United States Patent
Okano et al.

(10) Patent No.: US 8,476,287 B2
(45) Date of Patent: Jul. 2, 2013

(54) 3-HYDROXY-5-ARYLISOTHIAZOLE DERIVATIVE

(75) Inventors: Akihiro Okano, Tokyo (JP); Naoto Kosuga, Tokyo (JP); Munetaka Ohkouchi, Tokyo (JP); Daido Hotta, Tokyo (JP); Muneyoshi Makabe, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/392,350

(22) PCT Filed: Dec. 24, 2010

(86) PCT No.: PCT/JP2010/073464
§ 371 (c)(1),
(2), (4) Date: Feb. 24, 2012

(87) PCT Pub. No.: WO2011/078371
PCT Pub. Date: Jun. 30, 2011

(65) Prior Publication Data
US 2012/0157459 A1    Jun. 21, 2012

(30) Foreign Application Priority Data

Dec. 25, 2009 (JP) .................. 2009-295855
Feb. 26, 2010 (JP) .................. 2010-043420

(51) Int. Cl.
*A61K 31/506* (2006.01)
*A61K 31/425* (2006.01)
*A61K 31/4436* (2006.01)
*A61K 31/4535* (2006.01)
*C07D 239/24* (2006.01)
*C07D 275/02* (2006.01)
*C07D 417/02* (2006.01)

(52) U.S. Cl.
USPC ........... 514/274; 514/326; 514/342; 514/372; 544/316; 546/209; 546/271.1; 548/213

(58) Field of Classification Search
USPC ... 514/274, 326, 342, 372; 544/316; 546/209, 546/271.1; 548/213
See application file for complete search history.

(56) References Cited

U.S. PATENT DOCUMENTS

| | | | |
|---|---|---|---|
| 3,562,283 A | 2/1971 | Lewis et al. | |
| 3,801,575 A | 4/1974 | Lewis et al. | |
| 2003/0004193 A1 | 1/2003 | Barrett et al. | |
| 2006/0100261 A1 | 5/2006 | Hamamura et al. | |
| 2006/0258722 A1 | 11/2006 | Yasuma et al. | |
| 2009/0170908 A1 | 7/2009 | Shimada et al. | |
| 2009/0186909 A1 | 7/2009 | Negoro et al. | |
| 2010/0130559 A1 | 5/2010 | Hashimoto et al. | |
| 2010/0261645 A1 | 10/2010 | Defossa et al. | |
| 2010/0267775 A1 | 10/2010 | Negoro et al. | |
| 2011/0065739 A1 | 3/2011 | Ishikawa et al. | |

FOREIGN PATENT DOCUMENTS

| | | |
|---|---|---|
| CN | 101781268 A | 7/2010 |
| JP | 2000-204077 A | 7/2000 |
| JP | 2005-15461 A | 1/2005 |
| WO | WO 00/42029 A1 | 7/2000 |
| WO | WO 2004/011446 A1 | 2/2004 |
| WO | WO 2004/022551 A1 | 3/2004 |
| WO | WO 2004/041266 A1 | 5/2004 |
| WO | WO 2005/035551 A2 | 4/2005 |
| WO | WO 2005051890 A1 | 6/2005 |
| WO | WO 2005/063729 A1 | 7/2005 |
| WO | WO 2005/086661 A2 | 9/2005 |
| WO | WO 2007/033002 A1 | 3/2007 |
| WO | WO 2007/123225 A1 | 11/2007 |
| WO | WO 2008/001931 A2 | 1/2008 |
| WO | WO 2008/030520 A1 | 3/2008 |

(Continued)

OTHER PUBLICATIONS

PubMed Health, "Type 1 diabetes," Jun. 28, 2011.*

(Continued)

*Primary Examiner* — Samantha Shterengarts
(74) *Attorney, Agent, or Firm* — Birch, Stewart, Kolasch & Birch, LLP

(57) ABSTRACT

[Problem]
To provide a GPR40 activating agent having, as an active ingredient, a novel compound having a GPR40 agonist action, a salt of the compound, a solvate of the salt or the compound, or the like, particularly, an insulin secretagogue and a prophylactic and/or therapeutic agent against diabetes, obesity, or other diseases.

[Means of solving the problem]
A compound of Formula (I):

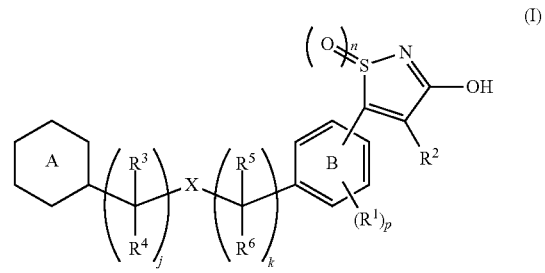

(where n is 0 to 2; p is 0 to 4; j is 0 to 3; k is 0 to 2; a ring A is an aryl group which is optionally substituted with L or a heterocyclic group which is optionally substituted with L; a ring B is a benzene ring, a pyridine ring, or a pyrimidine ring; X is O, S, —$NR^7$—; and $R^1$ to $R^7$ are specific groups), a salt of the compound, or a solvate of the salt or the compound.

36 Claims, No Drawings

FOREIGN PATENT DOCUMENTS

| | | |
|---|---|---|
| WO | WO 2008/033931 A1 | 3/2008 |
| WO | WO 2008/066131 A1 | 6/2008 |
| WO | WO 2008/130514 A1 | 10/2008 |
| WO | WO 2009/039943 A1 | 4/2009 |
| WO | WO 2009/048527 A1 | 4/2009 |
| WO | WO 2009/054390 A1 | 4/2009 |
| WO | WO 2009/054423 A1 | 4/2009 |
| WO | WO 2009/054479 A1 | 4/2009 |
| WO | WO 2009/111056 A1 | 9/2009 |
| WO | WO 2009/147990 A1 | 12/2009 |
| WO | WO 2010/085525 A1 | 7/2010 |
| WO | WO 2010/091176 A1 | 8/2010 |
| WO | WO 2010/143733 A1 | 12/2010 |
| WO | WO 2011/046851 A1 | 4/2011 |
| WO | WO 2011/052756 A1 | 5/2011 |
| WO | WO 2011/066183 A1 | 6/2011 |
| WO | WO 2011/078371 A1 | 6/2011 |
| WO | WO 2012/046869 A1 | 4/2012 |

OTHER PUBLICATIONS

Chiasson et al., "Acarbose Treatment and the Risk of Cardiovascular Disease and Hypertension in Patients With Impaired Glucose . . . ", Jama, http://jama.ama-assn.org/cgi/content/full/290/4/486, vol. 290, No. 4, 2003, pp. 486-494, (retrieved online Oct. 27, 2009).

International Preliminary Report on Patentability for Application No. PCT/JP2010/073464 dated Dec. 2, 2011 (with English translation).

Itoh et al., "Free fatty acids regulate insulin secretion from pancreatic β cells through GPR40", letters to nature, www.nature.com/nature, vol. 422, Mar. 13, 2003, pp. 173-176.

Japanese Amendment for Application No. PCT/JP2010/073464 dated Nov. 10, 2011 (with English translation).

Japanese Demand for International Preliminary Examination for Application No. PCT/JP2010/073464 dated Sep. 30, 2011.

Japanese Reply for Application No. PCT/JP2010/073464 dated Nov. 10, 2011 (with English translation).

Kotarsky et al., "A human cell surface receptor activated by free fatty acids and thiazolidinedione drugs", Biochemical and Biophysical Research Communications, vol. 301, 2003, pp. 406-410.

Technomics, Inc., "Saishin Soyaku Kagaku", The latest drug discovery chemistry, First Volume, Aug. 15, 1998, pp. 248-253.

English translation of Technomics, Inc., "Saishin Soyaku Kagaku", The latest drug discovery chemistry, First Volume, Aug. 15, 1998, pp. 248-253.

International Search Report and Written Opinion of the International Searching Authority in International Application No. PCT/JP2012/059933, mailed Jun. 19, 2012, with an English translation.

Notification of Transmittal of Translation of the International Preliminary Report of Patentability (Chapter I or Chapter II) for International application No. PCT/JP2010/073464 dated Aug. 9, 2012.

* cited by examiner

3-HYDROXY-5-ARYLISOTHIAZOLE DERIVATIVE

TECHNICAL FIELD

The present invention relates to a compound for modulating the functions of G protein-coupled receptor 40 (GPR40). In particular, the present invention relates to a compound having a 3-hydroxy-5-arylisothiazole ring of Formula (I), a salt of the compound, a solvate of the compound or the salt, a pharmaceutical composition containing the compound as an active ingredient, prophylactic and/or therapeutic agents against GPR40-involving diseases, especially diabetes, and an insulin secretagogues.

BACKGROUND ART

Diabetes is categorized into Type 1 diabetes (insulin-dependent diabetes) and Type 2 diabetes (non-insulin-dependent diabetes), and borderline type diabetes (glucose tolerance disorders) has also attracted attention as a pre-diabetic condition in recent years. Type 1 diabetes is characterized by a partial or complete inability to produce insulin, which is a blood glucose regulating hormone. Type 2 diabetes is characterized by induced peripheral insulin resistance and impaired insulin secretion. Borderline type diabetes is a pathological condition exhibiting impaired glucose tolerance (IGT) or impaired fasting glucose (IFG), associated with a risk of developing Type 2 diabetes or diabetes complications.

Diabetes is caused by several predisposing factors. It is a disease characterized by high glucose levels in blood plasma in fasting and postprandial states or during an oral glucose tolerance test or by chronic hyperglycemia, in general. Controlling chronic hyperglycemia is essential in clinical management and treatment of diabetes. In particular, reduced insulin secretion from beta cells of the pancreas can induce an abrupt increase in postprandial blood glucose levels in Type 2 diabetes or borderline type diabetes. An international large-scale clinical trial has revealed that it is essential to control postprandial hyperglycemia in impaired glucose tolerance for suppressing the development and progress of not only diabetes but also hypertension and cardiovascular diseases (JAMA, 290, 486-494 (2003) (Non-Patent Document 1)). On the basis of these findings, the International Diabetes Federation published new guidelines for diabetes treatment (postprandial blood glucose control guidelines) in 2007, which recommend control of postprandial blood glucose levels as essential for Type 1 and 2 diabetic patients to alleviate diabetes and reduce risk of complications. As a practical step, an increased administration of an alpha-glucosidase inhibitor (voglibose) that is a drug for alleviating excessive postprandial blood glucose levels associated with diabetes, has been approved in Japan as a prophylactic agent against diabetes, aiming to "inhibit the development of Type 2 diabetes from impaired glucose tolerance". As described above, there has been increasing awareness of the needs of nonpharmacological and pharmacological treatments against diabetes and borderline type diabetes, targeting the control of postprandial blood glucose levels in recent years.

Diabetes is treated mainly through diet regulation and exercise. When these fail to alleviate symptoms, pharmacological treatment is needed. Various types of drugs are available as prophylactic or therapeutic agents against diabetes. Among them, examples of insulin secretagogues include sulfonylurea agents (e.g., glibenclamide, glimepiride) and rapid-acting insulin secretagogues (e.g., mitiglinide), all of which stimulate beta cells of the pancreas so as to accelerate insulin secretion. These drugs are, however, known for their ineffectiveness (primary failure, secondary failure) and side effects such as induced hypoglycemic effects. Analogs (e.g., exenatide, liraglutide) of glucagon-like peptide-1 (GLP-1), which are hormones accelerating glucose-responsive insulin secretion in beta cells of the pancreas, have become available as novel insulin secretagogues, but they are administered by injection and known for their side effects of transient gastrointestinal tract disorders. Other examples of insulin secretagogues include dipeptidyl peptidase IV (DPP-IV) inhibitors (e.g., sitagliptin, vildagliptin), which inhibit the degradation of intrinsic GLP-1, but they are known for their side effects of epipharyngitis, headache, and infections. Alpha-glucosidase inhibitors (e.g., acarbose, voglibose) inhibit the degradation and digestion of carbohydrate and thus limit an abrupt increase in postprandial blood glucose levels, but they need to be taken immediately before meals and are known for their side effects such as distension and diarrhea and serious liver disorders. Biguanides (e.g., metformin, buformin) are insulin resistance improving agents enhancing insulin sensitivity and thereby alleviating hyperglycemia, but are known to potentially induce side effects such as lactic acidosis, nausea, and vomiting. Thiazolidinedione derivatives (e.g., pioglitazone, rosiglitazone) are peroxisome proliferator-activated receptor (PPAR) gamma agonists. The derivatives increase insulin sensitivity in adipose tissue, the liver, and skeletal muscles and thereby alleviate chronic hyperglycemia, but are known to cause edema, weight gain, and serious side effects of liver disorders. Side effects of these drugs do not always occur, but remain as a major obstacle to high satisfaction with treatment. Therefore, the demand has been increasing for insulin secretagogues, particularly orally administrable insulin secretagogues, entailing few problems and side effects caused by conventional prophylactic and therapeutic agents as described above and inhibiting postprandial hyperglycemia without inducing hypoglycemia.

Fatty acid plays an important role in insulin use in the liver and skeletal muscles, glucose-responsive insulin secretion from the pancreas, and inflammation associated with fat accumulation in adipose tissue. A strong correlation is known between increased levels of fatty acid in blood plasma and the development of diabetes, metabolic syndrome, obesity, and adiposity.

GPR40, one of the G-protein-coupled receptors, is categorized in the free fatty acid receptor (FFAR) family and activated by $C_{6\text{-}22}$ saturated or unsaturated fatty acid. It is reported that high expression of GPR40 is observed in beta cells of the pancreas where the receptor is involved in insulin secretion caused by fatty acid (Nature, 422, 173-176 (2003) (Non-Patent Document 2)). Non-fatty-acid low-molecular-weight compounds having a GPR40 agonist action have been found in recent years, and it is reported that thiazolidinediones, which are insulin sensitivity improving agents, and MEDICA 16, which is a hypolipidemic agent, also exhibit agonist actions (Biochem. Biophys. Res. Comm., 301, 406-410 (2003) (Non-Patent Document 3)).

In the pancreatic islets of Langerhans isolated from GPR40 knockout mice, the glucose-responsive insulin secretagogue action of fatty acid is lower than the case with normal mice. Accordingly, substances having a GPR40 agonist action like fatty acid are expected to have the effect of inhibiting postprandial hyperglycemia based on the glucose-responsive insulin secretagogue action in the pancreas. Therefore, substances having a GPR40 agonist action are considered to be effective as prophylactic and therapeutic agents against diabetes or borderline type diabetes.

Studies have been progressed on compounds having a GPR40 activating action as insulin secretagogues or therapeutic agents against diabetes. Technologies related to compounds having a GPR40 agonist action are disclosed, for example, in WO 2004/041266 pamphlet (Patent Document 1), WO 2005/086661 pamphlet (Patent Document 2), WO 2007/123225 pamphlet (Patent Document 3), WO 2008/001931 pamphlet (Patent Document 4), WO 2009/054390 pamphlet (Patent Document 5), and WO 2009/054423 pamphlet (Patent Document 6). These documents, however, do not disclose or suggest any compounds having a 3-hydroxy-5-arylisothiazolyl group.

A technique related to a compound having a 3-hydroxy-5-arylisothiazolyl group is disclosed in WO 2005/035551 pamphlet (Patent Document 7). The compound disclosed in Patent Document 7, however, is a compound having an inhibitory effect on protein tyrosine phosphatase 1B (PTP1B), and its structure is fundamentally different from that of the compounds according to the present invention. Another compound having a 3-hydroxy-5-arylisothiazolyl group is disclosed in WO 2000/042029 pamphlet (Patent Document 8). The compound disclosed in Patent Document 8, however, is a compound having an inhibitory effect on MAP kinase kinase (MEK) and containing a specific substituent on its side chain.

WO 2008/066131 pamphlet (Patent Document 9) and WO 2009/147990 pamphlet (Patent Document 10) disclose compounds having a 3-hydroxy-5-arylisoxazolyl group as compounds having a G protein-coupled receptor 120 (GPR120) agonist action. These documents, however, do not disclose or suggest any compounds having a GPR40 agonist action or a 3-hydroxy-5-arylisothiazolyl group as in the present invention.

In the development of drugs, various strict criteria must be met in terms of absorption, distribution, metabolism, excretion, and other factors as well as targeted pharmacological actions. There are various things to consider, for example, interaction with other drugs, desensitization or durability, digestive tract absorption after oral administration, speed to reach the small intestine, absorption speed and first pass effect, organ barriers, protein binding, drug metabolizing enzyme induction or inhibition, excretion route and clearance in the body, and application methods (application sites, methods, purposes). It is difficult to find a drug that meets all the criteria.

Several compounds are reported to have a GPR40 agonist action, but none of them has been marketed so far. Such agonists could also involve the above-mentioned general issues in the development phase of drugs. More specifically, they have problems in usefulness and safety, such as low metabolism stability and difficulty in systemic exposure by oral administration, unfavorable pharmacokinetic effects including absorption and persistence properties, an activity of inhibiting the human ether-a-go-go related gene (hERG) channel, possibly resulting in arrhythmia, and an activity of inducing or inhibiting drug metabolizing enzymes (e.g., cytochrome P450). Therefore, required is a compound that solves these problems as much as possible and still has high efficacy.

In addition, required as a GPR40 agonist is a compound with fewer problems or side effects as described above than the aforementioned conventional drugs that have been used to prevent or treat diabetes (particularly Type 2 diabetes or borderline type diabetes).

RELATED-ART DOCUMENTS

Patent Documents

Patent Document 1: WO 2004/041266 pamphlet
Patent Document 2: WO 2005/086661 pamphlet
Patent Document 3: WO 2007/123225 pamphlet
Patent Document 4: WO 2008/001931 pamphlet
Patent Document 5: WO 2009/054390 pamphlet
Patent Document 6: WO 2009/054423 pamphlet
Patent Document 7: WO 2005/035551 pamphlet
Patent Document 8: WO 2000/042029 pamphlet
Patent Document 9: WO 2008/066131 pamphlet
Patent Document 10: WO 2009/147990 pamphlet Non-Patent Documents Non-Patent Document 1: JAMA, 290, 486-494 (2003)
Non-Patent Document 2: Nature, 422, 173-176 (2003)
Non-Patent Document 3: Biochem. Biophys. Res. Comm., 301, 406-410 (2003)

DISCLOSURE OF THE INVENTION

Problem to be Solved by the Invention

In view of such medical circumstances related to diabetes, prophylactic and therapeutic drugs are required that accelerate insulin secretion, particularly glucose-responsive insulin secretion, through activation of GPR40, and thus exhibit the action of lowering blood glucose levels, particularly inhibiting postprandial hyperglycemia.

Particularly required are orally administrable GPR40 activating agents, insulin secretagogues, prophylactic and/or therapeutic agents against GPR40-involving diseases (particularly prophylactic and/or therapeutic agents against diabetes or obesity) all of which have high safety, excellent efficacy, and high selectivity with respect to other members of the FFAR family or similar receptors.

In particular, there are issues to be addressed as problems with the conventional techniques described above. More specifically, there are the following issues to be addressed with prophylactic and therapeutic agents against diabetes: ineffectiveness (primary failure, secondary failure) and side effects such as induced hypoglycemic effects caused by sulfonylurea agents and rapid-acting insulin secretagogues; transient gastrointestinal tract disorders caused by GLP-1 analogs; side effects of epipharyngitis, headache, and infections caused by DPP-IV inhibitors; side effects such as distension and diarrhea and serious liver disorders caused by alpha-glucosidase inhibitors; side effects such as lactic acidosis, nausea, and vomiting caused by biguanides; edema, weight gain, and serious liver disorders caused by thiazolidinedione derivatives; and so on. Other issues to be addressed include solubility, improvement in metabolism stability, enhancement of absorption properties, improvement in pharmacokinetic effects, reduction in the activity of inhibiting hERG, and reduction in the activity of inducing or inhibiting drug metabolizing enzymes (e.g., cytochrome P450). Consequently, there are the needs for insulin secretagogues and prophylactic and/or therapeutic agents against GPR40-involving diseases (particularly prophylactic and/or therapeutic agents against diabetes or obesity) all of which solve at least one of the issues, are orally administrable to mammals including human beings, and are clinically usable in particular.

Means for Solving the Problem

As a result of assiduous research for solving the above problems by obtaining a compound having high safety and/or excellent efficacy and modulating the functions of GPR40, the inventors of the present invention have found that a 3-hydroxy-5-arylisothiazole derivative of Formula (I) has a GPR40 agonist action. The compound of the present invention has an excellent glucose-responsive insulin secretagogue action and has a strong hyperglycemia-inhibiting action during glucose load.

Effects of Invention

The present invention provides: a compound of Formula (I), characterized by having a 3-hydroxy-5-arylisothiazole ring, a salt of the compound, or a solvate of the compound or the salt; and a pharmaceutical composition, characterized by containing as an active ingredient, the compound, a pharmaceutically acceptable salt of the compound, or a solvate of the compound or the pharmaceutically acceptable salt.

The compound of the present invention is a compound having a GPR40 agonist action, or a compound having an action of lowering a blood glucose level, particularly an action of inhibiting postprandial hyperglycemia, by activating GPR40 to accelerate an insulin secretion, particularly a glucose-responsive insulin secretion. The pharmaceutical composition containing the compound of the present invention as an active ingredient can be orally administrated and is expected as an insulin secretagogues or a prophylactic agent and/or a therapeutic agent for a GPR40-involving disease, particularly diabetes (particularly Type 2 diabetes or borderline type diabetes) or obesity and adiposity.

The group of the compounds of the present invention has at least one of characteristics such as having advantageous solubility, having high metabolism stability, having excellent oral absorption properties, and having a small activity of inhibiting the hERG channel, and thus is highly useful.

BEST MODE FOR CARRYING OUT THE INVENTION

The present invention provides: a compound of Formula (I), characterized by having a 3-hydroxy-5-arylisothiazole ring shown in the following aspects, a salt of the compound, or a solvate of the compound or the salt; and a pharmaceutical composition or GPR40 activating agent, characterized by containing the compound, the salt, or the solvate as an active ingredient.

ASPECTS OF THE PRESENT INVENTION

[1] Aspect [1] of the Present Invention
A first aspect of the present invention is,
a compound of Formula (I):

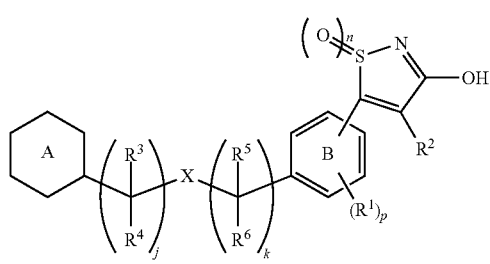

(where n is an integer of 0 to 2; p is an integer of 0 to 4; j is an integer of 0 to 3; k is an integer of 0 to 2;
a ring A is a $C_{6-14}$ aryl group which is optionally substituted with 1 to 5 L(s) or a 3- to 14-membered heterocyclic group which is optionally substituted with 1 to 5 L(s);

a ring B is a benzene ring, a pyridine ring, or a pyrimidine ring;
X is an oxygen atom, a sulfur atom, or —$NR^7$—;
$R^1$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group;
$R^2$ is a hydrogen atom, a halogen atom, a $C_{1-6}$ alkyl group, a $C_{2-6}$ alkenyl group, a $C_{2-6}$ alkynyl group, a $C_{1-6}$ alkoxy group, or a cyano group;
$R^3$, $R^4$, $R^5$, $R^6$, and $R^7$ are independently a group arbitrarily selected from a hydrogen atom, a $C_{1-6}$ alkyl group, a halogenated $C_{1-6}$ alkyl group, a $C_{2-6}$ alkenyl group, and a $C_{2-6}$ alkynyl group;
Ls are independently a halogen atom, —OH, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{1-10}$ alkenyloxy group which is optionally substituted with 1 to 5 substituent(s) RI, a $C_{1-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a —$S(O)_iR^a$ (i is an integer of 0 to 2) group, or a —$NR^bR^c$ group;
$R^a$ is a group arbitrarily selected from a $C_{1-6}$ alkyl group and a halogenated $C_{1-6}$ alkyl group;
$R^b$ and $R^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with —OH or a $C_{1-6}$ alkoxy group), a $C_{1-6}$ alkylsulfonyl group, an arylcarbonyl group, and a heterocyclic carbonyl group, where $R^b$ and $R^c$ optionally form together with a nitrogen atom to which they are bonded, a 3- to 8-membered cyclic group, where in the cyclic group, one carbon atom is optionally substituted with an atom arbitrarily selected from an oxygen atom, a sulfur atom, and a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;
where the substituents RI may be the same as or different from each other and be each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —$S(O)_iR^a$ (i is an integer of 0 to 2) group(s), 1 to 5

—SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a non-aromatic heterocyclic oxy group;

the substituents RII may be the same as or different from each other and be each a group arbitrarily selected from the substituents RI and a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s));

R$^d$ and R$^e$ are independently a hydrogen atom or a C$_{1-6}$ alkyl group;

R$^{b1}$ and R$^{c1}$ are independently a group arbitrarily selected from a hydrogen atom, a C$_{1-6}$ alkyl group, a C$_{2-7}$ alkanoyl group, and a C$_{1-6}$ alkylsulfonyl group, where R$^{b1}$ and R$^{c1}$ optionally form together with a nitrogen atom to which they are bonded, a 3- to 8-membered cyclic group, where in the cyclic group, one carbon atom is optionally substituted with an atom arbitrarily selected from an oxygen atom, a sulfur atom, and a nitrogen atom (the nitrogen atom is optionally substituted with a C$_{1-6}$ alkyl group) or with a carbonyl group;

(with the proviso that there are excluded a compound which is 5-(3-phenylmethoxyphenyl)-isothiazole-3-ol 1,1-dioxide or 5-(4-(((4-phenoxyphenyl)methoxy)methyl)phenyl)-isothiazole-3-ol 1,1-dioxide and a compound in which a 3-hydroxyisothiazolyl group is bonded to a carbon atom adjacent to a carbon atom to which a linker containing X is bonded in the ring B and the ring A is 4-iodophenyl, 2-chloro-4-iodophenyl, or 4-iodo-2-methylphenyl)), or a pharmaceutically acceptable salt of the compound, or a pharmaceutically acceptable solvate of the salt or a pharmaceutically acceptable solvate of the compound.

Each group in Formula (I) according to Aspect [1] is specifically described below.

In the explanation of the compound according to the present invention, for example, "C$_{1-6}$" indicates that the number of constituent carbon atoms, which is the number of carbon atoms in a linear, branched, or cyclic group unless otherwise indicated, is 1 to 6. The number of constituent carbon atoms includes the total number of carbon atoms in a group having a linear or branched group substituted with a cyclic group or a cyclic group substituted with a linear or branched group. Therefore, as for an acyclic group, "C$_{1-6}$" means a "linear or branched chain with the number of constituent carbon atoms of 1 to 6". As for a cyclic group, "C$_{1-6}$" means a "cyclic group with the number of ring-constituting carbon atoms of 1 to 6". As for a group having an acyclic group and a cyclic group, "C$_{1-6}$" means a "group with the total number of carbon atoms of 1 to 6".

The "alkyl group" is a linear, branched, or cyclic alkyl group. For example, examples of the "C$_{1-6}$ alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 3-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, 1-cyclopropylethyl, 2-cyclopropylethyl, 2-cyclobutylethyl, 2-methylcyclopropyl, and the like. Examples of the "C$_{1-10}$ alkyl group" include, in addition to the groups mentioned as the "C$_{1-6}$ alkyl group", heptyl, 1-methylhexyl, octyl, 2-ethylhexyl, 1,1-dimethylhexyl, nonyl, decyl, cycloheptyl, cyclohexylmethyl, 2-cyclohexylethyl, 4-methylcyclohexyl, 4,4-dimethylcyclohexyl, 3,3,5,5-tetramethylcyclohexyl, and the like.

The "alkenyl group" is a linear, branched, or cyclic alkenyl group. For example, examples of the "C$_{2-6}$ alkenyl group" include vinyl, allyl, isopropenyl, 2-methylallyl, butenyl, pentenyl, isopentenyl, hexenyl, 1-cyclopropen-1-yl, 2-cyclopropen-1-yl, 1-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclopentadien-1-yl, 2,5-cyclohexadien-1-yl, and the like. Examples of the "C$_{1-10}$ alkenyl group" include, in addition to the groups mentioned as the "C$_{1-6}$ alkenyl group", heptenyl, octenyl, nonenyl, decenyl, 1-cyclohepten-1-yl, 1-cyclohexen-1-ylmethyl, 4-methyl-1-cyclohexen-1-yl, 4,4-dimethyl-1-cyclohexen-1-yl, 3,3,5,5-tetramethyl-1-cyclohexen-1-yl, and the like.

The "alkynyl group" is a linear, branched, or cyclic alkynyl group. For example, examples of the "C$_{2-6}$ alkynyl group" include ethynyl, 1-propynyl, 2-propynyl, butynyl, pentynyl, hexynyl, and the like. Examples of the "C$_{1-10}$ alkynyl group" include, in addition to the groups mentioned as the "C$_{1-6}$ alkynyl group", heptynyl, octynyl, nonynyl, decynyl, and the like.

The "alkoxy group" is a linear, branched, or cyclic alkoxy group and comprehensively a group of RO— (as for the C$_{1-6}$ alkoxy group, R is the C$_{1-6}$ alkyl group listed above). For example, examples of the "C$_{1-6}$ alkoxy group" include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, 1-ethylpropoxy, hexyloxy, isohexyloxy, 1-methylpentyloxy, 2-methylpentyloxy, 3-methylpentyloxy, 1,1-dimethylbutyloxy, 1,2-dimethylbutyloxy, 2,2-dimethylbutyloxy, 1,3-dimethylbutyloxy, 2,3-dimethylbutyloxy, 3,3-dimethylbutoxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, cyclopropyloxy, cyclobutyloxy, cyclopentyloxy, cyclohexyloxy, cyclopropylmethoxy, cyclobutylmethoxy, cyclopentylmethoxy, 1-cyclopropylethoxy, 2-cyclopropylethoxy, 2-cyclobutylethoxy, 2-methylcyclopropyloxy, and the like. Examples of the "C$_{1-10}$ alkoxy group" include, in addition to the groups mentioned as the "C$_{1-6}$ alkoxy group", heptyloxy, octyloxy, 2-ethylhexyloxy, nonyloxy, decyloxy, cycloheptyloxy, cyclohexylmethoxy, 2-cyclohexylethoxy, 4-methylcyclohexyloxy, 4,4-dimethylcyclohexyloxy, 3,3,5,5-tetramethylcyclohexyloxy, and the like.

The "alkenyloxy group" is the "alkenyl group" which is substituted with an oxygen atom, denoting a linear, branched, or cyclic alkenyloxy group. For example, examples of the "C$_{2-6}$ alkenyloxy group" include vinyloxy, allyloxy, isopropenyloxy, 2-methylallyloxy, butenyloxy, pentenyloxy, isopentenyloxy, hexenyloxy, 1-cyclopropen-1-yloxy, 2-cyclopropen-1-yloxy, 1-cyclobuten-1-yloxy, 1-cyclopenten-1-yloxy, 2-cyclopenten-1-yloxy, 3-cyclopenten-1-yloxy, 1-cyclohexen-1-yloxy, 2-cyclohexen-1-yloxy, 3-cyclohexen-1-yloxy, 2,4-cyclopentadien-1-yloxy, 2,5-cyclohexadien-1-yloxy, and the like. Examples of the "C$_{2-10}$ alkenyloxy group" include, in addition to the groups mentioned as the "C$_{2-6}$ alkenyloxy group", heptenyloxy, octenyloxy, nonenyloxy, decenyloxy, 1-cyclohepten-1-yloxy, 1-cyclohexen-1-ylmethoxy, 4-methyl-1-cyclohexen-1-yloxy, 4,4-dimethyl-1-cyclohexen-1-yloxy, 3,3,5,5-tetramethyl-1-cyclohexen-1-yloxy, and the like.

The "alkynyloxy group" is the "alkynyl group" which is substituted with an oxygen atom, denoting a linear, branched, or cyclic alkynyloxy group. For example, examples of the "C$_{2-6}$ alkynyloxy group" include ethynyloxy, 1-propynyloxy, 2-propynyloxy, butynyloxy, pentynyloxy, hexynyloxy, and the like. Examples of the "$C_{2-10}$ alkynyloxy group" include, in addition to the groups mentioned as the "$C_{2-6}$ alkynyloxy group", heptynyloxy, octynyloxy, nonynyloxy, decynyloxy, and the like.

Examples of the "aryl group" include a monocyclic or ring-fused $C_{6-14}$ aryl group, for example, phenyl, 1-naphthyl, 2-naphthyl, anthryl, phenanthryl, acenaphthyl, and the like, or a fused aryl group which is partly hydrogenated such as (1-, 2-, 4-, or 5-)indanyl, indenyl, tetrahydronaphthyl, and the like. The aryl group which is partly hydrogenated means a monovalent group obtained by removing any hydrogen atom from a fused ring which is partly hydrogenated, and the hydrogen atom to be removed is optionally a hydrogen atom in an aromatic ring moiety or a hydrogen atom in a hydrogenated moiety of the fused ring. For example, tetrahydronaphthyl includes 1,2,3,4-tetrahydronaphthalen (-1-yl, -2-yl, -3-yl, -4-yl, -5-yl, -6-yl, -7-yl, -8-yl), and the like.

Examples of the "heterocyclic group" include a heteroaryl group, and a saturated or unsaturated non-aromatic heterocyclic group. The term "cyclic" used for these groups means a monovalent group obtained by removing any hydrogen atom from a ring having a 3- to 14-membered, preferably a 3- to 12-membered, monocyclic ring or fused ring containing, in addition to carbon atoms, at least one (preferably 1 to 4) heteroatom(s) arbitrarily selected from N, O, and S.

The "heteroaryl group" can be monocyclic or ring-fused, and the monocyclic heteroaryl group preferably has 5 to 7 ring members and includes, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, 1,4-oxazepinyl, and the like.

The ring-fused heteroaryl group preferably has 8 to 12 ring members and includes a monovalent group obtained by removing any hydrogen atom from a fused ring formed by fusing the 5- to 7-membered heterocyclic ring and a monocyclic aryl group or a monocyclic heteroaryl group, and the like. The hydrogen atom is optionally removed from any of the fused rings.

Specifically, indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, and the like are mentioned.

In addition, a ring-fused heteroaryl group, etc. which is partly hydrogenated, such as indolinyl, dihydrobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,3-benzodioxanyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl is mentioned. The ring-fused heteroaryl group, etc. which is partly hydrogenated is preferably one having 8 to 12 ring members, namely a monovalent group obtained by removing any hydrogen atom from a ring which is partly hydrogenated in the fused ring formed by fusing the 5- to 7-membered heterocyclic ring and a monocyclic aryl group or a monocyclic heteroaryl group. The hydrogen atom to be removed is optionally a hydrogen atom in the aryl group or in the heterocyclic moiety or a hydrogen atom in the hydrogenated moiety. In the case of tetrahydroquinolyl, examples of the partially hydrogenated ring-condensed heteroaryl group include 5,6,7,8-tetrahydroquinolyl and 1,2,3,4-tetrahydroquinolyl. Depending on the position in these groups from which the hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" include a 3- to 8-membered saturated or unsaturated non-aromatic heterocyclic group, for example, aziridinyl, azetidinyl, oxiranyl, oxetanyl, thietanyl, pyrrolidinyl, tetrahydrofuryl, thiolanyl, pyrazolinyl, pyrazolidinyl, piperidinyl, dihydropyranyl, tetrahydropyranyl(oxanyl), tetrahydrothiopyranyl, piperazinyl, dioxanyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, oxepanyl, and the like, and the "non-aromatic heterocyclic group" means a monovalent group obtained by removing any hydrogen atom from the ring.

Examples of the "non-aromatic heterocyclic group (the heterocyclic group is optionally substituted with a $C_{1-6}$ alkyl group)" include, in addition to the groups mentioned as the "non-aromatic heterocyclic group", a group in which the cyclic group is substituted with the "$C_{1-6}$ alkyl group" at any position. For example, methylaziridinyl, methylazetidinyl, methyloxiranyl, methyloxetanyl, methylthietanyl, methylpyrrolidinyl, methyltetrahydrofuryl, methylthiolanyl, methylpyrazolinyl, methylpyrazolidinyl, methylpiperidinyl, methyltetrahydropyranyl, methylpiperazinyl, methyloxazolinyl, methylisoxazolinyl, methyloxazolidinyl, methylisoxazolidinyl, methylthiazolinyl, methylisothiazolinyl, methylthiazolidinyl, methylisothiazolidinyl, methyloxadiazolinyl, methyloxadiazolidinyl, methylmorpholinyl, methylthiomorpholinyl, methylquinuclidinyl, methyloxepanyl, and the like are mentioned.

The "aralkyl group" is a group in which a linear or branched alkyl group of the "$C_{1-6}$ alkyl group" is substituted with the "aryl group", and examples of the "aralkyl group" include, for example, benzyl, phenethyl, 3-phenylpropyl, 1-naphthylmethyl, 2-naphthylmethyl, 2-(1-naphthyl)ethyl, 2-(2-naphthyl)ethyl, 1-indanylmethyl, 2-indanylmethyl, 1,2,3,4-tetrahydronaphthalen-1-ylmethyl, 1,2,3,4-tetrahydronaphthalen-2-ylmethyl, and the like.

The "heteroarylalkyl group" is a group in which a linear or branched alkyl group of the "$C_{1-6}$ alkyl group" is substituted with the "heteroaryl group", and examples of the "heteroarylalkyl group" include those substituted with the "monocyclic heteroaryl group", such as pyrrolylmethyl, furylmethyl, thienylmethyl, imidazolylmethyl, pyrazolylmethyl, oxazolylmethyl, isoxazolylmethyl, thiazolylmethyl, isothiazolylmethyl, 1,2,3-triazolylmethyl, 1,2,4-triazolylmethyl, 1,2,3-oxadiazolylmethyl, 1,2,4-oxadiazolylmethyl, 1,3,4-oxadiazolylmethyl, furazanylmethyl, 1,2,3- thiadiazolylmethyl, 1,2,4-thiadiazolylmethyl, 1,3,4-thiadiazolylmethyl, tetrazolylmethyl, pyridylmethyl, pyridazinylmethyl, pyrimidinylmethyl, pyrazinylmethyl, 1,2,3-triazinylmethyl, 1,2,4-triazinylmethyl, 1,3,5-triazinylmethyl, 2H-1,2,3-thiadiazinylmethyl, 4H-1,2,4-thiadiazinylmethyl, 6H-1,3,4-thiadiazinylmethyl, 1,4-diazepinylmethyl, 1,4-oxazepinylmethyl, and the like, and those substituted with the "ring-fused heteroaryl group", such as indolylmethyl, isoindolylmethyl, benzofuranylmethyl, isobenzofuranylmethyl, benzothienylmethyl, isobenzothienylmethyl, benzoxazolylmethyl, 1,2-benzisoxazolylmethyl, benzothiazolylmethyl, 1,2-benzisothiazolylmethyl, 1H-benzimidazolylmethyl, 1H-indazolylmethyl, 1H-benzotriazolylmethyl, 2,1,3-benzothiadiazinylmethyl, chromenylmethyl, isochromenylmethyl, 4H-1,4-benzoxazinylmethyl, 4H-1,4-benzothiazinylmethyl, quinolylmethyl, isoquinolylmethyl, cinnolinylmethyl, quinazolinylmethyl, quinoxalinylmethyl, phthalazinylmethyl, benzoxazepinylmethyl, benzoazepinylmethyl, benzodiazepinylmethyl, naphthyridinylmethyl, purinylmethyl, pteridinylmethyl, carbazolylmethyl, carbolinylmethyl, acridinylmethyl, phenoxazinylmethyl, phenothiazinylmethyl, phenazinylmethyl, phenoxathiinylmethyl, thianthrenylmethyl, phenanthridinylmethyl, phenanthrolinylmethyl, indolizinylmethyl, thieno[3,2-e]pyridylmethyl, thiazolo[5,4-c]pyridylmethyl, pyrrolo[1,2-b]pyridazinylmethyl, pyrazolo[1,5-a]pyridylmethyl, imidazo[1,2-a]pyridylmethyl, imidazo[1,5-a]pyridylmethyl, imidazo[1,2-b]pyridazinylmethyl, imidazo[1,5-a]pyrimidinylmethyl, 1,2,4-triazolo[4,3-a]pyridylmethyl, 1,2,4-triazolo[4,3-b]pyridazinylmethyl, 1H-pyrazolo[3,4-b]pyridylmethyl, 1,2,4-triazolo[1,5-a]pyrimidinylmethyl, indolinylmethyl, dihydrobenzofuranylmethyl, chromanylmethyl, tetrahydroquinolylmethyl, tetrahydroisoquinolylmethyl, 1,4-benzodioxanylmethyl, 1,3-benzodioxolylmethyl, and the like.

The "aryloxy group" is a group in which the "aryl group" is substituted with an oxygen atom, and examples thereof include, for example, phenoxy, 1-naphthyloxy, 2-naphthyloxy, 2-anthryloxy, phenanthryloxy, 1-indanyloxy, 2-indanyloxy, 1,2,3,4-tetrahydronaphthalen-1-yloxy, 1,2,3,4-tetrahydronaphthalen-2-yloxy, 1,2,3,4-tetrahydronaphthalen-8-yloxy, and the like.

The "heteroaryloxy group" is a group in which the "heteroaryl group" is substituted with an oxygen atom, and examples thereof include, for example, pyrrolyloxy, furyloxy, thienyloxy, imidazolyloxy, pyrazolyloxy, oxazolyloxy, isoxazolyloxy, thiazolyloxy, isothiazolyloxy, (2-, 3-, or 4-)pyridyloxy, pyridazinyloxy, pyrimidinyloxy, pyrazinyloxy, indolyloxy, quinolyloxy, isoquinolyloxy, indolinyloxy, dihydrobenzofuranyloxy, chromanyloxy, tetrahydroquinolyloxy, tetrahydroisoquinolyloxy, 1,4-benzodioxanyloxy, 1,3-benzodioxolyloxy, and the like.

The "aralkyloxy group" is a group in which the "aralkyl group" is substituted with an oxygen atom, and examples thereof include, for example, benzyloxy, phenethyloxy, 3-phenylpropoxy, 1-naphthylmethoxy, 2-naphthylmethoxy, 2-(1-naphthyl)ethoxy, 2-(2-naphthyl)ethoxy, 1-indanylmethoxy, 2-indanylmethoxy, 1,2,3,4-tetrahydronaphthalen-1-ylmethoxy, 1,2,3,4-tetrahydronaphthalen-2-ylmethoxy, and the like.

The "heteroarylalkyloxy group" is a group in which the "heteroarylalkyl group" is substituted with an oxygen atom, and examples thereof include a "monocyclic heteroarylalkyl group" substituted with an oxygen atom, such as pyrrolylmethoxy, furylmethoxy, thienylmethoxy, imidazolylmethoxy, pyrazolylmethoxy, oxazolylmethoxy, isoxazolylmethoxy, thiazolylmethoxy, isothiazolylmethoxy, 1,2,3-triazolylmethoxy, 1,2,4-triazolylmethoxy, 1,2,3-oxadiazolylmethoxy, 1,2,4-oxadiazolylmethoxy, 1,3,4-oxadiazolylmethoxy, furazanylmethoxy, 1,2,3-thiadiazolylmethoxy, 1,2,4-thiadiazolylmethoxy, 1,3,4-thiadiazolylmethoxy, tetrazolylmethoxy, pyridylmethoxy, pyridazinylmethoxy, pyrimidinylmethoxy, pyrazinylmethoxy, 1,2,3-triazinylmethoxy, 1,2,4-triazinylmethoxy, 1,3,5-triazinylmethoxy, 2H-1,2,3-thiadiazinylmethoxy, 4H-1,2,4-thiadiazinylmethoxy, 6H-1,3,4-thiadiazinylmethoxy, 1,4-diazepinylmethoxy, 1,4-oxazepinylmethoxy, and the like, and a "ring-fused heteroarylalkyl group" which is optionally partly hydrogenated and is substituted with an oxygen atom, such as indolylmethoxy, isoindolylmethoxy, benzofuranylmethoxy, isobenzofuranylmethoxy, benzothienylmethoxy, isobenzothienylmethoxy, benzoxazolylmethoxy, 1,2-benzisoxazolylmethoxy, benzothiazolylmethoxy, 1,2-benzisothiazolylmethoxy, 1H-benzimidazolylmethoxy, 1H-indazolylmethoxy, 1H-benzotriazolylmethoxy, 2,1,3-benzothiadiazinylmethoxy, chromenylmethoxy, isochromenylmethoxy, 4H-1,4-benzoxazinylmethoxy, 4H-1,4-benzothiazinylmethoxy, quinolylmethoxy, isoquinolylmethoxy, cinnolinylmethoxy, quinazolinylmethoxy, quinoxalinylmethoxy, phthalazinylmethoxy, benzoxazepinylmethoxy, benzoazepinylmethoxy, benzodiazepinylmethoxy, naphthyridinylmethoxy, purinylmethoxy, pteridinylmethoxy, carbazolylmethoxy, carbolinylmethoxy, acridinylmethoxy, phenoxazinylmethoxy, phenothiazinylmethoxy, phenazinylmethoxy, phenoxathiinylmethoxy, thianthrenylmethoxy, phenanthridinylmethoxy, phenanthrolinylmethoxy, indolizinylmethoxy, thieno[3,2-e]pyridylmethoxy, thiazolo[5,4-c]pyridylmethoxy, pyrrolo[1,2-b]pyridazinylmethoxy, pyrazolo[1,5-a]pyridylmethoxy, imidazo[1,2-a]pyridylmethoxy, imidazo[1,5-a]pyridylmethoxy, imidazo[1,2-b]pyridazinylmethoxy, imidazo[1,5-a]pyrimidinylmethoxy, 1,2,4-triazolo[4,3-a]pyridylmethoxy, 1,2,4-triazolo[4,3-b]pyridazinylmethoxy, 1H-pyrazolo[3,4-b]pyridylmethoxy, 1,2,4-triazolo[1,5-a]pyrimidinylmethoxy, indolinylmethoxy, dihydrobenzofuranylmethoxy, chromanylmethoxy, tetrahydroquinolylmethoxy, tetrahydroisoquinolylmethoxy, 1,4-benzodioxanylmethoxy, 1,3-benzodioxolylmethoxy, and the like.

The "non-aromatic heterocyclic oxy group" is a group in which the "non-aromatic heterocyclic group" is substituted with an oxygen atom, and examples thereof include, for example, a 3- to 8-membered saturated or unsaturated non-aromatic heterocyclic oxy group, such as aziridinyloxy, azetidinyloxy, oxiranyloxy, oxetanyloxy, thietanyloxy, pyrrolidinyloxy, tetrahydrofuryloxy, thiolanyloxy, pyrazolinyloxy, pyrazolidinyloxy, (1-, 2-, 3-, or 4-)piperidinyloxy, dihydropyranyloxy, (2-, 3-, or 4-)tetrahydropyranyloxy((2-, 3-, or 4-)oxanyloxy), tetrahydrothiopyranyloxy, piperazinyloxy, dioxanyloxy, oxazolinyloxy, isoxazolinyloxy, oxazolidinyloxy, isoxazolidinyloxy, thiazolinyloxy, isothiazolinyloxy, thiazolidinyloxy, isothiazolidinyloxy, oxadiazolinyloxy, oxadiazolidinyloxy, morpholinyloxy, thiomorpholinyloxy, quinuclidinyloxy, oxepanyloxy, and the like.

Examples of the "halogen atom" include a fluorine atom, a chlorine atom, a bromine atom, and an iodine atom.

The "halogenated $C_{1-6}$ alkyl group" is a group in which the "$C_{1-6}$ alkyl group" is optionally substituted with 1 to 5 halogen atom(s). For example, trifluoromethyl, trifluoroethyl, tetrafluoroethyl, pentafluoroethyl, and the like are mentioned.

The "$C_{2-7}$ alkanoyl group (the alkanoyl group is optionally substituted with —OH or a $C_{1-6}$ alkoxy group)" means a "linear, branched, or cyclic $C_{2-7}$ alkylcarbonyl group" which is optionally substituted with —OH or a $C_{1-6}$ alkoxy group and is R—CO— (R is the "$C_{1-6}$ alkyl group" which is optionally substituted with —OH or a $C_{1-6}$ alkoxy group). Examples thereof include, for example, acetyl, propionyl, butyryl, isobutyryl, valeryl, isovaleryl, pivaloyl, hexanoyl, heptanoyl, cyclopropylcarbonyl, cyclobutylcarbonyl, cyclopentylcarbonyl, cyclohexylcarbonyl, cyclopropylmethylcarbonyl, 2-methylcyclopropylcarbonyl, hydroxyacetyl, methoxyacetyl, and the like.

The "arylcarbonyl group" is a group in which a carbonyl group is bonded to the "aryl group", and examples thereof include, for example, $C_{6-14}$ arylcarbonyl such as benzoyl and naphthylcarbonyl.

The "heterocyclic carbonyl group" means a "heterocyclic carbonyl group", and examples thereof include the "heterocyclic group" (for example, a heteroaryl group, a saturated or unsaturated non-aromatic heterocyclic group, and the like) to which a carbonyl group is bonded, including a carbonyl group to which the "monocyclic heteroaryl group" is bonded, such as pyrrolylcarbonyl, furylcarbonyl, thienylcarbonyl, imidazolylcarbonyl, pyrazolylcarbonyl, oxazolylcarbonyl, isoxazolylcarbonyl, thiazolylcarbonyl, isothiazolylcarbonyl, 1,2,3-triazolylcarbonyl, 1,2,4-triazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, tetrazolylcarbonyl, pyridylcarbonyl, pyridazinylcarbonyl, pyrimidinylcarbonyl, pyrazinylcarbonyl, 1,2,3-triazinylcarbonyl, 1,2,4-triazinylcarbonyl, 1,3,5-triazinylcarbonyl, 2H-1,2,3-thiadiazinylcarbonyl, 4H-1,2,4-thiadiazinylcarbonyl, 6H-1,3,4-thiadiazinylcarbonyl, 1,4-diazepinylcarbonyl, and 1,4-oxazepinylcarbonyl; a carbonyl group to which the "ring-fused heteroaryl group" which is optionally partly hydrogenated is bonded, such as indolylcarbonyl, isoindolylcarbonyl, benzofuranylcarbonyl, isobenzofuranylcarbonyl, benzothienylcarbonyl, isobenzothienylcarbonyl, benzoxazolylcarbonyl, 1,2-benzisoxazolylcarbonyl, benzothiazolylcarbonyl, 1,2-benzisothiazolylcarbonyl, 1H-benzimidazolylcarbonyl, 1H-indazolylcarbonyl, 1H-benzotriazolylcarbonyl, 2,1,3-benzothiadiazinylcarbonyl, chromenylcarbonyl, isochromenylcarbonyl, 4H-1,4-benzoxazinylcarbonyl, 4H-1,4-benzothiazinylcarbonyl, quinolylcarbonyl, isoquinolylcarbonyl, cinnolinylcarbonyl, quinazolinylcarbonyl, quinoxalinylcarbonyl, phthalazinylcarbonyl, benzoxazepinylcarbonyl, benzoazepinylcarbonyl, benzodiazepinylcarbonyl, naphthyridinylcarbonyl, purinylcarbonyl, pteridinylcarbonyl, carbazolylcarbonyl, carbolinylcarbonyl, acridinylcarbonyl, phenoxazinylcarbonyl, phenothiazinylcarbonyl, phenazinylcarbonyl, phenoxathiinylcarbonyl, thianthrenylcarbonyl, phenanthridinylcarbonyl, phenanthrolinylcarbonyl, indolizinylcarbonyl, thieno[3,2-c]pyridylcarbonyl, thiazolo[5,4-c]pyridylcarbonyl, pyrrolo[1,2-b]pyridazinylcarbonyl, pyrazolo[1,5-a]pyridylcarbonyl, imidazo[1,2-a]pyridylcarbonyl, imidazo[1,5-a]pyridylcarbonyl, imidazo[1,2-b]pyridazinylcarbonyl, imidazo[1,5-a]pyrimidinylcarbonyl, 1,2,4-triazolo[4,3-a]pyridylcarbonyl, 1,2,4-triazolo[4,3-b]pyridazinylcarbonyl, 1H-pyrazolo[3,4-b]pyridylcarbonyl, 1,2,4-triazolo[1,5-a]pyrimidinylcarbonyl, indolinylcarbonyl, dihydrobenzofuranylcarbonyl, chromanylcarbonyl, tetrahydroquinolylcarbonyl, tetrahydroisoquinolylcarbonyl, 1,4-benzodioxanylcarbonyl, and 1,3-benzodioxolylcarbonyl, and a carbonyl group to which the "saturated or unsaturated non-aromatic heterocyclic group" is bonded, such as aziridinylcarbonyl, azetidinylcarbonyl, pyrrolidinylcarbonyl, tetrahydrofurylcarbonyl, piperidinylcarbonyl, tetrahydropyranylcarbonyl; piperazinylcarbonyl, and morpholinylcarbonyl.

In the "—S(O)$_i$R$^a$ group", i is an integer of 0 to 2, and R$^a$ is a group arbitrarily selected from a $C_{1-6}$ alkyl group and a halogenated $C_{1-6}$ alkyl group. When i is 0, examples of the "—S(O)$_i$R$^a$ group" include a "$C_{1-6}$ alkylthio group" and a "halogenated $C_{1-6}$ alkylthio group", when i is 1, examples of the "—S(O)$_i$R$^a$ group" include a "$C_{1-6}$ alkylsulfinyl group" and a "halogenated $C_{1-6}$ alkylsulfinyl group", and when i is 2, examples of the "—S(O)$_i$R$^a$ group" include a "$C_{1-6}$ alkylsulfonyl group" and a "halogenated $C_{1-6}$ alkylsulfonyl group".

The "$C_{1-6}$ alkylthio group" means a linear, branched, or cyclic $C_{1-6}$ alkylthio group, and examples thereof include, for example, methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, 2-methylbutylthio, 1,2-dimethylpropylthio, 1-ethylpropylthio, hexylthio, isohexylthio, 1-methylpentylthio, 2-methylpentylthio, 3-methylpentylthio, 1,1-dimethylbutylthio, 1,2-dimethylbutylthio, 2,2-dimethylbutylthio, 1,3-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, 1-ethyl-2-methylpropylthio, cyclopropylthio, cyclobutylthio, cyclopentylthio, cyclohexylthio, cyclopropylmethylthio, cyclobutylmethylthio, cyclopentylmethylthio, 1-cyclopropylethylthio, 2-cyclopropylethylthio, 2-cyclobutylethylthio, 2-methylcyclopropylthio, and the like. The "halogenated $C_{1-6}$ alkylthio group" is a group in which the "$C_{1-6}$ alkylthio group" is optionally substituted with 1 to 5 halogen atom(s), and examples thereof include, for example, trifluoromethylthio.

The "$C_{1-6}$ alkylsulfinyl group" means a linear, branched, or cyclic $C_{1-6}$ alkylsulfinyl group, and examples thereof include, for example, methylsulfinyl, ethylsulfinyl, propylsulfinyl, isopropylsulfinyl, cyclopropylsulfinyl, cyclopropylmethylsulfinyl, 2-methylcyclopropylsulfinyl, and the like. The "halogenated $C_{1-6}$ alkylsulfinyl group" is a group in which the "$C_{1-6}$ alkylsulfinyl group" is optionally substituted with 1 to 5 halogen atom(s), and examples thereof include, for example, trifluoromethylsulfinyl.

The "$C_{1-6}$ alkylsulfonyl group" means a linear, branched, or cyclic $C_{1-6}$ alkylsulfonyl group, and examples thereof include, for example, methylsulfonyl, ethylsulfonyl, propylsulfonyl, isopropylsulfonyl, cyclopropylsulfonyl, cyclopropylmethylsulfonyl, 2-methylcyclopropylsulfonyl, and the like. The "halogenated $C_{1-6}$ alkylsulfonyl group" is a group in which the "$C_{1-6}$ alkylsulfonyl group" is optionally substituted with 1 to 5 halogen atom(s), and examples thereof include, for example, trifluoromethylsulfonyl.

The "—SO$_2$NR$^d$R$^e$ group", in which R$^d$ and R$^e$ are independently a hydrogen atom or a $C_{1-6}$ alkyl group, means a sulfamoyl group in which 1 or 2 hydrogen atom(s) on a nitrogen atom of the sulfamoyl group is(are) optionally substituted with the "$C_{1-6}$ alkyl group". Specifically, for example, a sulfamoyl group, a methylsulfamoyl group, an ethylsulfamoyl group, a propylsulfamoyl group, an isopropylsulfamoyl group, a cyclopropylsulfamoyl group, a butylsulfamoyl group, an isobutylsulfamoyl group, a pentylsulfamoyl group, an isopentylsulfamoyl group, a hexylsulfamoyl group, an isohexylsulfamoyl group, a dimethylsulfamoyl group, a diethylsulfamoyl group, a dipropylsulfamoyl group, a di-isopropylsulfamoyl group, a dibutylsulfamoyl group, a dipentylsulfamoyl group, an ethylmethylsulfamoyl group, a methylpropylsulfamoyl group, an ethylpropylsulfamoyl group, a butylmethylsulfamoyl group, a butylethylsulfamoyl group, a butylpropylsulfamoyl group, and the like are mentioned.

The "—CONR$^d$R$^e$ group", in which R$^d$ and R$^e$ are independently a hydrogen atom or a $C_{1-6}$ alkyl group, means a carbamoyl group in which 1 or 2 hydrogen atom(s) on a nitrogen atom of the carbamoyl group is(are) optionally substituted with the "$C_{1-6}$ alkyl group". Specifically, for example, a carbamoyl group, a methylcarbamoyl group, an ethylcarbamoyl group, a propylcarbamoyl group, an isopropylcarbamoyl group, a cyclopropylcarbamoyl group, a butylcarbamoyl group, an isobutylcarbamoyl group, a pentylcarbamoyl group, an isopentylcarbamoyl group, a hexylcarbamoyl group, an isohexylcarbamoyl group, a dimethylcarbamoyl group, a diethylcarbamoyl group, a dipropylcarbamoyl group, a di-isopropylcarbamoyl group, a dibutylcarbamoyl group, a dipentylcarbamoyl group, an ethylmethylcarbamoyl group, a methylpropylcarbamoyl group, an ethylpropylcarbamoyl group, a butylmethylcarbamoyl group, a butylethylcarbamoyl group, a butylpropylcarbamoyl group, and the like are mentioned.

In the "—$NR^bR^c$ group", $R^b$ and $R^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with —OH or a $C_{1-6}$ alkoxy group), a $C_{1-6}$ alkylsulfonyl group, an arylcarbonyl group, and a heterocyclic carbonyl group. $R^b$ and $R^c$ optionally form, together with a nitrogen atom to which they are bonded, a 3- to 8-membered cyclic group, where in the cyclic group, one carbon atom is optionally substituted with an atom arbitrarily selected from an oxygen atom, a sulfur atom, and a nitrogen atom (the nitrogen atom is optionally substituted with a $C_{1-6}$ alkyl group which is optionally substituted with 1 to 5 substituents RI) or with a carbonyl group, and the cyclic group is optionally further substituted with 1 to 5 substituents RII. Examples of the "—$NR^bR^c$ group" include, for example, amino, "mono/di $C_{1-6}$ alkylamino", "halogenated mono/di $C_{1-6}$ alkylamino", "mono/di $C_{2-6}$ alkenylamino", "mono/di $C_{2-6}$ alkynylamino", "$C_{2-7}$ alkanoylamino which is optionally substituted with —OH or $C_{1-6}$ alkoxy", "$C_{1-6}$ alkylsulfonylamino", "arylcarbonylamino", "heterocyclic carbonylamino", and the like.

In the "—$NR^{b1}R^{c1}$ group", $R^{b1}$ and $R^{c1}$ are independently a group arbitrarily selected from a hydrogen atom, a $C_{1-6}$ alkyl group, a $C_{2-7}$ alkanoyl group, and a $C_{1-6}$ alkylsulfonyl group. $R^{b1}$ and $R^{c1}$ optionally form, together with a nitrogen atom to which they are bonded, a 3- to 8-membered cyclic group, where in the cyclic group, one carbon atom is optionally substituted with an atom arbitrarily selected from an oxygen atom, a sulfur atom, and a nitrogen atom (the nitrogen atom is optionally substituted with a $C_{1-6}$ alkyl group) or with a carbonyl group. Examples of the "—$NR^{b1}R^{c1}$ group" include, for example, amino, "mono/di $C_{1-6}$ alkylamino", "$C_{2-7}$ alkanoylamino", "$C_{1-6}$ alkylsulfonylamino", and the like.

The "mono/di $C_{1-6}$ alkylamino" means an amino group, 1 or 2 hydrogen atom(s) of which is(are) substituted with a linear, branched, or cyclic "$C_{1-6}$ alkyl group". Specifically, methylamino, ethylamino, propylamino, isopropylamino, butylamino, isobutylamino, pentylamino, isopentylamino, hexylamino, isohexylamino, cyclopropylamino, cyclobutylamino, cyclopentylamino, cyclohexylamino, 1-cyclopropylmethylamino, 1-cyclobutylmethylamino, 1-cyclopentylmethylamino, 1-cyclohexylmethylamino, dimethylamino, diethylamino, dipropylamino, diisopropylamino, dibutylamino, dipentylamino, ethylmethylamino, propylmethylamino, propylethylamino, butylmethylamino, butylethylamino, butylpropylamino, N-cyclopropyl-N-methylamino, N-cyclobutyl-N-methylamino, N-cyclopentyl-N-methylamino, N-cyclohexyl-N-methylamino, and the like are mentioned.

The "halogenated mono/di $C_{1-6}$ alkylamino" is a group in which the "mono/di $C_{1-6}$ alkylamino" is optionally substituted with 1 to 5 halogen atom(s). For example, trifluoromethylamino is mentioned.

The "mono/di $C_{2-6}$ alkenylamino" means an amino group, 1 or 2 hydrogen atom(s) of which is(are) substituted with a linear, branched, or cyclic "$C_{2-6}$ alkenyl group". Specifically, vinylamino, allylamino, isopropenylamino, 2-methylallylamino, butenylamino, pentenylamino, hexenylamino, 1-cyclopropen-1-ylamino, 2-cyclopropen-1-ylamino, 1-cyclobuten-1-ylamino, 1-cyclopenten-1-ylamino, 2-cyclopenten-1-ylamino, 3-cyclopenten-1-ylamino, 1-cyclohexen-1-ylamino, 2-cyclohexen-1-ylamino, 3-cyclohexen-1-ylamino, 2,4-cyclopentadien-1-ylamino, 2,5-cyclohexadien-1-ylamino, divinylamino, diallylamino, diisopropenylamino, di(2-methylallyl)amino, dibutenylamino, dipentenylamino, dihexenylamino, di(1-cyclopropen-1-yl)amino, di(2-cyclopropen-1-yl)amino, di(1-cyclobuten-1-yl)amino, di(1-cyclopenten-1-yl)amino, di(2-cyclopenten-1-yl)amino, di(3-cyclopenten-1-yl)amino, di(1-cyclohexen-1-yl)amino, di(2-cyclohexen-1-yl)amino, di(3-cyclohexen-1-yl)amino, di(2,4-cyclopentadien-1-yl)amino, di(2,5-cyclohexadien-1-yl)amino, and the like are mentioned.

The "mono/di $C_{2-6}$ alkynylamino" means an amino group, 1 or 2 hydrogen atom(s) of which is(are) substituted with a linear, branched, or cyclic "$C_{2-6}$ alkynyl group". Specifically, ethynylamino, 1-propynylamino, 2-propynylamino, butynylamino, pentynylamino, hexynylamino, diethynylamino, di(1-propynyl)amino, di(2-propynyl)amino, dibutynylamino, dipentynylamino, dihexynylamino, and the like are mentioned.

The "$C_{2-7}$ alkanoylamino which is optionally substituted with —OH or $C_{1-6}$ alkoxy" means an amino group, a hydrogen atom of which is substituted with a linear, branched, or cyclic "$C_{2-7}$ alkanoyl group (the alkanoyl group is optionally substituted with —OH or a $C_{1-6}$ alkoxy group)". Specifically, acetamido, propionamide, butylamide, isobutylamide, valeramide, isovaleramide, pivalamide, hexanamide, heptanamide, cyclopropanecarboxamide, cyclobutanecarboxamide, cyclopentanecarboxamide, cyclohexanecarboxamide, 2-methylcyclopropanecarboxamide, hydroxyacetylamino, methoxyacetylamino, and the like are mentioned.

The "$C_{1-6}$ alkylsulfonylamino" means an amino group, a hydrogen atom of which is substituted with a linear, branched, or cyclic $C_{1-6}$ alkylsulfonyl group. Specifically, methylsulfonylamino, ethylsulfonylamino, propylsulfonylamino, isopropylsulfonylamino, cyclopropylsulfonylamino, cyclopropylmethylsulfonylamino, 2-methylcyclopropylsulfonylamino, and the like are mentioned.

The "arylcarbonylamino" means an amino group, a hydrogen atom of which is substituted with the "arylcarbonyl group". Specifically, $C_{6-14}$ arylcarbonylamino such as benzamide and naphthamide is mentioned.

The "heterocyclic carbonylamino" means an amino group, a hydrogen atom of which is substituted with the "heterocyclic carbonyl group". Specifically, pyrrolecarboxamide, furancarboxamide, thiophenecarboxamide, imidazolecarboxamide, pyrazolecarboxamide, pyridinecarboxamide, indolecarboxamide, quinolinecarboxamide, piperidinecarboxamide, and the like are mentioned.

With regard to "$R^b$ and $R^c$ optionally form, together with a nitrogen atom to which they are bonded, a 3- to 8-membered cyclic group" and "$R^{b1}$ and $R^{c1}$ optionally form, together with a nitrogen atom to which they are bonded, a 3- to 8-membered cyclic group", the 3- to 8-membered cyclic group specifically means, for example, a monovalent cyclic group obtained by removing a hydrogen atom which is bonded to a nitrogen atom from a ring that has a nitrogen atom in addition to carbon atoms in a 3- to 8-membered saturated or unsaturated non-aromatic heterocyclic group that is one of the "non-aromatic heterocyclic groups". For example, aziridinyl, azetidinyl, pyrrolidinyl, pyrazolinyl, pyrazolidinyl, piperidinyl, piperazinyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, 2-oxopyrrolidinyl, and the like are mentioned. As for $R^b$ and $R^c$, and $R^{b1}$ and $R^{c1}$, with regard to "where in the cyclic group, one carbon atom is substituted with an oxygen atom, a sulfur atom, or a carbonyl group", examples of the cyclic group include, among the above-mentioned cyclic groups, for example, oxazolinyl, isoxazolinyl, oxazolidinyl, isoxazolidinyl, thiazolinyl, isothiazolinyl, thiazolidinyl, isothiazolidinyl, morpholinyl, thiomorpholinyl, 2-oxopyrrolidinyl, and the like.

As for $R^b$ and $R^c$, with regard to "where the nitrogen atom is substituted with a $C_{1-6}$ alkyl group which is optionally substituted with 1 to 5 substituents RI", examples of the cyclic group include, for example, 4-methylpiperazin-1-yl, 4-ethylpiperazin-1-yl, 4-propylpiperazin-1-yl, 4-trifluoromethylpiperazin-1-yl, and the like.

As for $R^{b1}$ and $R^{c1}$, with regard to "where the nitrogen atom is substituted with a $C_{1-6}$ alkyl group", examples of the cyclic group include, for example, 4-methylpiperazin-1-yl, 4-ethylpiperazin-1-yl, 4-propylpiperazin-1-yl, and the like.

As for $R^b$ and $R^c$, with regard to "where the cyclic group is further substituted with 1 to 5 substituents RII", examples of the cyclic group include, for example, 4,4-difluoropiperidin-1-yl.

The "substituent RI" is a group arbitrarily selected from a halogen atom, —OH, cyano, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with $C_{1-6}$ alkyl), 1 to 5 —S(O)$_i$R$^a$ (i is an integer of 0 to 2) group(s), 1 to 5 —SO$_2$NR$^d$R$^e$ group(s), 1 to 5-CONR$^d$R$^e$ group(s), or 1 to 5 —NR$^{b1}$R$^{c1}$ group(s)), a —NR$^{b1}$R$^{c1}$ group, and a non-aromatic heterocyclic oxy group.

The "substituent RII" is a group arbitrarily selected from the same groups as in the case of the "substituent RI", and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5—S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)).

$R^d$ and $R^e$ are independently a hydrogen atom or a $C_{1-6}$ alkyl group, and $R^{b1}$ and $R^{c1}$ are independently a group arbitrarily selected from a hydrogen atom, a $C_{1-6}$ alkyl group, a $C_{2-7}$ alkanoyl group, and a $C_{1-6}$ alkylsulfonyl group. $R^{b1}$ and $R^{c1}$ optionally form, together with a nitrogen atom to which they are bonded, a 3- to 8-membered cyclic group, where in the ring in the cyclic group, one carbon atom is optionally substituted with an atom arbitrarily selected from an oxygen atom, a sulfur atom, and a nitrogen atom (the nitrogen atom is optionally substituted with a $C_{1-6}$ alkyl group) or with a carbonyl group.

The "$C_{1-6}$ alkyl group which is optionally substituted with 1 to 5 substituents RI" is a "$C_{1-6}$ alkyl group which is optionally substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a non-aromatic heterocyclic oxy group, and specific examples thereof include the followings.

For example, a "$C_{1-6}$ alkyl group which is optionally substituted with 1 to 5 halogen atom(s)" includes, in addition to the "$C_{1-6}$ alkyl group", a group in which the alkyl group is optionally substituted with 1 to 5 halogen atom(s). Specifically, in addition to methyl, ethyl, propyl, isopropyl, butyl, isobutyl, sec-butyl, and tert-butyl, for example, trifluoromethyl, trifluoroethyl, tetrafluoroethyl, pentafluoroethyl, and the like are mentioned.

For example, a "$C_{1-6}$ alkyl group which is optionally substituted with 1 to 5 —OH" includes, in addition to the "$C_{1-6}$ alkyl group", a group in which the alkyl group is optionally substituted with 1 to 5 hydroxy, and there are many regioisomers depending on a substitution position. Specifically, in addition to methyl, ethyl, propyl, isopropyl, butyl, isobutyl, sec-butyl, and tert-butyl, for example, hydroxymethyl, 2-hydroxyethyl, 1-hydroxyethyl, 3-hydroxy-1-propyl, 2-hydroxy-1-propyl, 1-hydroxy-1-propyl, 2,3-dihydroxy-1-propyl, 1-hydroxy-1-methyl-1-ethyl, 2-hydroxy-1-methyl-1-ethyl, 4-hydroxy-1-butyl, 3-hydroxy-1-butyl, 2-hydroxy-1-butyl, 1-hydroxy-1-butyl, 3-hydroxy-2-methylpropyl, 2-hydroxy-2-methylpropyl, 3-hydroxy-2-hydroxymethylpropyl, 2-hydroxy-1,1-dimethyl-1-ethyl, 1-hydroxy-2-methylpropyl, 5-hydroxy-1-pentyl, 4-hydroxy-1-pentyl, 3-hydroxy-1-pentyl, 2-hydroxy-1-pentyl, 1-hydroxy-1-pentyl, 4-hydroxy-3-methylbutyl, 4-hydroxy-2-methylbutyl, 4-hydroxy-1-methylbutyl, 3-hydroxy-3-methylbutyl, 3-hydroxy-2-methylbutyl, 3-hydroxy-1-methylbutyl, 2-hydroxy-3-methylbutyl, 2-hydroxy-2-methylbutyl, 2-hydroxy-1-methylbutyl, 3-hydroxy-2,2-dimethylpropyl, 3-hydroxy-1,1-dimethylpropyl, 3-hydroxy-2-hydroxymethyl-2-methylpropyl, 6-hydroxy-1-hexyl, 4-hydroxy-1,1-dimethyl-1-butyl, 4-hydroxy-3,3-dimethyl-1-butyl, 2-hydroxycyclopropyl, 4-hydroxycyclohexyl, and the like are mentioned.

For example, a "$C_{1-6}$ alkyl group which is optionally substituted with 1 to 5 $C_{1-6}$ alkoxy group(s)" includes, in addition to the "$C_{1-6}$ alkyl group", a group in which the alkyl group is optionally substituted with 1 to 5 of the "$C_{1-6}$ alkoxy group(s)". Specifically, in addition to methyl, ethyl, propyl, isopropyl, butyl, isobutyl, sec-butyl, and tert-butyl, for example, methoxymethyl, methoxyethyl, methoxypropyl, and the like are mentioned.

For example, a "$C_{1-6}$ alkyl group which is optionally substituted with 1 to 5 $C_{1-6}$ alkoxy group(s) which is optionally substituted with 1 to 5 halogen atom(s)" includes, in addition to the "$C_{1-6}$ alkyl group" and the "$C_{1-6}$ alkyl group which is optionally substituted with 1 to 5 $C_{1-6}$ alkoxy group(s)", a group in which the alkyl group is optionally substituted with 1 to 5 of the "$C_{1-6}$ alkoxy group(s)" which is optionally substituted with 1 to 5 halogen atom(s). Specifically, in addition to methyl, ethyl, propyl, isopropyl, butyl, isobutyl, sec-butyl, tert-butyl, methoxymethyl, methoxyethyl, and methoxypropyl, for example, trifluoromethoxymethyl, trifluoromethoxyethyl, trifluoromethoxypropyl, and the like are mentioned.

Alternatively, the alkyl group is optionally substituted with 2 to 5 groups selected from two or more kinds of a halogen atom, —OH, cyano, and a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), or 1 to 5 —NR$^b$R$^c$ group(s)). For example, a $C_{1-6}$ alkyl group which is substituted with a single —OH and a single $C_{1-6}$ alkoxy group, such as 2-hydroxy-3-methoxypropyl and 3-hydroxy-2-methoxypropyl, and the like are mentioned.

Similarly, the "$C_{2-6}$ alkenyl group which is optionally substituted with 1 to 5 substituents RI" includes, in addition to the "$C_{2-6}$ alkenyl group", a group in which the alkenyl group is optionally substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a non-aromatic heterocyclic oxy group. Specifically, in addition to vinyl, allyl, isopropenyl, 2-methylallyl, butenyl, pentenyl, and hexenyl, for example, trifluorovinyl, 2-hydroxyvinyl, 2-methoxyvinyl, 2-trifluoromethoxyvinyl, and the like are mentioned.

The "$C_{2-6}$ alkynyl group which is optionally substituted with 1 to 5 substituents RI" includes, in addition to the "$C_{2-6}$ alkynyl group", a group in which the alkynyl group is optionally substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a non-aromatic heterocyclic oxy group. Specifically, in addition to ethynyl, 1-propynyl, 2-propynyl, butynyl, pentynyl, and hexynyl, for example, fluoroethynyl, 2-hydroxyethynyl, 2-methoxyethynyl, 2-trifluoromethoxyethynyl, and the like are mentioned.

The "$C_{1-6}$ alkoxy group which is optionally substituted with 1 to 5 substituents RI" includes, in addition to the "$C_{1-6}$ alkoxy group", a group in which the alkoxy group is optionally substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s) 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a non-aromatic heterocyclic oxy group. Specifically, in addition to methoxy, ethoxy, propoxy, isopropoxy, butoxy, isobutoxy, sec-butoxy, and tert-butoxy, for example, trifluoromethoxy, hydroxymethoxy, 2-hydroxyethoxy, 3-hydroxypropoxy, 3-hydroxybutoxy, 3-hydroxy-3-methylbutoxy, 2,3-dihydroxypropoxy, 3-hydroxy-2-hydroxymethylpropoxy, 3-hydroxy-2-hydroxymethyl-2 methylpropoxy, 2-methoxyethoxy, 2-ethoxyethoxy, 2-trifluoromethoxyethoxy, 2-methoxy-3-hydroxypropoxy, 2-hydroxy-3-methoxypropoxy, and the like are mentioned.

The "aryl group which is optionally substituted with 1 to 5 substituents RII" is a group in which any hydrogen atom in the "aryl group" is optionally substituted with 1 to 5 substituents RII. That is to say, the "aryl group which is optionally substituted with 1 to 5 substituents RII" includes, in addition to the "aryl group", an "aryl group which is substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 group(s)), a —NR$^{b1}$R$^{c1}$ group, a non-aromatic heterocyclic oxy group, and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5—S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))".

Specifically, in addition to the "aryl group", for example, an "aryl group which is optionally substituted with 1 to 5 halogen atom(s)", an "aryl group which is substituted with 1 to 5 group(s) arbitrarily selected from the "$C_{1-6}$ alkoxy group" (the $C_{1-6}$ alkoxy group is optionally substituted with a halogen atom, —OH, a $C_{1-6}$ alkoxy group, a non-aromatic heterocyclic group (the heterocyclic group is optionally substituted with a $C_{1-6}$ alkyl group), a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group)", an "aryl group which is substituted with 1 to 5 group(s) arbitrarily selected from the "$C_{1-6}$ alkyl group" (the $C_{1-6}$ alkyl group is optionally substituted with a halogen atom, —OH, a $C_{1-6}$ alkoxy group, a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group)", and the like are mentioned. More preferably, for example, an "aryl group which is optionally substituted with 1 or 2 of the "$C_{1-6}$ alkyl group(s)"" and the like are mentioned.

Alternatively, the aryl group is optionally substituted with 2 to 5 groups selected from two or more kinds of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclic oxy group, and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)). Specifically, for example, an "aryl group which is optionally substituted with 1 or 2 of the "$C_{1-6}$ alkyl group(s)" and 1 or 2 of the "$C_{1-6}$ alkoxy group(s)" (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))" and the like are mentioned. More preferably, for example, an "aryl group which is optionally substituted with 1 or 2 of the "$C_{1-6}$ alkyl group(s)" and one of the "$C_{1-6}$ alkoxy groups" (the alkoxy group is optionally substituted with 1 or 2 —OH, 1 or 2 $C_{1-6}$ alkoxy group(s), 1 or 2 non-aromatic heterocyclic group(s) (the heterocyclic group is optionally substituted with a $C_{1-6}$ alkyl group), 1 or 2 —S(O)$_i$R$^a$ (i is an integer of 0 to 2) group(s), or 1 or 2 —NR$^{b1}$R$^{c1}$ group(s))", and the like are mentioned.

Examples of the "aryl group which is optionally substituted with 1 to 5 substituents RII" more specifically include, in addition to phenyl, naphthyl, indanyl, and tetrahydronaphthyl, for example, (2-, 3-, or 4-)fluorophenyl, (2-, 3-, or 4-)chlorophenyl, (2-, 3-, or 4-)hydroxyphenyl, (2-, 3-, or 4-)methoxyphenyl, (2-, 3-, or 4-)ethoxyphenyl, (2-, 3-, or 4-)propoxyphenyl, (2-, 3-, or 4-)isopropoxyphenyl, (2-, 3-, or 4-)trifluoromethoxyphenyl, (2-, 3-, or 4-)methylphenyl, (2-, 3-, or 4-)trifluoromethylphenyl, 3,5-dimethoxyphenyl, (2,6-, 2,5-, 2,4-, or 2,3-)dimethylphenyl, 3,5-ditrifluoromethylphenyl, 4-methoxy-2-methylphenyl, 4-methoxy-(2,6-, 2,5-, or 2,3-)dimethylphenyl, 4-(2-hydroxyethoxy)-2-methylphenyl, 4-(2,3-dihydroxypropoxy)-2-methylphenyl, 4-(3-hydroxy-3-methylbutoxy)-2-methylphenyl, 3-(3-hydroxy-3-methylbutoxy)-2-methylphenyl, 4-(2-hydroxyethoxy)-(2,6-, 2,5-, or 2,3-)dimethylphenyl, 4-(3-hydroxypropoxy)-2-methylphenyl, 4-(3-hydroxypropoxy)-(2,6-, 2,5-, or 2,3-)dimethylphenyl, 4-(2,3-dihydroxypropoxy)-(2,6-, 2,5-, or 2,3-)dimethylphenyl, 4-((2R)-2,3-dihydroxypropoxy)-(2,6-, 2,5-, or 2,3-)dimethylphenyl, 4-((2S)-2,3-dihydroxypropoxy)-(2,6-, 2,5-, or 2,3-)dimethylphenyl, 4-(3-hydroxy-2-hydroxymethylpropoxy)-2-methylphenyl, 4-(3-hydroxy-2-hydroxymethyl-2-methylpropoxy)-2-methylphenyl, 4-(3-hydroxybutoxy)-2-methylphenyl, 4-((3S)-3-hydroxybutoxy)-2-methylphenyl, 4-((3R)-3-hydroxybutoxy)-2-methylphenyl, 4-(3-hydroxy-2-hydroxymethylpropoxy)-(2,6-, 2,5-, or 2,3-)dimethylphenyl, 4-(3-hydroxy-2-hydroxymethyl-2-methylpropoxy)-(2,6-, 2,5-, or 2,3-)dimethylphenyl, 4-(3-hydroxybutoxy)-(2,6-, 2,5-, or 2,3-)dimethylphenyl, 4-((3S)-3-hydroxybutoxy)-(2,6-, 2,5-, or 2,3-)dimethylphenyl, 4-((3R)-3-hydroxybutoxy)-(2,6-, 2,5-, or 2,3-)dimethylphenyl, 4-(3-hydroxy-3-methylbutoxy)-(2,6-, 2,5-, or 2,3-)dimethylphenyl, 4-(3-aminopropoxy)-2-methylphenyl, 4-(3-aminopropoxy)-(2,6-, 2,5-, or 2,3-)dimethylphenyl, 4-(2-(2-oxo-1-pyrrolidinyl)ethoxy)-2-methylphenyl, 4-(2-(2-oxo-1-pyrrolidinyl)ethoxy)-(2,6-, 2,5-, or 2,3-)dimethylphenyl, 4-(3-(2-oxo-1-pyrrolidinyl)propoxy)-2-methylphenyl, 4-(3-(2-oxo-1-pyrrolidinyl)propoxy)-(2,6-, 2,5-, or 2,3-)dimethylphenyl, 4-(2-ethoxy-ethoxy)-2-methylphenyl, 4-(2-ethoxy-ethoxy)-(2,6-, 2,5-, or 2,3-)dimethylphenyl, 4-(2-methylsulfonyl-ethoxy)-2-methylphenyl, 4-(2-methylsulfonyl-ethoxy)-(2,6-, 2,5-, or 2,3-)dimethylphenyl, 4-(3-methylsulfonyl-propoxy)-2-methylphenyl, 4-(3-methylsulfonyl-propoxy)-(2,6-, 2,5-, or 2,3-)dimethylphenyl, 4-((1,1-dioxytetrahydro-2H-thiopyran-4-yl)oxy)-2-methylphenyl, 4-((1,1-dioxytetrahydro-2H-thiopyran-4-yl)oxy)-(2,6-, 2,5-, or 2,3-)dimethylphenyl, 4-((4-hydroxy-1,1-dioxytetrahydro-2H-thiopyran-4-yl)methoxy)-2-methylphenyl, 4-((4-hydroxy-1,1-dioxytetrahydro-2H-thiopyran-4-yl)methoxy)-(2,6-, 2,5-, or 2,3-)dimethylphenyl, 4-((3-methyloxetan-3-yl)methoxy)-2-methylphenyl, 4-((3-methyloxetan-3-yl)methoxy)-(2,6-, 2,5-, or 2,3-)dimethylphenyl, 4-(2-acetylamino-ethoxy)-2-methylphenyl, 4-(2-acetylamino-ethoxy)-(2,6-, 2,5-, or 2,3-)dimethylphenyl, 4-(3-acetylamino-propoxy)-2-methylphenyl, 4-(3-acetylamino-propoxy)-(2,6-, 2,5-, or 2,3-)dimethylphenyl, 4-(2-methylsulfonylamino-ethoxy)-2-methylphenyl, 4-(2-methylsulfonylamino-ethoxy)-(2,6-, 2,5-, or 2,3-)dimethylphenyl, 4-(3-methylsulfonylamino-propoxy)-2-methylphenyl, 4-(3-methylsulfonylamino-propoxy)-(2,6-, 2,5-, or 2,3-)dimethylphenyl, 4-(2-carbamoyl-ethoxy)-2-methylphenyl, 4-(2-carbamoyl-ethoxy)-(2,6-, 2,5-, or 2,3-)dimethylphenyl, 4-(3-carbamoyl-propoxy)-2-methylphenyl, 4-(3-carbamoyl-propoxy)-(2,6-, 2,5-, or 2,3-)dimethylphenyl, 4-(2-methylcarbamoyl-ethoxy)-2-methylphenyl, 4-(2-methylcarbamoyl-ethoxy)-(2,6-, 2,5-, or 2,3-)dimethylphenyl, 4-(3-methylcarbamoyl-propoxy)-2-methylphenyl, 4-(3-methylcarbamoyl-propoxy)-(2,6-, 2,5-, or 2,3-)dimethylphenyl, 4-(2-dimethylcarbamoyl-ethoxy)-2-methylphenyl, 4-(2-dimethylcarbamoyl-ethoxy)-(2,6-, 2,5-, or 2,3-)dimethylphenyl, 4-(3-dimethylcarbamoyl-propoxy)-2-methylphenyl, 4-(3-dimethylcarbamoyl-propoxy)-(2,6-, 2,5-, or 2,3-)dimethylphenyl, 4-(2-sulfamoyl-ethoxy)-2-methylphenyl, 4-(2-sulfamoyl-ethoxy)-(2,6-, 2,5-, or 2,3-)dimethylphenyl, 4-(3-sulfamoyl-propoxy)-2-methylphenyl, 4-(3-sulfamoyl-propoxy)-(2,6-, 2,5-, or 2,3-)dimethylphenyl, 4-(2-methylsulfamoyl-ethoxy)-2-methylphenyl, 4-(2-methylsulfamoyl-ethoxy)-(2,6-, 2,5-, or 2,3-)dimethylphenyl, 4-(3-methylsulfamoyl-propoxy)-2-methylphenyl, 4-(3-methylsulfamoyl-propoxy)-(2,6-, 2,5-, or 2,3-)dimethylphenyl, 4-(2-dimethylsulfamoyl-ethoxy)-2-methylphenyl, 4-(2-dimethylsulfamoyl-ethoxy)-(2,6-, 2,5-, or 2,3-)dimethylphenyl, 4-(3-dimethylsulfamoyl-propoxy)-2-methylphenyl, 4-(3-dimethylsulfamoyl-propoxy)-(2,6-, 2,5-, or 2,3-)dimethylphenyl, 3-fluoro-4-(2-hydroxyethoxy)-2-methylphenyl, 3-fluoro-4-(2,3-dihydroxypropoxy)-2-methylphenyl, 3-fluoro-4-(3-hydroxy-3-methylbutoxy)-2-methylphenyl, 3-fluoro-4-(2-hydroxyethoxy)-(2,6- or 2,5-)dimethylphenyl, 4-((2R)-2,3-dihydroxypropoxy)-3-fluoro-(2,6- or 2,5-)dimethylphenyl, 4-((2S)-2,3-dihydroxypropoxy)-3-fluoro-(2,6- or 2,5-)dimethylphenyl, 3-fluoro-4-(3-hydroxypropoxy)-2-methylphenyl, 3-fluoro-4-(3-hydroxypropoxy)-(2,6- or 2,5-)dimethylphenyl, 3-fluoro-4-(2,3-dihydroxypropoxy)-(2,6- or 2,5-)dimethylphenyl, 3-fluoro-4-(3-hydroxy-2-hydroxymethylpropoxy)-2-methylphenyl, 3-fluoro-4-(3-hydroxy-2-hydroxymethylpropoxy)-(2,6- or 2,5-)dimethylphenyl, 3-fluoro-4-(3-hydroxy-2-hydroxymethyl-2-methylpropoxy)-2-methylphenyl, 3-fluoro-4-(3-hydroxy-2-hydroxymethyl-2-methylpropoxy)-(2,6- or 2,5-)dimethylphenyl, 3-fluoro-4-(3-hydroxybutoxy)-2-methylphenyl, 3-fluoro-4-(3-hydroxybutoxy)-(2,6- or 2,5-)dimethylphenyl, 3-fluoro-4-(3-hydroxy-3-methylbutoxy)-(2,6- or 2,5-)dimethylphenyl, 3-fluoro-4-(3-aminopropoxy)-2-methylphenyl, 3-fluoro-4-(3-aminopropoxy)-(2,6- or 2,5-)dimethylphenyl, 3-fluoro-4-(2-(2-oxo-1-pyrrolidinyl)ethoxy)-2-methylphenyl, 3-fluoro-4-(2-(2-oxo-1-pyrrolidinyl)ethoxy)-(2,6- or 2,5-)dimethylphenyl, 3-fluoro-4-(3-(2-oxo-1-pyrrolidinyl)propoxy)-2-methylphenyl, 3-fluoro-4-(3-(2-oxo-1-pyrrolidinyl)propoxy)-(2,6- or 2,5-)dimethylphenyl, 3-fluoro-4-(2-ethoxy-ethoxy)-2-methylphenyl, 3-fluoro-4-(2-ethoxy-ethoxy)-(2,6- or 2,5-)dimethylphenyl, 3-fluoro-4-(2-methylsulfonyl-ethoxy)-2-methylphenyl, 3-fluoro-4-(2-methylsulfonyl-ethoxy)-(2,6-, 2,5-, or 2,3-)dimethylphenyl, 3-fluoro-4-(3-methylsulfonyl-propoxy)-2-methylphenyl, 3-fluoro-4-(3-methylsulfonyl-propoxy)-(2,6- or 2,5-)dimethylphenyl, 3-fluoro-4-((1,1-dioxytetrahydro-2H-thiopyran-4-yl)oxy)-2-methylphenyl, 3-fluoro-4-((1,1-dioxytetrahydro-2H-thiopyran-4-yl)oxy)-(2,6- or 2,5-)dimethylphenyl, 3-fluoro-4-((4-hydroxy-1,1-dioxytetrahydro-2H-thiopyran-4-yl)methoxy)-2-methylphenyl, 3-fluoro-4-((4-hydroxy-1,1-dioxytetrahydro-2H-thiopyran-4-yl)methoxy)-(2,6- or 2,5-)dimethylphenyl, 3-fluoro-4-((3-methyloxetan-3-yl)methoxy)-2-methylphenyl, 3-fluoro-4-((3-methyloxetan-3-yl)methoxy)-(2,6- or 2,5-)dimethylphenyl, 3-fluoro-4-(2-acetylamino-ethoxy)-2-methylphenyl, 3-fluoro-4-(2-acetylamino-ethoxy)-(2,6- or 2,5-)dimethylphenyl, 3-fluoro-4-(3-acetylamino-propoxy)-2-methylphenyl, 3-fluoro-4-(3-acetylamino-propoxy)-(2,6- or 2,5-)dimethylphenyl, 3-fluoro-4-(2-methylsulfonylamino-ethoxy)-2-methylphenyl, 3-fluoro-4-(2-methylsulfonylamino-ethoxy)-(2,6- or 2,5-)dimethylphenyl, 3-fluoro-4-(3-methylsulfonylamino-propoxy)-2-methylphenyl, 3-fluoro-4-(3-methylsulfonylamino-propoxy)-(2,6- or 2,5-)dimethylphenyl, 3-fluoro-4-(2-carbamoyl-ethoxy)-2-methylphenyl, 3-fluoro-4-(2-carbamoyl-ethoxy)-(2,6- or 2,5-)dimethylphenyl, 3-fluoro-4-(3-carbamoyl-propoxy)-2-methylphenyl, 3-fluoro-4-(3-carbamoyl-propoxy)-(2,6- or 2,5-)dimethylphenyl, 3-fluoro- 4-(2-methylcarbamoyl-ethoxy)-2-methylphenyl, 3-fluoro-4-(2-methylcarbamoyl-ethoxy)-(2,6- or 2,5-)dimethylphenyl, 3-fluoro-4-(3-methylcarbamoyl-propoxy)-2-methylphenyl, 3-fluoro-4-(3-methylcarbamoyl-propoxy)-(2,6- or 2,5-)dimethylphenyl, 3-fluoro-4-(2-dimethylcarbamoyl-ethoxy)-2-methylphenyl, 3-fluoro-4-(2-dimethylcarbamoyl-ethoxy)-(2,6- or 2,5-)dimethylphenyl, 3-fluoro-4-(3-dimethylcarbamoyl-propoxy)-2-methylphenyl, 3-fluoro-4-(3-dimethylcarbamoyl-propoxy)-(2,6- or 2,5-)dimethylphenyl, 3-fluoro-4-(2-sulfamoyl-ethoxy)-2-methylphenyl, 3-fluoro-4-(2-sulfamoyl-ethoxy)-(2,6- or 2,5-)dimethylphenyl, 3-fluoro-4-(3-sulfamoyl-propoxy)-2-methylphenyl, 3-fluoro-4-(3-sulfamoyl-propoxy)-(2,6- or 2,5-)dimethylphenyl, 3-fluoro-4-(2-methylsulfamoyl-ethoxy)-2-methylphenyl, 3-fluoro-4-(2-methylsulfamoyl-ethoxy)-(2,6- or 2,5-)dimethylphenyl, 3-fluoro-4-(3-methylsulfamoyl-propoxy)-2-methylphenyl, 3-fluoro-4-(3-methylsulfamoyl-propoxy)-(2,6- or 2,5-)dimethylphenyl, 3-fluoro-4-(2-dimethylsulfamoyl-ethoxy)-2-methylphenyl, 3-fluoro-4-(2-dimethylsulfamoyl-ethoxy)-(2,6- or 2,5-)dimethylphenyl, 3-fluoro-4-(3-dimethylsulfamoyl-propoxy)-2-methylphenyl, 3-fluoro-4-(3-dimethylsulfamoyl-propoxy)-(2,6- or 2,5-)dimethylphenyl, 4-(2-hydroxyethoxy)-2-hydroxymethylphenyl, 4-(2,3-dihydroxypropoxy)-2-hydroxymethylphenyl, 4-(3-hydroxy-3-methylbutoxy)-2-hydroxymethylphenyl, 4-(2-hydroxyethoxy)-6-methyl-2-hydroxymethylphenyl, 4-(3-hydroxypropoxy)-2-hydroxymethylphenyl, 4-(3-hydroxypropoxy)-6-methyl-2-hydroxymethylphenyl, 4-(2,3-dihydroxypropoxy)-6-methyl-2-hydroxymethylphenyl, 4-(3-hydroxy-2-hydroxymethylpropoxy)-2-hydroxymethylphenyl, 4-(3-hydroxy-2-hydroxymethylpropoxy)-6-methyl-2-hydroxymethylphenyl, 4-(3-hydroxy-2-hydroxymethyl-2-methylpropoxy)-2-hydroxymethylphenyl, 4-(3-hydroxy-2-hydroxymethyl-2-methylpropoxy)-6-methyl-2-hydroxymethylphenyl, 4-(3-hydroxybutoxy)-2-hydroxymethylphenyl, 4-(3-hydroxybutoxy)-6-methyl-2-hydroxymethylphenyl, 4-(3-hydroxy-3-methylbutoxy)-6-methyl-2-hydroxymethylphenyl, 4-(3-aminopropoxy)-2-hydroxymethylphenyl, 4-(3-aminopropoxy)-6-methyl-2-hydroxymethylphenyl, 4-(2-(2-oxo-1-pyrrolidinyl)ethoxy)-2-hydroxymethylphenyl, 4-(2-(2-oxo-1-pyrrolidinyl)ethoxy)-6-methyl-2-hydroxymethylphenyl, 4-(3-(2-oxo-1-pyrrolidinyl)propoxy)-2-hydroxymethylphenyl, 4-(3-(2-oxo-1-pyrrolidinyl)propoxy)-6-methyl-2-hydroxymethylphenyl, 4-(2-ethoxy-ethoxy)-2-hydroxymethylphenyl, 4-(2-ethoxy-ethoxy)-6-methyl-2-hydroxymethylphenyl, 4-(2-methylsulfonyl-ethoxy)-2-hydroxymethylphenyl, 4-(2-methylsulfonyl-ethoxy)-6-methyl-2-hydroxymethylphenyl, 4-(3-methylsulfonyl-propoxy)-2-hydroxymethylphenyl, 4-(3-methylsulfonyl-propoxy)-6-methyl-2-hydroxymethylphenyl, 4-((1,1-dioxytetrahydro-2H-thiopyran-4-yl)oxy)-2-hydroxymethylphenyl, 4-((1,1-dioxytetrahydro-2H-thiopyran-4-yl)oxy)-6-methyl-2-hydroxymethylphenyl, 4-((4-hydroxy-1,1-dioxytetrahydro-2H-thiopyran-4-yl)methoxy)-2-hydroxymethylphenyl, 4-((4-hydroxy-1,1-dioxytetrahydro-2H-thiopyran-4-yl)methoxy)-6-methyl-2-hydroxymethylphenyl, 4-((3-methyloxetan-3-yl)methoxy)-2-hydroxymethylphenyl, 4-((3-methyloxetan-3-yl)methoxy)-6-methyl-2-hydroxymethylphenyl, 4-(2-acetylamino-ethoxy)-2-hydroxymethylphenyl, 4-(2-acetylamino-ethoxy)-6-methyl-2-hydroxymethylphenyl, 4-(3-acetylamino-propoxy)-2-hydroxymethylphenyl, 4-(3-acetylamino-propoxy)-6-methyl-2-hydroxymethylphenyl, 4-(2-methylsulfonylamino-ethoxy)-2-hydroxymethylphenyl, 4-(2-methylsulfonylamino-ethoxy)-6-methyl-2-hydroxymethylphenyl, 4-(3-methylsulfonylamino-propoxy)-2-hydroxymethylphenyl, 4-(3-methylsulfonylamino-propoxy)-6-methyl-2-hydroxymethylphenyl, 4-(2-carbamoyl-ethoxy)-2-hydroxymethylphenyl, 4-(2-carbamoyl-ethoxy)-6-methyl-2-hydroxymethylphenyl, 4-(3-carbamoyl-propoxy)-2-hydroxymethylphenyl, 4-(3-carbamoyl-propoxy)-6-methyl-2-hydroxymethylphenyl, 4-(2-methylcarbamoyl-ethoxy)-2-hydroxymethylphenyl, 4-(2-methylcarbamoyl-ethoxy)-6-methyl-2-hydroxymethylphenyl, 4-(3-methylcarbamoyl-propoxy)-2-hydroxymethylphenyl, 4-(3-methylcarbamoyl-propoxy)-6-methyl-2-hydroxymethylphenyl, 4-(2-dimethylcarbamoyl-ethoxy)-2-hydroxymethylphenyl, 4-(2-dimethylcarbamoyl-ethoxy)-6-methyl-2-hydroxymethylphenyl, 4-(3-dimethylcarbamoyl-propoxy)-2-hydroxymethylphenyl, 4-(3-dimethylcarbamoyl-propoxy)-6-methyl-2-hydroxymethylphenyl, 4-(2-sulfamoyl-ethoxy)-2-hydroxymethylphenyl, 4-(2-sulfamoyl-ethoxy)-6-methyl-2-hydroxymethylphenyl, 4-(3-sulfamoyl-propoxy)-2-hydroxymethylphenyl, 4-(3-sulfamoyl-propoxy)-6-methyl-2-hydroxymethylphenyl, 4-(2-methylsulfamoyl-ethoxy)-2-hydroxymethylphenyl, 4-(2-methylsulfamoyl-ethoxy)-6-methyl-2-hydroxymethylphenyl, 4-(3-methylsulfamoyl-propoxy)-2-hydroxymethylphenyl, 4-(3-methylsulfamoyl-propoxy)-6-methyl-2-hydroxymethylphenyl, 4-(2-dimethylsulfamoyl-ethoxy)-2-hydroxymethylphenyl, 4-(2-dimethylsulfamoyl-ethoxy)-6-methyl-2-hydroxymethylphenyl, 4-(3-dimethylsulfamoyl-propoxy)-2-hydroxymethylphenyl, 4-(3-dimethylsulfamoyl-propoxy)-6-methyl-2-hydroxymethylphenyl, (4-, 5-, 6-, or 7-)fluoro-1-indanyl, (4-, 5-, 6-, or 7-)chloro-1-indanyl, (4-, 5-, 6-, or 7-)bromo-1-indanyl, (4-, 5-, 6-, or 7-)trifluoromethyl-1-indanyl, (4-, 5-, 6-, or 7-)fluoro-2-indanyl, (4-, 5-, 6-, or 7-)chloro-2-indanyl, (4-, 5-, 6-, or 7-)bromo-2-indanyl, (4-, 5-, 6-, or 7-)trifluoromethyl-2-indanyl, and the like.

The "heterocyclic group which is optionally substituted with 1 to 5 substituent(s) RII" is a group in which any hydrogen atom in the "heterocyclic group" is optionally substituted with 1 to 5 substituent(s) RII. Namely, the "heterocyclic group which is optionally substituted with 1 to 5 substituent(s) RII" is, in addition to the unsubstituted "heteroaryl group" and the "non-aromatic heterocyclic group" both exemplified above as a "heterocyclic group" (these rings are each a monovalent group obtained by removing any hydrogen atom from a ring having a monocycle or a fused ring that is a 3- to 14-membered ring, or preferably, a 3- to 12-membered ring, containing, in addition to carbon atoms, at least one hetero atom (preferably 1 to 4 atom(s)) arbitrarily selected from N, O, and S): a "heterocyclic group which is substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))".

Specific examples of the "heterocyclic group which is optionally substituted with 1 to 5 substituent(s) RII" include, in addition to the "heterocyclic group", a "heterocyclic group arbitrarily substituted with 1 to 5 halogen atom(s)", a "heterocyclic group substituted with 1 to 5 group(s) arbitrarily selected from a "$C_{1-6}$ alkoxy group" (the $C_{1-6}$ alkoxy group is optionally substituted with a halogen atom, —OH, a $C_{1-6}$ alkoxy group, a non-aromatic heterocyclic group (the heterocyclic group is optionally substituted with a $C_{1-6}$ alkyl group), a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group)", and a "heterocyclic group substituted with 1 to 5 group(s) arbitrarily selected from a "$C_{1-6}$ alkyl group" (the $C_{1-6}$ alkyl group is optionally substituted with a halogen atom, —OH, a $C_{1-6}$ alkoxy group, a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group)". More specific examples thereof include a "heteroaryl group substituted with 1 to 5 group(s) arbitrarily selected from a "$C_{1-6}$ alkyl group" (the $C_{1-6}$ alkyl group is optionally substituted with a halogen atom, —OH, a $C_{1-6}$ alkoxy group, a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group)" and a "heteroaryl group substituted with 1 to 5 groups(s) arbitrarily selected from a "$C_{1-6}$ alkoxy group" (the $C_{1-6}$ alkoxy group is optionally substituted with a halogen atom, —OH, a $C_{1-6}$ alkoxy group, a non-aromatic heterocyclic group (the heterocyclic group is optionally substituted with a $C_{1-6}$ alkyl group), a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group)". More preferred examples thereof include a "heteroaryl group optionally substituted with 1 or 2 "$C_{1-6}$ alkyl group(s)"".

Furthermore, the heterocyclic group is optionally substituted at 2 to 5 positions with a group selected from 2 or more types of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)). Specific examples thereof include a "heterocyclic group optionally substituted with 1 or 2 "$C_{1-6}$ alkyl group(s)" and 1 or 2 "$C_{1-6}$ alkoxy group(s)" (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". More preferred examples thereof include a "heteroaryl group optionally substituted with 1 or 2 "$C_{1-6}$ alkyl group(s)" and one "$C_{1-6}$ alkoxy group" (the $C_{1-6}$ alkoxy group is optionally substituted with 1 or 2 —OH, 1 or 2 $C_{1-6}$ alkoxy group(s), 1 or 2 non-aromatic heterocyclic group(s) (the heterocyclic group is optionally substituted with a $C_{1-6}$ alkyl group), 1 or 2 —S(O)$_i$R$^a$ (i is an integer of 0 to 2) group(s), or 1 or 2 —NR$^{b1}$R$^{c1}$ group(s))".

The "heteroaryl group" in the "heterocyclic group which is optionally substituted with 1 to 5 substituent(s) RII" may be monocyclic or ring-fused. The monocyclic heteroaryl group preferably has a 5- to 7-membered ring, and examples thereof include those groups described in the definition of the "heteroaryl group", such as pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, and 1,4-oxazepinyl. The ring-fused heteroaryl group preferably has an 8- to 12-membered ring, and examples thereof include a monovalent group obtained by removing any hydrogen atom from a fused ring formed by fusing the 5- to 7-membered heterocyclic ring and a monocyclic aryl group (such as a benzene ring) or a monocyclic heteroaryl group. The hydrogen atom is optionally removed from any of the fused rings. Specific examples include those groups described in the definition of the "heteroaryl group", such as indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, and 1,2,4-triazolo[1,5-a]pyrimidinyl. Specific examples thereof also include a ring-fused heteroaryl group which is partly hydrogenated, such as indolinyl, dihydrobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl. The ring-fused heteroaryl group which is partly hydrogenated preferably has an 8- to 12-membered ring, namely a monovalent group obtained by removing any hydrogen atom from a fused ring which is partly hydrogenated and formed by fusing the 5- to 7-membered heterocyclic ring and a monocyclic aryl group (such as a benzene ring) or a monocyclic heteroaryl group. Any of the hydrogen atom in the aryl group or in the heterocyclic moiety and of the hydrogen atom in the hydrogenated moiety is optionally removed. In the case of tetrahydroquinolyl, examples of the partially hydrogenated ring-fused heteroaryl group include 5,6,7,8-tetrahydroquinolyl and 1,2,3,4-tetrahydroquinolyl. Depending on the position in these groups from which any hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" in the "heterocyclic group which is optionally substituted with 1 to 5 substituent(s) RII" include a 3- to 8-membered saturated or unsaturated non-aromatic heterocyclic group. Specific examples thereof include aziridinyl, azetidinyl, oxiranyl, oxetanyl, thietanyl, pyrrolidinyl, tetrahydrofuryl, thiolanyl, pyrazolinyl, pyrazolidinyl, piperidinyl, dihydropyranyl, tetrahydropyranyl (oxanyl), tetrahydrothiopyranyl, piperazinyl, dioxanyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, and oxepanyl. The "non-aromatic heterocyclic group" means a monovalent group obtained by removing any hydrogen atom from the ring.

Specific examples of the "heterocyclic group which is optionally substituted with 1 to 5 substituent(s) RII" include pyrrolyl, furyl, pyrazolyl, isoxazolyl, pyridyl, pyrimidinyl, indolyl, quinolyl, dihydrobenzofuranyl, chromanyl, 1,3-benzodioxanyl, 1,4-benzodioxanyl, piperidinyl, dihydropyranyl, and tetrahydropyranyl(oxanyl). Specific examples thereof include 2-pyrrolyl, 3-pyrrolyl, 2-furyl, 3-furyl, 1-pyrazolyl, 3-pyrazolyl, 4-pyrazolyl, 5-pyrazolyl, 3-isoxazolyl, 4-isoxazolyl, 5-isoxazolyl, 2-pyridyl, 3-pyridyl, 4-pyridyl, 2-pyrimidinyl, 4-pyrimidinyl, 5-pyrimidinyl, 1-indolyl, 2-indolyl, 3-indolyl, 4-indolyl, 5-indolyl, 6-indolyl, 7-indolyl, 2-quinolyl, 3-quinolyl, 4-quinolyl, 5-quinolyl, 6-quinolyl, 7-quinolyl, 8-quinolyl, 1,4-benzodioxazin-2-yl, 1,4-benzodioxazin-3-yl, 1,4-benzodioxazin-5-yl, 1,4-benzodioxazin-6-yl, piperidin-1-yl, piperidin-2-yl, piperidin-3-yl, piperidin-4-yl, 3,6-dihydro-2H-pyran-4-yl, and 4-tetrahydropyranyl (4-oxanyl). Any hydrogen atom of the groups is optionally substituted with 1 to 5 substituent(s) RII. Specific examples thereof include 1-methylpyrazol-4-yl, 3,5-dimethylisoxazol-4-yl, (2-, 4-, 5-, or 6-)fluoropyridin-3-yl, (2-, 4-, 5-, or 6-)chloropyridin-3-yl, (2-, 4-, 5-, or 6-)hydroxypyridin-3-yl, (2-, 4-, 5-, or 6-)methoxypyridin-3-yl, (2-, 4-, 5-, or 6-)methylpyridin-3-yl, (2-, 4-, 5-, or 6-)trifluoromethylpyridin-3-yl, (2,4-, 2,5-, 2,6-, 4,5-, 4,6-, or 5,6-)dimethylpyridin-3-yl, (2,4-, 2,5-, 2,6-, 4,5-, 4,6-, or 5,6-)dimethoxypyridin-3-yl, 6-methoxy-(2-, 4-, or 5-)methylpyridin-3-yl, 6-(2-hydroxyethoxy)-(2-, or 4-)methylpyridin-3-yl, 6-(3-hydroxypropoxy)-(2-, or 4-)methylpyridin-3-yl, 6-(2,3-dihydroxypropoxy)-(2-, or 4-)methylpyridin-3-yl, 6-((2R)-2,3-dihydroxypropoxy)-(2-, or 4-)methylpyridin-3-yl, 6-((2S)-2,3-dihydroxypropoxy)-(2-, or 4-)methylpyridyl-3-yl, 6-((3S)-3-hydroxybutoxy)-(2-, or 4-)methylpyridyl-3-yl, 6-((3R)-3-hydroxybutoxy)-(2-, or 4-)methylpyridin-3-yl, 6-(3-hydroxy-3-methylbutoxy)-(2-, or 4-)methylpyridin-3-yl, 6-(3-hydroxy-2-hydroxymethylpropoxy)-(2-, or 4-)methylpyridin-3-yl, 6-(3-hydroxy-2-hydroxymethyl-2-methylpropoxy)-(2-, or 4-)methylpyridin-3-yl, 6-(3-hydroxybutoxy)-(2-, or 4-)methylpyridin-3-yl, 6-(2-ethoxyethoxy)-(2-, or 4-)methylpyridin-3-yl, 6-(2-methylsulfonylethoxy)-(2-, or 4-)methylpyridin-3-yl, 6-(3-methylsulfonyl-propoxy)-(2-, or 4-)methylpyridin-3-yl, 6-((1,1-dioxytetrahydro-2H-thiopyran-4-yl)oxy)-(2-, or 4-)methylpyridin-3-yl, 6-((4-hydroxy-1,1-dioxytetrahydro-2H-thiopyran-4-yl)methoxy)-(2-, or 4-)methylpyridin-3-yl, 6-((3-methyloxetan-3-yl)methoxy)-(2-, or 4-)methylpyridin-3-yl, 6-(2-hydroxyethoxy)-(2,4-, 2,5-, or 4,5-)dimethylpyridin-3-yl, 6-(3-hydroxypropoxy)-(2,4-, 2,5-, or 4,5-)dimethylpyridin-3-yl, 6-(2,3-dihydroxypropoxy)-(2,4-, 2,5-, or 4,5-)dimethylpyridin-3-yl, 6-(3-hydroxy-2-hydroxymethylpropoxy)-(2,4-, 2,5-, or 4,5-)dimethylpyridin-3-yl, 6-(3-hydroxy-2-hydroxymethyl-2-methylpropoxy)-(2,4-, 2,5-, or 4,5-)dimethylpyridin-3-yl, 6-(3-hydroxybutoxy)-(2,4-, 2,5-, or 4,5-)dimethylpyridin-3-yl, 6-(3-hydroxy-3-methylbutoxy)-(2,4-, 2,5-, or 4,5-)dimethylpyridin-3-yl, 6-(2-ethoxyethoxy)-(2,4-, 2,5-, or 4,5-)dimethylpyridin-3-yl, 6-(2-methylsulfonylethoxy)-(2,4-, 2,5-, or 4,5-)dimethylpyridin-3-yl, 6-(3-methylsulfonyl-propoxy)-(2,4-, 2,5-, or 4,5-)dimethylpyridin-3-yl, 6-((1,1-dioxytetrahydro-2H-thiopyran-4-yl)oxy)-(2,4-, 2,5-, or 4,5-)dimethylpyridin-3-yl, 6-((4-hydroxy-1,1-dioxytetrahydro-2H-thiopyran-4-yl)methoxy)-(2,4-, 2,5-, or 4,5-)dimethylpyridin-3-yl, 6-((3-methyloxetan-3-yl)methoxy)-(2,4-, 2,5-, or 4,5-)dimethylpyridin-3-yl, 6-(3-hydroxy-3-methylbutoxy)-(2-, or 4-)methoxypyridin-3-yl, 6-(2-aminoethoxy)-(2-, or 4-)methylpyridin-3-yl, 6-(2-aminoethoxy)-(2,4-, 2,5-, or 4,5-)dimethylpyridin-3-yl, 6-(3-aminopropoxy)-(2-, or 4-)methylpyridin-3-yl, 6-(3-aminopropoxy)-(2,4-, 2,5-, or 4,5-)dimethylpyridin-3-yl, 6-(2-acetylamino-ethoxy)-(2-, or 4-)methylpyridin-3-yl, 6-(2-acetylamino-ethoxy)-(2,4-, 2,5-, or 4,5-)dimethylpyridin-3-yl, 6-(3-acetylamino-propoxy)-(2-, or 4-)methylpyridin-3-yl, 6-(3-acetylamino-propoxy)-(2,4-, 2,5-, or 4,5-)dimethylpyridin-3-yl, 6-(2-methylsulfonylamino-ethoxy)-(2-, or 4-)methylpyridin-3-yl, 6-(2-methylsulfonylamino-ethoxy)-(2,4-, 2,5-, or 4,5-)dimethylpyridin-3-yl, 6-(3-methylsulfonylamino-propoxy)-(2-, or 4-)methylpyridin-3-yl, 6-(3-methylsulfonylamino-propoxy)-(2,4-, 2,5-, or 4,5-)dimethylpyridin-3-yl, 6-(2-carbamoyl-ethoxy)-(2-, or 4-)methylpyridin-3-yl, 6-(2-carbamoyl-ethoxy)-(2,4-, 2,5-, or 4,5-)dimethylpyridin-3-yl, 6-(3-carbamoyl-propoxy)-(2-, or 4-)methylpyridin-3-yl, 6-(3-carbamoyl-propoxy)-(2,4-, 2,5-, or 4,5-)dimethylpyridin-3-yl, 6-(2-methylcarbamoyl-ethoxy)-(2-, or 4-)methylpyridin-3-yl, 6-(2-methylcarbamoyl-ethoxy)-(2,4-, 2,5-, or 4,5-)dimethylpyridin-3-yl, 6-(3-methylcarbamoyl-propoxy)-(2-, or 4-)methylpyridin-3-yl, 6-(3-methylcarbamoyl-propoxy)-(2,4-, 2,5-, or 4,5-)dimethylpyridin-3-yl, 6-(2-dimethylcarbamoyl-ethoxy)-(2-, or 4-)methylpyridin-3-yl, 6-(2-dimethylcarbamoyl-ethoxy)-(2,4-, 2,5-, or 4,5-)dimethylpyridin-3-yl, 6-(3-dimethylcarbamoyl-propoxy)-(2-, or 4-)methylpyridin-3-yl, 6-(3-dimethylcarbamoyl-propoxy)-(2,4-, 2,5-, or 4,5-)dimethylpyridin-3-yl, 6-(2-sulfamoyl-ethoxy)-(2-, or 4-)methylpyridin-3-yl, 6-(2-sulfamoyl-ethoxy)-(2,4-, 2,5-, or 4,5-)dimethylpyridin-3-yl, 6-(3-sulfamoyl-propoxy)-(2-, or 4-)methylpyridin-3-yl, 6-(3-sulfamoyl-propoxy)-(2,4-, 2,5-, or 4,5-)dimethylpyridin-3-yl, 6-(2-methylsulfamoyl-ethoxy)-(2-, or 4-)methylpyridin-3-yl, 6-(2-methylsulfamoyl-ethoxy)-(2,4-, 2,5-, or 4,5-)dimethylpyridin-3-yl, 6-(3-methylsulfamoyl-propoxy)-(2-, or 4-)methylpyridin-3-yl, 6-(3-methylsulfamoyl-propoxy)-(2,4-, 2,5-, or 4,5-)dimethylpyridin-3-yl, 6-(2-dimethylsulfamoyl-ethoxy)-(2-, or 4-)methylpyridin-3-yl, 6-(2-dimethylsulfamoyl-ethoxy)-(2,4-, 2,5-, or 4,5-)dimethylpyridin-3-yl, 6-(3-dimethylsulfamoyl-propoxy)-(2-, or 4-)methylpyridin-3-yl, 6-(3-dimethylsulfamoyl-propoxy)-(2,4-, 2,5-, or 4,5-)dimethylpyridin-3-yl, 6-(2-(2-oxo-1-pyrrolidinyl)ethoxy)-(2-, or 4-)methylpyridin-3-yl, 6-(2-(2-oxo-1-pyrrolidinyl)ethoxy)-(2,4-, 2,5-, or 4,5-)dimethylpyridin-3-yl, 6-(3-(2-oxo-1-pyrrolidinyl)propoxy)-(2-, or 4-)methylpyridin-3-yl, 6-(3-(2-oxo-1-pyrrolidinyl)propoxy)-(2,4-, 2,5-, or 4,5-)dimethylpyridin-3-yl, 6-(1-piperidinyl)pyridin-3-yl, (2-, or 4-)methoxypyrimidin-5-yl, 2-(2-hydroxyethoxy)-4-methylpyrimidin-5-yl, 2-(3-hydroxypropoxy)-4-methylpyrimidin-5-yl, 2-(2,3-dihydroxypropoxy)-4-methylpyrimidin-5-yl, 2-(3-hydroxy-3-methylbutoxy)-4-methylpyrimidin-5-yl, 2-(3-hydroxy-2-hydroxymethylpropoxy)-4-methylpyrimidin-5-yl, 2-(3-hydroxy-2-hydroxymethyl-2-methylpropoxy)-4-methylpyrimidin-5-yl, 2-(3-hydroxybutoxy)-4-methylpyrimidin-5-yl, 2-(2-ethoxyethoxy)-4-methylpyrimidin-5-yl, 2-(2-methylsulfonylethoxy)-4-methylpyrimidin-5-yl, 2-(3-methylsulfonyl-propoxy)-4-methylpyrimidin-5-yl, 2-((1,1-dioxytetrahydro-2H-thiopyran-4-yl)oxy)-4-methylpyrimidin-5-yl, 2-((4-hydroxy-1,1-dioxytetrahydro-2H-thiopyran-4-yl)methoxy)-4-methylpyrimidin-5-yl, 2-((3-methyloxetan-3-yl)methoxy)-4-methylpyrimidin-5-yl, 2-(2-hydroxyethoxy)-4,6-dimethylpyrimidin-5-yl, 2-(3-hydroxypropoxy)-4,6-dimethylpyrimidin-5-yl, 2-(2,3-dihydroxypropoxy)-4,6-dimethylpyrimidin-5-yl, 2-(3-hydroxy-2-hydroxymethylpropoxy)-4,6-dimethylpyrimidin-5-yl, 2-(3-hydroxy-2-hydroxymethyl-2-methylpropoxy)-4,6-dimethylpyrimidin-5-yl, 2-(3-hydroxybutoxy)-4,6-dimethylpyrimidin-5-yl, 2-((2R)-2,3-dihydroxypropoxy)-4,6-dimethylpyrimidin-5-yl, 2-((2S)-2,3-dihydroxypropoxy)-

4,6-dimethylpyrimidin-5-yl, 2-((3S)-3-hydroxybutoxy)-4,6-dimethylpyrimidin-5-yl, 6-((3R)-3-hydroxybutoxy)-4,6-dimethylpyrimidin-5-yl, 2-(3-hydroxy-3-methylbutoxy)-4,6-dimethylpyrimidin-5-yl, 2-(2-ethoxyethoxy)-4,6-dimethylpyrimidin-5-yl, 2-(2-methylsulfonylethoxy)-4,6-dimethylpyrimidin-5-yl, 2-(3-methylsulfonyl-propoxy)-4,6-dimethylpyrimidin-5-yl, 2-((1,1-dioxytetrahydro-2H-thiopyran-4-yl)oxy)-4,6-dimethylpyrimidin-5-yl, 6-((4-hydroxy-1,1-dioxytetrahydro-2H-thiopyran-4-yl)methoxy)-4,6-dimethylpyrimidin-5-yl, 2-((3-methyloxetan-3-yl)methoxy)-4,6-dimethylpyrimidin-5-yl, 2-(2-aminoethoxy)-4-methylpyrimidin-5-yl, 2-(2-aminoethoxy)-4,6-dimethylpyrimidin-5-yl, 2-(3-aminopropoxy)-4-methylpyrimidin-5-yl, 2-(3-aminopropoxy)-4,6-dimethylpyrimidin-5-yl, 2-(2-acetylamino-ethoxy)-4-methylpyrimidin-5-yl, 2-(2-acetylamino-ethoxy)-4,6-dimethylpyrimidin-5-yl, 2-(3-acetylamino-propoxy)-4-methylpyrimidin-5-yl, 2-(3-acetylamino-propoxy)-4,6-dimethylpyrimidin-5-yl, 2-(2-methylsulfonylamino-ethoxy)-4-methylpyrimidin-5-yl, 2-(2-methylsulfonylamino-ethoxy)-4,6-dimethylpyrimidin-5-yl, 2-(3-methylsulfonylamino-propoxy)-4-methylpyrimidin-5-yl, 2-(3-methylsulfonylamino-propoxy)-4,6-dimethylpyrimidin-5-yl, 2-(2-carbamoyl-ethoxy)-4-methylpyrimidin-5-yl, 2-(2-carbamoyl-ethoxy)-4,6-dimethylpyrimidin-5-yl, 2-(3-carbamoyl-propoxy)-4-methylpyrimidin-5-yl, 2-(3-carbamoyl-propoxy)-4,6-dimethylpyrimidin-5-yl, 2-(2-methylcarbamoyl-ethoxy)-4-methylpyrimidin-5-yl, 2-(2-methylcarbamoyl-ethoxy)-4,6-dimethylpyrimidin-5-yl, 2-(3-methylcarbamoyl-propoxy)-4-methylpyrimidin-5-yl, 2-(3-methylcarbamoyl-propoxy)-4,6-dimethylpyrimidin-5-yl, 2-(2-dimethylcarbamoyl-ethoxy)-4-methylpyrimidin-5-yl, 2-(2-dimethylcarbamoyl-ethoxy)-4,6-dimethylpyrimidin-5-yl, 2-(3-dimethylcarbamoyl-propoxy)-4-methylpyrimidin-5-yl, 2-(3-dimethylcarbamoyl-propoxy)-4,6-dimethylpyrimidin-5-yl, 2-(2-sulfamoyl-ethoxy)-4-methylpyrimidin-5-yl, 2-(2-sulfamoyl-ethoxy)-4,6-dimethylpyrimidin-5-yl, 2-(3-sulfamoyl-propoxy)-4-methylpyrimidin-5-yl, 2-(3-sulfamoyl-propoxy)-4,6-dimethylpyrimidin-5-yl, 2-(2-methylsulfamoyl-ethoxy)-4-methylpyrimidin-5-yl, 2-(2-methylsulfamoyl-ethoxy)-4,6-dimethylpyrimidin-5-yl, 2-(3-methylsulfamoyl-propoxy)-4-methylpyrimidin-5-yl, 2-(3-methylsulfamoyl-propoxy)-4,6-dimethylpyrimidin-5-yl, 2-(2-dimethylsulfamoyl-ethoxy)-4-methylpyrimidin-5-yl, 2-(2-dimethylsulfamoyl-ethoxy)-4,6-dimethylpyrimidin-5-yl, 2-(3-dimethylsulfamoyl-propoxy)-4-methylpyrimidin-5-yl, 2-(3-dimethylsulfamoyl-propoxy)-4,6-dimethylpyrimidin-5-yl, 2-(2-(2-oxo-1-pyrrolidinyl)ethoxy)-4-methylpyrimidin-5-yl, 2-(2-(2-oxo-1-pyrrolidinyl)ethoxy)-4,6-dimethylpyrimidin-5-yl, 2-(3-(2-oxo-1-pyrrolidinyl)propoxy)-4-methylpyrimidin-5-yl, 2-(3-(2-oxo-1-pyrrolidinyl)propoxy)-4,6-dimethylpyrimidin-5-yl, (2-, 4-, 5-, 6-, 7-, or 8-)methylquinolin-3-yl, 6-(1-piperidinyl)pyridin-3-yl, 1-methylpiperidin-4-yl, and 4,4-difluoropiperidin-1-yl.

The "aralkyl group which is optionally substituted with 1 to 5 substituent(s) RII" is the "aralkyl group" in which any hydrogen atom is optionally substituted with 1 to 5 substituent(s) RII. That is to say, the "aralkyl group which is optionally substituted with 1 to 5 substituent(s) RII" includes, in addition the unsubstituted groups exemplified as the "aralkyl group": "an aralkyl group which is substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5—S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". The substituent(s) of the aralkyl group may be substituted with either the aryl moiety or the alkyl moiety. Specific examples thereof include, in addition to unsubstituted benzyl, phenethyl, 1-naphthylmethyl, or 2-naphthylmethyl: (2-, 3-, or 4-)fluorobenzyl, (2-, 3-, or 4-)chlorobenzyl, (2-, 3-, or 4-)hydroxybenzyl, (2-, 3-, or 4-)methoxybenzyl, (2-, 3-, or 4-)trifluoromethoxybenzyl, (2-, 3-, or 4-)methylbenzyl, (2-, 3-, or 4-)trifluoromethylbenzyl, (2,6-, 2,5-, 2,4-, or 2,3-)dimethylbenzyl, 3,5-trifluoromethylbenzyl, 4-(2-hydroxyethoxy)-2,6-dimethylbenzyl, 4-(2,3-dihydroxypropoxy)-2,6-dimethylbenzyl, and 4-(3-hydroxy-3-methylbutoxy)-2,6-dimethylbenzyl.

The "heteroarylalkyl group which is optionally substituted with 1 to 5 substituent(s) RII" is the "heteroarylalkyl group" in which any hydrogen atom is optionally substituted with 1 to 5 substituent(s) RII. That is to say, the "heteroarylalkyl group which is optionally substituted with 1 to 5 substituent(s) RII" includes, in addition to the unsubstituted groups exemplified as the "heteroarylalkyl group": "a heteroarylalkyl group which is substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5—S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". The substituent(s) of the heteroarylalkyl group may be substituted with either the heteroaryl moiety or the alkyl moiety. Specific examples thereof include, in addition to unsubstituted pyrrolylmethyl, furylmethyl, pyridylmethyl, or quinolylmethyl: (2-, 4-, 5-, or 6-)chloropyridin-3-ylmethyl, (2-, 4-, 5-, or 6-)hydroxypyridin-3-ylmethyl, (2-, 4-, 5-, or 6-)methoxypyridin-3-ylmethyl, (2-, 4-, 5-, or 6-)methylpyridin-3-ylmethyl, (2,4-, 2,5-, 2,6-, 4,5-, or 4,6-)dimethylpyridin-3-ylmethyl, 6-(2-hydroxyethoxy)-2,4-dimethylpyridin-3-ylmethyl, 6-(2,3-dihydroxypropoxy)-2,4-dimethylpyridin-3-ylmethyl, and 6-(3-hydroxy-3-methylbutoxy)-2,4-dimethylpyridin-3-ylmethyl.

The "aryloxy group which is optionally substituted with 1 to 5 substituent(s) RII" is the "aryloxy group" in which any hydrogen atom is optionally substituted with 1 to 5 substituent(s) RII. That is to say, the "aryloxy group which is optionally substituted with 1 to 5 substituent(s) RII" includes, in addition to the unsubstituted groups exemplified as the "aryloxy group": "an aryloxy group which is substituted with 1 to 5 group(s) arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5—S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a C$_{1-6}$ alkyl group (the C$_{1-6}$ alkyl group is optionally substituted with 1 to 5 halogen atom(s), 1 to 5 —OH, 1 to 5 C$_{1-5}$ alkoxy group(s), 1 to 5 —S(O)$_i$R$^a$, (i is an integer of 0 to 2) group(s), 1 to 5 —SO$_2$NR$^d$R$^e$ group(s), 1 to 5 —CONR$^d$R$^e$ group(s), or 1 to 5 group(s))" Specific examples thereof include, in addition to unsubstituted phenoxy, 1-naphthyloxy, 2-naphthyloxy, 1-indanyloxy, or 2-indanyloxy: (2-, 3-, or 4-)fluorophenoxy, (2-, 3-, or 4-)chlorophenoxy, (2-, 3-, or 4-)hydroxyphenoxy, (2-, 3-, or 4-)methoxyphenoxy, (2-, 3-, or 4-)trifluoromethoxyphenoxy, (2-, 3-, or 4-)methylphenoxy, (2-, 3-, or 4-)trifluoromethylphenoxy, (2,6-, 2,5-, 2,4-, or 2,3-)dimethylphenoxy, 4-(2-hydroxyethoxy)phenoxy, 4-(2,3-dihydroxypropoxy)phenoxy, 4-(3-hydroxy-3-methylbutoxy)phenoxy, 4-(2-hydroxyethoxy)-2,6-dimethylphenoxy, 4-(2,3-dihydroxypropoxy)-2,6-dimethylphenoxy, and 4-(3-hydroxy-3-methylbutoxy)-2,6-dimethylphenoxy.

The "heteroaryloxy group which is optionally substituted with 1 to 5 substituent(s) RII" is the "heteroaryloxy group" in which any hydrogen atom is optionally substituted with 1 to 5 substituent(s) RII. That is to say, the "heteroaryloxy group which is optionally substituted with 1 to 5 substituent(s) RII" includes, in addition to the unsubstituted groups exemplified as the "heteroaryloxy group":"a heteroaryloxy group which is substituted with 1 to 5 group(s) arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with a C$_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5—S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". Specific examples thereof include, in addition to pyrrolyloxy, furyloxy, (2-, 3-, or 4-)pyridyloxy, or quinolyloxy: (2-, 4-, 5-, or 6-)chloropyridin-3-yloxy, (2-, or 3-)chloropyridin-4-yloxy, (2-, 4-, 5-, or 6-)hydroxypyridin-3-yloxy, (2-, or 3-)hydroxypyridin-4-yloxy, (2-, 4-, 5-, or 6-)methoxypyridin-3-yloxy, (2-, or 3-)methoxypyridin-4-yloxy, (2-, 4-, 5-, or 6-)methylpyridin-3-yloxy, (2-, or 3-)methylpyridin-4-yloxy, (2,4-, 2,5-, 2,6-, 4,5-, or 4,6-)dimethylpyridin-3-yloxy, (2,3-, 2,5-, 2,6-, or 3,5-)dimethylpyridin-4-yloxy, 6-(2-hydroxyethoxy)pyridin-3-yloxy, 6-(2,3-dihydroxypropoxy)pyridin-3-yloxy, 6-(3-hydroxy-3-methylbutoxy)pyridin-3-yloxy, 6-(2-hydroxyethoxy)-2,4-dimethylpyridin-3-yloxy, 6-(2,3-dihydroxypropoxy)-2,4-dimethylpyridin-3-yloxy, and 6-(3-hydroxy-3-methylbutoxy)-2,4-dimethylpyridin-3-yloxy.

The "non-aromatic heterocyclic oxy group which is optionally substituted with 1 to 5 substituent(s) RII" is the "non-aromatic heterocyclic oxy group" in which any hydrogen atom is optionally substituted with 1 to 5 substituent(s) RII. That is to say, the "non-aromatic heterocyclic oxy group which is optionally substituted with 1 to 5 substituent(s) RII" includes, in addition to the unsubstituted groups exemplified as the "non-aromatic heterocyclic oxy group":"a non-aromatic heterocyclic oxy group which is substituted with 1 to 5 group(s) arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with a C$_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". For example, a 3- to 8-membered saturated or unsaturated non-aromatic heterocyclic oxy group optionally substituted with 1 to 5 substituent(s) RII is included. Examples thereof include, in addition to pyrrolidinyloxy, tetrahydrofuryloxy, piperidinyloxy, dihydropyranyloxy, or tetrahydropyranyloxy(oxanyloxy): (2-, or 3-)fluorooxan-4-yloxy, (2-, or 3-)chlorooxan-4-yloxy, (2-, or 3-)hydroxyoxan-4-yloxy, (2-, or 3-)methoxyoxan-4-yloxy, (2-, or 3-)trifluoromethoxyoxan-4-yloxy, (2-, or 3-)methyloxan-4-yloxy, (2-, or 3-)trifluoromethyloxan-4-yloxy, (2,3-, 2,5-, 2,6-, or 3,5-)dimethyloxan-4-yloxy, 1-methylpiperidin-4-yloxy, and (1,2-, or 1,3-)dimethylpiperidin-4-yloxy.

The "aralkyloxy group which is optionally substituted with 1 to 5 substituent(s) RII" is the "aralkyloxy group" in which any hydrogen atom is optionally substituted with 1 to 5 substituent(s) RII. That is to say, the "aralkyloxy group which is optionally substituted with 1 to 5 substituent(s) RII" includes, in addition to the unsubstituted groups exemplified as the "aralkyloxy group":"an aralkyloxy group which is substituted with 1 to 5 group(s) arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with a C$_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group(s)), a group, a non-aromatic heterocyclicoxy group, and a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". The substituent(s) of the aralkyloxy group may be substituted with the aryl moiety or the alkyl moiety. Specific examples thereof include, in addition to benzyloxy, phenethyloxy, 1-naphthylmethoxy, or 2-naphthylmethoxy: (2-, 3-, or 4-)fluorobenzyloxy, (2-, 3-, or 4-)chlorobenzyloxy, (2-, 3-, or 4-)hydroxybenzyloxy, (2-, 3-, or 4-)methoxybenzyloxy, (2-, 3-, or 4-)trifluoromethoxybenzyloxy, (2-, 3-, or 4-)methylbenzyloxy, (2-, 3-, or 4-)trifluoromethylbenzyloxy, (2-, 3-, or 4-)methoxyphenethyloxy, (2,6-, 2,5-, 2,4-, or 2,3-)dimethylbenzyloxy, 4-(2-hydroxyethoxy)-2,6-dimethylbenzyloxy, 4-(2,3-dihydroxypropoxy)-2,6-dimethylbenzyloxy, and 4-(3-hydroxy-3-methylbutoxy)-2,6-dimethylbenzyloxy.

The "heteroarylalkyloxy group which is optionally substituted with 1 to 5 substituent(s) RII" is the "heteroarylalkyloxy group" in which any hydrogen atom is optionally substituted with 1 to 5 substituent(s) RII. That is to say, the "heteroarylalkyloxy group which is optionally substituted with 1 to 5 substituent(s) RII" includes, in addition to the unsubstituted groups exemplified as the "heteroarylalkyloxy group": "a heteroarylalkyloxy group which is substituted with 1 to 5 group(s) arbitrarily selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 non-aromatic heterocyclic group(s) (the heterocyclic group is optionally substituted with a C$_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclicoxy group, and a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". The substituent(s) of the heteroarylalkyloxy group may be substituted with either the heteroaryl moiety or the alkyl moiety. Specific examples thereof include, in addition to pyrrolylmethoxy, furylmethoxy, pyridylmethoxy, or quinolylmethoxy: (2-, 4-, 5-, or 6-)chloropyridin-3-ylmethoxy, (2-, 4-, 5-, or 6-)hydroxypyridin-3-ylmethoxy, (2-, 4-, 5-, or 6-)methoxypyridin-3-ylmethoxy, (2-, 4-, 5-, or 6-)methylpyridin-3-ylmethoxy, (2,4-, 2,5-, 2,6-, 4,5-, or 4,6-)dimethylpyridin-3-ylmethoxy, 6-(2-hydroxyethoxy)-2,4-dimethylpyridin-3-ylmethoxy, 6-(2,3-dihydroxypropoxy)-2,4-dimethylpyridin-3-ylmethoxy, and 6-(3-hydroxy-3-methylbutoxy)-2,4-dimethylpyridin-3-ylmethoxy.

In the compound of Formula (I), the 3-hydroxy-isothiazolyl group is a group that can be a 3(2H)-isothiazolonyl group by proton tautomerism, and the resultant tautomer is included in Formula (I). The abundance ratio of this structure can vary depending on whether the compound of Formula (I) is in the solid state or in the dissolved state in a liquid.

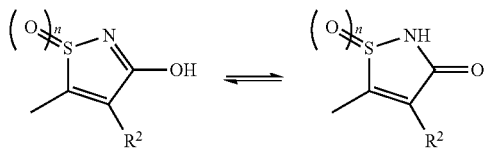

The description of any specific types of tautomers in any structural formulae of the present specification is not intended to limit the present invention, but is intended to represent the whole set of tautomers that are applicable.

Specifically, for example, a tautomer, namely, 5-(4-((3-phenoxyphenyl)methoxy)phenyl)-3(2H)-isothiazolone, of the compounds described as 5-(4-((3-phenoxyphenyl)methoxy)phenyl)isothiazol-3-ol among compounds of Example 1 is also categorized as a compound of Example 1.

[1-1] In the compound of Formula (I) according to Aspect [1], Ls are independently a halogen atom, —OH, a cyano group, a C$_{1-10}$ alkyl group which is optionally substituted with 1 to 5 substituent(s) RI, a C$_{2-10}$ alkenyl group which is optionally substituted with 1 to 5 substituent(s) RI, a C$_{2-10}$ alkynyl group which is optionally substituted with 1 to 5 substituent(s) RI, a C$_{1-10}$ alkoxy group which is optionally substituted with 1 to 5 substituent(s) RI, a C$_{1-10}$ alkenyloxy group which is optionally substituted with 1 to 5 substituent(s) RI, a C$_{1-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a —S(O)$_i$R$^a$ (i is an integer of 0 to 2) group, or a —NR$^b$R$^c$ group; and the substituent(s) RI, the substituent(s) RII, i, R$^a$, R$^b$, R$^c$ are the same as defined in Aspect [1].

[1-1-a] Preferable examples of Ls include a halogen atom, a cyano group, a C$_{1-10}$ alkyl group which is optionally substituted with 1 to 5 substituent(s) RI, a C$_{2-10}$ alkenyl group which is optionally substituted with 1 to 5 substituent(s) RI, a C$_{2-10}$ alkynyl group which is optionally substituted with 1 to 5 substituent(s) RI, a C$_{1-10}$ alkoxy group which is optionally substituted with 1 to 5 substituent(s) RI, a C$_{1-10}$ alkenyloxy group which is optionally substituted with 1 to 5 substituent(s) RI, a C$_{1-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, and a —NR$^b$R$^c$ group (the substituent(s) RI and the substituent(s) RII are the same as defined in Aspect [1]).

[1-1-b] More preferable examples of Ls include a halogen atom, a cyano group, a C$_{1-10}$ alkyl group which is optionally substituted with 1 to 5 substituent(s) RI, a C$_{2-10}$ alkenyl group which is optionally substituted with 1 to 5 substituent(s) RI, a C$_{1-10}$ alkoxy group which is optionally substituted with 1 to 5 substituent(s) RI, a C$_{1-10}$ alkenyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, and a —NR$^b$R$^c$ group (the substituent(s) RI and the substituent(s) RII are the same as defined in Aspect [1]).

[1-1-c] Further preferable examples of Ls include a halogen atom, a cyano group, a C$_{1-10}$ alkyl group which is optionally substituted with 1 to 5 substituent(s) RI, a C$_{2-10}$ alkenyl group which is optionally substituted with 1 to 5 substituent(s) RI, a C$_{1-10}$ alkoxy group which is optionally substituted with 1 to 5 substituent(s) RI, a C$_{1-10}$ alkenyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, and an aralkyloxy group which is optionally substituted with 1 to 5 substituent(s) RII (the substituent(s) RI and the substituent(s) RII are the same as defined in Aspect [1]).

[1-1-d] Most preferable examples of Ls include a halogen atom, a cyano group, a $C_{1-10}$ alkyl group (the $C_{1-10}$ alkyl group is optionally substituted with 1 to 5 halogen atom(s), 1 to 5 —OH, or 1 to 5 $C_{1-4}$ alkoxy group(s)), a $C_{1-10}$ alkenyl group (the $C_{1-10}$ alkenyl group is optionally substituted with 1 to 5 halogen atom(s), 1 to 5 —OH, or 1 to 5 $C_{1-4}$ alkoxy group(s)), a $C_{1-10}$ alkoxy group (the $C_{1-10}$ alkoxy group is optionally substituted with 1 to 5 halogen atom(s), 1 to 5 —OH, or 1 to 5 $C_{1-4}$ alkoxy group(s)), a $C_{1-10}$ alkenyloxy group (the $C_{1-10}$ alkenyloxy group is optionally substituted with 1 to 5 halogen atom(s), 1 to 5 —OH, or 1 to 5 $C_{1-4}$ alkoxy group(s)), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, an aryloxy group which is optionally substituted with 1 to 5 substituent(s) RIIa, a heteroaryloxy group which is optionally substituted with 1 to 5 substituent(s) RIIa, a non-aromatic heterocyclic oxy group which is optionally substituted with 1 to 5 substituent(s) RIIa, or an aralkyloxy group which is optionally substituted with 1 to 5 substituent(s) RIIa (the substituent(s) RIIa are the same as or different from each other and are each a group arbitrarily selected from a halogen atom, a $C_{1-6}$ alkoxy group (the $C_{1-6}$ alkoxy group is optionally substituted with 1 to 5 halogen atom(s), 1 to 5 —OH, or 1 to 5 $C_{1-4}$ alkoxy group(s)), 1 to 5 non-aromatic heterocyclic group(s) (the heterocyclic group(s) is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclic oxy group, and a $C_{1-6}$ alkyl group (the $C_{1-6}$ alkyl group is optionally substituted with 1 to 5 halogen atom(s), 1 to 5 —OH, 1 to 5 $C_{1-4}$ alkoxy group(s), or 1 to 5 —NR$^{b1}$R$^{c1}$ group(s)). Substitution with one to three substituent(s) RIIa is preferable.

Specific examples of Ls include a fluorine atom, a chlorine atom, a bromine atom, cyano, methyl, ethyl, trifluoromethyl, cyclopropyl, cyclohexyl, 4,4-dimethylcyclohexyl, vinyl, allyl, 1-cyclohexen-1-yl, 4,4-dimethyl-1-cyclohexen-1-yl, methoxy, ethoxy, isopropoxy, cyclohexyloxy, vinyloxy, allyloxy, pentenyloxy, isopentenyloxy, phenyl, (2-, 3-, or 4-)fluorophenyl, (2-, 3-, or 4-)chlorophenyl, (2-, 3-, or 4-)hydroxyphenyl, (2-, 3-, or 4-)methoxyphenyl, (2-, 3-, or 4-)ethoxyphenyl, (2-, 3-, or 4-)propoxyphenyl, (2-, 3-, or 4-)isopropoxyphenyl, (2-, 3-, or 4-)trifluoromethoxyphenyl, (2-, 3-, or 4-)methylphenyl, (2-, 3-, or 4-)trifluoromethylphenyl, 3,5-dimethoxyphenyl, (2,6-, 2,5-, 2,4-, or 2,3-)dimethylphenyl, 3,5-ditrifluoromethylphenyl, 4-methoxy-2-methylphenyl, 4-methoxy-(2,6-, 2,5-, or 2,3-)dimethylphenyl, 4-(2-hydroxyethoxy)-2-methylphenyl, 4-(2,3-dihydroxypropoxy)-2-methylphenyl, 4-(3-hydroxy-3-methylbutoxy)-2-methylphenyl, 3-(3-hydroxy-3-methylbutoxy)-2-methylphenyl, 4-(2-hydroxyethoxy)-(2,6-, 2,5-, or 2,3-)dimethylphenyl, 4-(3-hydroxypropoxy)-2-methylphenyl, 4-(3-hydroxypropoxy)-(2,6-, 2,5-, or 2,3-)dimethylphenyl, 4-(2,3-dihydroxypropoxy)-(2,6-, 2,5-, or 2,3-)dimethylphenyl, 4-((2R)-2,3-dihydroxypropoxy)-(2,6-, 2,5-, or 2,3-)dimethylphenyl, 4-((2S)-2,3-dihydroxypropoxy)-(2,6-, 2,5-, or 2,3-)dimethylphenyl, 4-(3-hydroxy-2-hydroxymethylpropoxy)-2-methylphenyl, 4-(3-hydroxy-2-hydroxymethyl-2-methylpropoxy)-2-methylphenyl, 4-(3-hydroxybutoxy)-2-methylphenyl, 4-((3S)-3-hydroxybutoxy)-2-methylphenyl, 4-((3R)-3-hydroxybutoxy)-2-methylphenyl, 4-(3-hydroxy-2-hydroxymethylpropoxy)-(2,6-, 2,5-, or 2,3-)dimethylphenyl, 4-(3-hydroxy-2-hydroxymethyl-2-methylpropoxy)-(2,6-, 2,5-, or 2,3-)dimethylphenyl, 4-(3-hydroxybutoxy)-(2,6-, 2,5-, or 2,3-)dimethylphenyl, 4-((3S)-3-hydroxybutoxy)-(2,6-, 2,5-, or 2,3-)dimethylphenyl, 4-((3R)-3-hydroxybutoxy)-(2,6-, 2,5-, or 2,3-)dimethylphenyl, 4-(3-hydroxy-3-methylbutoxy)-(2,6-, 2,5-, or 2,3-)dimethylphenyl, 4-(3-aminopropoxy)-2-methylphenyl, 4-(3-aminopropoxy)-(2,6-, 2,5-, or 2,3-)dimethylphenyl, 4-(2-(2-oxo-1-pyrrolidinyl)ethoxy)-2-methylphenyl, 4-(2-(2-oxo-1-pyrrolidinyl)ethoxy)-(2,6-, 2,5-, or 2,3-)dimethylphenyl, 4-(3-(2-oxo-1-pyrrolidinyl)propoxy)-2-methylphenyl, 4-(3-(2-oxo-1-pyrrolidinyl)propoxy)-(2,6-, 2,5-, or 2,3-)dimethylphenyl, 4-(2-ethoxy-ethoxy)-2-methylphenyl, 4-(2-ethoxy-ethoxy)-(2,6-, 2,5-, or 2,3-)dimethylphenyl, 4-(2-methylsulfonyl-ethoxy)-2-methylphenyl, 4-(2-methylsulfonyl-ethoxy)-(2,6-, 2,5-, or 2,3-)dimethylphenyl, 4-(3-methylsulfonyl-propoxy)-2-methylphenyl, 4-(3-methylsulfonyl-propoxy)-(2,6-, 2,5-, or 2,3-)dimethylphenyl, 4-((1,1-dioxytetrahydro-2H-thiopyran-4-yl)oxy)-2-methylphenyl, 4-((1,1-dioxytetrahydro-2H-thiopyran-4-yl)oxy)-(2,6-, 2,5-, or 2,3-)dimethylphenyl, 4-((4-hydroxy-1,1-dioxytetrahydro-2H-thiopyran-4-yl)methoxy)-2-methylphenyl, 4-((4-hydroxy-1,1-dioxytetrahydro-2H-thiopyran-4-yl)methoxy)-(2,6-, 2,5-, or 2,3-)dimethylphenyl, 4-((3-methyloxetan-3-yl)methoxy)-2-methylphenyl, 4-((3-methyloxetan-3-yl)methoxy)-(2,6-, 2,5-, or 2,3-)dimethylphenyl, 4-(2-acetylamino-ethoxy)-2-methylphenyl, 4-(2-acetylamino-ethoxy)-(2,6-, 2,5-, or 2,3-)dimethylphenyl, 4-(3-acetylamino-propoxy)-2-methylphenyl, 4-(3-acetylamino-propoxy)-(2,6-, 2,5-, or 2,3-)dimethylphenyl, 4-(2-methylsulfonylamino-ethoxy)-2-methylphenyl, 4-(2-methylsulfonylamino-ethoxy)-(2,6-, 2,5-, or 2,3-)dimethylphenyl, 4-(3-methylsulfonylamino-propoxy)-2-methylphenyl, 4-(3-methylsulfonylamino-propoxy)-(2,6-, 2,5-, or 2,3-)dimethylphenyl, 4-(2-carbamoyl-ethoxy)-2-methylphenyl, 4-(2-carbamoyl-ethoxy)-(2,6-, 2,5-, or 2,3-)dimethylphenyl, 4-(3-carbamoyl-propoxy)-2-methylphenyl, 4-(3-carbamoyl-propoxy)-(2,6-, 2,5-, or 2,3-)dimethylphenyl, 4-(2-methylcarbamoyl-ethoxy)-2-methylphenyl, 4-(2-methylcarbamoyl-ethoxy)-(2,6-, 2,5-, or 2,3-)dimethylphenyl, 4-(3-methylcarbamoyl-propoxy)-2-methylphenyl, 4-(3-methylcarbamoyl-propoxy)-(2,6-, 2,5-, or 2,3-)dimethylphenyl, 4-(2-dimethylcarbamoyl-ethoxy)-2-methylphenyl, 4-(2-dimethylcarbamoyl-ethoxy)-(2,6-, 2,5-, or 2,3-)dimethylphenyl, 4-(3-dimethylcarbamoyl-propoxy)-2-methylphenyl, 4-(3-dimethylcarbamoyl-propoxy)-(2,6-, 2,5-, or 2,3-)dimethylphenyl, 4-(2-methylsulfamoyl-ethoxy)-2-methylphenyl, 4-(2-sulfamoyl-ethoxy)-(2,6-, 2,5-, or 2,3-)dimethylphenyl, 4-(3-sulfamoyl-propoxy)-2-methylphenyl, 4-(3-sulfamoyl-propoxy)-(2,6-, 2,5-, or 2,3-)dimethylphenyl, 4-(2-methylsulfamoyl-ethoxy)-2-methylphenyl, 4-(2-methylsulfamoyl-ethoxy)-(2,6-, 2,5-, or 2,3-)dimethylphenyl, 4-(3-methylsulfamoyl-propoxy)-2-methylphenyl, 4-(3-methylsulfamoyl-propoxy)-(2,6-, 2,5-, or 2,3-)dimethylphenyl, 4-(2-dimethylsulfamoyl-ethoxy)-2-methylphenyl, 4-(2-dimethylsulfamoyl-ethoxy)-(2,6-, 2,5-, or 2,3-)dimethylphenyl, 4-(3-dimethylsulfamoyl-propoxy)-2-methylphenyl, 4-(3-dimethylsulfamoyl-propoxy)-(2,6-, 2,5-, or 2,3-)dimethylphenyl, 3-fluoro-4-(2-hydroxyethoxy)-2-methylphenyl, 3-fluoro-4-(2,3-dihydroxypropoxy)-2-methylphenyl, 3-fluoro-4-(3-hydroxy-3-methylbutoxy)-2-methylphenyl, 3-fluoro-4-(2-hydroxyethoxy)-(2,6-, or 2,5-)dimethylphenyl, 4-((2R)-2,3-dihydroxypropoxy)-3-fluoro-(2,6-, or 2,5-)dimethylphenyl, 4-((2S)-2,3-dihydroxypropoxy)-3-fluoro-(2,6-, or 2,5-)dimethylphenyl, 3-fluoro-4-(3-hydroxypropoxy)-2-methylphenyl, 3-fluoro-4-(3-hydroxypropoxy)-(2,6-, or 2,5-)dimethylphenyl, 3-fluoro-4-(2,3-dihydroxypropoxy)-(2,6-, or 2,5-)dimethylphenyl, 3-fluoro-4-(3-hydroxy-2-hydroxymethylpropoxy)-2-methylphenyl, 3-fluoro-4-(3-hydroxy-2-hydroxyethylpropoxy)-(2,6-, or 2,5-)dimethylphenyl, 3-fluoro-4-(3-hydroxy-2-hydroxymethyl-2-methylpropoxy)-2-methylphenyl, 3-fluoro-4-(3-hydroxy-2-hydroxymethyl-2-methylpropoxy)-(2,6-, or 2,5-)dimethylphenyl, 3-fluoro-4-(3-hydroxybutoxy)-2-methylphenyl, 3-fluoro-4-(3-hydroxybutoxy)-(2,6-, or 2,5-)dimethylphenyl, 3-fluoro-4-(3-hydroxy-3-methylbutoxy)-(2,6-, or 2,5-)dimethylphenyl, 3-fluoro-4-(3-aminopropoxy)-2-methylphenyl, 3-fluoro-4-(3-aminopropoxy)-(2,6-, or 2,5-)dimethylphenyl, 3-fluoro-4-(2-(2-oxo-1-pyrrolidinyl)ethoxy)-2-methylphenyl, 3-fluoro-4-(2-(2-oxo-1-pyrrolidinyl)ethoxy)-(2,6-, or 2,5-)dimethylphenyl, 3-fluoro-4-(3-(2-oxo-1-pyrrolidinyl)propoxy)-2-methylphenyl, 3-fluoro-4-(3-(2-oxo-1-pyrrolidinyl)propoxy)-(2,6-, or 2,5-)dimethylphenyl, 3-fluoro-4-(2-ethoxy-ethoxy)-2-methylphenyl, 3-fluoro-4-(2-ethoxy-ethoxy)-(2,6-, or 2,5-)dimethylphenyl, 3-fluoro-4-(2-methylsulfonyl-ethoxy)-2-methylphenyl, 3-fluoro-4-(2-methylsulfonyl-ethoxy)-(2,6-, 2,5-, or 2,3-)dimethylphenyl, 3-fluoro-4-(3-methylsulfonyl-propoxy)-2-methylphenyl, 3-fluoro-4-(3-methylsulfonyl-propoxy)-(2,6-, or 2,5-)dimethylphenyl, 3-fluoro-4-((1,1-dioxytetrahydro-2H-thiopyran-4-yl)oxy)-2-methylphenyl, 3-fluoro-4-((1,1-dioxytetrahydro-2H-thiopyran-4-yl)oxy)-(2,6-, or 2,5-)dimethylphenyl, 3-fluoro-4-((4-hydroxy-1,1-dioxytetrahydro-2H-thiopyran-4-yl)methoxy)-2-methylphenyl, 3-fluoro-4-((4-hydroxy-1,1-dioxytetrahydro-2H-thiopyran-4-yl)methoxy)-(2,6-, or 2,5-)dimethylphenyl, 3-fluoro-4-((3-methyloxetan-3-yl)methoxy)-2-methylphenyl, 3-fluoro-4-((3-methyloxetan-3-yl)methoxy)-(2,6-, or 2,5-)dimethylphenyl, 3-fluoro-4-(2-acetylamino-ethoxy)-2-methylphenyl, 3-fluoro-4-(2-acetylamino-ethoxy)-(2,6-, or 2,5-)dimethylphenyl, 3-fluoro-4-(3-acetylamino-propoxy)-2-methylphenyl, 3-fluoro-4-(3-acetylamino-propoxy)-(2,6-, or 2,5-)dimethylphenyl, 3-fluoro-4-(2-methylsulfonylamino-ethoxy)-2-methylphenyl, 3-fluoro-4-(2-methylsulfonylamino-ethoxy)-(2,6-, or 2,5-)dimethylphenyl, 3-fluoro-4-(3-methylsulfonylamino-propoxy)-2-methylphenyl, 3-fluoro-4-(3-methylsulfonylamino-propoxy)-(2,6-, or 2,5-)dimethylphenyl, 3-fluoro-4-(2-carbamoyl-ethoxy)-2-methylphenyl, 3-fluoro-4-(2-carbamoyl-ethoxy)-(2,6-, or 2,5-)dimethylphenyl, 3-fluoro-4-(3-carbamoyl-propoxy)-2-methylphenyl, 3-fluoro-4-(3-carbamoyl-propoxy)-(2,6-, or 2,5-)dimethylphenyl, 3-fluoro-4-(2-methylcarbamoyl-ethoxy)-2-methylphenyl, 3-fluoro-4-(2-methylcarbamoyl-ethoxy)-(2,6-, or 2,5-)dimethylphenyl, 3-fluoro-4-(3-methylcarbamoyl-propoxy)-2-methylphenyl, 3-fluoro-4-(3-methylcarbamoyl-propoxy)-(2,6-, or 2,5-)dimethylphenyl, 3-fluoro-4-(2-dimethylcarbamoyl-ethoxy)-2-methylphenyl, 3-fluoro-4-(2-dimethylcarbamoyl-ethoxy)-(2,6-, or 2,5-)dimethylphenyl, 3-fluoro-4-(3-dimethylcarbamoyl-propoxy)-2-methylphenyl, 3-fluoro-4-(3-dimethylcarbamoyl-propoxy)-(2,6-, or 2,5-)dimethylphenyl, 3-fluoro-4-(2-sulfamoyl-ethoxy)-2-methylphenyl, 3-fluoro-4-(2-sulfamoyl-ethoxy)-(2,6-, or 2,5-)dimethylphenyl, 3-fluoro-4-(3-sulfamoyl-propoxy)-2-methylphenyl, 3-fluoro-4-(3-sulfamoyl-propoxy)-(2,6-, or 2,5-)dimethylphenyl, 3-fluoro-4-(2-methylsulfamoyl-ethoxy)-2-methylphenyl, 3-fluoro-4-(2-methylsulfamoyl-ethoxy)-(2,6-, or 2,5-)dimethylphenyl, 3-fluoro-4-(3-methylsulfamoyl-propoxy)-2-methylphenyl, 3-fluoro-4-(3-methylsulfamoyl-propoxy)-(2,6-, or 2,5-)dimethylphenyl, 3-fluoro-4-(2-dimethylsulfamoyl-ethoxy)-2-methylphenyl, 3-fluoro-4-(2-dimethylsulfamoyl-ethoxy)-(2,6-, or 2,5-)dimethylphenyl, 3-fluoro-4-(3-dimethylsulfamoyl-propoxy)-2-methylphenyl, 3-fluoro-4-(3-dimethylsulfamoyl-propoxy)-(2,6-, or 2,5-)dimethylphenyl, 4-(2-hydroxyethoxy)-2-hydroxymethylphenyl, 4-(2,3-dihydroxypropoxy)-2-hydroxymethylphenyl, 4-(3-hydroxy-3-methylbutoxy)-2-hydroxymethylphenyl, 4-(2-hydroxyethoxy)-6-methyl-2-hydroxymethylphenyl, 4-(3-hydroxypropoxy)-2-hydroxymethylphenyl, 4-(3-hydroxypropoxy)-6-methyl-2-hydroxymethylphenyl, 4-(2,3-dihydroxypropoxy)-6-methyl-2-hydroxymethylphenyl, 4-(3-hydroxy-2-hydroxymethylpropoxy)-2-hydroxymethylphenyl, 4-(3-hydroxy-2-hydroxymethylpropoxy)-6-methyl-2-hydroxymethylphenyl, 4-(3-hydroxy-2-hydroxymethyl-2-methylpropoxy)-2-hydroxymethylphenyl, 4-(3-hydroxy-2-hydroxymethyl-2-methylpropoxy)-6-methyl-2-hydroxymethylphenyl, 4-(3-hydroxybutoxy)-2-hydroxymethylphenyl, 4-(3-hydroxybutoxy)-6-methyl-2-hydroxymethylphenyl, 4-(3-hydroxy-3-methylbutoxy)-6-methyl-2-hydroxymethylphenyl, 4-(3-aminopropoxy)-2-hydroxymethylphenyl, 4-(3-aminopropoxy)-6-methyl-2-hydroxymethylphenyl, 4-(2-(2-oxo-1-pyrrolidinyl)ethoxy)-2-hydroxymethylphenyl, 4-(2-(2-oxo-1-pyrrolidinyl)ethoxy)-6-methyl-2-hydroxymethylphenyl, 4-(3-(2-oxo-1-pyrrolidinyl)propoxy)-2-hydroxymethylphenyl, 4-(3-(2-oxo-1-pyrrolidinyl)propoxy)-6-methyl-2-hydroxymethylphenyl, 4-(2-ethoxy-ethoxy)-2-hydroxymethylphenyl, 4-(2-ethoxy-ethoxy)-6-methyl-2-hydroxymethylphenyl, 4-(2-methylsulfonyl-ethoxy)-2-hydroxymethylphenyl, 4-(2-methylsulfonyl-ethoxy)-6-methyl-2-hydroxymethylphenyl, 4-(3-methylsulfonyl-propoxy)-2-hydroxymethylphenyl, 4-(3-methylsulfonyl-propoxy)-6-methyl-2-hydroxymethylphenyl, 4-((1,1-dioxytetrahydro-2H-thiopyran-4-yl)oxy)-2-hydroxymethylphenyl, 4-((1,1-dioxytetrahydro-2H-thiopyran-4-yl)oxy)-6-methyl-2-hydroxymethylphenyl, 4-((4-hydroxy-1,1-dioxytetrahydro-2H-thiopyran-4-yl)methoxy)-2-hydroxymethylphenyl, 4-((4-hydroxy-1,1-dioxytetrahydro-2H-thiopyran-4-yl)methoxy)-6-methyl-2-hydroxymethylphenyl, 4-((3-methyloxetan-3-yl)methoxy)-2-hydroxymethylphenyl, 4-((3-methyloxetan-3-yl)methoxy)-6-methyl-2-hydroxymethylphenyl, 4-(2-acetylamino-ethoxy)-2-hydroxymethylphenyl, 4-(2-acetylamino-ethoxy)-6-methyl-2-hydroxymethylphenyl, 4-(3-acetylamino-propoxy)-2-hydroxymethylphenyl, 4-(3-acetylamino-propoxy)-6-methyl-2-hydroxymethylphenyl, 4-(2-methylsulfonylamino-ethoxy)-2-hydroxymethylphenyl, 4-(2-methylsulfonylamino-ethoxy)-6-methyl-2-hydroxymethylphenyl, 4-(3-methylsulfonylamino-propoxy)-2-hydroxymethylphenyl, 4-(3-methylsulfonylamino-propoxy)-6-methyl-2-hydroxymethylphenyl, 4-(2-carbamoyl-ethoxy)-2-hydroxymethylphenyl, 4-(2-carbamoyl-ethoxy)-6-methyl-2-hydroxymethylphenyl, 4-(3-carbamoyl-propoxy)-2-hydroxymethylphenyl, 4-(3-carbamoyl-propoxy)-6-methyl-2-hydroxymethylphenyl, 4-(2-methylcarbamoyl-ethoxy)-2-hydroxymethylphenyl, 4-(2-methylcarbamoyl-ethoxy)-6-methyl-2-hydroxymethylphenyl, 4-(3-methylcarbamoyl-propoxy)-2-hydroxymethylphenyl, 4-(3-methylcarbamoyl-propoxy)-6-methyl-2-hydroxymethylphenyl, 4-(2-dimethylcarbamoyl-ethoxy)-2-hydroxymethylphenyl, 4-(2-dimethylcarbamoyl-ethoxy)-6-methyl-2-hydroxymethylphenyl, 4-(3-dimethylcarbamoyl-propoxy)-2-hydroxymethylphenyl, 4-(3-dimethylcarbamoyl-propoxy)-6-methyl-2-hydroxymethylphenyl, 4-(2-sulfamoyl-ethoxy)-2-hydroxymethylphenyl, 4-(2-sulfamoyl-ethoxy)-6-methyl-2-hydroxymethylphenyl, 4-(3-sulfamoyl-propoxy)-2-hydroxymethylphenyl, 4-(3-sulfamoyl-propoxy)-6-methyl-2-hydroxymethylphenyl, 4-(2-methylsulfamoyl-ethoxy)-2- hydroxymethylphenyl, 4-(2-methylsulfamoyl-ethoxy)-6-methyl-2-hydroxymethylphenyl, 4-(3-methylsulfamoyl-propoxy)-2-hydroxymethylphenyl, 4-(3-methylsulfamoyl-propoxy)-6-methyl-2-hydroxymethylphenyl, 4-(2-dimethylsulfamoyl-ethoxy)-2-hydroxymethylphenyl, 4-(2-dimethylsulfamoyl-ethoxy)-6-methyl-2-hydroxymethylphenyl, 4-(3-dimethylsulfamoyl-propoxy)-2-hydroxymethylphenyl, 4-(3-dimethylsulfamoyl-propoxy)-6-methyl-2-hydroxymethylphenyl, (4-,5-,6-, or 7-)fluoro-1-indanyl, (4-,5-,6-, or 7-)chloro-1-indanyl, (4-,5-,6-, or 7-)bromo-1-indanyl, (4-,5-,6-, or 7-)trifluoromethyl-1-indanyl, (4-,5-,6-, or 7-)fluoro-2-indanyl, (4-,5-,6-, or 7-)chloro-2-indanyl, (4-,5-,6-, or 7-)bromo-2-indanyl, (4-,5-,6-, or 7-)trifluoromethyl-2-indanyl, 1-methylpyrazol-4-yl, 3,5-dimethylisoxazol-4-yl, (2,3-, or 4-)pyridyl, (2-, 4-, 5-, or 6-)fluoropyridin-3-yl, (2-, 4-, 5-, or 6-)chloropyridin-3-yl, (2-, 4-, 5-, or 6-)hydroxypyridin-3-yl, (2-, 4-, 5-, or 6-)methoxypyridin-3-yl, (2-, 4-, 5-, or 6-)methylpyridin-3-yl, (2-, 4-, 5-, or 6-)trifluoromethylpyridin-3-yl, (2,4-, 2,5-, 2,6-, 4,5-, 4,6-, or 5,6-)dimethylpyridin-3-yl, (2,4-, 2,5-, 2,6-, 4,5-, 4,6-, or 5,6-)dimethoxypyridin-3-yl, 6-methoxy-(2-, 4-, or 5-)methylpyridin-3-yl, 6-(2-hydroxyethoxy)-(2-, or 4-)methylpyridin-3-yl, 6-(3-hydroxypropoxy)-(2-, or 4-)methylpyridin-3-yl, 6-(2,3-dihydroxypropoxy)-(2-, or 4-)methylpyridin-3-yl, 6-((2R)-2,3-dihydroxypropoxy)-(2-, or 4-)methylpyridin-3-yl, 6-((2S)-2,3-dihydroxypropoxy)-(2-, or 4-)methylpyridin-3-yl, 6-((3S)-3-hydroxybutoxy)-(2-, or 4-)methylpyridin-3-yl, 6-((3R)-3-hydroxybutoxy)-(2-, or 4-)methylpyridin-3-yl, 6-(3-hydroxy-3-methylbutoxy)-(2-, or 4-)methylpyridin-3-yl, 6-(3-hydroxy-2-hydroxymethylpropoxy)-(2-, or 4-)methylpyridin-3-yl, 6-(3-hydroxy-2-hydroxymethyl-2-methylpropoxy)-(2-, or 4-)methylpyridin-3-yl, 6-(3-hydroxybutoxy)-(2-, or 4-)methylpyridin-3-yl, 6-(2-ethoxyethoxy)-(2-, or 4-)methylpyridin-3-yl, 6-(2-methylsulfonylethoxy)-(2-, or 4-)methylpyridin-3-yl, 6-(3-methylsulfonyl-propoxy)-(2-, or 4-)methylpyridin-3-yl, 6-((1,1-dioxytetrahydro-2H-thiopyran-4-yl)oxy)-(2-, or 4-)methylpyridin-3-yl, 6-((4-hydroxy-1,1-dioxytetrahydro-2H-thiopyran-4-yl)methoxy)-(2-, or 4-)methylpyridin-3-yl, 6-((3-methyloxetan-3-yl)methoxy)-(2-, or 4-)methylpyridin-3-yl, 6-(2-hydroxyethoxy)-(2,4-, 2,5-, or 4,5-)dimethylpyridin-3-yl, 6-(3-hydroxypropoxy)-(2,4-, 2,5-, or 4,5-)dimethylpyridin-3-yl, 6-(2,3-dihydroxypropoxy)-(2,4-, 2,5-, or 4,5-)dimethylpyridin-3-yl, 6-(3-hydroxy-2-hydroxymethylpropoxy)-(2,4-, 2,5-, or 4,5-)dimethylpyridin-3-yl, 6-(3-hydroxy-2-hydroxymethyl-2-methylpropoxy)-(2,4-, 2,5-, or 4,5-)dimethylpyridin-3-yl, 6-(3-hydroxybutoxy)-(2,4-, 2,5-, or 4,5-)dimethylpyridin-3-yl, 6-(3-hydroxy-3-methylbutoxy)-(2,4-, 2,5-, or 4,5-)dimethylpyridin-3-yl, 6-(2-ethoxyethoxy)-(2,4-, 2,5-, or 4,5-)dimethylpyridin-3-yl, 6-(2-methylsulfonylethoxy)-(2,4-, 2,5-, or 4,5-)dimethylpyridin-3-yl, 6-(3-methylsulfonyl-propoxy)-(2,4-, 2,5-, or 4,5-)dimethylpyridin-3-yl, 6-((1,1-dioxytetrahydro-2H-thiopyran-4-yl)oxy)-(2,4-, 2,5-, or 4,5-)dimethylpyridin-3-yl, 6-((4-hydroxy-1,1-dioxytetrahydro-2H-thiopyran-4-yl)methoxy)-(2,4-, 2,5-, or 4,5-)dimethylpyridin-3-yl, 6-((3-methyloxetan-3-yl)methoxy)-(2,4-, 2,5-, or 4,5-)dimethylpyridin-3-yl, 6-(3-hydroxy-3-methylbutoxy)-(2-, or 4-)methoxypyridin-3-yl, 6-(2-aminoethoxy)-(2-, or 4-)methylpyridin-3-yl, 6-(2-aminoethoxy)-(2,4-, 2,5-, or 4,5-)dimethylpyridin-3-yl, 6-(3-aminopropoxy)-(2-, or 4-)methylpyridin-3-yl, 6-(3-aminopropoxy)-(2,4-, 2,5-, or 4,5-)dimethylpyridin-3-yl, 6-(2-acetylamino-ethoxy)-(2-, or 4-)methylpyridin-3-yl, 6-(2-acetylamino-ethoxy)-(2,4-, 2,5-, or 4,5-)dimethylpyridin-3-yl, 6-(3-acetylamino-propoxy)-(2-, or 4-)methylpyridin-3-yl, 6-(3-acetylamino-propoxy)-(2,4-, 2,5-, or 4,5-)dimethylpyridin-3-yl, 6-(2-methylsulfonylamino-ethoxy)-(2-, or 4-)methylpyridin-3-yl, 6-(2-methylsulfonylamino-ethoxy)-(2,4-, 2,5-, or 4,5-)dimethylpyridin-3-yl, 6-(3-methylsulfonylamino-propoxy)-(2-, or 4-)methylpyridin-3-yl, 6-(3-methylsulfonylamino-propoxy)-(2,4-, 2,5-, or 4,5-)dimethylpyridin-3-yl, 6-(2-carbamoyl-ethoxy)-(2-, or 4-)methylpyridin-3-yl, 6-(2-carbamoyl-ethoxy)-(2,4-, 2,5-, or 4,5-)dimethylpyridin-3-yl, 6-(3-carbamoyl-propoxy)-(2-, or 4-)methylpyridin-3-yl, 6-(3-carbamoyl-propoxy)-(2,4-, 2,5-, or 4,5-)dimethylpyridin-3-yl, 6-(2-methylcarbamoyl-ethoxy)-(2-, or 4-)methylpyridin-3-yl, 6-(2-methylcarbamoyl-ethoxy)-(2,4-, 2,5-, or 4,5-)dimethylpyridin-3-yl, 6-(3-methylcarbamoyl-propoxy)-(2-, or 4-)methylpyridin-3-yl, 6-(3-methylcarbamoyl-propoxy)-(2,4-, 2,5-, or 4,5-)dimethylpyridin-3-yl, 6-(2-dimethylcarbamoyl-ethoxy)-(2-, or 4-)methylpyridin-3-yl, 6-(2-dimethylcarbamoyl-ethoxy)-(2,4-, 2,5-, or 4,5-)dimethylpyridin-3-yl, 6-(3-dimethylcarbamoyl-propoxy)-(2-, or 4-)methylpyridin-3-yl, 6-(3-dimethylcarbamoyl-propoxy)-(2,4-, 2,5-, or 4,5-)dimethylpyridin-3-yl, 6-(2-sulfamoyl-ethoxy)-(2-, or 4-)methylpyridin-3-yl, 6-(2-sulfamoyl-ethoxy)-(2,4-, 2,5-, or 4,5-)dimethylpyridin-3-yl, 6-(3-sulfamoyl-propoxy)-(2-, or 4-)methylpyridin-3-yl, 6-(3-sulfamoyl-propoxy)-(2,4-, 2,5-, or 4,5-)dimethylpyridin-3-yl, 6-(2-methylsulfamoyl-ethoxy)-(2-, or 4-)methylpyridin-3-yl, 6-(2-methylsulfamoyl-ethoxy)-(2,4-, 2,5-, or 4,5-)dimethylpyridin-3-yl, 6-(3-methylsulfamoyl-propoxy)-(2-, or 4-)methylpyridin-3-yl, 6-(3-methylsulfamoyl-propoxy)-(2,4-, 2,5-, or 4,5-)dimethylpyridin-3-yl, 6-(2-dimethylsulfamoyl-ethoxy)-(2-, or 4-)methylpyridin-3-yl, 6-(2-dimethylsulfamoyl-ethoxy)-(2,4-, 2,5-, or 4,5-)dimethylpyridin-3-yl, 6-(3-dimethylsulfamoyl-propoxy)-(2-, or 4-)methylpyridin-3-yl, 6-(3-dimethylsulfamoyl-propoxy)-(2,4-, 2,5-, or 4,5-)dimethylpyridin-3-yl, 6-(2-(2-oxo-1-pyrrolidinyl)ethoxy)-(2-, or 4-)methylpyridin-3-yl, 6-(2-(2-oxo-1-pyrrolidinyl)ethoxy)-(2,4-, 2,5-, or 4,5-)dimethylpyridin-3-yl, 6-(3-(2-oxo-1-pyrrolidinyl)propoxy)-(2-, or 4-)methylpyridin-3-yl, 6-(3-(2-oxo-1-pyrrolidinyl)propoxy)-(2,4-, 2,5-, or 4,5-)dimethylpyridin-3-yl, 6-(1-piperidinyl)pyridin-3-yl, (2,4-, or 5-)pyrimidinyl, (2-, or 4-)methoxypyrimidin-5-yl, 2-(2-hydroxyethoxy)-4-methylpyrimidin-5-yl, 2-(3-hydroxypropoxy)-4-methylpyrimidin-5-yl, 2-(2,3-dihydroxypropoxy)-4-methylpyrimidin-5-yl, 2-(3-hydroxy-3-methylbutoxy)-4-methylpyrimidin-5-yl, 2-(3-hydroxy-2-hydroxymethylpropoxy)-4-methylpyrimidin-5-yl, 2-(3-hydroxy-2-hydroxymethyl-2-methylpropoxy)-4-methylpyrimidin-5-yl, 2-(3-hydroxybutoxy)-4-methylpyrimidin-5-yl, 2-(2-ethoxyethoxy)-4-methylpyrimidin-5-yl, 2-(2-methylsulfonylethoxy)-4-methylpyrimidin-5-yl, 2-(3-methylsulfonyl-propoxy)-4-methylpyrimidin-5-yl, 2-((1,1-dioxytetrahydro-2H-thiopyran-4-yl)oxy)-4-methylpyrimidin-5-yl, 2-((4-hydroxy-1,1-dioxytetrahydro-2H-thiopyran-4-yl)methoxy)-4-methylpyrimidin-5-yl, 2-((3-methyloxetan-3-yl)methoxy)-4-methylpyrimidin-5-yl, 2-(2-hydroxyethoxy)-4,6-dimethylpyrimidin-5-yl, 2-(3-hydroxypropoxy)-4,6-dimethylpyrimidin-5-yl, 2-(2,3-dihydroxypropoxy)-4,6-dimethylpyrimidin-5-yl, 2-(3-hydroxy-2-hydroxymethylpropoxy)-4,6-dimethylpyrimidin-5-yl, 2-(3-hydroxy-2-hydroxymethyl-2-methylpropoxy)-4,6-dimethylpyrimidin-5-yl, 2-(3-hydroxybutoxy)-4,6-dimethylpyrimidin-5-yl, 2-((2R)-2,3-dihydroxypropoxy)-4,6-dimethylpyrimidin-5-yl, 2-((2S)-2,3-dihydroxypropoxy)-4,6-dimethylpyrimidin-5-yl, 2-((3S)-3-hydroxybutoxy)-4,6-dimethylpyrimidin-5-yl, 6-((3R)-3-hydroxybutoxy)-4,6-dimethylpyrimidin-5-yl, 2-(3-hydroxy-3-methylbutoxy)-4,6-dimethylpyrimidin-5-yl, 2-(2-ethoxyethoxy)-4,6-dimethylpyrimidin-5-yl, 2-(2-methylsulfonylethoxy)-4,6-dimethylpyrimidin-5-yl, 2-(3-methylsulfonyl-propoxy)-4,6- dimethylpyrimidin-5-yl, 2-((1,1-dioxytetrahydro-2H-thiopyran-4-yl)oxy)-4,6-dimethylpyrimidin-5-yl, 6-((4-hydroxy-1,1-dioxytetrahydro-2H-thiopyran-4-yl)methoxy)-4,6-dimethylpyrimidin-5-yl, 2-((3-methyloxetan-3-yl)methoxy)-4,6-dimethylpyrimidin-5-yl, 2-(2-aminoethoxy)-4-methylpyrimidin-5-yl, 2-(2-aminoethoxy)-4,6-dimethylpyrimidin-5-yl, 2-(3-aminopropoxy)-4-methylpyrimidin-5-yl, 2-(3-aminopropoxy)-4,6-dimethylpyrimidin-5-yl, 2-(2-acetylamino-ethoxy)-4-methylpyrimidin-5-yl, 2-(2-acetylamino-ethoxy)-4,6-dimethylpyrimidin-5-yl, 2-(3-acetylamino-propoxy)-4-methylpyrimidin-5-yl, 2-(3-acetylamino-propoxy)-4,6-dimethylpyrimidin-5-yl, 2-(2-methylsulfonylamino-ethoxy)-4-methylpyrimidin-5-yl, 2-(2-methylsulfonylamino-ethoxy)-4,6-dimethylpyrimidin-5-yl, 2-(3-methylsulfonylamino-propoxy)-4-methylpyrimidin-5-yl, 2-(3-methylsulfonylamino-prop oxy)-4,6-dimethylpyrimidin-5-yl, 2-(2-carbamoyl-ethoxy)-4-methylpyrimidin-5-yl, 2-(2-carbamoyl-ethoxy)-4,6-dimethylpyrimidin-5-yl, 2-(3-carbamoyl-propoxy)-4-methylpyrimidin-5-yl, 2-(3-carbamoyl-propoxy)-4,6-dimethylpyrimidin-5-yl, 2-(2-methylcarbamoyl-ethoxy)-4-methylpyrimidin-5-yl, 2-(2-methylcarbamoyl-ethoxy)-4,6-dimethylpyrimidin-5-yl, 2-(3-methylcarbamoyl-propoxy)-4-methylpyrimidin-5-yl, 2-(3-methylcarbamoyl-propoxy)-4,6-dimethylpyrimidin-5-yl, 2-(2-dimethylcarbamoyl-ethoxy)-4-methylpyrimidin-5-yl, 2-(2-dimethylcarbamoyl-ethoxy)-4,6-dimethylpyrimidin-5-yl, 2-(3-dimethylcarbamoyl-propoxy)-4-methylpyrimidin-5-yl, 2-(3-dimethylcarbamoyl-propoxy)-4,6-dimethylpyrimidin-5-yl, 2-(2-sulfamoyl-ethoxy)-4-methylpyrimidin-5-yl, 2-(2-sulfamoyl-ethoxy)-4,6-dimethylpyrimidin-5-yl, 2-(3-sulfamoyl-propoxy)-4-methylpyrimidin-5-yl, 2-(3-sulfamoyl-propoxy)-4,6-dimethylpyrimidin-5-yl, 2-(2-methylsulfamoyl-ethoxy)-4-methylpyrimidin-5-yl, 2-(2-methylsulfamoyl-ethoxy)-4,6-dimethylpyrimidin-5-yl, 2-(3-methylsulfamoyl-propoxy)-4-methylpyrimidin-5-yl, 2-(3-methylsulfamoyl-propoxy)-4,6-dimethylpyrimidin-5-yl, 2-(2-dimethylsulfamoyl-ethoxy)-4-methylpyrimidin-5-yl, 2-(2-dimethylsulfamoyl-ethoxy)-4,6-dimethylpyrimidin-5-yl, 2-(3-dimethylsulfamoyl-propoxy)-4-methylpyrimidin-5-yl, 2-(3-dimethylsulfamoyl-propoxy)-4,6-dimethylpyrimidin-5-yl, 2-(2-(2-oxo-1-pyrrolidinyl)ethoxy)-4-methylpyrimidin-5-yl, 2-(2-(2-oxo-1-pyrrolidinyl)ethoxy)-4,6-dimethylpyrimidin-5-yl, 2-(3-(2-oxo-1-pyrrolidinyl)propoxy)-4-methylpyrimidin-5-yl, 2-(3-(2-oxo-1-pyrrolidinyl)propoxy)-4,6-dimethylpyrimidin-5-yl, (2-, 4-, 5-, 6-, 7-, or 8-)methylquinolin-3-yl, 6-(1-piperidinyl)pyridin-3-yl, 5-pyrimidinyl, 6-indolyl, 3-quinolyl, 1,4-benzodioxan-6-yl, piperidin-1-yl, piperidin-4-yl, 1-methylpiperidin-4-yl, 4,4-difluoropiperidin-1-yl, 3,6-dihydro-2H-pyran-4-yl, 4-oxanyl, benzyl, phenoxy, (2-, 3-, or 4-)methoxyphenoxy, (2-, 3-, or 4-)methylphenoxy, (2,6-, 2,5-, 2,4-, or 2,3-)dimethylphenoxy, (2-, 3-, or 4-)pyridyloxy, (2-, 4-, 5-, or 6-)methoxypyridin-3-yloxy, (2- or 3-)methoxypyridin-4-yloxy, (2-, 4-, 5-, or 6-)methylpyridin-3-yloxy, (2-, or 3-)methylpyridin-4-yloxy, oxan-4-yloxy, 1-methylpiperidin-4-yloxy, benzyloxy, phenethyloxy, (2-, 3-, or 4-)methoxybenzyloxy, (2-, 3-, or 4-)trifluoromethylbenzyloxy, and (2-, 3-, or 4-)methoxyphenethyloxy.

[1-2] In the compound of Formula (I) according to Aspect [1], $R^1$s are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group (the substituent(s) RI are the same as or different from each other and are the same as defined as the substituent(s) RI above).

[1-2-a] Preferable examples of $R^1$s include a halogen atom, a $C_{1-6}$ alkyl group which is optionally substituted with 1 to 5 substituent(s) RI, a $C_{1-6}$ alkoxy group which is optionally substituted with 1 to 5 substituent(s) RI, and a cyano group (the substituent(s) RI are the same as or different from each other and are the same as defined as the substituent(s) RI above).

[1-2-b] More preferable examples of $R^1$s include a halogen atom, a $C_{1-4}$ alkyl group which is optionally substituted with 1 to 5 halogen atoms, a $C_{1-4}$ alkoxy group which is optionally substituted with 1 to 5 halogen atoms, and a cyano group. Specific examples of $R^1$ include a fluorine atom, a chlorine atom, a bromine atom, methyl, ethyl, propyl, isopropyl, butyl, isobutyl, sec-butyl, tert-butyl, trifluoromethyl, methoxy, trifluoromethoxy, and cyano.

[1-3] In the compound of Formula (I) according to Aspect [1], $R^2$ is a hydrogen atom, a halogen atom, a $C_{1-6}$ alkyl group, a $C_{2-6}$ alkenyl group, a $C_{2-6}$ alkynyl group, a $C_{1-6}$ alkoxy group, or a cyano group.

[1-3-a] Preferable examples of $R^2$ include a hydrogen atom and a halogen atom, and specific examples thereof include a hydrogen atom, a fluorine atom, a chlorine atom, and a bromine atom.

[1-4] In the compound of Formula (I) according to Aspect [1], $R^3$, $R^4$, $R^5$, $R^6$, $R^7$ are independently a group arbitrarily selected from a hydrogen atom, a $C_{1-6}$ alkyl group, a halogenated $C_{1-6}$ alkyl group, a $C_{2-6}$ alkenyl group, and a $C_{2-6}$ alkynyl group. Preferable examples of $R^3$, $R^4$, $R^5$, $R^6$, $R^7$ include a hydrogen atom and a $C_{1-4}$ alkyl group.

[1-4-a] More preferably, $R^3$, $R^4$, $R^5$, $R^6$, $R^7$ are a hydrogen atom.

[1-5] In the compound of Formula (I) according to Aspect [1], X is an oxygen atom, a sulfur atom, or —$NR^7$— ($R^7$ is the same as defined as $R^7$ above).

[1-5-a] Preferably, X is an oxygen atom or —NH—.

[1-5-b] More preferably, X is an oxygen atom.

[1-6] In the compound of Formula (I) according to Aspect [1], j is an integer of 0 to 3, while k is an integer of 0 to 2. Preferably, j is 0, 1, or 2, while k is 0 or 1. More preferably, j is 0 or 1, while k is 0.

[1-7] In the compound of Formula (I) according to Aspect [1], the ring B is a benzene ring, a pyridine ring, or a pyrimidine ring. The ring B is preferably a benzene ring or a pyridine ring, and more preferably a benzene ring.

[1-8] In the compound of Formula (I) according to Aspect [1], p is an integer of 0 to 4. p is preferably 0 or 1.

[1-9] In the compound of Formula (I) according to Aspect [1], n is an integer of 0 to 2. n is preferably 1 or 2, and more preferably 1.

[1-10] In the compound of Formula (I) according to Aspect [1], the ring A is a $C_{6-14}$ aryl group which is optionally substituted with 1 to 5 L(s) or a 3- to 14-membered heterocyclic group which is optionally substituted with 1 to 5 L(s).

[1-10-a] Preferably, the ring A is phenyl which is optionally substituted with 1 to 5 L(s), a fused aryl group which is optionally substituted with 1 to 5 L(s) and partially hydrogenated, a 5- to 7-membered monocyclic heteroaryl group which is optionally substituted with 1 to 5 L(s), an 8- to 12-membered ring-fused heteroaryl group which is optionally substituted with 1 to 5 L(s) and partially hydrogenated, or a 3- to 8-membered non-aromatic heterocyclic group which is optionally substituted with 1 to 5 L(s). Specific examples thereof include phenyl, indanyl, tetrahydronaphthyl, oxazolyl, thiazolyl, pyridyl, pyrimidinyl, dihydrobenzofuranyl, chromanyl, 1,3-benzodioxanyl, pyrrolidinyl, and piperidinyl. They are optionally substituted with 1 to 5 L(s)

[1-10-b] More preferably, the ring A is phenyl which is optionally substituted with 1 to 5 L(s), indanyl which is optionally substituted with 1 to 5 L(s), tetrahydronaphthyl which is optionally substituted with 1 to 5 L(s), pyridyl which is optionally substituted with 1 to 5 L(s), dihydrobenzofuranyl which is optionally substituted with 1 to 5 L(s), chromanyl which is optionally substituted with 1 to 5 L(s), 1,3-benzodioxanyl which is optionally substituted with 1 to 5 L(s), pyrrolidinyl which is optionally substituted with 1 to 5 L(s), or piperidinyl which is optionally substituted with 1 to 5 L(s).

[1-10-c] The ring A in Formula (I) is preferably the Partial Structural Formula (A):

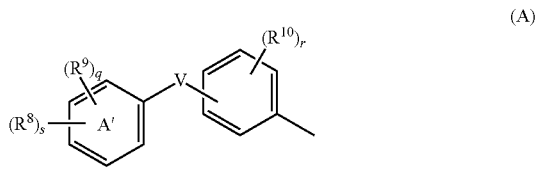

(A)

(where q and r are independently an integer of 0 to 4; s is an integer of 0 to 2; a ring A' is a benzene ring, a pyridine ring, or a pyrimidine ring; V is a single bond or an oxygen atom;

$R^8$s are independently a $C_{1-6}$ alkoxy group which is optionally substituted with 1 to 5 substituent(s) RIII, or a non-aromatic heterocyclic oxy group; the substituent RIII is a group arbitrarily selected from —OH, a $C_{1-6}$ alkoxy group, a non-aromatic heterocyclic group (the heterocyclic group is optionally substituted with a $C_{1-6}$ alkyl group), a —S(O)$_i$R$^a$ (i is an integer of 0 to 2, R$^a$ is the same as defined as R$^a$ in Formula (I)) group, a —SO$_2$NR$^d$R$^e$ (R$^d$ and R$^e$ are the same as defined as R$^d$ and R$^e$ in Formula (I)) group, a —CONR$^d$R$^e$ (R$^d$ and R$^e$ are the same as defined as R$^d$ and R$^e$ in Formula (I)) group, and a —NR$^{b1}$R$^{c1}$ ((R$^{b1}$ and R$^{c1}$ are the same as defined as R$^{b1}$ and R$^{c1}$ in Formula (I)) group;

$R^9$s and $R^{10}$s are independently a halogen atom, a $C_{1-6}$ alkyl group (the $C_{1-6}$ alkyl group is optionally substituted with 1 to 5 halogen atoms, 1 to 5 —OH, or 1 to 5 $C_{1-6}$ alkoxy group(s)), or a $C_{1-6}$ alkoxy group (the $C_{1-6}$ alkoxy group is optionally substituted with 1 to 5 halogen atom(s)). In Formula (A), the binding positions of the ring A'-V— and $R^{10}$s are any positions at which they can be optionally bonded in the benzene ring, and the binding positions of $R^8$s and $R^9$s are any positions at which they can be optionally bonded in the ring A'.

Preferable examples of Formula (A) include Formula (A1) or Formula (A2):

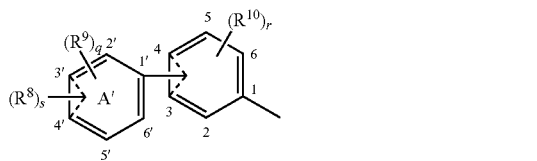

(A1)

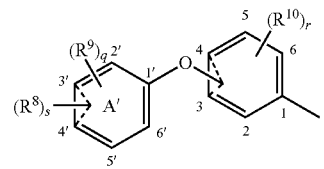

(A2)

(where q, r, s, the ring A', $R^8$s, $R^9$s, and $R^{10}$s are the same as defined in the above Formula (A), and the broken lines and the FIGS. 3 and 4 or the FIGS. 3' and 4' indicate where the ring A', the ring A'-O—, or $R^8$s are bonded).

In Formula (A1), when the position of the single bond of the phenyl group (the binding position of the linker moiety containing X) is determined as the first position, the binding position of the ring A' is preferably at the third or fourth position, and more preferably at the third position. In Formula (A1), when the binding position of the ring A' with the phenyl group is determined as the first' position, the binding position of $R^8$s is preferably at the third' or fourth' position.

In Formula (A2), when the position of the single bond of the phenyl group (the binding position of the linker moiety containing X) is determined as the first position, the binding position of the ring A'-O— is preferably at the third or fourth position, and more preferably at the third position. In Formula (A2), when the binding position of the ring A' with the phenyl group —O— is determined as the first' position, the binding position of $R^8$s is preferably at the third' or fourth' position.

[1-10-c-1] Specifically, Formula (A) is preferably the above Partial Structural Formula (A1).

[1-10-c-2] Specifically, Formula (A) is preferably the above Partial Structural Formula (A1), where s is 0 or 1.

[1-10-c-3] More preferably, Formula (A) is Formula (A1a) or Formula (A1b) when is 1 in Formula (A1), and Formula (A) is Formula (A1c) when s is 0 in Formula (A1):

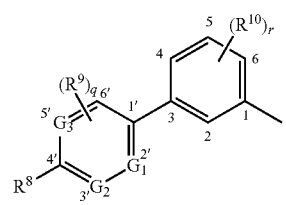

(A1a)

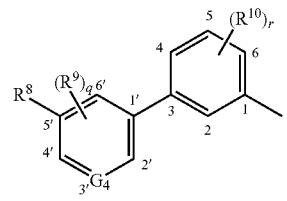

(A1b)

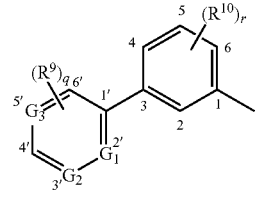

(A1c)

(where q, r, $R^8$, $R^9$ and $R^{10}$ are the same as defined in the above Formula (A), $G_1$, $G_2$, $G_3$, and $G_4$ is a =CH— group, a =CR$^9$— group or a nitrogen atom (with the proviso that when $G_1$ is a nitrogen atom, $G_2$ and $G_3$ are each a =CH— group or a =CR$^9$— group)).

In Formula (A1a), Formula (A1b), or Formula (A1c), when the position of the single bond of the phenyl group (the binding position of the linker moiety containing X) is determined as the first position, $R^{10}$ can be bonded at the second, fourth, fifth, or sixth positions. The binding position of $R^9$ is any positions in the ring including $G_1$ or $G_4$.

Formula (A) is more preferably Formula (A1a) or Formula (A1c).

[1-10-c-4] In Formula (A1a), preferably, $G_1$ is a =CH— group or a =CR$^9$— group, $G_2$ and $G_3$ are independently a =CH— group, a =CR$^9$— group, or a nitrogen atom. More preferably, $G_1$ and $G_3$ are independently a =CH— group or a =CR$^9$— group, $G_2$ is a =CH— group, a =CR$^9$— group, or a nitrogen atom.

In Formula (A1c), preferably, $G_1$ is a =CH— group or a =CR$^9$— group, $G_2$ and $G_3$ are independently a =CH— group, a =CR$^9$— group or a nitrogen atom. More preferably, $G_1$ and $G_3$ are independently a =CH— group or a =CR$^9$— group, $G_2$ is a =CH— group, a =CR$^9$— group, or a nitrogen atom.

[1-10-c-5] In Formula (A1a), Formula (A1b), or Formula (A1c), when r is not 0, at least one of the binding positions of $R^{10}$(s) is preferably the second position, and when r is 1, the binding position of $R^{10}$(s) is preferably the second position.

[1-10-c-6] In Formula (A1a), when the binding position of the ring containing $G_1$ with the third position of the phenyl group is determined as the first' position, when q is 1, the binding position of $R^9$ is preferably the second' position (except for the case in which $G_1$ is a nitrogen atom) or the sixth' position. When q is 2, the binding positions of $R^9$s are preferably the second' and sixth' positions, the second' and fifth' positions, or the fifth' and sixth' positions (except for the case in which the binding position is a nitrogen atom), and more preferably, the second' and sixth' positions.

In Formula (A1c), when the binding position of the ring containing $G_1$ with the third position of the phenyl group is determined as the first' position, when q is 1, the binding position of $R^9$ is preferably the second' position (except for the case in which $G_1$ is a nitrogen atom) or the sixth' position. When q is 2, the binding positions of $R^9$s are preferably the second' and sixth' positions, the second' and fifth' positions, the second' and the fourth' positions, the fourth' and the sixth' positions, or the fifth' and sixth' positions (except for the case in which the binding position is a nitrogen atom), and more preferably, the second' and sixth' positions.

[1-10-c-7] In Formula (A1a), r is preferably 0 or 1. When r is 1, the binding position of $R^{10}$ is preferably the second position. When $G_1$ is a =CH— group or a =CR$^9$— group, $G_2$ is a =CH— group or a nitrogen atom, $G_3$ is a =CH— group, and q is 1 or 2, the binding position(s) of $R^9$(s) is more preferably the second' and/or the sixth' positions.

In Formula (A1c), r is preferably 0 or 1. When r is 1, the binding position of $R^{10}$ is preferably the second position. When $G_1$ is a =CH— group or a =CR$^9$— group, $G_2$ is a =CH— group or a nitrogen atom, $G_3$ is a =CH— group, and q is 1 or 2, the binding position(s) of $R^9$(s) is more preferably the second' and/or the sixth' positions.

[1-10-c-8] In Formula (A), preferable examples of $R^8$ include a $C_{1-6}$ alkoxy group (the $C_{1-6}$ alkoxy group is optionally substituted with 1 to 5 group(s) arbitrarily selected from —OH, a $C_{1-6}$ alkoxy group, a non-aromatic heterocyclic group (the heterocyclic group is optionally substituted with a $C_{1-6}$ alkyl group), a —S(O)$_i$R$^a$ (i is an integer of 0 to 2) group, a —SO$_2$NR$^d$R$^e$ group, a —CONR$^d$R$^e$ group, or a —NR$^{b1}$R$^{c1}$ group) and a non-aromatic heterocyclic oxy group. $R^{b1}$ and $R^{c1}$ are independently a group arbitrarily selected from a hydrogen atom, a $C_{2-7}$ alkanoyl group, a $C_{1-6}$ alkylsulfonyl group, and a $C_{1-6}$ alkyl group. $R^{b1}$ and $R^{c1}$ optionally form together with a nitrogen atom to which they are bonded, a 3- to 8-membered cyclic group. In the cyclic group, one carbon atom is optionally substituted with a carbonyl group.

More preferably, $R^8$ is, for example, a $C_{1-6}$ alkoxy group substituted with 1 to 5 —OH, ethoxy, methylsulfonyl, sulfamoyl, methylsulfamoyl, dimethylsulfamoyl, carbamoyl, methylcarbamoyl, dimethylcarbamoyl, —NH$_2$, acetylamino, methylsulfonylamino, 2-oxo-1-pyrrolidinyl, or 3-methyloxetan-3-yl, and (1,1-dioxytetrahydro-2H-thiopyran-4-yl)oxy.

The number of groups substituted with —OH, ethoxy, methylsulfonyl, sulfamoyl, methylsulfamoyl, dimethylsulfamoyl, carbamoyl, methylcarbamoyl, dimethylcarbamoyl, —NH$_2$, acetylamino, methylsulfonylamino, 2-oxo-1-pyrrolidinyl, or 3-methyloxetan-3-yl is preferably 1 or 2.

Specific examples of $R^8$ include 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-aminoethoxy, 3-aminopropoxy, 2-(2-oxo-1-pyrrolidinyl)ethoxy, 3-(2-oxo-1-pyrrolidinyl)propoxy, 2-ethoxyethoxy, 2-methylsulfonylethoxy, 3-methylsulfonyl-propoxy, (1,1-dioxytetrahydro-2H-thiopyran-4-yl)oxy, (4-hydroxy-1,1-dioxytetrahydro-2H-thiopyran-4-yl)methoxy, (3-methyloxetan-3-yl)methoxy, 2-acetylamino-ethoxy, 2-acetylamino-ethoxy, 3-acetylamino-propoxy, 2-methylsulfonylamino-ethoxy, 3-methylsulfonylamino-propoxy, 2-carbamoyl-ethoxy, 3-carbamoyl-propoxy, 2-methylcarbamoyl-ethoxy, 3-methylcarbamoyl-propoxy, 2-dimethylcarbamoyl-ethoxy, 3-dimethylcarbamoyl-propoxy, 2-sulfamoyl-ethoxy, 3-sulfamoyl-propoxy, 2-methylsulfamoyl-ethoxy, 3-methylsulfamoyl-propoxy, 2-dimethylsulfamoyl-ethoxy, and 3-dimethylsulfamoyl-propoxy.

[1-10-c-9] In Formula (A), $R^9$ and $R^{10}$ are preferably independently a halogen atom, a $C_{1-4}$ alkyl group which is optionally substituted with 1 to 5 halogen atom(s), a $C_{1-4}$ alkoxy group which is optionally substituted with 1 to 5 halogen atom(s), or the like. Specific examples thereof include a fluorine atom, a chlorine atom, a bromine atom, methyl, ethyl, propyl, isopropyl, butyl, isobutyl, sec-butyl, tert-butyl, trifluoromethyl, methoxy, ethoxy, trifluoromethoxy, and trifluoroethoxy. More preferably, examples of $R^9$ include a fluorine atom, methyl, or methoxy, and examples of $R^{10}$ include methyl.

[1-10-c-10] In Formula (A), the preferred aspect of Partial Structural Formula (A') is, for example, when V is a single bond, among the preferred aspects of L described in Aspects [1-1-d], a group including a benzene ring, a pyridine ring or a pyrimidine ring:

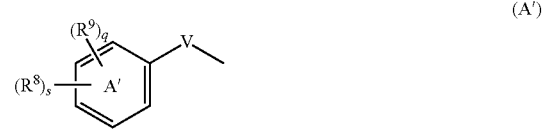

(A')

(where q, s, the ring A', V, $R^8$ and $R^9$ are the same as defined in the above Formula (A)). When V is an oxygen atom, among the preferred aspects of L described in Aspects [1-1-d], the preferred aspect of Partial Structural Formula (A') is, for example, the group including a benzene ring, a pyridine ring or a pyrimidine ring which is substituted with an oxygen atom.

[1-10-c-11] In Formula (A), Formula (A1), and Formula (A2), q is preferably 1, 2, or 3, and s is preferably 0 or 1.

[1-10-c-12] In Formula (A), Formula (A1), Formula (A2), Formula (A1a), Formula (A1b), Formula (A1c), r is preferably 0 or 1.

[1-10-d] In Formula (I), the ring A is preferably Partial Structural Formula (AA):

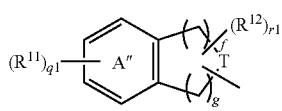
(AA)

(where f is an integer of 0 to 2; g is an integer of 1 to 4; q1 is an integer of 0 to 4; r1 is an integer of 0 to 2;
the ring A'' is a benzene ring or a pyridine ring;
T is —$CH_2$—, an oxygen atom, —$S(O)_i$— (i is an integer of 0 to 2), or —$NR^7$ ($R^7$ is the same as defined as $R^7$ in Formula (I));
$R^{12}$s are independently a halogen atom, —OH, a cyano group, a $C_{1-6}$ alkyl group optionally substituted with 1 to 5 substituent(s) RI, a $C_{2-6}$ alkenyl group optionally substituted with 1 to 5 substituent(s) RI, a $C_{2-6}$ alkynyl group optionally substituted with 1 to 5 substituent(s) RI, a $C_{1-6}$ alkoxy group optionally substituted with 1 to 5 substituent(s) RI, —SH, a —$S(O)_iR^a$ (i is an integer of 0 to 2, $R^a$ is the same as defined as $R^a$ in Formula (I)) group, or a —$NR^bR^c$ ($R^b$ and $R^c$ are the same as defined as $R^b$ and $R^c$ in Formula (I)) group;
$R^{11}$ corresponds to L in Formula (I) and is the same as defined as L;
the substituent(s) RI is the same as defined in the above Formula (I)).

Specifically, examples of Formula (AA) include Formula (AA'):

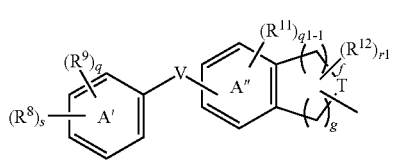
(AA')

(where f, g, r1, the ring A'', T, $R^{11}$, and $R^{12}$ are the same as defined in the above Formula (AA), q, s, the ring A', V, $R^8$, and $R^9$ are the same as defined in the above Formula (A) described in Aspect [1-10-c], q1-1 is an integer of 0 to 3).

Specifically, examples of Formula (AA) include Formula (AA1) and Formula (AA2):

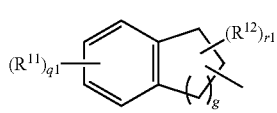
(AA1)

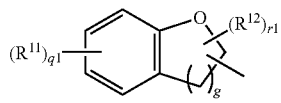
(AA2)

(where q1, r1, $R^{11}$, and $R^{12}$ are the same as defined in the above Formula (AA), g' is an integer of 1 or 2).

[1-10-d-1] Specifically, Formula (AA) is preferably Formula (AA1).

[1-10-d-2] Specifically, Formula (AA) is more preferably Formula (AA1) where g' is 1.

[1-10-d-3] The binding position of the linker moiety containing X in the fused ring including T in Formula (AA) is any position at which it can be optionally bonded in the ring including T, and is Formula (AA1a) or Formula (AA1b) when g' is 1 in Formula (AA1):

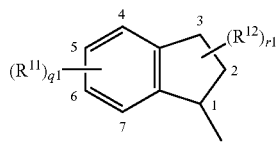
(AA1a)

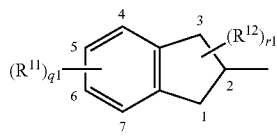
(AA1b)

(where q1, r1, $R^{11}$, and $R^{12}$ are the same as defined in the above Formula (AA)). In Formula (AA1a), when the binding position of the linker moiety containing X is determined as the first position, $R^{11}$ can be bonded at the fourth, fifth, sixth, or seventh position, and $R^{12}$ can be bonded at the first, second, or third position. In Formula (AA1b), when the binding position of the linker moiety containing X is determined as the second position, $R^{11}$ can be bonded at the fourth, fifth, sixth, or seventh position, and $R^{12}$ can be bonded at the first, second, or third position. Specifically, Formula (AA) is Formula (AA1a).

[1-10-d-4] In Formula (AA1a), the substitution position of $R^{11}$ is preferably the fourth or fifth position, and more preferably the fourth position.

[1-10-d-5] The definition and preferable aspects of $R^{11}$ in Formula (AA) are the same as defined as L in Aspect [1-1]. Specific examples of $R^{11}$ include the specific examples of L described in Aspect [1-1].

Specific examples of $R^{11}$ include Partial Structural Formula (A').

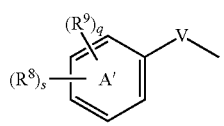
(A')

(where q, s, the ring A', V, $R^8$, and $R^9$ are the same as defined in the above Formula (A)). More specifically, Formula (A') is, for example, when V is a single bond, among the specific groups of L described in Aspects [1-1-d], a group including a benzene ring, a pyridine ring or a pyrimidine ring. When V is an oxygen atom, among the specific groups of L described in Aspects [1-1-d], the specific aspect of Partial Structural Formula (A') is, for example, the group including a benzene ring, a pyridine ring or a pyrimidine ring which is substituted with an oxygen atom.

[1-10-d-6] In Formula (AA), preferable examples of $R^{12}$ include a halogen atom or a $C_{1-4}$ alkyl group optionally substituted with 1 to 5 halogen atom(s). Specific examples of $R^{12}$ include a fluorine atom, a chlorine atom, a bromine atom, methyl, ethyl, propyl, isopropyl, butyl, isobutyl, sec-butyl, tert-butyl, and trifluoromethyl.

[1-10-d-7] In Formula (AA), Formula (AA1), Formula (AA2), Formula (AA1a), and Formula (AA1b), q1 is preferably 0, 1, or 2, more preferably 1 or 2, and further preferably 1. In Formula (AA'), q1-1 is preferably 0 or 1, and more preferably 0.

[1-10-d-8] In Formula (AA), Formula (AA'), Formula (AA1), Formula (AA2), Formula (AA1a), Formula (AA1b), r1 is preferably 0 or 1, and more preferably 0.

[1-11] The isothiazolyl group and the substituent of $R^1$ in the ring B in Formula (I) can be bonded at the second, third, fourth, fifth, or sixth position when the binding position of the linker moiety containing X is determined as the first position in Partial Structural Formula (B):

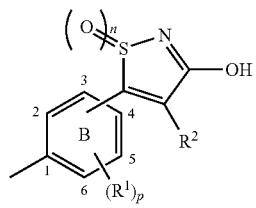

(B)

(where n, p, the ring B, $R^1$, and $R^2$ are the same as defined in the above Formula (I)).

Preferable examples of Formula (B) include Formula (B1) or Formula (B2):

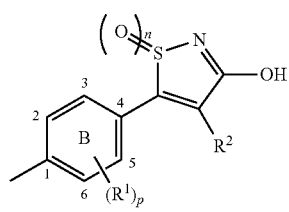

(B1)

(B2)

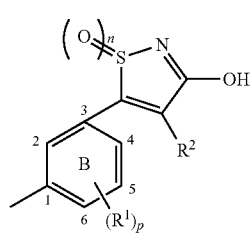

(where n, p, the ring B, $R^1$, and $R^2$ are the same as defined in the above Formula (I)). When the binding position of the linker moiety containing X is determined as the first position, $R^1$ can be bonded at the second, third, fifth, or sixth position in Formula (B1), and $R^1$ can be bonded at the second, fourth, fifth, or sixth position in Formula (B2).

[1-11-a] Formula (B) is preferably Formula (B1).

[1-11-b] More preferable examples of Formula (B) include Formula (B1a) and Formula (B1b):

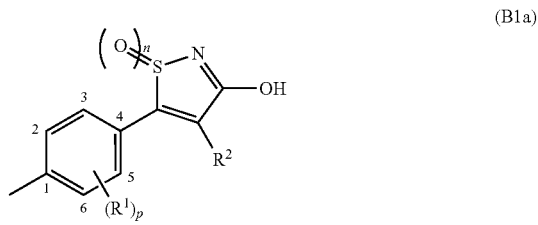

(B1a)

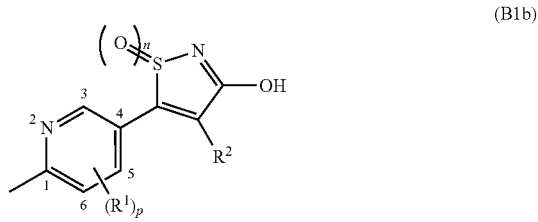

(B1b)

(where n, p, $R^1$, and $R^2$ are the same as defined in the above Formula (I)).

In Formula (B1a) and Formula (B1b), $R^1$ is preferably a halogen atom, a $C_{1-4}$ alkyl group optionally substituted with 1 to 5 halogen atom(s), a $C_{1-4}$ alkoxy group optionally substituted with 1 to 5 halogen atom(s) or a cyano group. Specifically, $R^1$ is preferably a fluorine atom, a chlorine atom, a bromine atom, methyl, ethyl, propyl, isopropyl, butyl, isobutyl, sec-butyl, tert-butyl, trifluoromethyl, methoxy, trifluoromethoxy, or cyano. p is preferably 0 or 1.

In Formula (B1a) and Formula (Bib), $R^2$ is preferably a hydrogen atom or a halogen atom, more specifically, a hydrogen atom, a fluorine atom, a chlorine atom, or a bromine atom, and more preferably, a hydrogen atom. n is preferably 1 or 2, and more preferably, 1.

[1-11-c] Further preferable examples of Formula (B) include Formula (B1a).

[1-12] In a combination of j, k, X, $R^3$, $R^4$, $R^5$, and $R^6$, in Formula (I), the linker moiety containing X bonded to the ring A and the ring B is Partial Structural Formula (C):

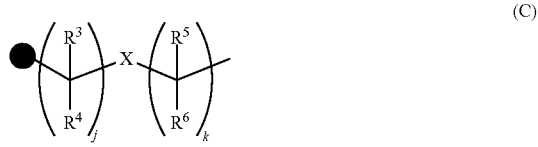

(C)

(where j, k, X, $R^3$, $R^4$, $R^5$, and $R^6$ are the same as defined in the above Formula (I), and ● is a single bond with the ring A).

Specific examples of Formula (C) include Formula (c1) to Formula (c6):

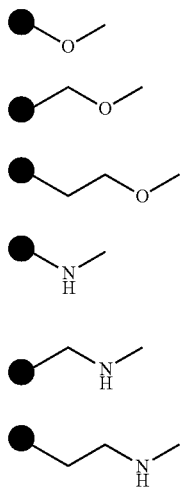

(c1)
(c2)
(c3)
(c4)
(c5)
(c6)

[1-12-a] More preferably, Formula (C) is Formula (c1), Formula (c2), Formula (c4), or Formula (c5).

[1-12-b] When the ring A is monocyclic, Formula (C) is preferably Formula (c2) or Formula (c5), and more preferably Formula (c2).

[1-12-c] When the ring A is Formula (AA), Formula (C) is preferably Formula (c1) or Formula (c4), and more preferably Formula (c1).

[1-13] In the compound of Formula (I) according to Aspect [1], a preferable compound is a compound of Formula (II):

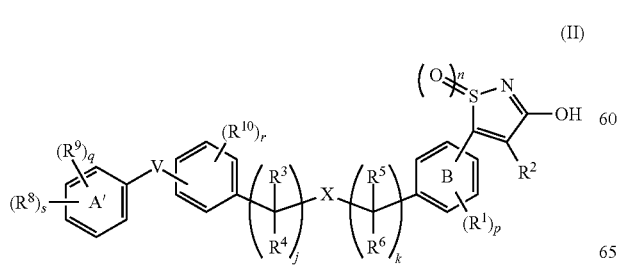

(II)

(where n, p, j, k, the ring B, X, $R^1$, $R^2$, $R^3$, $R^4$, $R^5$, and $R^6$ are the same as defined in the above Formula (I), q, r, s, the ring A', V, $R^8$, $R^9$, and $R^{10}$ are the same as defined in the above Formula (A) described in Aspect [1-10-c] (except for 5-(4-(((4-phenoxyphenyl)methoxy)methyl)phenyl)-isothiazole-3-ol 1,1-dioxide)), or a pharmaceutically acceptable salt of the compound, or a pharmaceutically acceptable solvate of the salt or a pharmaceutically acceptable solvate of the compound.

Specifically, the definition and preferable aspects of n, p, q, r, s, j, k, the ring A', the ring B, X, V, $R^1$, $R^2$, $R^3$, $R^4$, $R^5$, $R^6$, $R^8$, $R^9$, and $R^{10}$ are the same as defined in any one of Aspects [1-1] to [1-12].

[1-13-a] In the compound of Formula (II) according to Aspect [1-13], compounds produced by optionally combining the groups of Partial Structural Formula (A) (on the left of the left wavy line), Partial Structural Formula (B) (on the right of the right wavy line), Partial Structural Formula (C) (between the two wavy lines) in Formula (II) can be produced optionally:

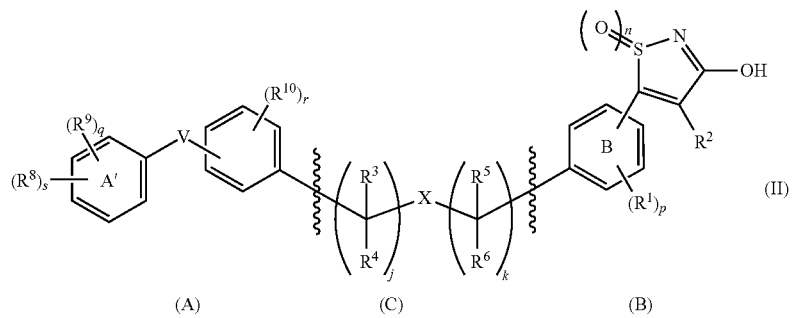

(A) (C) (B) (II)

Specifically, Partial Structural Formula (A) is a group arbitrarily selected from Formula (A1), Formula (A2), Formula (A1a), Formula (A1b), and Formula (A1c) described in Aspects [1-10-c] and [1-10-c-3], Partial Structural Formula (B) is a group arbitrarily selected from Formula (B1), Formula (B2), Formula (B1a), and Formula (B1b) described in Aspects [1-11] and [1-11-b], and Partial Structural Formula (C) is a group arbitrarily selected from Formula (c1) to Formula (c6) described in Aspect [1-12]. An optional combination of each formula forms part of the compound of Formula (I) or Formula (II) according to the present invention.

[1-13-a-1] In the compound of Formula (II) according to Aspect [1-13], preferably, Partial Structural Formula (A) is Formula (A1a), Formula (A1b), or Formula (A1c), Partial Structural Formula (B) is Formula (B1a) or Formula (B1b), and Partial Structural Formula (C) is Formula (c2) or Formula (c5). More preferably, Partial Structural Formula (A) is Formula (A1a) or Formula (A1c), Partial Structural Formula (B) is Formula (B1a), and Partial Structural Formula (C) is Formula (c2). An optional combination of each formula forms part of the preferable compound of Formula (I) or Formula (II) according to the present invention.

[1-13-b] The compound of Formula (II) according to Aspect [1-13] is more preferably Formula (II-A):

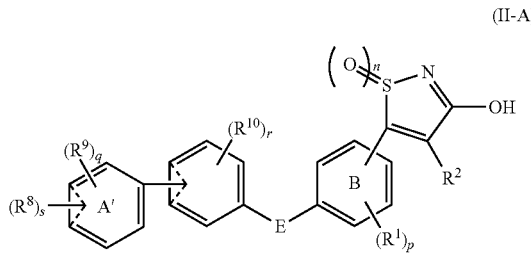

(II-A)

(where n, p, the ring B, R¹, and R² are the same as defined in the above Formula (I), q, r, s, the ring A', R⁸, R⁹, and R¹⁰ are the same as defined in the above Formula (A) described in Aspect [1-10-c], the broken lines are defined as the same as with Formula (A1) described in Aspect [1-10-c], E is a group arbitrarily selected from Formula (c1) to Formula (c6) serving as specific examples of Formula (C) described in Aspect [1-12]).

Specifically, the definition and preferable aspects of n, p, q, r, s, the ring A', the ring B, R¹, R², R⁸, R⁹, R¹⁰, and E are the same as defined in any one of Aspects [1-1] to [1-12].

[1-13-c] The compound of Formula (II) according to Aspect [1-13] is further preferably Formula (II-B):

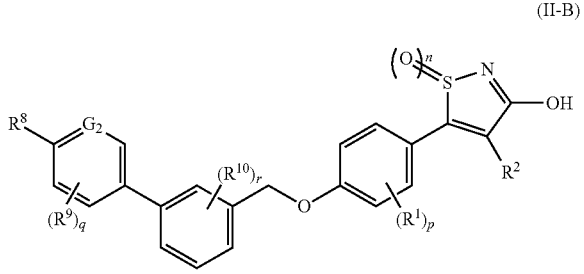

(II-B)

(where n, p, R¹ and R² are the same as defined in the above Formula (I), q, r, R⁸, R⁹ and R¹⁰ are the same as defined in the above Formula (A) described in Aspect [1-10-c], G₂ is the same as defined in the above Formula (A1a) described in Aspect [1-10-c-3]).

Specifically, the definition and preferable aspects of n, p, q, r, R¹, R², R⁸, R⁹, R¹⁰, and G₂ are the same as defined in any one of Aspects [1-1] to [1-12].

[1-13-c-1] In Formula (II-B), preferably, r is 0 or 1 and R¹⁰ is a C₁₋₄ alkyl group. Preferably, q is 1, 2, or 3, and R⁹s are independently a halogen atom or a C₁₋₄ alkyl group. R⁸ is a C₁₋₆ alkoxy group (the C₁₋₆ alkoxy group is substituted with 1 to 5 —OH, 1 to 5 ethoxy, 1 to 5 methylsulfonyl, 1 to 5 sulfamoyl, 1 to 5 methylsulfamoyl, 1 to 5 dimethylsulfamoyl, 1 to 5 carbamoyl, 1 to 5 methylcarbamoyl, 1 to 5 dimethylcarbamoyl, 1 to 5 —NH₂, 1 to 5 acetylamino, 1 to 5 methylsulfonylamino, 1 to 5 2-oxo-1-pyrrolidinyl, or 1 to 5 3-methyloxetan-3-yl) or a (1,1-dioxytetrahydro-2H-thiopyran-4-yl)oxy group. G₂ is preferably a =CH— group or a nitrogen atom.

More preferably, r is 0 or 1, R¹⁰ is a methyl group, q is 1, 2, or 3, R⁹s are independently a fluorine atom or a methyl group, R⁸ is a C₂₋₆ alkoxy group (the C₂₋₆ alkoxy group is 1 or 2 —OH, 1 or 2 ethoxy, 1 or 2 methylsulfonyl, 1 or 2 —NH₂, 1 or 2 acetylamino, 1 or 2 methylsulfonylamino, 1 or 2 2-oxo-1-pyrrolidinyl, or 1 or 2 3-methyloxetan-3-yl) or a (1,1-dioxytetrahydro-2H-thiopyran-4-yl)oxy group, and G₂ is a =CH— group or a nitrogen atom.

Particularly preferable examples of R⁸ include a 2-hydroxyethoxy group, 3-hydroxypropoxy group, 3-hydroxybutoxy group, 3-hydroxy-3-methylbutoxy group, 2,3-dihydroxypropoxy group, 3-hydroxy-2-hydroxymethylpropoxy group, 2-ethoxyethoxy group, 3-(methylsulfonyl)propoxy group, 3-aminopropoxy group, 3-acetylaminopropoxy group, 3-methylsulfonylaminopropoxy group, 2-(2-oxopyrrolidin-1-yl)ethoxy group, 3-(2-oxopyrrolidin-1-yl)propoxy group, (3-methyl-3-oxetanyl)methoxy group, and (1,1-dioxytetrahydro-2H-thiopyran-4-yl)oxy group.

[1-13-d] The compound of Formula (II) according to Aspect [1-13] is further even preferably Formula (II-C):

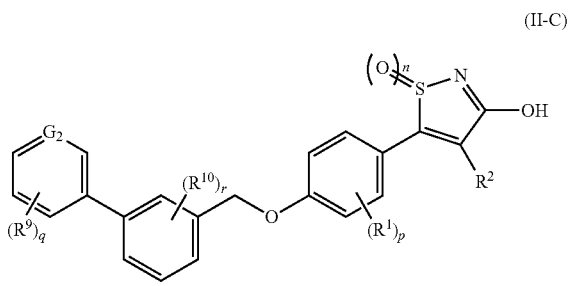

(II-C)

(where n, p, R¹, and R² are the same as defined in the above Formula (I), q, r, R⁹, and R¹⁰ are the same as defined in the above Formula (A) described in Aspect [1-10-c], G₂ are the same as defined in the above Formula (A1a) described in Aspect [1-10-c-3]).

Specifically, the definition and preferable aspects of n, p, q, r, R¹, R², R⁹, R¹⁰, and G₂ is the same as defined in any one of Aspects [1-1] to [1-12].

[1-13-d-1] In Formula (II-C), preferably, r is 0 or 1, and R¹⁰ is a C₁₋₄ alkyl group. Preferably, q is 1 or 2, and R⁹ is a C₁₋₄ alkyl group.

[1-14] In the compound of Formula (I) according to Aspect [1], a preferable compound is a compound of Formula (III):

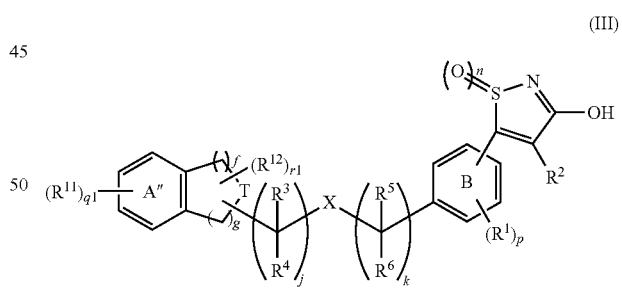

(III)

(where n, p, j, k, the ring B, X, R¹, R², R³, R⁴, R⁵, and R⁶ are the same as defined in the above Formula (I), and f, g, q1, r1, the ring A", T, R¹¹, and R¹² are the same as defined in the above Formula (AA) described in Aspect [1-10-d]), or a pharmaceutically acceptable salt of the compound, or a pharmaceutically acceptable solvate of the salt or a pharmaceutically acceptable solvate of the compound.

t.

Specifically, the definition and preferable aspects of n, f, g, p, q1, r1, j, k, the ring A", the ring B, X, T, R¹, R², R³, R⁴, R⁵, R⁶, R¹¹, and R¹² are the same as defined in any one of Aspects [1-1] to [1-12].

[1-14-a] In the compound of Formula (III) according to Aspect [1-14], compounds produced by optionally combining the groups of Partial Structural Formula (AA) (on the left of the left wavy line), Partial Structural Formula (B) (on the right of the right wavy line), Partial Structural Formula (C) (between the two wavy lines) in Formula (III) can be produced optionally:

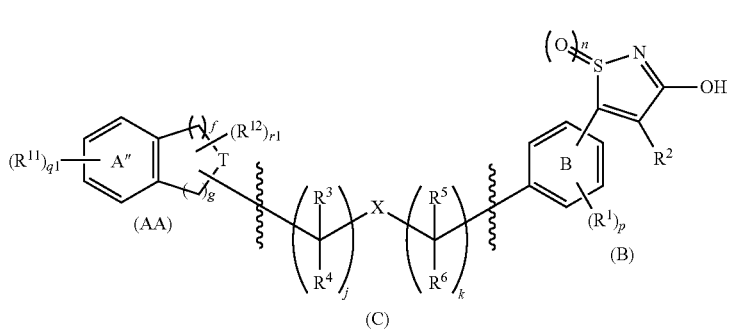

Specifically, Partial Structural Formula (AA) is a group arbitrarily selected from Formula (AA1), Formula (AA2), Formula (AA1a), and Formula (AA1b) described in Aspects [1-10-d] and [1-10-d-3], Partial Structural Formula (B) is a group arbitrarily selected from Formula (B1), Formula (B2), Formula (B1a), and Formula (B1b) described in Aspects [1-11] and [1-11-b], and Partial Structural Formula (C) is a group arbitrarily selected from Formula (c1) to Formula (c6) described in Aspect [1-12]. An optional combination of each formula forms part of the compound of Formula (I) or Formula (III) according to the present invention.

[1-14-a-1] In the compound of Formula (III) according to Aspect [1-14], preferably, Partial Structural Formula (AA) is Formula (AA1a) or Formula (AA1b), Partial Structural Formula (B) is Formula (B1a) or Formula (B1b), and Partial Structural Formula (C) is Formula (c1) or Formula (c4). More preferably, Partial Structural Formula (AA) is Formula (AA1a), Partial Structural Formula (B) is Formula (B1a), and Partial Structural Formula (C) is Formula (c1). An optional combination of each formula forms part of the preferable compound of Formula (I) or Formula (III) according to the present invention.

[1-14-b] The compound of Formula (III) according to Aspect [1-14] is more preferably Formula (III-A):

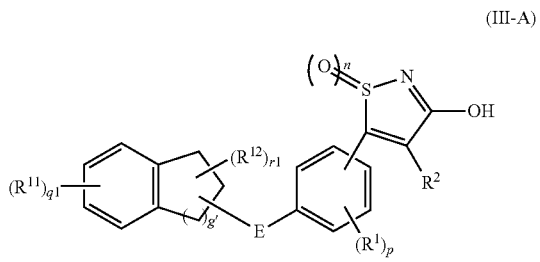

(where n, p, $R^1$, and $R^2$ are the same as defined in the above Formula (I), q1, r1, $R^{11}$, and $R^{12}$ are the same as defined in the above Formula (AA) described in Aspect [1-10-d], g' is the same as defined in the above Formula (AA1) described in Aspect [1-10-d], and E is a group arbitrarily selected from Formula (c1) to Formula (c6) serving as specific examples of Formula (C) described in Aspect [1-12]).

Specifically, the definition and preferable aspects of n, g', p, q1, r1, $R^1$, $R^2$, $R^{11}$, $R^{12}$, and E are the same as defined in any one of Aspects [1-1] to [1-12].

[1-14-c] The compound of Formula (III) according to Aspect [1-14] is further preferably a compound of Formula (III-B):

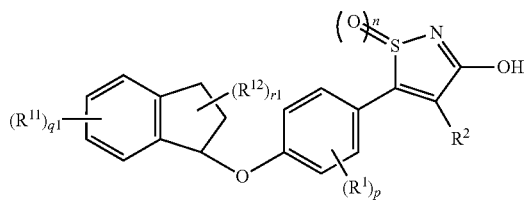

(where n, p, $R^1$, and $R^2$ are the same as defined in the above Formula (I), and q1, r1, $R^{11}$, and $R^{12}$ are the same as defined in the above Formula (AA) described in Aspect [1-10-d]).

Specifically, the definition and preferable aspects of n, p, q1, r1, $R^1$, $R^2$, $R^{11}$, and $R^{12}$ are the same as defined in any one of Aspects [1-1] to [1-12].

Examples of particularly preferable aspects of $R^{11}$ include the same as the preferable aspects of L described in [1-1-d].

[1-14-c-1] In Formula (III-B), preferably, r1 is 0. q1 is an integer of 1 or 2. Preferable examples of $R^{11}$ include a halogen atom, a cyano group, a $C_{1-10}$ alkyl group (the $C_{1-10}$ alkyl group is optionally substituted with 1 to 5 halogen atom(s), 1 to 5 —OH, or 1 to 5 $C_{1-4}$ alkoxy group(s)), a $C_{1-10}$ alkenyl group (the $C_{1-10}$ alkenyl group is optionally substituted with 1 to 5 halogen atom(s), 1 to 5 —OH, or 1 to 5 $C_{1-4}$ alkoxy group(s)), a $C_{1-10}$ alkoxy group (the $C_{1-10}$ alkoxy group is optionally substituted with 1 to 5 halogen atom(s), 1 to 5 —OH, or 1 to 5 $C_{1-4}$ alkoxy group(s)), a $C_{1-10}$ alkenyloxy group (the $C_{1-10}$ alkenyloxy group is optionally substituted with 1 to 5 halogen atom(s), 1 to 5 —OH, or 1 to 5 $C_{1-4}$ alkoxy group(s)), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, an aryloxy group which is optionally substituted with 1 to 5 substituent(s) RIIa, a heteroaryloxy group which is optionally substituted with 1 to 5 substituent(s) RIIa, a non-aromatic heterocyclic oxy group which is optionally substituted with 1 to 5 substituent(s) RIIa, or an aralkyloxy group which is optionally substituted with 1 to 5 substituent(s) RIIa (the substituent(s) RIIa are the same as or different from each other and are each a group arbitrarily selected from a halogen atom, a $C_{1-6}$ alkyl group (the $C_{1-6}$ alkoxy group is optionally substituted with 1 to 5 halogen atom(s), 1 to 5 —OH, or 1 to 5 $C_{1-4}$ alkoxy group(s), 1 to 5 non-aromatic heterocyclic group(s) (the heterocyclic group(s) is optionally substituted with a $C_{1-6}$ alkyl group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclic oxy group, and a $C_{1-6}$ alkyl group (the $C_{1-6}$ alkyl group is optionally substituted with 1 to 5 halogen atom(s), 1 to 5 —OH, 1 to 5 $C_{1-4}$ alkoxy group(s), or 1 to 5 —NR$^{b1}$R$^{c1}$ group(s)).

[1-15] Aspects [1-1] to [1-14] of the present invention, respective preferable aspects described above, and the definition of the substituents can be optionally combined, so that the preferable aspects of the compound of Formula (I) according to Aspect [1] can be optionally provided.

[1-16] Examples of preferable compounds as the compound of Formula (I) according to Aspects [1] include the following:

5-(4-((3-phenoxyphenyl)methoxy)phenyl)isothiazol-3-ol (Example 1);
5-(4-((3-phenoxyphenyl)methoxy)phenyl)isothiazol-3-ol 1-oxide (Example 2);
5-(4-(benzyloxy)phenyl)isothiazol-3-ol (Example 3);
5-(4-(benzyloxy)phenyl)isothiazol-3-ol 1-oxide (Example 4);
5-(4-(5-chloro-2,3-dihydro-1H-inden-1-yloxy)phenyl) isothiazol-3-ol (Example 5);
5-(4-(5-chloro-2,3-dihydro-1H-inden-1-yloxy)phenyl) isothiazol-3-ol 1-oxide (Example 6);
5-(4-((3-(2,6-dimethylphenyl)phenyl)methoxy)phenyl) isothiazol-3-ol (Example 7);
5-(4-((3-(2,6-dimethylphenyl)phenyl)methoxy)phenyl) isothiazol-3-ol 1-oxide (Example 8);
5-(4-((3-(2,6-dimethylphenyl)phenyl)methoxy)phenyl) isothiazol-3-ol 1,1-dioxide (Example 9);
5-(4-((3-(6-(3-hydroxy-3-methylbutoxy)-4-methylpyridin-3-yl)-2-methylphenyl)methoxy)phenyl)isothiazol-3-ol 1-oxide (Example 10);
5-(4-((3-(6-(3-hydroxy-3-methylbutoxy)-2-methylpyridin-3-yl)-2-methylphenyl)methoxy)phenyl)isothiazol-3-ol 1-oxide (Example 11);
5-(4-((3-(2,4-dimethyl-6-(3-hydroxy-3-methylbutoxy)pyridin-3-yl)-2-methylphenyl)methoxy)phenyl)isothiazol-3-ol 1-oxide (Example 12);
5-(4-((3-(2,6-dimethyl-4-(3-hydroxy-3-methylbutoxy)phenyl)-2-methylphenyl)methoxy)phenyl)isothiazol-3-ol 1-oxide (Example 13);
5-(4-((3-(2,6-dimethylphenyl)phenyl)methoxy)phenyl) isothiazol-3-ol 1-oxide (Example 14);
5-(4-((3-(2,6-dimethylphenyl)phenyl)methoxy)phenyl) isothiazol-3-ol 1-oxide(A) (Example 15);
5-(4-((3-(2,6-dimethylphenyl)phenyl)methoxy)phenyl) isothiazol-3-ol 1-oxide(B) (Example 16);
5-(4-((3-(2,6-dimethyl-4-(2-ethoxyethoxy)phenyl)phenyl) methoxy)phenyl)isothiazol-3-ol 1-oxide(A) (Example 17);
5-(4-((3-(2,6-dimethyl-4-(2-ethoxyethoxy)phenyl)-2-methylphenyl)methoxy)phenyl)isothiazol-3-ol 1-oxide(A) (Example 18);
5-(4-((3-(2,4-dimethyl-6-(2-ethoxyethoxy)pyridin-3-yl)phenyl)methoxy)phenyl)isothiazol-3-ol 1-oxide(A) (Example 19);
5-(4-((3-(6-(2-ethoxyethoxy)-2-methylpyridin-3-yl)-2-methylphenyl)methoxy)phenyl)isothiazol-3-ol 1-oxide(A) (Example 20);
5-(4-((3-(4,6-dimethyl-2-(2-ethoxyethoxy)pyrimidin-5-yl)-2-methylphenyl)methoxy)phenyl)isothiazol-3-ol 1-oxide (A) (Example 21);
5-(4-((3-(2,6-dimethyl-4-(2-ethoxyethoxy)-3-fluorophenyl) phenyl)methoxy)phenyl)isothiazol-3-ol 1-oxide(A) (Example 22);
5-(4-((3-(2,6-dimethyl-4-(3-(methylsulfonyl)propoxy)phenyl)-2-methylphenyl)methoxy)phenyl)isothiazol-3-ol 1-oxide(A) (Example 23);
5-(4-((3-(2,4-dimethyl-6-(3-(methylsulfonyl)propoxy)pyridin-3-yl)phenyl)methoxy)phenyl)isothiazol-3-ol 1-oxide (A) (Example 24);
5-(4-((3-(2-methyl-6-(3-(methylsulfonyl)propoxy)pyridin-3-yl)-2-methylphenyl)methoxy)phenyl)isothiazol-3-ol 1-oxide(A) (Example 25);
5-(4-((3-(4,6-dimethyl-2-(3-(methylsulfonyl)propoxy)pyrimidin-5-yl)-2-methylphenyl)methoxy)phenyl)isothiazol-3-ol 1-oxide(A) (Example 26);
5-(4-((3-(2,6-dimethyl-3-fluoro-4-(3-(methylsulfonyl)propoxy)phenyl)phenyl)methoxy)phenyl)isothiazol-3-ol 1-oxide(A) (Example 27);
5-(4-((3-(2,6-dimethyl-4-((1,1-dioxidetetrahydro-2H-thiopyran-4-yl)oxy)phenyl)phenyl)methoxy)phenyl)isothiazol-3-ol 1-oxide(A) (Example 28);
5-(4-((3-(2,6-dimethyl-4-((1,1-dioxidetetrahydro-2H-thiopyran-4-yl)oxy)phenyl)-2-methylphenyl)methoxy)phenyl)isothiazol-3-ol 1-oxide(A) (Example 29);
5-(4-((3-(2,4-dimethyl-6-(3-hydroxy-3-methylbutoxy)pyridin-3-yl)phenyl)methoxy)phenyl)isothiazol-3-ol 1-oxide (A) (Example 30);
5-(4-((3-(2,6-dimethyl-4-(3-hydroxy-3-methylbutoxy)phenyl)-2-methylphenyl)methoxy)phenyl)isothiazol-3-ol 1-oxide(A) (Example 31);
5-(4-(3-(2,6-dimethyl-3-fluoro-4-(3-hydroxy-3-methylbutoxy)phenyl)phenyl)methoxy)phenyl)isothiazol-3-ol 1-oxide(A) (Example 32);
5-(4-(3-(2,6-dimethyl-4-(3-(2-oxopyrrolidin-1-yl)propoxy) phenyl)phenyl)methoxy)phenyl)isothiazol-3-ol 1-oxide (A) (Example 33);
5-(4-(3-(2,6-dimethyl-4-(3-(2-oxopyrrolidin-1-yl)propoxy) phenyl)-2-methylphenyl)methoxy)phenyl)isothiazol-3-ol 1-oxide(A) (Example 34);
5-(4-((3-(2,4-dimethyl-6-(3-(2-oxopyrrolidin-1-yl)propoxy) pyridin-3-yl)phenyl)methoxy)phenyl)isothiazol-3-ol 1-oxide(A) (Example 35);
5-(4-((3-(2-methyl-6-(3-(2-oxopyrrolidin-1-yl)propoxy)pyridin-3-yl)-2-methylphenyl)methoxy)phenyl)isothiazol-3-ol 1-oxide(A) (Example 36);
5-(4-((3-(4,6-dimethyl-2-(3-(2-oxopyrrolidin-1-yl)propoxy) pyrimidin-5-yl)-2-methylphenyl)methoxy)phenyl) isothiazol-3-ol 1-oxide(A) (Example 37);
5-(4-((3-(2,6-dimethyl-3-fluoro-4-(3-(2-oxopyrrolidin-1-yl) propoxy)phenyl)phenyl)methoxy)phenyl)isothiazol-3-ol 1-oxide(A) (Example 38);
5-(4-((3-(2,4-dimethyl-6-(2-(2-oxopyrrolidin-1-yl)ethoxy) pyridin-3-yl)phenyl)methoxy)phenyl)isothiazol-3-ol 1-oxide(A) (Example 39);
5-(4-((3-(2-methyl-6-(2-(2-oxopyrrolidin-1-yl)ethoxy)pyridin-3-yl)-2-methylphenyl)methoxy)phenyl)isothiazol-3-ol 1-oxide(A) (Example 40);
5-(4-((3-(2,6-dimethyl-4-(2-(2-oxopyrrolidin-1-yl)ethoxy) phenyl)-2-methylphenyl)methoxy)phenyl)isothiazol-3-ol 1-oxide(A) (Example 41);
5-(4-((3-(2,6-dimethyl-4-((3-methyl-3-oxetanyl)methoxy) phenyl)-2-methylphenyl)methoxy)phenyl)isothiazol-3-ol 1-oxide(A) (Example 42);

5-(4-((3-(2,6-dimethyl-3-fluoro-4-(3-methyl-3-oxetanyl)methoxy)phenyl)phenyl)methoxy)phenyl)isothiazol-3-ol 1-oxide(A) (Example 43);

5-(4-((3-(2,6-dimethyl-4-(3-(methylsulfonyl)propoxy)phenyl)phenyl)methoxy)phenyl)isothiazol-3-ol 1-oxide(A) (Example 44);

5-(4-((3-(2,6-dimethyl-4-(2-(2-oxopyrrolidin-1-yl)ethoxy)phenyl)phenyl)methoxy)phenyl)isothiazol-3-ol 1-oxide(A) (Example 45);

5-(4-((3-(2,6-dimethyl-4-(3-methyl-3-oxetanyl)methoxy)phenyl)phenyl)methoxy)phenyl)isothiazol-3-ol 1-oxide(A) (Example 46);

5-(4-((3-(2,6-dimethyl-4-(3-hydroxypropoxy)phenyl)phenyl)methoxy)phenyl)isothiazol-3-ol 1-oxide(A) (Example 47);

5-(4-((3-(2,6-dimethyl-4-(3-hydroxypropoxy)phenyl)-2-methylphenyl)methoxy)phenyl)isothiazol-3-ol 1-oxide(A) (Example 48);

5-(4-((3-(2,4-dimethyl-6-(3-hydroxypropoxy)pyridin-3-yl)phenyl)methoxy)phenyl)isothiazol-3-ol 1-oxide(A) (Example 49);

5-(4-((3-(2-methyl-6-(3-hydroxypropoxy)pyridin-3-yl)-2-methylphenyl)methoxy)phenyl)isothiazol-3-ol 1-oxide(A) (Example 50);

5-(4-((3-(2,6-dimethyl-4-(2-hydroxyethoxy)phenyl)-2-methylphenyl)methoxy)phenyl)isothiazol-3-ol 1-oxide(A) (Example 51);

5-(4-((3-(2-methyl-6-(2-hydroxyethoxy)pyridin-3-yl)-2-methylphenyl)methoxy)phenyl)isothiazol-3-ol 1-oxide(A) (Example 52);

5-(4-((3-(2,4-dimethyl-6-(2-hydroxyethoxy)pyridin-3-yl)phenyl)methoxy)phenyl)isothiazol-3-ol 1-oxide(A) (Example 53);

5-(4-((3-(4,6-dimethyl-2-(2-hydroxyethoxy)pyrimidin-5-yl)-2-methylphenyl)methoxy)phenyl)isothiazol-3-ol 1-oxide(A) (Example 54);

5-(4-((3-(4-((2R)-2,3-dihydroxypropoxy)-2,6-dimethylphenyl)phenyl)methoxy)phenyl)isothiazol-3-ol 1-oxide(A) (Example 55);

5-(4-((3-(4-((2R)-2,3-dihydroxypropoxy)-2,6-dimethylphenyl)-2-methylphenyl)methoxy)phenyl)isothiazol-3-ol 1-oxide(A) (Example 56);

5-(4-((3-(6-((2R)-2,3-dihydroxypropoxy)-2-methylpyridin-3-yl)-2-methylphenyl)methoxy)phenyl)isothiazol-3-ol 1-oxide(A) (Example 57);

5-(4-((3-(2-((2R)-2,3-dihydroxypropoxy)-4,6-dimethylpyrimidin-5-yl)-2-methylphenyl)methoxy)phenyl)isothiazol-3-ol 1-oxide(A) (Example 58);

5-(4-((3-(4-((2R)-2,3-dihydroxypropoxy)-2,6-dimethyl-3-fluorophenyl)phenyl)methoxy)phenyl)isothiazol-3-ol 1-oxide(A) (Example 59);

5-(4-((3-(6-((2S)-2,3-dihydroxypropoxy)-2-methylpyridin-3-yl)-2-methylphenyl)methoxy)phenyl)isothiazol-3-ol 1-oxide(A) (Example 60);

5-(4-((3-(2,6-dimethyl-4-((3S)-3-hydroxybutoxy)phenyl)-2-methylphenyl)methoxy)phenyl)isothiazol-3-ol 1-oxide(A) (Example 61);

5-(4-((3-(2-methyl-6-((3S)-3-hydroxybutoxy)pyridin-3-yl)-2-methylphenyl)methoxy)phenyl)isothiazol-3-ol 1-oxide(A) (Example 62)

5-(4-((3-(2,6-dimethyl-4-((3R)-3-hydroxybutoxy)phenyl)phenyl)methoxy)phenyl)isothiazol-3-ol 1-oxide(A) (Example 63);

5-(4-((3-(2,6-dimethyl-4-((3R)-3-hydroxybutoxy)phenyl)-2-methylphenyl)methoxy)phenyl)isothiazol-3-ol 1-oxide(A) (Example 64);

5-(4-((3-(2-methyl-6-((3R)-3-hydroxybutoxy)pyridin-3-yl)-2-methylphenyl)methoxy)phenyl)isothiazol-3-ol 1-oxide(A) (Example 65);

5-(4-((1R)-4-bromo-2,3-dihydro-1H-inden-1-yloxy)phenyl)isothiazol-3-ol 1-oxide(A) (Example 66);

5-(4-((1S)-4-bromo-2,3-dihydro-1H-inden-1-yloxy)phenyl)isothiazol-3-ol 1-oxide(A) (Example 67);

5-(4-(4-chloro-2,3-dihydro-1H-inden-1-yloxy)phenyl)isothiazol-3-ol 1-oxide(A) (Example 68);

5-(4-(4-trifluoromethyl-2,3-dihydro-1H-inden-1-yloxy)phenyl)isothiazol-3-ol 1-oxide(A) (Example 69);

N-[3-[4-[3-[[4-(3-hydroxy-1-oxo-isothiazol-5-yl)phenoxy]methyl]phenyl]-3,5-dimethylphenoxy]propyl]acetamide (A) (Example 70);

N-[3-[5-[[4-(3-hydroxy-1-oxo-isothiazol-5-yl)phenoxy]methyl]-2-methylphenyl]-6-methylpyridin-2-yl]oxypropyl]acetamide(A) (Example 71);

N-[3-[4-[3-[[4-(3-hydroxy-1-oxo-isothiazol-5-yl)phenoxy]methyl]phenyl]-3,5-dimethylphenoxy]propyl]methanesulfonamide(A) (Example 72);

5-[4-[[3-[2,5-dimethyl-4-(3-methylsulfonylpropoxy)phenyl]phenyl]methoxy]phenyl]isothiazol-3-ol 1-oxide(A) (Example 73);

5-[4-[[3-[2,5-dimethyl-6-(3-methylsulfonylpropoxy)pyridin-3-yl] phenyl]methoxy]phenyl]isothiazol-3-ol 1-oxide (A) (Example 74);

5-[4-[[3-4-(3-hydroxy-3-methylbutoxy)-2,5-dimethylphenyl]phenyl]methoxy]phenyl]isothiazol-3-ol 1-oxide(A) (Example 75);

5-[4-[[3-[4-(3-hydroxy-3-methylbutoxy)-2,6-dimethylphenyl]phenyl]methoxy]phenyl] isothiazol-3-ol 1-oxide(A) (Example 76);

2-[[4-[3-[[4-(3-hydroxy-1-oxo-isothiazol-5-yl)phenoxy]methyl]phenyl]-3,5-dimethylphenoxy]methyl]propane-1,3-diol(A) (Example 77);

5-[4-[[3-[4-(3-aminopropoxy)-2,6-dimethylphenyl]phenyl]methoxy]phenyl]isothiazol-3-ol 1-oxide(A) (Example 78);

5-[2-chloro-4-[[3-[2,4-dimethyl-6-(3-methylsulfonylpropoxy)pyridin-3-yl]phenyl]methoxy]phenyl]isothiazol-3-ol 1-oxide(A) (Example 79);

1-oxo-5-[4-[[7-(trifluoromethyl)-2,3-dihydro-1-benzofuran-3-yl]oxy]phenyl]-1,2-thiazol-3-ol (A) (Example 80);

5-[4-[[8-(trifluoromethyl)-3,4-dihydro-2H-chromen-4-yl]oxy]phenyl]isothiazol-3-ol 1-oxide(A) (Example 81);

5-[4-[(2,2-dimethyl-4H-1,3-benzodioxin-5-yl)methoxy]phenyl]isothiazol-3-ol 1-oxide(A) (Example 82);

5-[4-[[7-(trifluoromethyl)-3,4-dihydro-2H-chromen-4-yl]oxy]phenyl]isothiazol-3-ol 1-oxide(A) (Example 83);

5-[4-[(2,6-dimethylphenyl)methoxy]phenyl]isothiazol-3-ol 1-oxide(A) (Example 84);

5-[4-[(5,5,8,8-tetramethyl-6,7-dihydronaphthalen-2-yl)methoxy]phenyl]isothiazol-3-ol 1-oxide(A) (Example 85);

5-[4-[(2,3-dichlorophenyl)methoxy]phenyl]isothiazol-3-ol 1-oxide(A) (Example 86);

5-[4-[(1R)-1-(3-chlorophenyl)ethoxy]phenyl]isothiazol-3-ol 1-oxide(A) (Example 87);

5-[4-[(1R)-1-(3-bromophenyl)ethoxy]phenyl]isothiazol-3-ol 1-oxide(A) (Example 88);

5-[4-[(3-chlorophenyl)methoxy]phenyl]isothiazol-3-ol 1-oxide(A) (Example 89);

5-[4-[(1S)-1-(3-bromophenyl)ethoxy]phenyl]isothiazol-3-ol 1-oxide(A) (Example 90);

5-[4-[(3-bromo-2-methylphenyl)methoxy]phenyl]isothiazol-3-ol 1-oxide(A) (Example 91);

5-[4-[2-(4-methoxyphenyl)ethoxy]phenyl]isothiazol-3-ol 1-oxide(A) (Example 92);

5-[4-[[3-(4,4-difluoropiperidin-1-yl)phenyl]methoxy]phenyl]isothiazol-3-ol 1-oxide(A) (Example 93);

5-[4-[[3-(2,6-dimethylphenyl)-2-methoxyphenyl]methoxy]phenyl]isothiazol-3-ol 1-oxide (A) (Example 94);

5-[4-(2,3-dihydro-1-benzofuran-7-ylmethoxy)phenyl]isothiazol-3-ol 1-oxide(A) (Example 95);

5-[4-[[(3S)-1-(2,6-dimethylphenyl)piperidin-3-yl]methoxy]phenyl]isothiazol-3-ol 1-oxide (A) (Example 96);

5-[4-[[(3R)-1-(2,6-dimethylphenyl)piperidin-3-yl]methoxy]phenyl]isothiazol-3-ol 1-oxide(A) (Example 97);

5-[4-[[3-(4,4-difluoropiperidin-1-yl)-2-methoxyphenoxy]methyl]phenyl]isothiazol-3-ol 1-oxide(A) (Example 98);

5-[4-[[3-(trifluoromethyl)phenyl]methoxy]phenyl]isothiazol-3-ol 1-oxide (Example 99);

5-[4-[2-chloro-4-(trifluoromethyl)phenoxy]phenyl]isothiazol-3-ol 1-oxide (Example 100);

5-[4-[(3-bromophenyl)methylamino]phenyl]isothiazol-3-ol 1-oxide (Example 101);

5-[4-[(3-bromophenyl)methoxy]phenyl]isothiazol-3-ol 1-oxide(A) (Example 102);

5-[4-[(3-bromophenoxy)methyl]phenyl]isothiazol-3-ol 1-oxide (Example 103);

5-[3-[(3-bromophenyl)methoxy]phenyl]isothiazol-3-ol 1-oxide (Example 104);

5-[4-[(2R)-1-(3-propan-2-yloxyphenyl)propan-2-yl]oxyphenyl]isothiazol-3-ol 1-oxide (Example 105);

5-[4-[2-(3-phenoxyphenyl)ethoxy]phenyl]isothiazol-3-ol 1-oxide (Example 106);

5-[4-[[(1R)-4-(2,6-dimethylphenyl)-2,3-dihydro-1H-inden-1-yl]oxy]phenyl]isothiazol-3-ol 1-oxide(A) (Example 107);

5-[4-[[(1R)-4-(cyclohexen-1-yl)-2,3-dihydro-1H-inden-1-yl]oxy]phenyl]isothiazol-3-ol 1-oxide(A) (Example 108);

5-[4-[[(1R)-4-cyclopropyl-2,3-dihydro-1H-inden-1-yl]oxy]phenyl]isothiazol-3-ol 1-oxide (A) (Example 109);

5-[4-[[(1R)-4-phenyl-2,3-dihydro-1H-inden-1-yl]oxy]phenyl]isothiazol-3-ol 1-oxide(A) (Example 110);

5-[4-[[(1R)-4-pyridin-3-yl-2,3-dihydro-1H-inden-1-yl]oxy]phenyl]isothiazol-3-ol 1-oxide (A) (Example 111);

5-[4-[[(1R)-4-(6-methoxypyridin-3-yl)-2,3-dihydro-1H-inden-1-yl]oxy]phenyl]isothiazol-3-ol 1-oxide(A)trifluoroacetate salt (Example 112);

5-[4-[[(1R)-4-(2-methylpyridin-3-yl)-2,3-dihydro-1H-inden-1-yl]oxy]phenyl] isothiazol-3-ol 1-oxide(A)trifluoroacetate salt (Example 113);

5-[4-[[(1R)-4-(2-methoxypyridin-3-yl)-2,3-dihydro-1H-inden-1-yl]oxy]phenyl]isothiazol-3-ol 1-oxide(A) (Example 114);

5-[4-[[(1R)-4-(4-methoxy-2,6-dimethylphenyl)-2,3-dihydro-1H-inden-1-yl]oxy]phenyl]isothiazol-3-ol 1-oxide (A) (Example 115);

5-[4-[[(1R)-4-(2,6-dimethoxypyridin-3-yl)-2,3-dihydro-1H-inden-1-yl]oxy]phenyl]isothiazol-3-ol 1-oxide(A) (Example 116);

5-[4-[[(1R)-4-[2-(trifluoromethyl)pyridin-3-yl]-2,3-dihydro-1H-inden-1-yl]oxy]phenyl]isothiazol-3-ol 1-oxide (A) (Example 117);

5-[4-[[(1R)-4-(6-(piperidin-1-yl)pyridin-3-yl)-2,3-dihydro-1H-inden-1-yl]oxy]phenyl] isothiazol-3-ol 1-oxide(A) (Example 118);

5-[4-[[(1R)-4-(6-methoxy-2-methylpyridin-3-yl)-2,3-dihydro-1H-inden-1-yl]oxy]phenyl]isothiazol-3-ol 1-oxide(A)trifluoroacetate salt (Example 119);

5-[4-[[(1R)-4-(4,4-dimethylcyclohexen-1-yl)-2,3-dihydro-1H-inden-1-yl]oxy]phenyl]isothiazol-3-ol 1-oxide(A) (Example 120);

5-[4-[[(1R)-4-(3,6-dihydro-2H-pyran-4-yl)-2,3-dihydro-1H-inden-1-yl]oxy]phenyl]isothiazol-3-ol 1-oxide(A) (Example 121);

5-[4-[[(1R)-4-(pyridin-4-yl)-2,3-dihydro-1H-inden-1-yl]oxy]phenyl]isothiazol-3-ol 1-oxide(A)trifluoroacetate salt (Example 122);

5-[4-[[(1R)-4-(2-methoxypyrimidin-5-yl)-2,3-dihydro-1H-inden-1-yl]oxy]phenyl]isothiazol-3-ol 1-oxide(A) (Example 123);

5-[4-[(4-phenoxy-2,3-dihydro-1H-inden-1-yl)oxy]phenyl]isothiazol-3-ol 1-oxide(A) (Example 124);

5-[4-[[4-(2-methylpyridin-3-yl)oxy-2,3-dihydro-1H-inden-1-yl]oxy]phenyl]isothiazol-3-ol 1-oxide(A) (Example 125);

5-[4-[[4-(2-methoxypyridin-4-yl)oxy-2,3-dihydro-1H-inden-1-yl]oxy]phenyl]isothiazol-3-ol 1-oxide(A) (Example 126);

5-[4-[(4-pyridin-4-yloxy-2,3-dihydro-1H-inden-1-yl)oxy]phenyl]isothiazol-3-ol 1-oxide(A) (Example 127);

5-[4-[[3-(2-methoxypyridin-3-yl)phenyl]methoxy]phenyl]isothiazol-3-ol 1-oxide(A) (Example 128);

5-[4-[(4-phenylmethoxy-2,3-dihydro-1H-inden-1-yl)oxy]phenyl]isothiazol-3-ol 1-oxide(A) (Example 129);

5-[4-[[4-(2,2,2-trifluoroethoxy)-2,3-dihydro-1H-inden-1-yl]oxy]phenyl]isothiazole-3-ol 1-oxide(A) (Example 130);

5-[4-[(4-cyclohexyloxy-2,3-dihydro-1H-inden-1-yl)oxy]phenyl]isothiazol-3-ol 1-oxide(A) (Example 131);

5-[4-[[4-(oxan-4-yloxy)-2,3-dihydro-1H-inden-1-yl]oxy]phenyl]isothiazol-3-ol 1-oxide(A) (Example 132);

5-[4-[[4-(2-ethoxyethoxy)-2,3-dihydro-1H-inden-1-yl]oxy]phenyl]isothiazol-3-ol 1-oxide(A) (Example 133);

[5-[4-[[4-(1-methylpiperidin-4-yl)oxy-2,3-dihydro-1H-inden-1-yl]oxy]phenyl]-1-oxo-isothiazol-3-yl]oxysodium salt (Example 134);

5-[4-[[(1R)-4-[6-(3-hydroxy-3-methylbutoxy)-2-methylpyridin-3-yl]-2,3-dihydro-1H-inden-1-yl]oxy]phenyl] isothiazol-3-ol 1-oxide(A) (Example 135);

5-[4-[[(1R)-4-[6-(2-ethoxyethoxy)-2-methylpyridin-3-yl]-2,3-dihydro-1,4-inden-1-yl]oxy]-phenyl]isothiazol-3-ol 1-oxide(A) (Example 136);

5-[4-[[(1R)-4-[2-methyl-6-(3-methylsulfonylpropoxy)pyridin-3-yl]-2,3-dihydro-1H-inden-1-yl]oxy]phenyl]isothiazol-3-ol 1-oxide(A) (Example 137);

5-[4-[[(1R)-4-[2,6-dimethyl-4-(3-methylsulfonylpropoxy)phenyl]-2,3-dihydro-1H-inden-1-yl]oxy]phenyl]isothiazol-3-ol 1-oxide(A) (Example 138);

5-[4-[[(1R)-4-[4-(2-ethoxyethoxy)-2,6-dimethylphenyl]-2,3-dihydro-1H-inden-1-yl]oxy]phenyl]isothiazol-3-ol 1-oxide(A) (Example 139);

5-[4-[[(1R)-4-[4-(3-hydroxy-3-methylbutoxy)-2,6-dimethylphenyl]-2,3-dihydro-1H-inden-1-yl]oxy]phenyl] isothiazol-3-ol 1-oxide(A) (Example 140);

5-[4-[(3-bromophenyl)methoxymethyl]phenyl]isothiazol-3-ol 1-oxide (Example 141);

5-(4-((1R)-4-trifluoromethyl-2,3-dihydro-1H-inden-1-yloxy)phenyl)isothiazol-3-ol 1-oxide(A) (Example 142);

5-(4-((1R)-4-chloro-2,3-dihydro-1H-inden-1-yloxy)phenyl)isothiazol-3-ol 1-oxide(A) (Example 143);

5-[4-[[(1R)-4-(6-fluoropyridin-3-yl)-2,3-dihydro-1H-inden-1-yl]oxy]phenyl]isothiazol-3-ol 1-oxide(A) (Example 144); and salts of these compounds, solvates of the compounds or the salts, and optical isomers of the compounds, the salts, or the solvates.

[2] A second aspect of the present invention is a pharmaceutical composition, characterized by containing as an active ingredient, at least one of the compound of Formula (I), a pharmaceutically acceptable salt of the compound, and a pharmaceutically acceptable solvate of the compound or the salt.

[3] A third aspect of the present invention is a prophylactic agent and/or a therapeutic agent for a GPR40-involving disease, characterized by containing as an active ingredient, at least one of the compound of Formula (I), a pharmaceutically acceptable salt of the compound, and a pharmaceutically acceptable solvate of the compound or the salt.

[3-1] Specifically, a prophylactic agent and/or a therapeutic agent for each disease of diabetes [more specifically, any one of or all of Type 1 diabetes (insulin-dependent diabetes), Type 2 diabetes (non-insulin-dependent diabetes), and borderline type diabetes (impaired glucose tolerance (IGT) and/or impaired fasting glycemia (IFG))], obesity, and adiposity, characterized by containing as an active ingredient, at least one of the compound of Formula (I), a pharmaceutically acceptable salt of the compound, and a pharmaceutically acceptable solvate of the compound or the salt. An inhibitor of Type 2 diabetes in the impaired glucose tolerance is also included in examples of the above prophylactic agent and therapeutic agent. A therapeutic agent for sulfonylurea secondary failure diabetes is also included in the examples thereof, and by the therapeutic agent, also in (administration-ineffective) diabetic patients who cannot obtain a satisfactory hypoglycemic effect even by being administrated with a sulfonylurea agent (such as glibenclamide and glimepiride) or a rapid-acting insulin secretagogues (such as mitiglinide), insulin secretion effect or hypoglycemic effect can be obtained.

Here, in relationship between the blood glucose level and the disease, the diabetes is characterized by exhibiting a fasting blood glucose level of 126 mg/dL or more, or a casual blood glucose level or a 2 hours value of the 75 g oral glucose tolerance test (OGTT) of 200 mg/dL or more. The borderline type diabetes (called also as glucose tolerance disorders) refers to an impaired fasting glycemia (IFG) in which the fasting blood glucose level is 110 mg/dL or more and less than 126 mg/dL and/or an impaired glucose tolerance (IGT) in which a 2 hours value of the 75 g OGTT is 140 mg/dL or more and less than 200 mg/dL.

The insulin resistance refers to a pathological condition in which insulin becomes unable to lower the blood glucose level in the organism and is evaluated by a quantitative glucose clamp technique or HOMA-IR in clinical practice. It is known that the insulin resistance causes a hyperinsulinemia and becomes a risk of a hypertension and a coronary artery disease.

The "adiposity" is defined by the Japan Society for the Study of Obesity as "a pathological condition requiring medically a weight reduction in the case where an obesity-derived or -related health impairment is combined or such a combination is expected". The "obesity" defined here is evaluated by measuring BMI (body mass index, kg/m$^2$). Generally, a body having a BMI of 25 or more is diagnosed as obesity. Examples of the result of the therapy include the reduction of BMI.

[4] A fourth aspect of the present invention is an insulin secretagogues, characterized by containing as an active ingredient, at least one of the compound of Formula (I), a pharmaceutically acceptable salt of the compound, and a pharmaceutically acceptable solvate of the compound or the salt.

[5] A fifth aspect of the present invention is a GPR40 activating agent containing one or more of the compound of Formula (I), a pharmaceutically acceptable salt of the compound, and a pharmaceutically acceptable solvate of the compound or the salt.

In the second to fifth aspects and preferred aspects thereof, more preferred substituents and a combination thereof in Formula (I) are according to descriptions described in the first aspect.

In each aspect as described in [1] to [5] of the present invention, it is preferred to use a compound having a $EC_{50}$ value of preferably, 3 μM or less, more preferably, 1 μM or less, further preferably, 300 nM or less, and most preferably, 100 nM or less, when the GPR40 agonist action is measured by a method accordingly selected (for example, the below described pharmacological test example 1 (an agonist action on GPR40 of human origin)).

[6] A sixth aspect of the present invention is a production method of a compound of Formula (I):

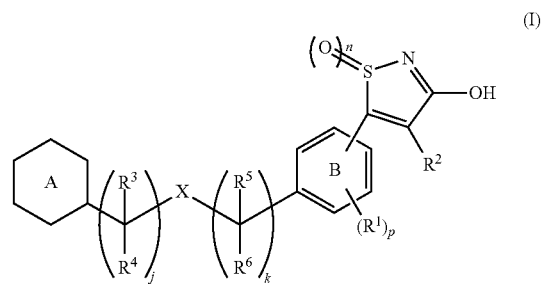

(where p, j, k, n, a ring A, a ring B, $R^1$, $R^2$, $R^3$, $R^4$, $R^5$, and $R^6$ are the same as defined in the above Formula (I)), characterized in that: a compound of Formula (VI):

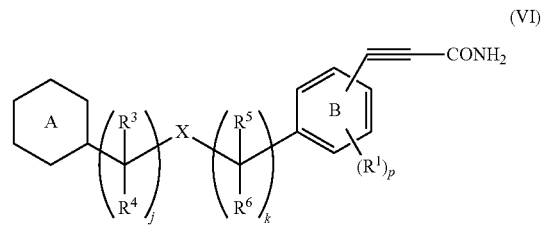

(where p, j, k, a ring A, a ring B, $R^1$, $R^3$, $R^4$, $R^5$, and $R^6$ are the same as defined in the above Formula (I)) is reacted with a thiol (SH) source such as sodium hydrosulfide and a hydrogen sulfide gas in a reaction inert solvent at a temperature from 0° C. to a temperature at which the solvent refluxes; the resultant thiol adduct is subjected to a reaction in the presence of a halogen and further, in the presence or absence of a base in a reaction inert solvent at a temperature from 0° C. to a temperature at which the solvent refluxes to produce a compound of Formula (I)-a:

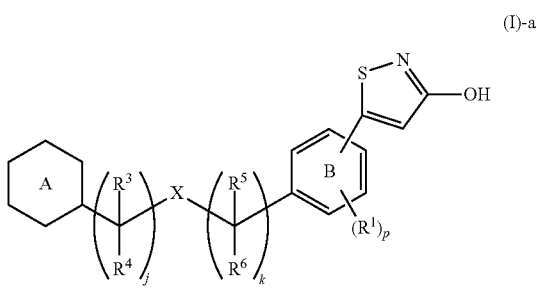

(where p, j, k, a ring A, a ring B, $R^1$, $R^3$, $R^4$, $R^5$, and $R^6$ are the same as defined in the above Formula (I)); and if necessary, the compound of Formula (I)-a is subjected to a reaction in the presence of a peracid or a peroxide such as hydrogen peroxide water, m-chloro perbenzoic acid (MCPBA), peracetic acid, trifluoro peracetic acid, and tert-butylhydroperoxide (TBHP) in a reaction inert solvent at a temperature from 0° C. to a temperature at which the solvent refluxes to obtain a compound of Formula (I)-b:

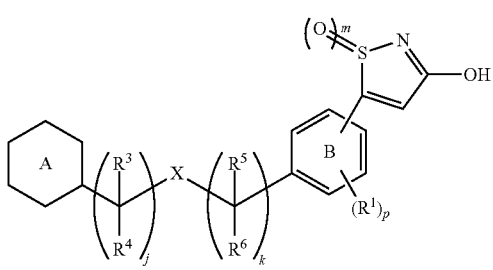

(where p, j, k, a ring A, a ring B, $R^1$, $R^3$, $R^4$, $R^5$, and $R^6$ are the same as defined in the above Formula (I); and m is an integer of 1 or 2), or characterized in that: a phenolic hydroxy group of the compound of Formula (I)-a is protected with a group selected from an alkoxyalkyl group, an arylmethyl group, a silyl group, an alkanoyl group, an aroyl group, an alkylcarbonyl group, and an arylmethylcarbonyl group as $P^2$ to obtain a compound of Formula (B-VI):

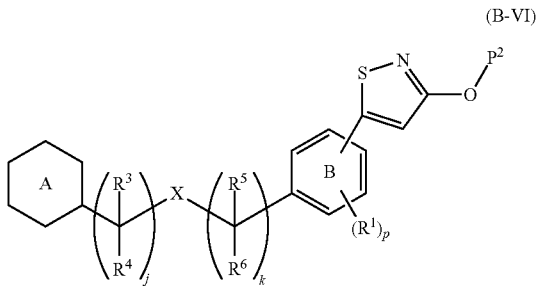

(where p, j, k, a ring A, a ring B, $R^1$, $R^3$, $R^4$, $R^5$, and $R^6$ are the same as defined in the above Formula (I); and $P^2$ is a group selected from an alkoxyalkyl group, an arylmethyl group, a silyl group, an alkanoyl group, an aroyl group, an alkylcarbonyl group, and an arylmethylcarbonyl group);

the obtained compound is subjected to a reaction in the presence of a halogenating agent and a base in a reaction inert solvent at a temperature from −78° C. to a temperature at which the solvent refluxes; if necessary, the resultant reaction product is subjected to a reaction in the presence of a corresponding cyanating agent, a palladium catalyst, a phosphine-based reagent or instead of the phosphine-based reagent, tetramethylammonium chloride, tetrabutylammonium chloride, or the like, and a base in a reaction inert solvent at a temperature from 0° C. to a temperature at which the solvent refluxes to produce a compound of Formula (D-I):

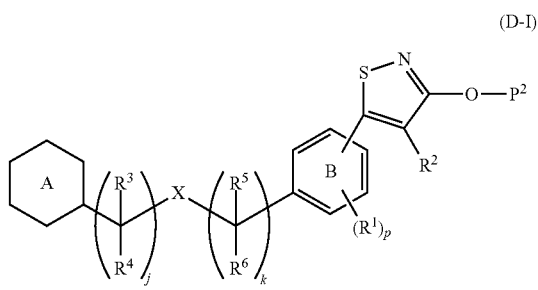

(where p, j, k, a ring A, a ring B, $R^1$, $R^2$, $R^3$, $R^4$, $R^5$, and $R^6$ are the same as defined in the above Formula (I); and $P^2$ is a group selected from an alkoxyalkyl group, an arylmethyl group, a silyl group, an alkanoyl group, an aroyl group, an alkylcarbonyl group, and an arylmethylcarbonyl group); if necessary, an oxidation reaction of a sulfur atom of the compound of Formula (D-I) is effected in the presence of a peracid or a peroxide such as hydrogen peroxide water, m-chloro perbenzoic acid (MCPBA), peracetic acid, trifluoro peracetic acid, and tert-butylhydroperoxide (TBHP) in a reaction inert solvent at a temperature from 0° C. to a temperature at which the solvent refluxes to produce a compound of Formula (D-II):

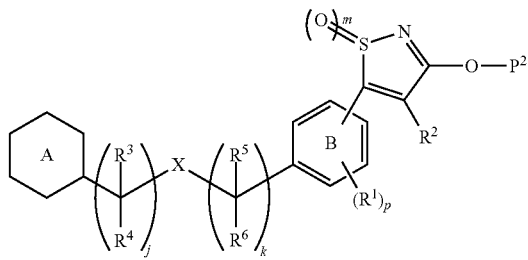

(where p, j, k, a ring A, a ring B, $R^1$, $R^2$, $R^3$, $R^4$, $R^5$, $R^6$, and $P^2$ are the same as defined in the above Formula (D-I); and m is an integer of 1 or 2);

and the compound of Formula (D-I) or the compound of Formula (D-II) is subjected to a deprotection reaction of the protecting group $P^2$.

[7] A seventh aspect of the present invention is a production method of a compound of Formula (I):

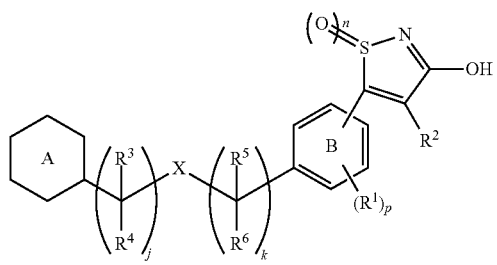

(where p, j, k, n, a ring A, a ring B, $R^1$, $R^2$, $R^3$, $R^4$, $R^5$, and $R^6$ are the same as defined in the above Formula), characterized in that the compound of Formula (C-I):

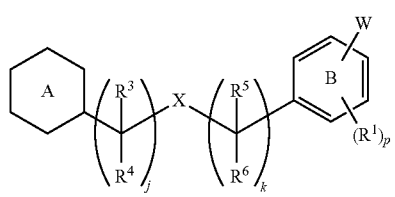

(where p, j, k, n, a ring A, a ring B, $R^1$, $R^3$, $R^4$, $R^5$, and $R^6$ are the same as defined in the above Formula (I); and W is boronic acid, a boronic acid ester, or a trifluoroborate salt) and a compound of Formula (C-II):

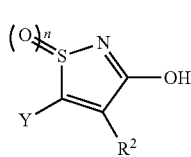

(where n and $R^2$ are the same as defined in the above Formula (I); and Y is a halogen atom) are subjected to a reaction in the presence of a palladium catalyst, a phosphine-based reagent or instead of the phosphine-based reagent, tetramethylammonium chloride, tetrabutylammonium chloride, or the like, and a base in a reaction inert solvent at a temperature from 0° C. to a temperature at which the solvent refluxes.

[8] An eighth aspect of the present invention is a compound of Formula (I-I):

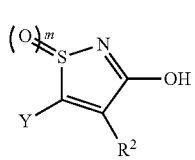

(where $R^2$ is the same as defined in the above Formula (I); Y is a halogen atom; and m is an integer of 1 or 2, with the proviso that when m is 1, the case where Y and $R^2$ are chlorine atoms is excluded), a salt of the compound, or a solvate of the compound or the salt.

In Formula (I-I), when m is 1, the compound of Formula (I-I) has optical isomers. When there is, besides the asymmetry of an oxygen atom, an asymmetry (for example, the presence of an asymmetric carbon) in another moiety of the molecule of the compound of Formula (I) which is the compound of the present invention, the compound has diastereomers.

In the above aspects of the present invention, the "therapeutic agent" is not only for treating diseases or symptoms, but also for improving diseases or symptoms.

In all of the above aspects, when the term "compound" is used, the compound refers also to a "pharmaceutically acceptable salt of the compound". In addition, there is the case where the compound of the present invention has an asymmetric carbon, and thus, the compound of the present invention includes a mixture of various stereoisomers such as a geometric isomer, a tautomer, and an optical isomer, and an isolated stereoisomer. The compound of Formula (I) may have an axial asymmetry due to a steric hindrance and an isomer caused by the axial asymmetry (axial chirality) is also included in the compound of Formula (I). The isolation and the purification of such stereoisomers can be performed by a person skilled in the art by an ordinary technique through an optical resolution or an asymmetric synthesis using a preferential crystallization or a column chromatography.

The compound of Formula (I) of the present invention may form an acid addition salt or a salt with a base depending on the type of the substituent. Such salt is not particularly limited so long as the salt is a pharmaceutically acceptable salt. Specific examples thereof include acid addition salts with: mineral acids such as hydrochloric acid, hydrobromic acid, hydriodic acid, sulfuric acid, nitric acid, and phosphoric acid; organic carboxylic acids, for example, an aliphatic monocarboxylic acid such as formic acid, acetic acid, propionic acid, butyric acid, valeric acid, enanthic acid, capric acid, myristic acid, palmitic acid, stearic acid, lactic acid, sorbic acid, and mandelic acid, an aromatic monocarboxylic acid such as benzoic acid and salicylic acid, an aliphatic dicarboxylic acid such as oxalic acid, malonic acid, succinic acid, fumaric acid, maleic acid, malic acid, and tartaric acid, an aliphatic tricarboxylic acid such as citric acid, cinnamic acid, glycolic acid, pyruvic acid, oxylic acid, salicylic acid, and N-acetylcysteine; organic sulfonic acids, for example, an aliphatic sulfonic acid such as methanesulfonic acid, ethanesulfonic acid, and 2-hydroxyethanesulfonic acid, and an aromatic sulfonic acid such as benzenesulfonic acid and p-toluenesulfonic acid; and acidic amino acids such as aspartic acid and glutamic acid, salts (including besides mono salts, disodium salts and dipotassium salts) with a metal, for example, alkali metals such as lithium, sodium, potassium, and cesium, and alkaline earth metals such as magnesium, calcium, and barium, salts with a metal such as aluminum, iron, copper, nickel, cobalt, and zinc, salts with an organic base such as methylamine, ethylamine, tert-butylamine, tert-octylamine, diethylamine, triethylamine, cyclohexylamine, dibenzylamine, ethanolamine, diethanolamine, triethanolamine, piperidine, morpholine, pyridine, lysine, arginine, ornithine, ethylenediamine, N-methylglucamine, glucosamine, a phenylglycine alkyl ester, and guanidine, and salts with glycine, histidine, choline, and ammonium.

These salts can be obtained by an ordinary method including, for example, mixing an equivalent of the compound of the present invention with a solution containing a desired acid, base, or the like, and collecting a desired salt by filtration or distillation-off of a solvent. The compound of the present invention or a salt of the compound can form a solvate with a solvent such as water, ethanol, and glycerol.

The salt of the compound of the present invention includes a mono-salt and a di-salt. The compound of the present invention can form both of an acid addition salt and a salt with a base simultaneously depending on the type of the substituent in the side chains. Further, the present invention encompasses also hydrates, various pharmaceutically acceptable solvates, and crystal polymorphs of the compound of Formula (I) of the present invention. Here, needless to say, the present invention is not limited to the compounds described in Examples below and encompasses all of the compounds of Formula (I) of the present invention and pharmaceutically acceptable salts of the compounds.

The compound of the present invention may be labeled with an isotope (such as $^3$H, $^{14}$C, and $^{35}$S).

[Method for Producing the Compound of the Present Invention]

Methods for producing the compound of Formula (I) of the present invention will be described below.

The compound of Formula (I) of the present invention, a salt of the compound, and a solvate of the compound or the salt can be produced by a combination of commonly known chemical production methods. Typical production methods will be described below.

In each Formula in the production methods below, each definition of ring A, ring A', ring A", ring B, $R^1$, $R^2$, $R^3$, $R^4$, $R^5$, $R^6$, $R^7$, $R^8$, $R^9$, $R^{10}$, $R^{11}$, $R^{12}$, X, V, T, f, g, n, p, q, q1, q1-1, r, r1, s, j, and k is the same as each definition in Formula (I), Formula (II), Formula (III), Formula (A), Formula (AA), Formula (AA') described in the first aspect above unless otherwise specified.

In the production methods, the definition of m is an integer of 1 or 2.

In the production methods, the definition of g-1 is an integer of 1 to 3.

In the production methods, the definition of R' is a lower alkyl group such as a methyl group and an ethyl group unless otherwise specified.

In the production methods, the definition of R" is a hydrogen atom, a hydroxy group, or a lower alkoxy group such as a methoxy group and an ethoxy group unless otherwise specified.

In the production methods, the definition of Y is a halogen atom unless otherwise specified.

In the production methods, the definition of Z is a hydroxy group, a halogen atom, or a sulfonyloxy group such as a methanesulfonyloxy group, a p-toluenesulfonyloxy group, and a trifluoromethanesulfonyloxy group unless otherwise specified.

In the production methods, the definition of W is boronic acid, a boronic acid ester, or a trifluoroborate salt unless otherwise specified.

In the production methods, for the definitions of $W^1$ and $W^2$, $W^2$ is boronic acid, a boronic acid ester, or a trifluoroborate salt when $W^1$ is a hydroxy group, a halogen atom, or a trifluoromethanesulfonyloxy group, and $W^2$ is a hydroxy group, a halogen atom, or a trifluoromethanesulfonyloxy group when $W^1$ is boronic acid, a boronic acid ester, or a trifluoroborate salt unless otherwise specified.

In the production methods, the definition of $P^1$ is a protective group for a hydroxy group (—OH), a thiol group (—SH), or an imino group (—NH—) unless otherwise specified. Examples of the protective group for a hydroxy group include an alkoxyalkyl group such as a methoxymethyl group, a methoxyethoxymethyl group, and a tetrahydropyranyl group; an arylmethyl group such as a benzyl group and a triphenyl-methyl group; a silyl group such as a triethylsilyl group and a t-butyldimethylsilyl group; an alkanoyl group such as an acetyl group; an aroyl group such as a benzoyl group; an alkylcarbonyl group such as a methoxycarbonyl group; and an arylmethylcarbonyl group such as a benzyloxycarbonyl group. Examples of the protective group for a thiol group include an arylmethyl group such as a benzyl group and a triphenylmethyl group; an alkanoyl group such as an acetyl group and a pivaloyl group; and an aroyl group such as a benzoyl group. Examples of the protective group for an imino group include an alkanoyl group such as an acetyl group; an alkoxycarbonyl group such as a methoxycarbonyl group, an ethoxycarbonyl group, and a t-butoxycarbonyl group; an arylmethoxycarbonyl group such as a benzyloxycarbonyl group, a para-methoxybenzyloxycarbonyl group, and a para-nitrobenzyloxycarbonyl group; an arylmethyl group such as a benzyl group and a triphenylmethyl group; and an aroyl group such as a benzoyl group.

In the production methods, the definition of $P^2$ is a protective group for a phenolic hydroxy group unless otherwise specified. Examples of the protective group include an alkoxyalkyl group such as a methoxymethyl group, a methoxyethoxymethyl group, and a tetrahydropyranyl group; an arylmethyl group such as a benzyl group; a silyl group such as a trimethylsilyl group and a t-butyldimethylsilyl group; an alkanoyl group such as an acetyl group and a pivaloyl group; an aroyl group such as a benzoyl group; an alkylcarbonyl group such as a methoxycarbonyl group; and an arylmethylcarbonyl group such as a benzyloxycarbonyl group.

In the production methods, the definition of $P^3$ is a protective group for an imino group (—NH—) unless otherwise specified. Examples of the protective group include an arylmethyl group such as a benzyl group and a triphenylmethyl group; an alkoxyalkyl group such as a methoxymethyl group and a methoxyethoxymethyl group; an alkyl group such as a tert-butyl group; an alkanoyl group such as an acetyl group; an alkoxycarbonyl group such as a methoxycarbonyl group, an ethoxycarbonyl group, and a t-butoxycarbonyl group; an arylmethoxycarbonyl group such as a benzyloxycarbonyl group, a para-methoxybenzyloxycarbonyl group, and a para-nitrobenzyloxycarbonyl group; and an aroyl group such as a benzoyl group.

Deprotection methods of such protective groups are different depending on the chemical properties of a protected reactive group (a hydroxy group, a thiol group, or an imino group) and an employed protective group. For example, an acyl-type protective group such as an alkanoyl group, an alkoxycarbonyl group, and an aroyl group can be hydrolyzed using a suitable base such as an alkali metal hydroxide including lithium hydroxide, sodium hydroxide, and potassium hydroxide for the deprotection. An alkoxyalkyl-type protective group such as a methoxymethyl group, a methoxyethoxymethyl group, and a tetrahydropyranyl group, a substituted methoxycarbonyl-type protective group such as a t-butoxycarbonyl group and a para-methoxybenzyloxycarbonyl group, and a silyl-type protective group such as a triethylsilyl group and a t-butyldimethylsilyl group can be removed using a suitable acid such as acetic acid, hydrochloric acid, hydrobromic acid, sulfuric acid, phosphoric acid, trifluoroacetic acid, and trifluoromethanesulfonic acid or a combination of them. The silyl-type protective group can also be removed using a suitable fluorine ion ($F^-$) generating reagent such as tetrabutylammonium fluoride and hydrogen fluoride. An arylmethoxycarbonyl group such as a benzyloxycarbonyl group, a para-methoxybenzyloxycarbonyl group, and a para-nitrobenzyloxycarbonyl group and an arylmethyl group such as a benzyl group can be removed by hydrogenolysis using a palladium carbon catalyst. A benzyl group can be removed by Birch reduction using metallic sodium in liquid ammonia. A triphenylmethyl group can be removed using a suitable acid such as acetic acid, hydrochloric acid, hydrobromic acid, sulfuric acid, phosphoric acid, trifluoroacetic acid, and trifluoromethanesulfonic acid or a combination of them. It can also be removed by Birch reduction using metallic sodium in liquid ammonia and removed by hydrogenolysis using a palladium carbon catalyst.

During the production of the compound of Formula (I) of the present invention, when it has a reactive group such as a hydroxy group, an amino group, and a carboxy group, such group may be properly protected in any reaction step, and the protective group may be removed in a suitable step. Methods for introducing and removing such protective groups are properly employed depending on the type of a group to be protected or a protective group. For example, such introduction and removal can be performed by methods described in [Protective Groups in Organic Synthesis, edited by Greene et al, the fourth edition (2007), John Wiley & Sons].

In each production step below, when X is a sulfur atom, the sulfur atom can be oxidized after an intermediate is properly selected or other functional groups are properly protected depending on the intermediate or the functional groups in each step. In accordance with a method known in the literature, for example, the method described in [*Jikken Kagaku Koza* (Experimental Chemistry Course), the fourth edition, vol. 20, Organic Synthesis V, Oxidation Reaction, pp. 276-280 (1992), Maruzen Co., Ltd.], the oxide can be produced by reacting the intermediate, in the presence of the compound to be reacted, in the presence of a peracid or a peroxide such as hydrogen peroxide water, m-chloroperbenzoic acid (MCPBA), peracetic acid, trifluoroperacetic acid, Oxone (registered trademark) (DuPont), and tert-butylhydroperoxide (TBHP), in a reaction inert solvent including a halogenated solvent such as dichloromethane and chloroform, an aromatic hydrocarbon solvent such as toluene and benzene, and a polar solvent such as acetonitrile, methanol, acetone, and water, at a temperature from 0° C. to a reflux temperature of the solvent. In the oxidation reaction, selection of an oxidizing agent and suitable selection of equivalent weight of a reagent, a reaction temperature, a reaction time, a solvent, and the like can produce a sulfoxide and a sulfone separately. Such sulfoxide and sulfone can be separated by common techniques such as column chromatography.

Required starting materials are commercially available or can be easily obtained from commercial products by usual production methods in organic chemistry.

Reaction conditions in the production methods are as follows unless otherwise specified. The reaction temperature is in a range from −78° C. to the reflux temperature of a solvent, and the reaction time is a time sufficient for a reaction. Examples of the reaction inert solvent include, but are not limited to, an aromatic hydrocarbon solvent such as toluene and benzene; a polar solvent such as water, methanol, N,N-dimethylformamide, dimethyl sulfoxide, and 1,3-dimethyl-2-imidazolidinone; a basic solvent such as triethylamine and pyridine; a halogenated solvent such as chloroform, methylene chloride, and 1,2-dichloroethane; an ether solvent such as diethyl ether, tetrahydrofuran, and dioxane; and a mixed solvent of them. Such solvents are properly selected depending on reaction conditions. Examples of the base include, but are not limited to, an inorganic base such as potassium carbonate, cesium carbonate, sodium hydroxide, potassium hydroxide, and sodium hydride; and an organic base such as triethylamine, pyridine, N,N-dialkylaniline, and lithium diisopropylamide. Examples of the acid include, but are not limited to, a mineral acid such as hydrochloric acid and sulfuric acid, and an organic acid such as methanesulfonic acid and p-toluenesulfonic acid.

Hereinafter, production methods will be described, but the present invention is not limited to these methods.

The compound of Formula (I) of the present invention can be obtained from a compound of Formula (VI).

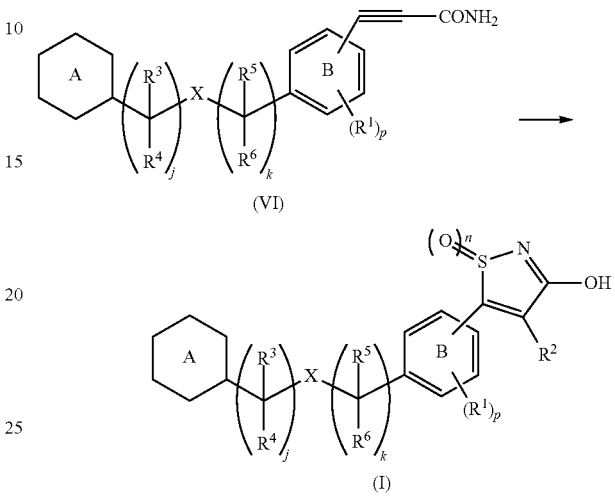

(1) Methods for producing the compound of Formula (I) of the present invention will be described below.
<Production Method A>
<When $R^2$=H in Formula (I)>

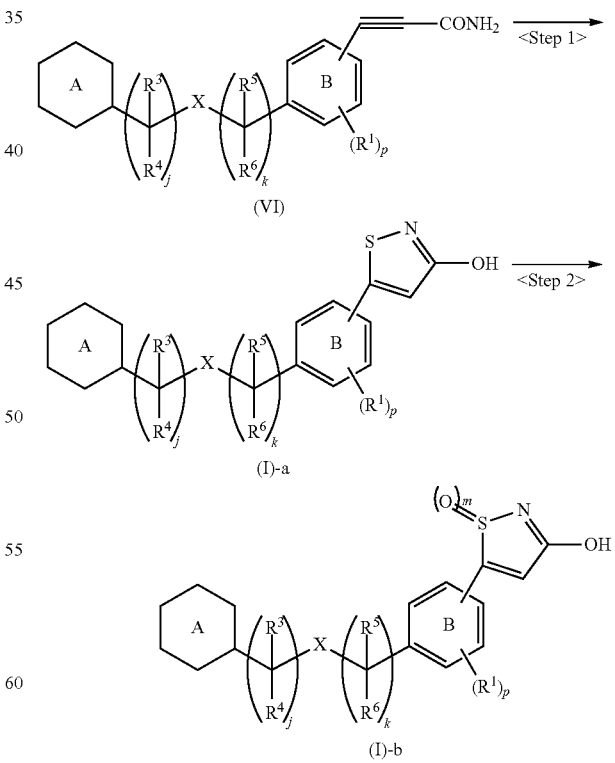

<Step 1>
The compound of Formula (VI) is subjected to isothiazole ring formation reaction. In accordance with a method known in the literature, for example, the method described in [Heterocyclic Compounds, New Edition, Applications, pp. 41-57 (2004), Kodansha Ltd.], [Chemische Berichte, vol. 94, p. 2950 (1961)], or [Chemische Berichte, vol. 96, p. 944 (1963)], a compound of Formula (I)-a can be produced by reacting the compound of Formula (VI) with a thiol (SH) source such as sodium hydrosulfide and hydrogen sulfide gas in a reaction inert solvent such as methanol, ethanol, and water or a mixed solvent of them at a temperature from 0° C. to a reflux temperature of the solvent, and then by reacting the obtained thiol adduct in the presence of a halogen such as iodine and bromine and in the presence or absence of a base such as pyridine and potassium carbonate in a reaction inert solvent such as methanol, ethanol, ethyl acetate, and water or a mixed solvent of them at a temperature from 0° C. to a reflux temperature of the solvent.

<Step 2>

The sulfur atom in the compound of Formula (I)-a is oxidized. In accordance with a method known in the literature, for example, the method described in [*Jikken Kagaku Koza* (Experimental Chemistry Course), the fourth edition, vol. 20, Organic Synthesis V, Oxidation Reaction, pp. 276-280 (1992), Maruzen Co., Ltd.], a compound of Formula (I)-b can be produced by reacting the compound of Formula (I)-a in the presence of a peracid or a peroxide such as hydrogen peroxide water, m-chloroperbenzoic acid (MCPBA), peracetic acid, trifluoroperacetic acid, Oxone (registered trademark) (DuPont), and tert-butylhydroperoxide (TBHP) in a reaction inert solvent including a halogenated solvent such as dichloromethane and chloroform, an aromatic hydrocarbon solvent such as toluene and benzene, and a polar solvent such as acetonitrile and water or in a mixed solvent of them at a temperature from 0° C. to a reflux temperature of the solvent.

In (Production Method A), the compound of Formula (I)-a and the compound of Formula (I)-b are included in the compound of Formula (I).

<Production Method B>
<When $R^2$=H in Formula (I)>

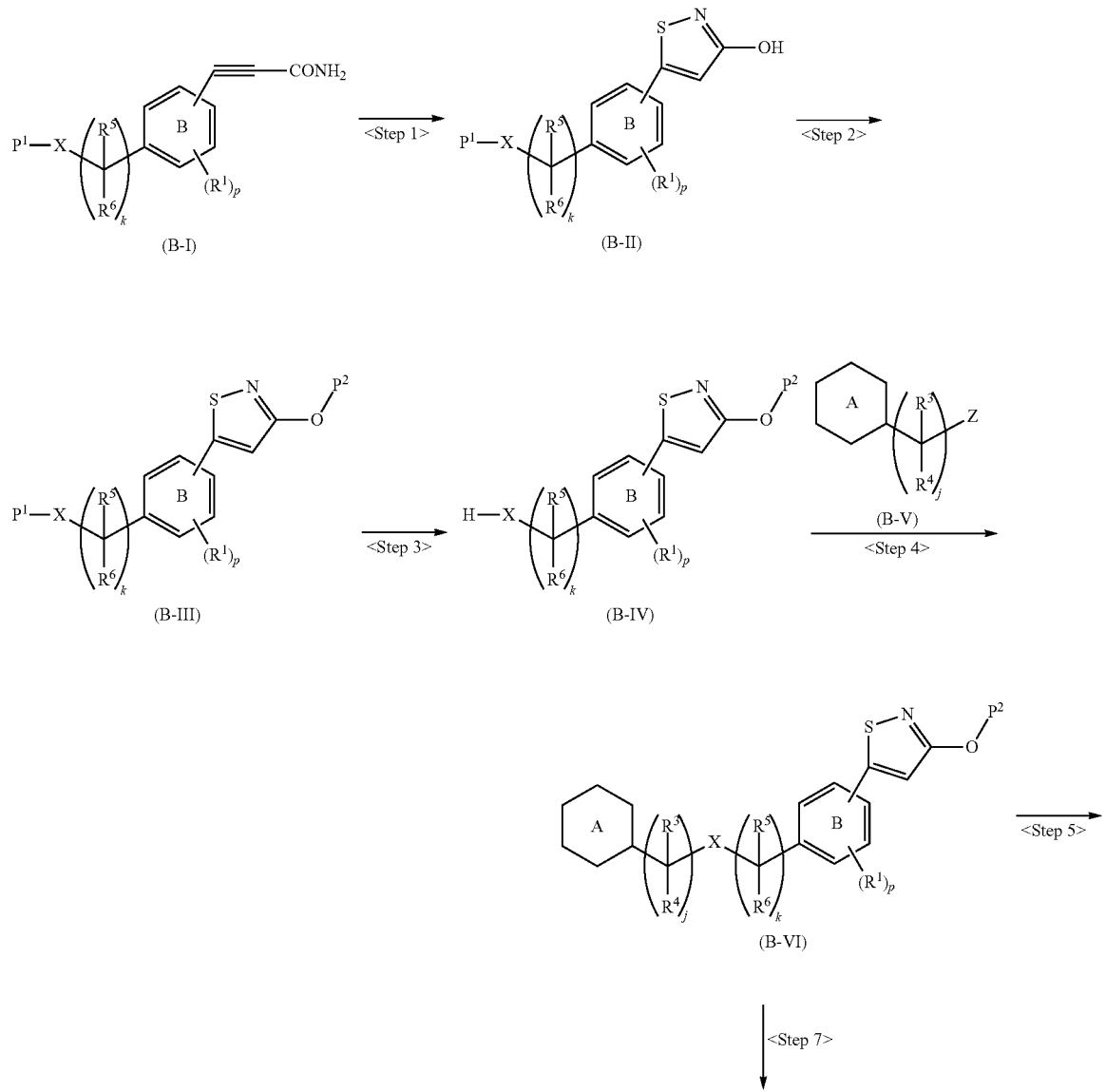

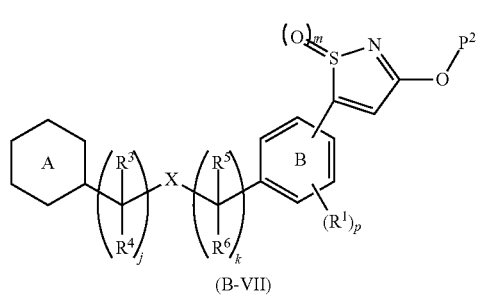

(B-VII)

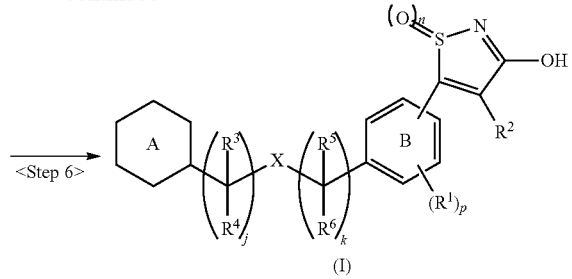

(I)

<Step 1>

A compound of Formula (B-I) is subjected to isothiazole ring formation reaction. A compound of Formula (B-II) can be produced by reacting the compound of Formula (B-I) (it is known in the art or can be easily produced from a known compound as described later in (Production Method E), and, for example, is a compound that is obtained by properly protecting a compound in Step 2 in Example 1 described later) in a similar manner to that in <Step 1> in (Production Method A).

<Step 2>

The compound of Formula (B-II) is protected with a protective group $P^2$. A compound of Formula (B-III) can be produced by reacting the compound of Formula (B-II) with the protective group $P^2$ by a method suitable for the protective group.

<Step 3>

The protective group $P^1$ in the compound of Formula (B-III) is deprotected. A compound of Formula (B-IV) (for example, a compound in Step 2 in Example 8 described later) can be produced by deprotecting the protective group $P^1$ in the compound of Formula (B-III) by a method suitable for the protective group.

<Step 4>

The compound of Formula (B-IV) is subjected to substitution reaction with a compound of Formula (B-V).

<When Z≠Hydroxy Group>

In accordance with a method known in the literature, for example, the methods described in [*Jikken Kagaku Koza* (Experimental Chemistry Course), the fourth edition, vol. 20, Organic Synthesis II, Alcohol and Amine, pp. 187-200 and 284-292 (1992), Maruzen Co., Ltd.] and [*Jikken Kagaku Koza* (Experimental Chemistry Course), the fourth edition, vol. 20, Organic Synthesis VI, Hetero Element- or Main Group Metal Element-Containing Compound, pp. 319-350 (1992), Maruzen Co., Ltd.], a compound of Formula (B-VI) can be produced by the substitution reaction of the compound of Formula (B-IV) in the presence of the compound of Formula (B-V) in the presence or absence of a base such as triethylamine, pyridine, sodium hydride, sodium hydroxide, and potassium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<When Z=Hydroxy Group, X≠—$NR^7$—, and k=0>

In accordance with a method known in the literature, for example, the method described in [Journal of Medicinal Chemistry, vol. 51 (23), pp. 7640-7644 (2008)], a compound of Formula (B-VI) (for example, compounds in Examples 4-1 and 8-3 described later) can be produced by Mitsunobu reaction of the compound of Formula (B-IV) in the presence of the compound of Formula (B-V) in the presence of an organo-phosphorus compound such as triphenylphosphine and an azo compound such as azodicarboxylic acid ester and azodicarboxylic amide in a reaction inert solvent such as a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

The compound of Formula (B-V) used in this step is known in the art or can be produced from a corresponding known compound in accordance with a method known in the literature as described in (Production Method N), (Production Method O), (Production Method P), and (Production Method Q) below. For example, it can be produced from a corresponding compound in accordance with the methods described in [WO 2005/063729 pamphlet, Reference Examples 2 and 3 and the like], [WO 2008/001931 pamphlet, Reaction Scheme 2, Reference Examples 15-19, and the like], and [WO 2009/054423 pamphlet, Production Examples 12, 24, and 37 and the like]. Examples of the compound of Formula (B-V) include compounds that are obtained by properly protecting the compounds in Reference Example 2, Reference Example 3, Example 10-3, Example 124-2, and the like described later.

<When n≠0>

<Step 5>

The sulfur atom in the compound of Formula (B-VI) is oxidized. A compound of Formula (B-VII) can be produced by reacting the compound of Formula (B-VI) in a similar manner to that in <Step 2> in (Production Method A).

<Step 6>

The protective group $P^2$ in the compound of Formula (B-VII) is deprotected. The compound of Formula (I) can be produced by deprotecting the protective group $P^2$ in the compound of Formula (B-VII) by a method suitable for the protective group.

<When n=0>

<Step 7>

The protective group $P^2$ in the compound of Formula (B-VI) is deprotected. The compound of Formula (I) can be produced by reacting the compound of Formula (B-VI) in a similar manner to that in <Step 6> in (Production Method B).

Production Method C

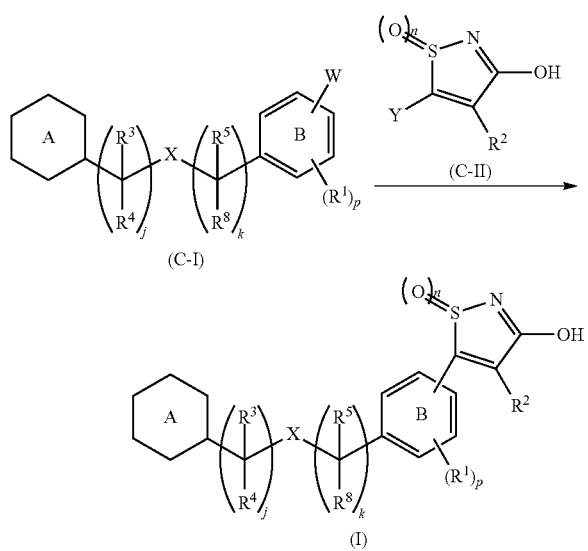

A compound of Formula (C-I) is subjected to substitution reaction with a compound of Formula (C-II). In accordance with a method known in the literature, for example, the methods described in [*Jikken Kagaku Koza* (Experimental Chemistry Course), the fifth edition, vol. 18, Synthesis of Organic Compound VI, Organic Synthesis Using Metal, pp. 327-352 (2004), Maruzen Co., Ltd.] and [Journal of Medicinal Chemistry, vol. 48 (20), pp. 6326-6339 (2005)], the compound of Formula (I) can be produced by reacting the compound of Formula (C-I) in the presence of the compound of Formula (C-II) in the presence of a palladium catalyst such as palladium (II) acetate, tetrakis triphenylphosphine palladium, tris (dibenzylideneacetone)dipalladium, bis(dibenzylideneacetone)palladium, and [1,1'-bis(diphenylphosphino)ferrocene]dichloropalladium (II), a phosphine reagent such as triphenylphosphine, tris(tert-butyl)phosphine, tris(o-tolyl)phosphine, 2-dicyclohexylphosphino-2',6'-dimethoxybiphenyl, and 2-dicyclohexylphosphino-2',4',6'-triisopropylbiphenyl, and an organic or inorganic base such as triethylamine, N,N-diisopropylethylamine, and potassium phosphate using a reaction inert solvent such as toluene, xylene, N,N-dimethylformamide, and N,N-dimethylacetamide or a mixed solvent of them at a temperature from 0° C. to a reflux temperature of the solvent. Alternatively, it can be produced using tetramethylammonium chloride, tetrabutylammonium chloride, or the like in place of the phosphine reagent in a similar method.

Formula (C-II) used in the step is a compound of Formula (G-III) below when n=0 and a compound of Formula (I-I) below when n≠0.

Production Method D

When R² ≠ Hydrogen Atom in Formula (I)

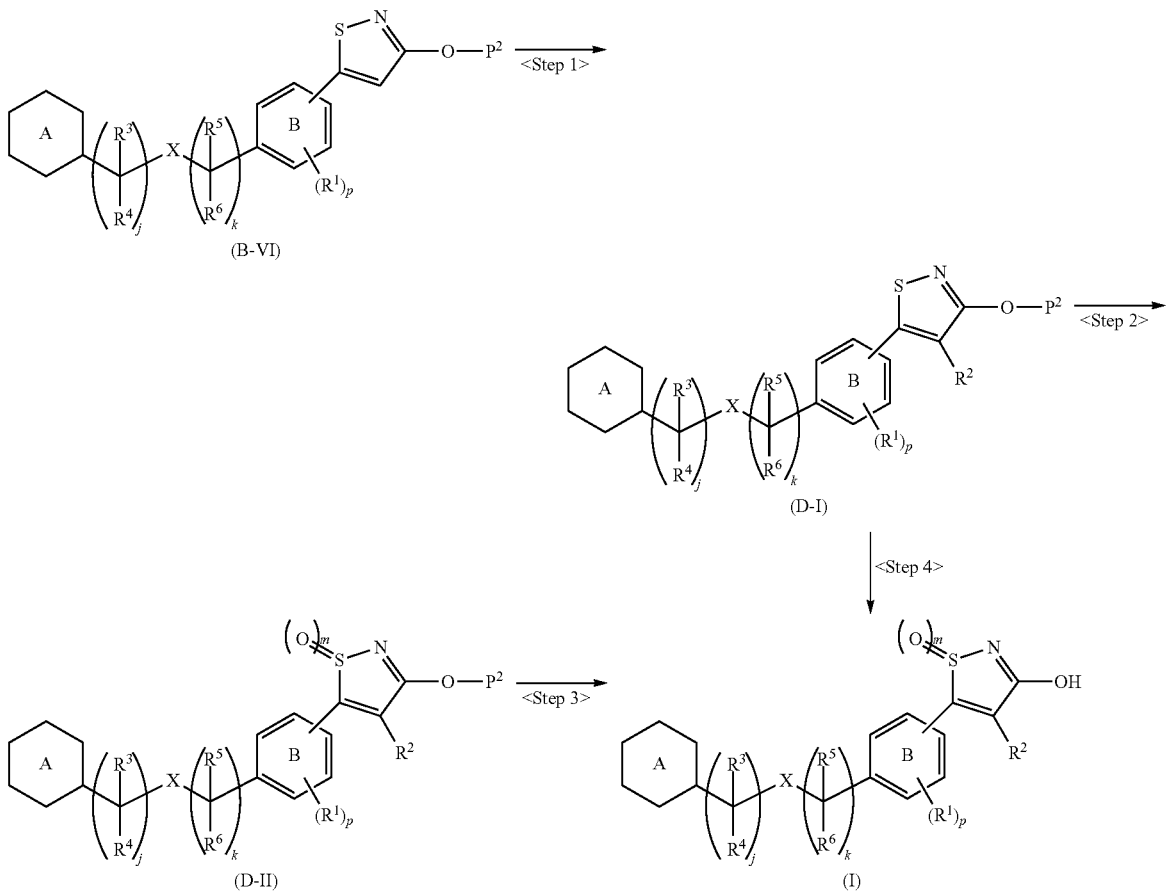

<Step 1>

The compound of Formula (B-VI) is subjected to substitution reaction on the isothiazole ring.

<When $R^2$=Halogen Atom>

In accordance with a method known in the literature, for example, the method described in [WO 1997/031906 pamphlet, Example 68], a compound of Formula (D-I) can be produced by reacting the compound of Formula (B-VI) in the presence of a corresponding halogenating agent such as N-fluorodibenzenesulfonimide, N-chlorosuccinimide, N-bromosuccinimide, and N-iodosuccinimide in the presence of a base such as n-butyllithium, lithium diisopropylamide, lithium bis(trimethylsilyl)amide, sodium bis(trimethylsilyl)amide, and potassium bis(trimethylsilyl)amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from −78° C. to a reflux temperature of the solvent.

<When $R^2$=Cyano Group>

In accordance with a method known in the literature, for example, the method described in [Tetrahedron Letters, vol. 40 (47), pp. 8193-8195 (1999)], a compound of Formula (D-I) can be produced by reacting the compound of Formula (D-I) ($R^2$=I, Br) obtained in <When $R^2$=halogen atom> in <Step 1> in (Production Method D) in the presence of a corresponding cyanating agent such as zinc cyanide and potassium ferrocyanide in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, and potassium phosphate or in the presence of tetramethylammonium chloride, tetrabutylammonium chloride, or the like in place of the phosphine reagent using a reaction inert solvent such as toluene, xylene, N,N-dimethylformamide, and N,N-dimethylacetamide or a mixed solvent of them at a temperature from 0° C. to a reflux temperature of the solvent.

<When n≠0>

<Step 2>

The sulfur atom in the compound of Formula (D-I) is oxidized. A compound of Formula (D-II) can be produced by reacting the compound of Formula (D-I) in a similar manner to that in <Step 2> in (Production Method A).

<Step 3>

The protective group $P^2$ in the compound of Formula (D-II) is deprotected. The compound of Formula (I) can be produced by reacting the compound of Formula (D-II) in a similar manner to that in <Step 6> in (Production Method B).

<When n=0>

<Step 4>

The protective group $P^2$ in the compound of Formula (D-I) is deprotected. The compound of Formula (I) can be produced by reacting the compound of Formula (D-I) in a similar manner to that in <Step 6> in (Production Method B).

(2) Next, methods for producing compounds of Formula (VI), Formula (B-I), and Formula (B-II) will be described.

The compounds of Formula (VI) and Formula (B-I) can be produced by the methods below.

<Production Method E>

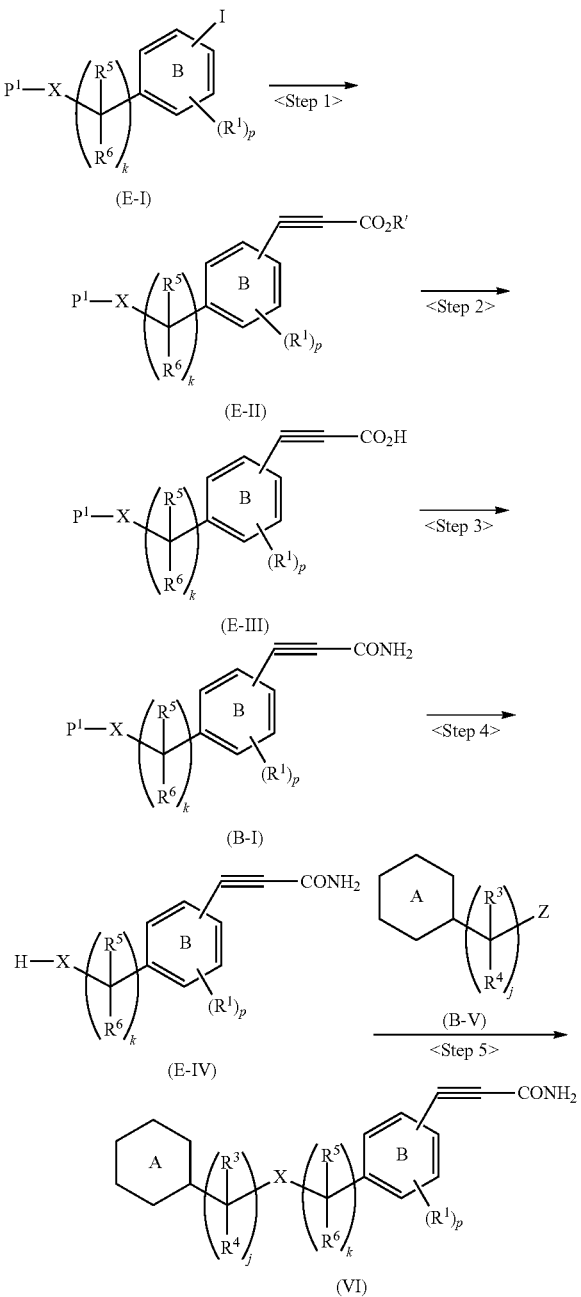

<Step 1>

A compound of Formula (E-I) is subjected to alkynylation. In accordance with a method known in the literature, for example, the methods described in [Jikken Kagaku Koza (Experimental Chemistry Course), the fourth edition, vol. 19, Organic Synthesis I, Hydrocarbon and Halogenated Compounds, pp. 318-335 (1992), Maruzen Co., Ltd.] and [WO 2008/066131 pamphlet, Reference Example 1], a compound of Formula (E-II) (for example, a compound obtained by properly protecting a compound in Reference Example 1 described later) can be produced by reacting the compound of Formula (E-I) that is known in the art or can be easily produced from a known compound, in the presence of a corresponding propiolic acid ester such as methyl propiolate and ethyl propiolate and copper oxide (II) using a reaction inert solvent such as toluene, xylene, N,N-dimethylformamide, and N,N-dimethylacetamide or a mixed solvent of them at a temperature from 0° C. to a reflux temperature of the solvent.

Alternatively, the compound of Formula (E-II) can be produced by reaction in the presence of an ortho ester of a corresponding propiolic acid such as 3,3,3-triethoxypropyne or a corresponding propiolic acid ester such as methyl propiolate and ethyl propiolate in the presence of copper iodide (I) or zinc bromide in the presence of a palladium catalyst such as palladium (II) acetate, tetrakis triphenylphosphine palladium, tris(dibenzylideneacetone)dipalladium, and [1,1'-bis (diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, potassium phosphate, and potassium carbonate using a reaction inert solvent such as toluene, xylene, N,N-dimethylformamide, and N,N-dimethylacetamide or a mixed solvent of them at a temperature from 0° C. to a reflux temperature of the solvent.

<Step 2>

The compound of Formula (E-II) is hydrolyzed. In accordance with a method known in the literature, for example, the method described in [*Jikken Kagaku Koza* (Experimental Chemistry Course), the fourth edition, vol. 22, Organic Synthesis IV, Acid, Amino Acid, and Peptide, pp. 1-43 (1992), Maruzen Co., Ltd.], a compound of Formula (E-III) (for example, a compound obtained by properly protecting a compound in Step 1 in Example 1 described later) can be produced by reacting the compound of Formula (E-II) in the presence of a base such as lithium hydroxide, sodium hydroxide, potassium hydroxide, lithium carbonate, sodium carbonate, and potassium carbonate using a reaction inert solvent such as water, methanol, ethanol, 2-propanol, N,N-dimethylformamide, 1,4-dioxane, and tetrahydrofuran or a mixed solvent of them at a temperature from 0° C. to a reflux temperature of the solvent.

<Step 3>

The compound of Formula (E-III) is subjected to amidation reaction. In accordance with a method known in the literature, for example, the method described in [*Jikken Kagaku Koza* (Experimental Chemistry Course), the fourth edition, vol. 22, Organic Synthesis IV, Acid, Amino Acid, and Peptide, pp. 191-309 (1992), Maruzen Co., Ltd.], a compound of Formula (B-I) can be produced by reacting the compound of Formula (E-III) with aqueous ammonia or ammonia gas in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxytris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), and 4-(4,6-dimethoxy-1,3,5-triazin-2-yl)-4-methylmorpholinium chloride (DMTMM) in a reaction inert solvent including a halogenated solvent such as dichloromethane and chloroform, an ether solvent such as diethyl ether and tetrahydrofuran, an aromatic hydrocarbon solvent such as toluene and benzene, a polar solvent such as N,N-dimethylformamide, and an alcoholic solvent such as methanol, ethanol, and 2-propanol or in a mixed solvent of them in the presence or absence of a base such as triethylamine and pyridine at a temperature from 0° C. to a reflux temperature of the solvent. When the compound of Formula (E-III) is converted into an acid chloride, in accordance with the method described in [*Jikken Kagaku Koza* (Experimental Chemistry Course), the fourth edition, vol. 22, Organic Synthesis IV, Acid, Amino Acid, and Peptide, pp. 144-146 (1992), Maruzen Co., Ltd.] and the like, the compound of Formula (B-I) can be produced by reacting the acid chloride in the presence of a base such as triethylamine and pyridine in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<Step 4>

The protective group $P^1$ in the compound of Formula (B-I) is deprotected. A compound of Formula (E-IV) can be produced by reacting the compound of Formula (B-I) in a similar manner to that in <Step 3> in (Production Method B).

<Step 5>

The compound of Formula (E-IV) is subjected to substitution reaction with a compound of Formula (B-V). A compound of Formula (VI) can be produced by reacting the compound of Formula (E-IV) with the compound of Formula (B-V) in a similar manner to that in <Step 4> in (Production Method B).

The compound of Formula (VI) can also be produced by the following method.

<Production Method F>

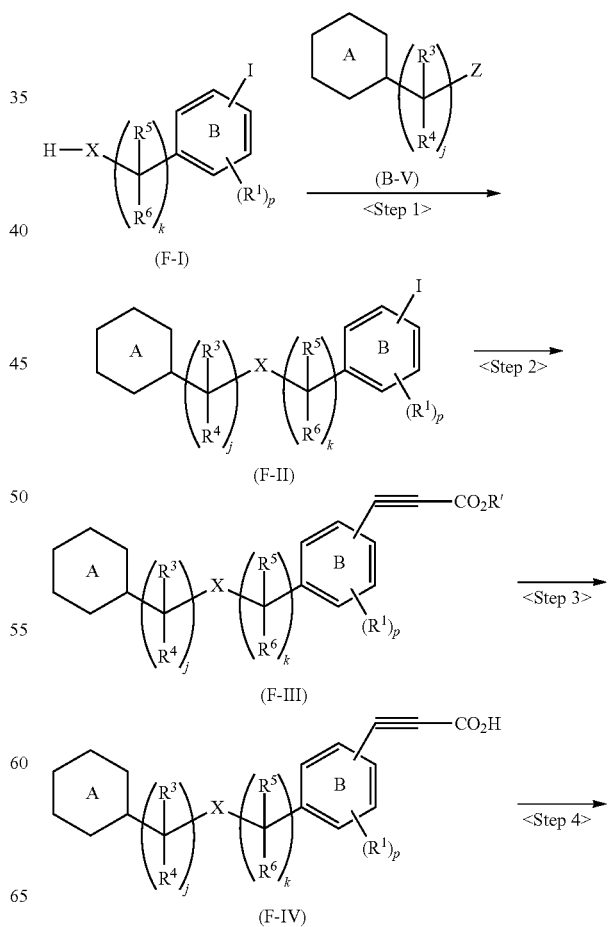

-continued

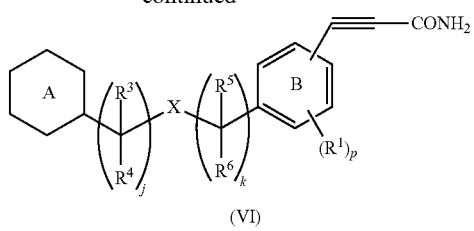

(VI)

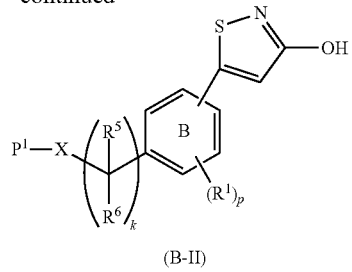

(B-II)

<Step 1>

A compound of Formula (F-I) is subjected to substitution reaction with a compound of Formula (B-V). A compound of Formula (F-II) can be produced by reacting the compound of Formula (F-I) that is known in the art or can be easily produced from a known compound with the compound of Formula (B-V) in a similar manner to that in <Step 4> in (Production Method B).

<Step 2>

The compound of Formula (F-II) is subjected to alkynylation. A compound of Formula (F-III) (for example, a compound in Step 1 in Example 3 described later) can be produced by reacting the compound of Formula (F-II) in a similar manner to that in <Step 1> in (Production Method E).

<Step 3>

The compound of Formula (F-III) is hydrolyzed. A compound of Formula (F-IV) (for example, compounds in Examples 3-2, 5-1, and 7-1 described later) can be produced by reacting the compound of Formula (F-III) in a similar manner to that in <Step 2> in (Production Method E).

<Step 4>

The compound of Formula (F-IV) is subjected to amidation reaction. A compound of Formula (VI) can be produced by reacting the compound of Formula (F-IV) in a similar manner to that in <Step 3> in (Production Method E).

The compound of Formula (B-II) can also be produced by the following method.

<Production Method G>

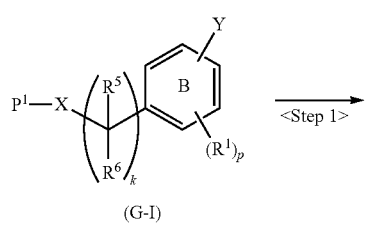

(G-I)

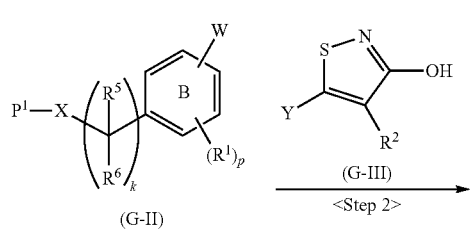

<Step 1>

A compound of Formula (G-I) is subjected to boration reaction.

<When W=Boronic Acid Ester>

In accordance with a method known in the literature, for example, the method described in [The Journal of Organic Chemistry, vol. 60, pp. 7508-2665 (1995)], a boronic acid ester of Formula (G-II) can be produced by reacting the compound of Formula (G-I) that is known in the art or can be easily produced from a known compound in the presence of a diboronic acid ester such as bis(pinacolato)diboron and bis(neopentylglycolato)diboron in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II) in the presence or absence of a phosphine reagent such as triphenylphosphine, tris(tert-butyl)phosphine, tris(o-tolyl)phosphine, and 2-dicyclohexylphosphino-2',6'-dimethoxybiphenyl and an organic or inorganic base such as triethylamine, N,N-diisopropylethylamine, and potassium acetate or in the presence or absence of tetramethylammonium chloride, tetrabutylammonium chloride, or the like in place of the phosphine reagent using a reaction inert solvent such as toluene, N,N-dimethylformamide, dimethyl sulfoxide, and 1,4-dioxane or a mixed solvent of them at a temperature from 0° C. to a reflux temperature of the solvent.

<When W=Boronic Acid>

In accordance with a method known in the literature, for example, the method described in [Chemische Berichte, vol. 42, p. 3090 (1909)], a boronic acid of Formula (G-II) can be produced by reacting the compound of Formula (G-I) using a reaction inert solvent such as toluene, tetrahydrofuran, and 1,4-dioxane or a mixed solvent of them in the presence of an alkyllithium such as n-butyllithium and sec-butyllithium, a Grignard reagent such as isopropyl magnesium chloride, or metal magnesium, with a trialkyl borate such as trimethyl borate and triisopropyl borate at a temperature from −78° C. to room temperature, followed by reaction with an acid such as hydrochloric acid and sulfuric acid at a temperature from 0° C. to a reflux temperature of the solvent.

<When W=Trifluoroborate Salt>

In accordance with a method known in the literature, for example, the method described in [Chemical Reviews, vol. 108, pp. 288-325 (2008)], a trifluoroborate salt of Formula (G-II) can be produced by reacting the compound of Formula (G-II) (W=boronic acid ester or boronic acid) obtained in <When W=boronic acid ester or boronic acid> in <Step 1> in (Production Method G) in the presence of potassium hydrogen difluoride ($KHF_2$) using a reaction inert solvent such as methanol, ethanol, and water or a mixed solvent of them at a temperature from 0° C. to a reflux temperature of the solvent.

<When W=Boronic Acid N-Methylimino Diacetic Acid (MIDA) Ester>

In accordance with a method known in the literature, for example, the method described in [Journal of Organometallic Chemistry, vol. 307 (1), pp. 1-6 (1986)], a boronic acid N-methylimino diacetic acid (MIDA) ester of Formula (G-II) can be produced by reacting the compound of Formula (G-II) (W=boronic acid) obtained in <When W=boronic acid> in <Step 1> in (Production Method G) in the presence of N-methyliminodiacetic acid (MIDA) using a reaction inert solvent such as benzene, toluene, xylene, and dimethyl sulfoxide or a mixed solvent of them at a temperature from 0° C. to a reflux temperature of the solvent.

<Step 2>

The compound of Formula (G-II) is subjected to substitution reaction with a compound of Formula (G-III). A compound of Formula (B-II) can be produced by reacting the compound of Formula (G-II) with the compound of Formula (G-III) that is known in the art or can be easily produced from a known compound in a similar manner to that in (Production Method C).

(3) Next, a method for producing the compound of Formula (C-I) will be described.

<Production Method H>

<Step 1>

A compound of Formula (C-I) is subjected to substitution reaction with a compound of Formula (B-V). A compound of Formula (H-II) can be produced by reacting the compound of Formula (H-I) that is known in the art or can be easily produced from a known compound with the compound of Formula (B-V) in a similar manner to that in <Step 4> in (Production Method B).

<Step 2>

The compound of Formula (H-II) is subjected to boration reaction. The compound of Formula (C-I) can be produced by reacting the compound of Formula (H-II) in a similar manner to that in <Step 1> in (Production Method G).

<Step 3>

The compound of Formula (H-I) is subjected to boration reaction. A compound of Formula (H-III) can be produced by reacting the compound of Formula (H-I) in a similar manner to that in <Step 1> in (Production Method G).

<Step 4>

The compound of Formula (H-III) is subjected to substitution reaction with the compound of Formula (B-V). The compound of Formula (C-I) can be produced by reacting the compound of Formula (H-III) with the compound of Formula (B-V) in a similar manner to that in <Step 4> in (Production Method B).

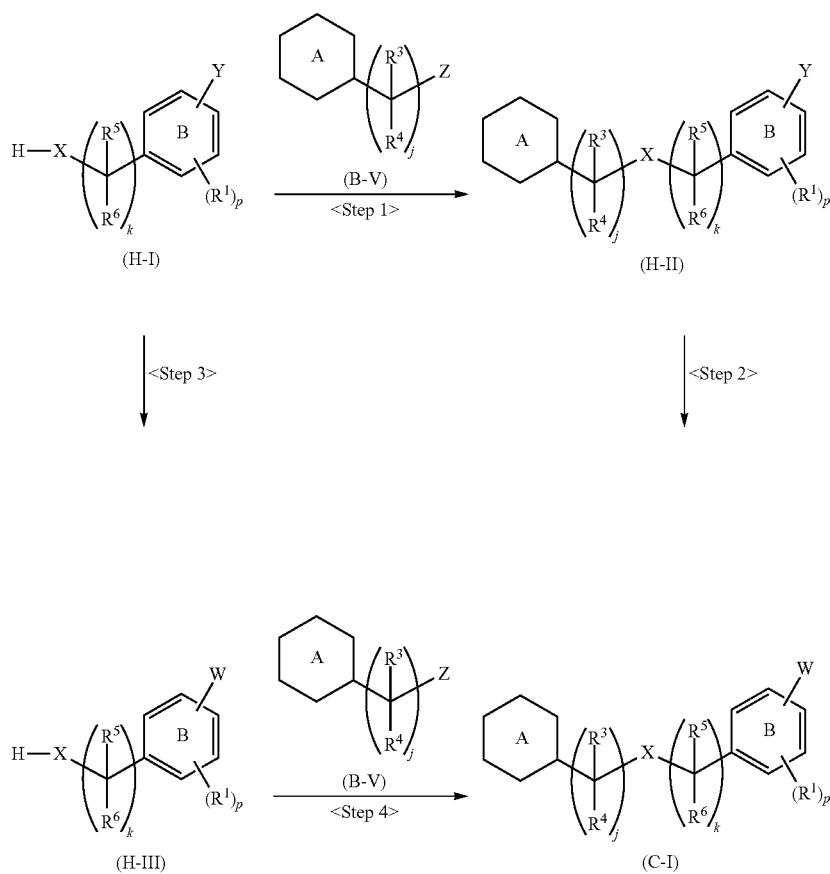

(4) Next, a method for producing the compound of Formula (C-II) will be described.

<Production Method I>

<When n is 1 or 2 in Formula (C-II) Above>

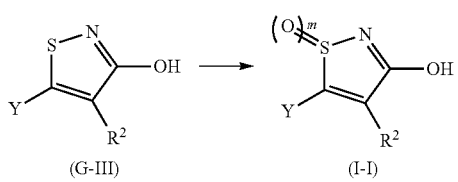

The sulfur atom in a compound of Formula (G-III) is oxidized. A compound of Formula (I-I) can be produced by reacting the compound of Formula (G-III) in a similar manner to that in <Step 2> in (Production Method A).

The compound of Formula (I-I) in (Production Method I) is included in the compound of Formula (C-II).

The compound of Formula (I-I) includes optical isomers when m is 1 in Formula (I-I). As for the optical isomers, each enantiomer can be obtained through optical resolution using column chromatography or asymmetric synthesis by a person skilled in the art based on conventional techniques. For example, each enantiomer can be obtained using preparative chromatography as described in Step 1 in Example 15 described later.

(5) The compound of Formula (I)-b can also be produced by the following method.

<Production Method J>

<When X=Oxygen Atom in Formula (I)-b Above>

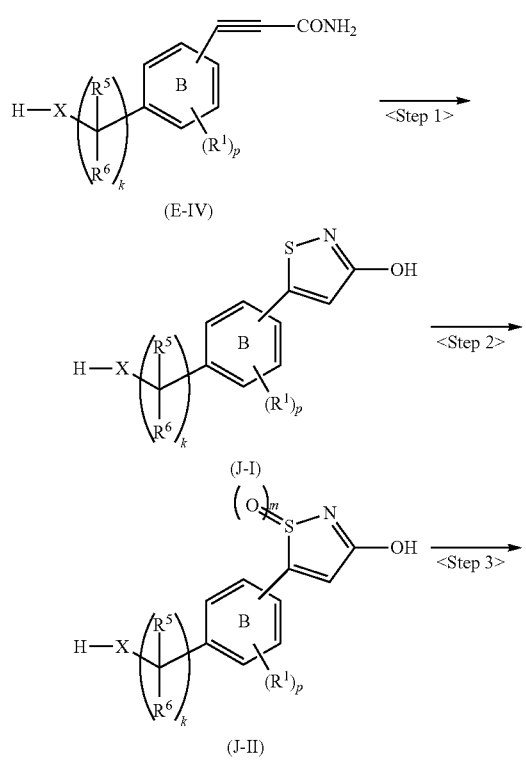

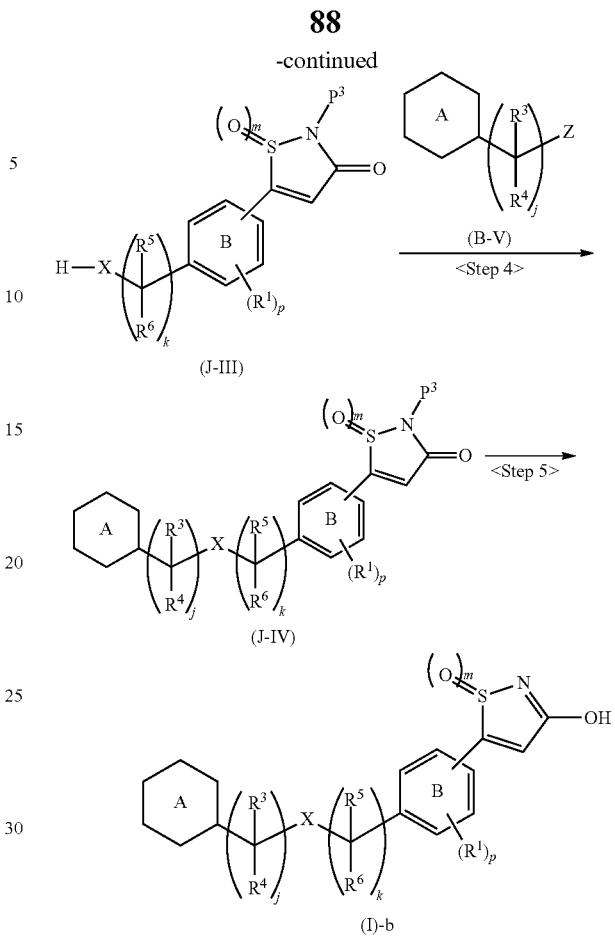

<Step 1>

A compound of Formula (E-IV) is subjected to isothiazole ring formation reaction. A compound of Formula (J-I) can be produced by reacting the compound of Formula (E-IV) in a similar manner to that in <Step 1> in (Production Method A).

<Step 2>

The sulfur atom in the compound of Formula (J-I) is oxidized. A compound of Formula (J-II) can be produced by reacting the compound of Formula (J-I) in a similar manner to that in <Step 2> in (Production Method A).

<Step 3>

The compound of Formula (J-II) is protected with a protective group $P^3$. A compound of Formula (J-III) can be produced by reacting the compound of Formula (J-II) with the protective group $P^3$ by a method suitable for the protective group.

<Step 4>

The compound of Formula (J-III) is subjected to substitution reaction with a compound of Formula (B-V). A compound of Formula (J-IV) can be produced by reacting the compound of (J-III) with the compound of Formula (B-V) in a similar manner to that in <Step 4> in (Production Method B).

<Step 5>

The protective group $P^3$ in the compound of Formula (J-IV) is deprotected. The compound of Formula (I)-b can be produced by deprotecting the protective group $P^3$ in the compound of Formula (J-IV) by a method suitable for the protective group.

<Production Method K>
<When the Ring A is Partial Structural Formula (A):

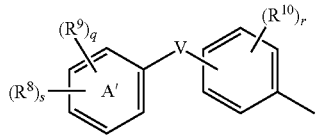

and X=Oxygen Atom in Formula (I)-B Above>

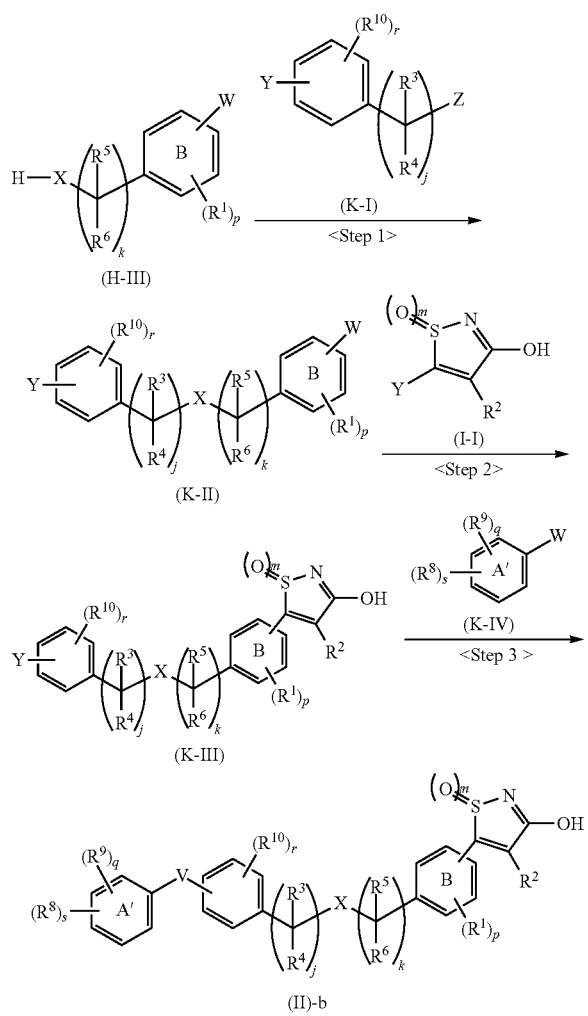

<Step 1>
A compound of Formula (H-III) is subjected to substitution reaction with a compound of Formula (K-I). A compound of Formula (K-II) can be produced by reacting the compound of Formula (H-III) that is known in the art or can be easily produced from a known compound with the compound of Formula (K-I) in a similar manner to that in <Step 4> in (Production Method B).

<Step 2>
The compound of Formula (K-II) is subjected to substitution reaction with a compound of Formula (I-I). A compound of Formula (K-III) can be produced by reacting the compound of Formula (K-II) and the compound of Formula (I-I) in a similar manner to that in (Production Method C).

<Step 3>
The compound of Formula (K-III) is subjected to substitution reaction with a compound of Formula (K-IV).
<When V=Single Bond>
A compound of Formula (II)-b can be produced by reacting the compound of Formula (K-III) with the compound of Formula (K-IV) in a similar manner to that in (Production Method C).
<When V=Oxygen Atom>
In accordance with a method known in the literature, for example, the method described in [Tetrahedron Letters, vol. 49, pp. 1851-1855 (2008)], a compound of Formula (II)-b can be produced by reacting the compound of Formula (K-III) in the presence of the compound of Formula (K-IV) in the presence of a copper catalyst such as copper iodide (I), copper bromide (I), copper chloride (I), and copper oxide (I), a base such as potassium phosphate, potassium carbonate, and sodium tert-butoxide, and an additive such as 1-butylimidazole, 1-methylimidazole, and 2,2'-bipyridine using a reaction inert solvent such as toluene, xylene, 1,4-dioxane, and N-methylpyrrolidone or a mixed solvent of them at a temperature from 0° C. to a reflux temperature of the solvent.

In accordance with another method known in the literature, for example, the method described in [Journal of the American Chemical Society, vol. 121, pp. 4369-4378 (1999)], the compound of Formula (II)-b can also be produced by reaction in the presence of the compounds of Formula (K-III) and Formula (K-IV) in the presence of a palladium catalyst such as palladium (II) acetate, tetrakis triphenylphosphine palladium, tris(dibenzylideneacetone)dipalladium, bis(dibenzylideneacetone)palladium, and [1,1'-bis(diphenylphosphino)ferrocene]dichloropalladium (II), a phosphine reagent such as (2-biphenyl)di-(tert-butyl)phosphine, 2-di-(tert-butyl)-2'-(N,N-dimethylamino)biphenyl, and 2-dicyclohexyl-2'-(N,N-dimethylamino)biphenyl, and a base such as potassium phosphate, sodium hydride, and sodium tert-butoxide using a reaction inert solvent such as dichloromethane, 1,4-dioxane, tetrahydrofuran, toluene, and N,N-dimethylformamide or a mixed solvent of them at a temperature from 0° C. to a reflux temperature of the solvent.

The compound of Formula (K-IV) used in this step is known in the art or can be easily produced from a known compound. Specifically, in accordance with a method known in the literature, for example, the methods described in [WO 2005/063729 pamphlet, Reference Example 1 and the like], [WO 2008/001931 pamphlet, <Step 4A> in Reaction Scheme 2, Reference Examples 1 and 54, and the like], and [WO 2009/054423 pamphlet, Production Example 37 and the like], a corresponding halogenated derivative can be produced from a corresponding compound, and the compound of Formula (K-IV) can be produced by boration reaction of the halogenated derivative in a similar manner to that in <Step 1> in (Production Method G).

<Production Method L>
<When the Ring A is Partial Structural Formula (AA'):

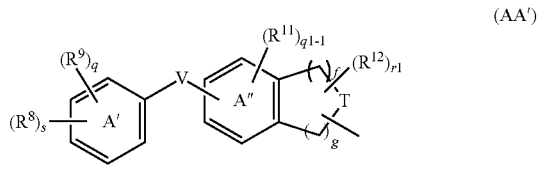

and X=Oxygen Atom in Formula (I)-b Above>

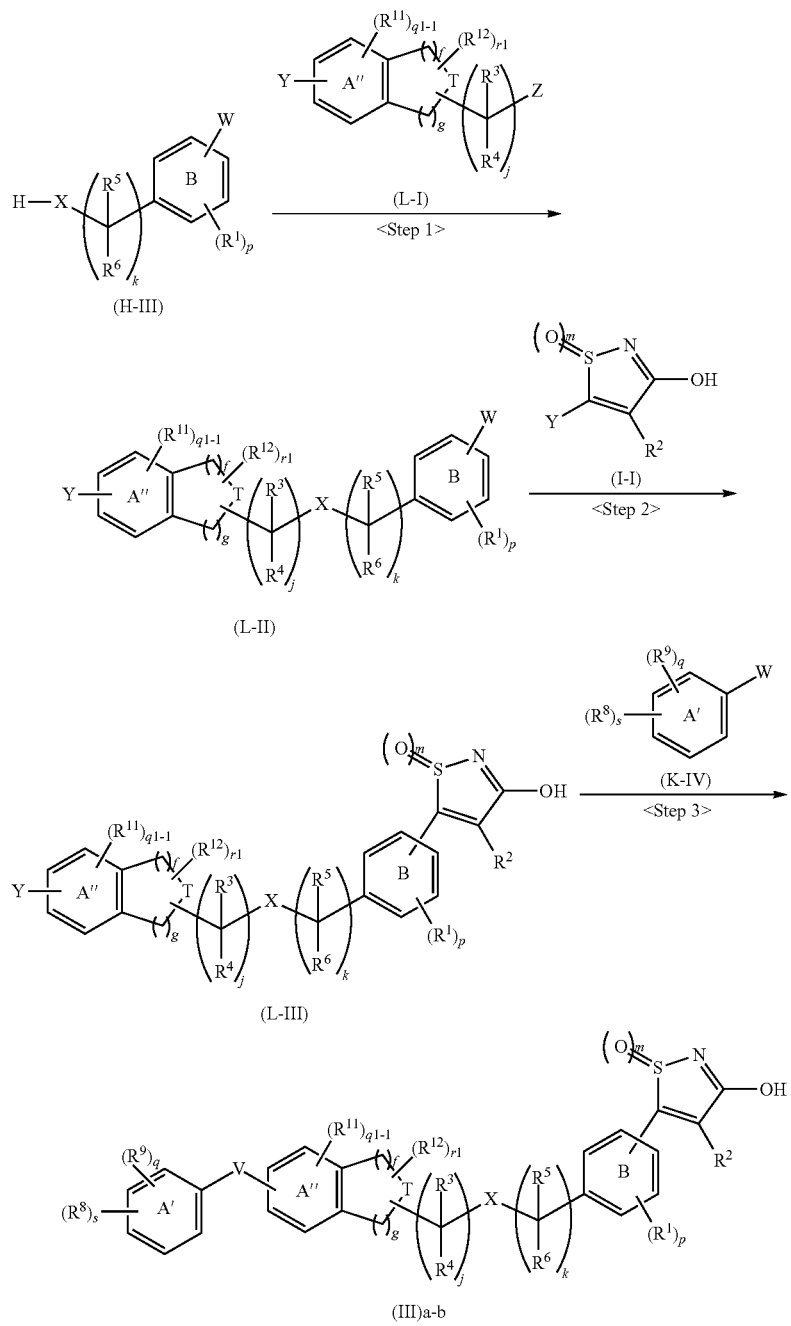

<Step 1>

A compound of Formula (H-III) is subjected to substitution reaction with a compound of Formula (L-I). A compound of Formula (L-II) can be produced by reacting the compound of Formula (H-III) that is known in the art or can be easily produced from a known compound with the compound of Formula (L-I) in a similar manner to that in <Step 4> in (Production Method B).

<Step 2>

The compound of Formula (L-II) is subjected to substitution reaction with a compound of Formula (I-I). A compound of Formula (L-III) can be produced by reacting the compound of Formula (L-II) with the compound of Formula (I-I) in a similar manner to that in (Production Method C).

<Step 3>

The compound of Formula (L-III) is subjected to substitution reaction with a compound of Formula (K-IV). Each compound of Formula (III)a-b can be produced by reacting the compound of Formula (L-III) with the compound of Formula (K-IV) in a similar manner to that in <Step 3> in (Production Method K).

The compound of Formula (L-I) includes optical isomers when a carbon atom in the ring including T is an asymmetric carbon by bonding the carbon atom to the linker moiety including Z. Such isomers are known in the art or can be easily produced from a known compound. Each enantiomer can be obtained through optical resolution using column chromatography or asymmetric synthesis by a person skilled in the art based on conventional techniques. For example, the isomers are separated with an optical resolution column, and each absolute configuration can be determined in accordance with [Agric. Biol. Chem., vol. 46 (10), pp. 2579-2585 (1982)]. Furthermore, the enantiomers can be obtained in accordance with the method described in [WO 2009/157418 pamphlet, Example 51 and Example 52].

Each enantiomer of Formula (L-II), Formula (L-III), and Formula (III)a-b (for example, compounds in Example 66 and Example 107 described later) can be produced using such an enantiomer.

(6) The compound of Formula (E-IV) can also be produced by the following method.

<Production Method M>

<When X=Oxygen Atom in Formula (E-IV) Above>

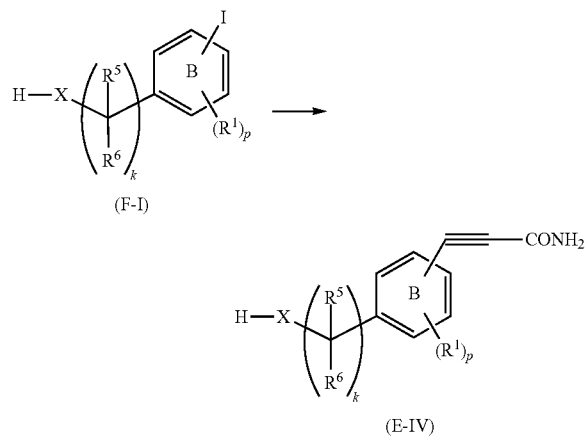

A compound of Formula (F-I) is subjected to alkynylation. The compound of Formula (E-IV) can be produced by reacting the compound of Formula (F-I) that is known in the art or can be easily produced from a known compound with propiolic amide in a similar manner to that in <Step 1> in (Production Method E).

(7) Hereinafter, the method for producing the compound of Formula (B-V) of the present invention will be described in further detail. As typical examples, methods for producing a compound of Formula (Ba-V) having Partial Structural Formula (A) above and a compound of Formula (Bb-V) having Partial Structural Formula (AA') above will be described.

<Production Method N>

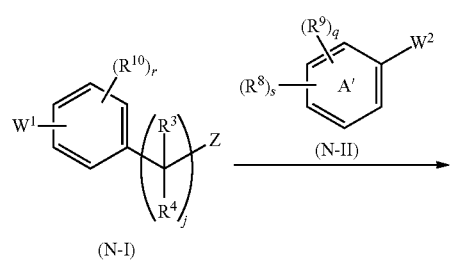

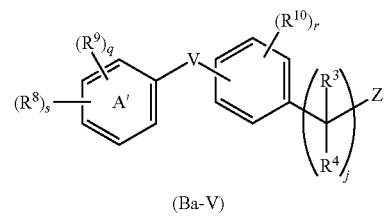

A compound of Formula (N-I) is subjected to substitution reaction on the benzene ring.

<When V=Single Bond>

A compound of Formula (Ba-V) can be produced by reacting the compound of Formula (N-I) that is known in the art or can be easily produced from a known compound with a compound of Formula (N-II) in a similar manner to that in (Production Method C).

<When V=Oxygen Atom>

In accordance with a method known in the literature, for example, the method described in [Tetrahedron Letters, vol. 44, pp. 3863-3865 (2003)], a compound of Formula (Ba-V) can be produced by reacting the compound of Formula (N-I) in the presence of a compound of Formula (N-II) in the presence of a copper catalyst such as copper (II) acetate and copper (II) trifluoroacetate and a base such as triethylamine, N,N-diisopropylethylamine, and pyridine using a reaction inert solvent such as dichloromethane, 1,4-dioxane, tetrahydrofuran, and N,N-dimethylformamide or a mixed solvent of them at a temperature from 0° C. to a reflux temperature of the solvent.

The compound of Formula (N-II) used in this step is known in the art or can be easily produced from a known compound. Specifically, in accordance with a method known in the literature, for example, the methods described in [WO 2005/063729 pamphlet, Reference Example 1 and the like], [WO 2008/001931 pamphlet, <Step 4A> in Reaction Scheme 2, Reference Examples 1 and 54, and the like], and [WO 2009/054423 pamphlet, Production Example 37 and the like], a corresponding halogenated derivative can be produced from a corresponding compound. Furthermore, a boronic acid derivative can be produced by boration reaction of the halogenated derivative in a similar manner to that in <Step 1> in (Production Method G).

<Production Method O>

<When j=1, $R^3$, $R^4$=H, and Z=OH in Formula (Ba-V) Above>

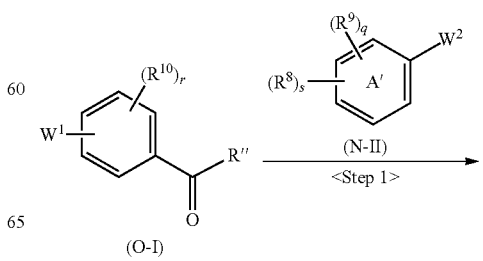

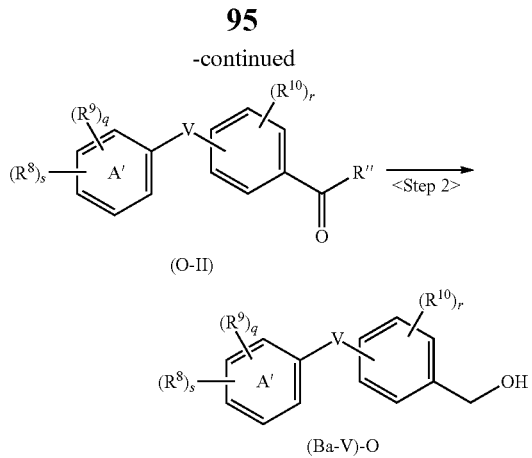

(O-II)

(Ba-V)-O

<Step 1>

A compound of Formula (O-I) is subjected to substitution reaction on the benzene ring.

<When V=Single Bond>

A compound of Formula (O-II) can be produced by reacting the compound of Formula (O-I) that is known in the art or can be easily produced from a known compound with a compound of Formula (N-II) in a similar manner to that in <When V=single bond> in (Production Method N).

<When V=Oxygen Atom>

A compound of Formula (O-II) can be produced by reacting the compound of Formula (O-I) with a compound of Formula (N-II) in a similar manner to that in <When V=oxygen atom> in (Production Method N).

<Step 2>

The compound of Formula (O-II) is subjected to reduction. In accordance with a method known in the literature, for example, the methods described in [*Jikken Kagaku Koza* (Experimental Chemistry Course), the fourth edition, vol. 26, Organic Synthesis VIII, Asymmetric Synthesis, Reduction, Sugar, and Labelled Compound, pp. 234-245 (1992), Maruzen Co., Ltd.] and the like, a compound of Formula (Ba-V)-O can be produced by reacting the compound of Formula (O-II) in the presence of sodium borohydride, diisobutyl aluminum hydride (DIBAH), lithium aluminum hydride (LAH), lithium triethoxyaluminum hydride, borane-tetrahydrofuran ($BH_3 \cdot THF$), or borane-dimethyl sulfide ($BH_3 \cdot Me_2S$), and the like using a reaction inert solvent including an ether solvent such as diethyl ether, tetrahydrofuran, 1,2-dimethoxyethane, and 1,4-dioxane, a halogenated solvent such as dichloromethane, chloroform, and 1,2-dichloroethane, and an alcoholic solvent such as methanol and ethanol or a mixed solvent of them at a temperature from 0° C. to a reflux temperature of the solvent.

In accordance with a method known in the literature, for example, the methods described in [WO 2005/063729 pamphlet, Reference Examples 2 and 3 and the like], [WO 2008/001931 pamphlet, Reaction Scheme 2, Reference Examples 15-19, and the like], and [WO 2009/054423 pamphlet, Production Examples 12, 24, and 37 and the like], the compound of Formula (Ba-V)-O can also be produced from a corresponding compound.

<Production Method P>

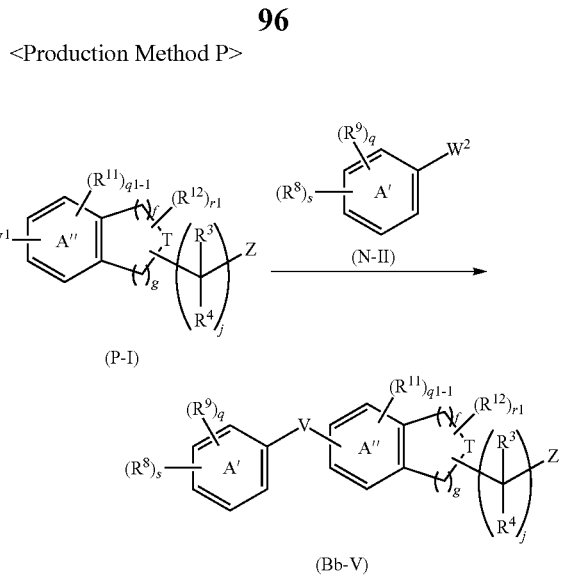

A compound of Formula (P-I) is subjected to substitution reaction on the ring A".

<When V=Single Bond>

A compound of Formula (Bb-V) can be produced by reacting the compound of Formula (P-I) that is known in the art or can be easily produced from a known compound with a compound of Formula (N-II) in a similar manner to that in <When V=single bond> in (Production Method N).

<When V=Oxygen Atom>

A compound of Formula (Bb-V) can be produced by reacting the compound of Formula (P-I) with the compound of Formula (N-II) in a similar manner to that in <When V=oxygen atom> in (Production Method N).

<Production Method Q>

<When j=0 and Z=OH in Formula (Bb-V) Above>

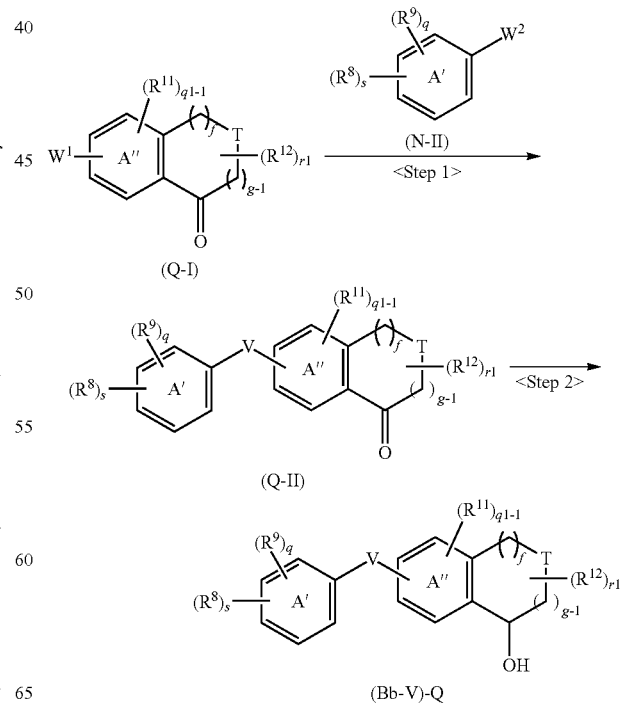

<Step 1>

A compound of Formula (Q-I) is subjected to substitution reaction on the ring A″.

<When V=Single Bond>

A compound of Formula (Q-II) can be produced by reacting the compound of Formula (Q-I) that is known in the art or can be easily produced from a known compound with a compound of Formula (N-II) in a similar manner to that in <When V=single bond> in (Production Method N).

<When V=Oxygen Atom>

A compound of Formula (Q-II) can be produced by reacting the compound of Formula (Q-I) with a compound of Formula (N-II) in a similar manner to that in <When V=oxygen atom> in (Production Method N).

<Step 2>

The compound of Formula (Q-II) is subjected to reduction. A compound of Formula (Bb-V)-Q can be produced by reacting the compound of Formula (Q-II) in a similar manner to that in <Step 2> in (Production Method N).

The Formula (Bb-V)-Q can also be produced from a corresponding compound in accordance with a method known in the literature, for example, the methods described in [WO 2005/063729 pamphlet, Reference Examples 2 and 3 and the like], [WO 2008/001931 pamphlet, Reaction Scheme 2, Reference Examples 15-19, and the like], and [WO 2009/054423 pamphlet, Production Examples 12, 24, and 37 and the like].

(8) The compound of Formula (C-I) can also be produced by the following method.

<Production Method R>

<When the Ring A is Partial Structural Formula (A) Above, j=1, k=0, $R^3$, $R^4$=H, and X=$NR^7$ in Formula (C-I) Above>

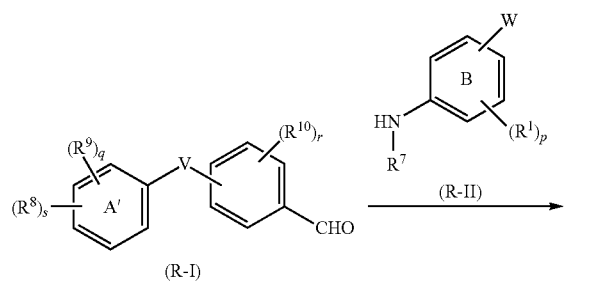

A compound of Formula (R-I) is subjected to reductive amination. In accordance with a method known in the literature, for example, the method described in [The Journal of Organic Chemistry, vol. 61, pp. 3849-3862 (1996)], a compound of Formula (Ca-I) can be produced by reacting the compound of Formula (R-I) (the compound of Formula (R-I) is included in the compound of Formula (O-II), and can be easily produced from a known compound as described in <Step 1> in (Production Method O) above) with a compound of Formula (R-II) (it is known in the art or can be easily produced from a known compound) in the presence of a reducing agent such as sodium triacetoxyborohydride and sodium cyanoborohydride in the presence or absence of a catalytic amount of acetic acid using a reaction inert solvent such as dichloromethane, 1,2-dichloroethane, tetrahydrofuran, acetonitrile, and toluene or a mixed solvent of them at a temperature from 0° C. to a reflux temperature of the solvent.

<Production Method S>

<When the Ring A is Partial Structural Formula (AA):

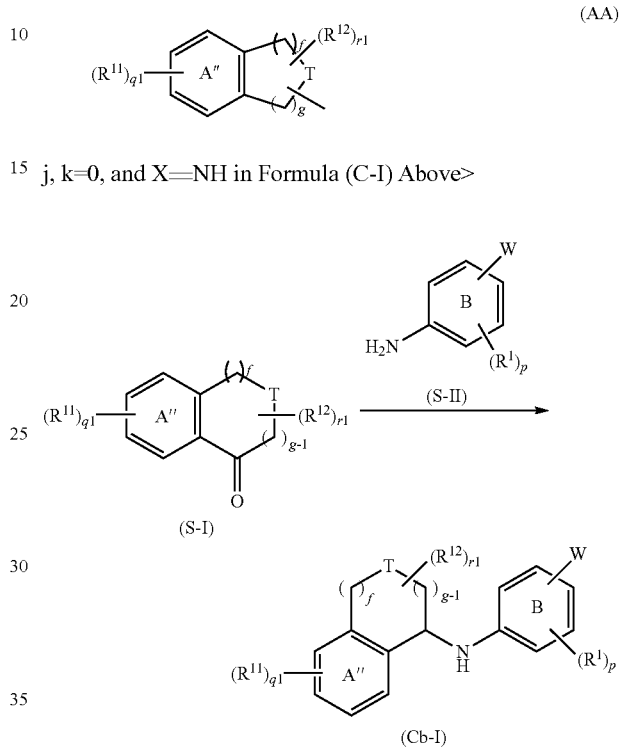

j, k=0, and X=NH in Formula (C-I) Above>

A compound of Formula (S-I) is subjected to reductive amination. A compound of Formula (Cb-I) can be produced by reacting the compound of Formula (S-I) (it is known in the art or can be easily produced from a known compound as described above in <Step 1> in (Production Method Q) and the like) with a compound of Formula (S-II) (it is known in the art or can be easily produced from a known compound) in a similar manner to that in (Production Method R).

[Concomitant Drug Containing Compound of the Present Invention]

The compound and pharmaceutical composition of the present invention can be used in combination with other drugs or medicines by a general method performed in medical practice. Particularly, such combination is used for the prevention, progress delay, and therapies of the mediating state of the GPR40 agonist, and is further particularly used against at least one disease selected from a group consisting of diabetes (Type 1 diabetes, Type 2 diabetes, and borderline type diabetes (impaired glucose tolerance (IGT) and/or impaired fasting glycemia (IFG))), insulin resistance, hyperinsulinemia, obesity, adiposity, and various diseases derived from or related to there diseases.

Examples of an insulin sensitizer and an anti-diabetic drug include 1) PPAR gamma agonists (specifically, pioglitazone, rosiglitazone, troglitazone, ciglitazone, darglitazone, englitazone, netoglitazone, etc.), 2) biguanide agents (specifically, metformin, buformin, phenformin, etc.), 3) sulfonylureas (specifically, tolbutamide, acetohexamide, chlorpropamide, glibenclamide, gliclazide, glipizide, glimepiride, glipentide, gliquidone, glisolamide, tolazamide, etc.), 4) rapid-acting insulin secretagogues (specifically, nateglinide, mitiglinide, repaglinide, etc.), 5) alpha-glucosidase inhibitors (specifically, acarbose, voglibose, miglitol, camiglibose, adiposin, emiglitate, pradimicin Q, salbostatin, etc.), 6) insulin or insulin derivatives (specifically, insulin zinc suspensions, insulin lispro, insulin aspart, regular insulin, NPH insulin, insulin glargine, insulin detemir, mixed insulin, etc.), 7) GLP-1 and GLP-1 agonists (specifically, exenatide, liraglutide, lixisenatide, taspoglutide, etc.), 8) DPP-IV inhibitors (specifically, sitagliptin, vildagliptin, alogliptin, saxagliptin, linagliptin, teneligliptin, NVP-DPP-728, etc.), 9) alpha-2 antagonists (specifically, midaglizole, isaglidole, deriglidole, idazoxan, efaroxan, etc.), and 10) SGLT2 inhibitors. Examples of the insulin sensitizer and the anti-diabetic drug also include a combination drug containing two or more of the components described above (specifically, pioglitazone/metformin, pioglitazone/glimepiride, etc.).

Examples of the insulin sensitizer and the anti-diabetic drug also include a hypolipidemic agent and a dyslipidemia therapeutic agent. Examples of the hypolipidemic agent and the dyslipidemia therapeutic agent include 1) omega-3 fatty acids (specifically, ethyl icosapentate (EPA-E preparation), docosahexaenoic acid (DHA), etc.), 2) HMG-CoA reductase inhibitors (specifically, atorvastatin, simvastatin, pitavastatin, itavastatin, fluvastatin, lovastatin, pravastatin, rivastatin, rosuvastatin, etc.), 3) HMG-CoA synthase inhibitors, 4) cholesterol absorption inhibitors (specifically, ezetimibe), 5) acyl-CoA-cholesterol acyltransferase (ACAT) inhibitors, 6) CETP inhibitors, 7) squalene synthase inhibitors, 8) antioxidants (specifically, probucol, etc.), 9) PPAR alpha agonists (specifically, clofibrate, etofibrate, fenofibrate, bezafibrate, ciprofibrate, gemfibrozil, KRP-101, etc.), 10) PPAR delta agonists, 11) LXR agonists, 12) FXR agonists (specifically, INT-747, etc.), 13) MTTP inhibitors, 14) squalene epoxidase inhibitors, and 15) bile acid absorption inhibitors (specifically, cholestyramine, colestipol, etc).

In addition, examples of the insulin sensitizer and the anti-diabetic drug also include an anti-obesity agent. Specific examples of the anti-obesity agent include 1) CB-1 receptor antagonists (specifically, rimonabant, SR-147778, BAY-65-2520, etc.), 2) monoamine reuptake inhibitors (specifically, sibutramine, mazindol, etc.), 3) serotonin reuptake inhibitors (specifically, fluoxetine, paroxetine, etc.), 4) lipase inhibitors (specifically, orlistat, cetilistat, etc.), 5) neuropeptide Y (NPY) receptor antagonists (specifically, S-2367, etc.), 6) peptide YY (PYY) receptor antagonists, and 7) adrenergic beta-3 receptor agonists (specifically, KRP-204, TRK-380/TAC-301, etc).

The therapies can be performed in combination with not only other drugs, but also other therapies. Examples of the therapies include the improvement of lifestyle through weight control, exercise therapy, and diet therapy, and radiotherapy.

Against GPR40-involving diseases except for diabetes and obesity, the therapies can be performed in combination with drugs used in respective fields.

Examples of the concomitant drug include, preferably, PPAR gamma agonists (more preferably, pioglitazone and rosiglitazone), biguanide agents (more preferably, metformin and buformin), sulfonylureas (more preferably, glibenclamide, gliclazide, and glimepiride), rapid-acting insulin secretagogues (more preferably, nateglinide and mitiglinide), alpha-glucosidase inhibitors (more preferably, acarbose, voglibose, and miglitol), insulin or insulin derivatives, and DPP-IV inhibitors (more preferably, sitagliptin, vildagliptin, and alogliptin).

The combined use of the concomitant drug and conventional drugs against the diseases described above enables the dosage of the conventional drugs to be reduced, which can reduce the side effects of the conventional drugs. It is needless to say the combining method using the drugs is not limited to the diseases, and the drugs to be used in combination are not limited to the compounds exemplified above.

To use the compound of the present invention in combination with the drug to be used in combination, they may be individual preparations or be a drug combination. In the form of individual preparations, the compound and the drug can be taken at the same time or can be administered at different time.

[Producing Preparations of Prophylactic or Therapeutic Agents of the Present Invention]

The medicines of the present invention are administered in the form of pharmaceutical compositions.

The pharmaceutical compositions of the present invention may include at least the compound of Formula (I) or Formula (II) of the present invention and are produced in combination with pharmaceutically acceptable additives. More in detail, various dosage forms can be prepared by appropriately combining the compound of the present invention and, for example, excipients (for example, lactose, white soft sugar, mannitol, microcrystalline cellulose, silicic acid, corn starch, and potato starch), bonding agents (for example, celluloses (hydroxypropylcellulose (HPC), hydroxypropylmethylcellulose (HPMC), microcrystalline cellulose, saccharide (lactose, mannitol, white soft sugar, sorbitol, erythritol, and xylitol), starches (corn starch and potato starch), gelatinized starch, dextrin, polyvinylpyrrolidone (PVP), macrogol, polyvinyl alcohol (PVA)), lubricants (for example, magnesium stearate, calcium stearate, talc, and carboxymethylcellulose), disintegrants (for example, starches (corn starch and potato starch), sodium carboxymethyl starch, carmellose, carmellose calcium, croscarmellose sodium, and, crospovidone), coating agents (for example, celluloses (hydroxypropylcellulose (HPC), hydroxypropylmethylcellulose (HPMC), aminoalkylmethacrylate copolymers E, and methacrylic copolymers LD), plasticizers (for example, triethyl citrate and macrogol), masking agents (for example, titanium oxide), colorants, flavoring agents, antiseptics (for example, benzalkonium chloride and p-hydroxybenzoate esters), tonicity agents (for example, glycerin, sodium chloride, calcium chloride, mannitol, and dextrose), pH regulators (for example, sodium hydroxide, potassium hydroxide, sodium carbonate, hydrochloric acid, sulfuric acid, and buffer solutions such as phosphate buffer solutions), stabilizing agents (for example, sugar, sugar alcohol, and xanthan gum), dispersants, antioxidants (for example, ascorbic acid, butylated hydroxyanisole (BHA), propyl gallate, and dl-alpha-tocopherol), buffer agents, preservatives (for example, paraben, benzyl alcohol, and benzalkonium chloride), perfumes (for example, vanillin, l-menthol, and rose oil), solubilizing agents (for example, polyoxyethylene hydrogenated castor oil, polysorbate 80, polyethylene glycol, phospholipid cholesterol, and triethanolamine), absorbefacients (for example, sodium glycolate, sodium edetate, sodium caprate, acylcarnitines, and limonene), gelators, suspending agents, emulsifiers, and, generally used suitable additives and solvents.

Examples of the various dosage forms include tablets, capsules, granules, powderes, pills, aerosols, inhalants, ointments, adhesive patches, suppositories, injections, troches, liquids, spirits, suspensions, extracts, and elixirs. The dosage forms can be administered to patients through oral administration, subcutaneous injection, intramuscular injection, intranasal administration, transdermal administration, intravenous injection, intraarterial injection, perineural administration, epidural administration, administration in subdural cavity, intraventricular administration, rectal administration, inhalation, or the like.

The dosage of the compound of the present invention is generally, 0.005 mg to 3.0 g, preferably, 0.05 mg to 2.5 g, and more preferably, 0.1 mg to 1.5 g per day for adults, but can be reduced or increased as needed depending on symptoms or administration routes.

The compound can be administered as a whole at once or be separately administered by being divided into two to six doses through oral administration or parenteral administration, or can be administered through repeated administration such as intravenous infusion.

The present specification incorporates, as references, the whole publications cited in the present specification, for example, related-art documents, publications of unexamined applications, patent publications, and other patent documents.

PHARMACOLOGICAL TEST EXAMPLES

The present invention is specifically described below with reference to test examples but is not limited to them.

The following pharmacological test examples 1 to 7 provide methods for investigating the efficacy of the compound of the present invention.

Pharmacological Test Example 1

Agonist Action on GPR40 of Human Origin

A CHO cell strain stably expressing GPR40 of human origin was used to determine the agonist action of a subject compound. This cell strain was seeded in a clear bottom 96 well plate at $4\times10^4$ cells/100 µL/well. The cell strain was cultured in a $CO_2$ incubator overnight using a Ham's F-12 medium containing a 10% fetal bovine serum, 100 U/mL penicillin, 0.1 mg/mL streptomycin, and 400 µg/mL Geneticin. Calcium 4 Assay Kit (Molecular Devices) was used as a fluorescent calcium indicator. One mL of 77 mg/mL probenecid (Invitrogen) was added to 100 mL of a calcium indicator solution to prepare a solution (loading solution) mixed with a 20 mM HEPES-containing Hanks' balanced salt solution (HBSS) in equal proportions. 200 µL of the loading solution was added to the cells from which the culture solution was removed, and the cells were cultured in a $CO_2$ incubator for 1 hour. The subject compound was diluted with a 20 mM HEPES-containing HBSS and was added to the cells by 50 µL, and the fluctuation of the $Ca^{2+}$ concentration was measured by an intracellular ion analyzer. The $EC_{50}$ value of the subject compound was calculated using the dose-response curve of fluorescence intensity variation. Table 1 indicates the compound of the present invention having an $EC_{50}$ value of less than 0.3 µM as A and the compound of the present invention having an $EC_{50}$ value of 0.3 µM or more and less than 3 µM as B.

TABLE 1

| Compound of Examples | $EC_{50}$ values |
|---|---|
| 2 | B |
| 6 | B |
| 8 | A |
| 9 | B |
| 10 | A |

TABLE 1-continued

| Compound of Examples | $EC_{50}$ values |
|---|---|
| 11 | A |
| 12 | A |
| 13 | A |
| 17 | A |
| 19 | A |
| 22 | A |
| 23 | A |
| 24 | A |
| 27 | A |
| 28 | A |
| 29 | A |
| 31 | A |
| 33 | A |
| 35 | A |
| 37 | B |
| 42 | A |
| 43 | A |
| 44 | A |
| 47 | A |
| 49 | A |
| 51 | A |
| 52 | B |
| 55 | A |
| 59 | A |
| 61 | A |
| 63 | A |
| 64 | A |
| 66 | A |
| 67 | B |
| 68 | A |
| 69 | A |
| 71 | B |
| 72 | A |
| 78 | A |
| 80 | A |
| 83 | B |
| 85 | A |
| 86 | A |
| 88 | B |
| 89 | A |
| 91 | B |
| 93 | B |
| 95 | B |
| 96 | A |
| 106 | B |
| 107 | A |
| 109 | A |
| 111 | A |
| 117 | B |
| 118 | A |
| 119 | A |
| 120 | B |
| 121 | B |
| 124 | A |
| 125 | A |
| 126 | A |
| 129 | A |
| 131 | A |
| 132 | A |
| 135 | A |
| 138 | A |
| 139 | A |
| 141 | B |

Pharmacological Test Example 2

Oral Glucose Tolerance Test for Mouse

A reduction of blood glucose excursion of a subject compound after glucose load is examined using male C57BL/6J mice fasted overnight. The subject compound is suspended with a solvent (for example, 0.5% carboxymethylcellulose) and is orally administered before glucose load. The solvent is singly administered to the control group. Blood specimen collection is performed before compound administration (pre-administration blood collection), after compound administration and immediately before glucose load, during glucose load, after 15, 30, 60, and 120 minutes, and the blood glucose level of the collected blood is measured. The reduction of blood glucose excursion is obtained by orally administering a dosage of 3 to 10 mg/kg of the preferable compound of the compound of the present invention.

Pharmacological Test Example 3

Solubility Test (1) DMSO Precipitation Solubility (Kinetic Solubility)

A 10 mM DMSO solution of the compound of the present invention is added to a 50 mM phosphate buffer solution (pH 7.4) to the final concentration of 100 μM. The resultant solution is incubated with stirring at 600 rpm for 1.5 hours at room temperature, and then is filtered through a filter plate (4 μm, MultiScreen Solubility Filter Plate, Millipore). The absorbance of the obtained filtrate is measured at the maximum absorption wavelength using a plate reader (Powerscan HT, (Dainippon Pharmaceutical)). In this process, DMSO solutions of known concentration of the test compound (1, 3, 10, 30, and 100 μM) are prepared as standard solutions for a calibration curve. The absorbance of each of the standard solutions is measured to generate a calibration curve. The solubility (μM) of the compound is calculated using the absorbance values of the filtrate and the standard solutions.

(2) Crystal Solubility (Thermodynamic Solubility)

The compound of the present invention is added to water so as to be 1 mg/mL. The resultant solution is incubated at 37° C. for 24 hours, and then is centrifuged. The obtained supernatant is analyzed by HPLC to detect the peak at the maximum absorption wavelength, and thus, the peak area is calculated. Similarly, DMSO solutions of known concentration of the test compound (0.03, 0.1, 0.3, 1, 3, and 10 μg/mL) are prepared as standard solutions for a calibration curve. The peak area of each of the standard solutions is measured. The solubility (μg/mL) of the compound is calculated using the peak areas of the obtained calibration curve.

Pharmacological Test Example 4

Metabolic Stability Test

The 10 mM DMSO solution of the compound of the present invention is added to a solution containing liver microsome (human or mouse; XenoTech) and a NADPH generating systems (water containing beta-NADP, Glucose-6-Phosphate, G-6-PDH(Y), and $MgCl_2$) to the final concentration of 1 μM. The resultant solution is incubated at 37° C. for 20 minutes, and then the reaction is terminated by adding acetonitrile. The reaction solution is filtrated by centrifugation using a filter plate (MultiScreen HTS-HV plate, Millipore). The test compound in the filtrate is measured by high performance liquid chromatogram/mass spectrometry. Similarly, a sample with a reaction time of 0 is measured as a control, and the decomposition rate (%) is calculated from the ratio between the microsome reaction sample and the control.

Pharmacological Test Example 5 hERG Inhibition Test by Patch-Clamp Technique

An effect against a human ether-a-go-go related gene (hERG) channel is measured using a fully automatic patch-clamp system (Patchliner (Nanion)). To confirm the hERG $I_{kr}$, current of a cell (hERG-HEK (Upstate)), the membrane potential is kept at −80 mV, and a depolarizing pulse is applied to the cell on a regular basis. After the generated current became stable, a test compound is added. The effect of the test compound against the hERG channel is confirmed from the change in tail current induced by a repolarizing pulse at −40 mV for 0.5 second subsequent to a depolarizing pulse at 40 mV for 0.5 second. The stimulation is performed at a frequency of once every 10 seconds. The measurement is performed at room temperature. The hERG channel inhibition rate is calculated as the reduction rate (suppression rate) of a tail current two minutes after the application of the test compound relative to the maximum tail current before the application.

The calculated suppression rate shows the possibility that drug-induced QT prolongation followed by fatal side effects (such as ventricular tachycardia and sudden death).

Pharmacological Test Example 6

Pharmacokinetics Study (Mouse Cassette Dosing PK)

The compound of the present invention is orally administrated in a single dose to 7- or 8-week-old male C57BL/6J Jcl at 1 mg/kg (the vehicle is DMSO:Tween 80:ultrapure water=1:1:8 and 10 mL/kg), and then the blood is collected from the abdominal aorta 0.25, 0.5, 1, and 2 hours after dosing. The blood is centrifuged (3000 rpm, 15 minutes, and 4° C.) to obtain plasma, and the test compound in the plasma is measured by high performance liquid chromatogram/mass spectrometry. Similarly, standard solutions of known concentration of the test compound (0.01, 0.02, 0.05, 0.1, 0.2, 0.5, and 1 μg/mL) are measured to generate a calibration curve. The concentration (μg/mL) of the compound in the plasma is calculated using the calibration curve, and the maximum concentration in the plasma is indicated by $C_{max}$ (μg/mL).

Pharmacological Test Example 7

Safety Assessment Study

The compound of the present invention is orally administrated in a single dose to mice or rats. When no death and no noticeable behavior disorder is observed, the safety of the compound of the present invention is shown.

As a result, the compound of the present invention showed an excellent GPR40 agonist action and reduced blood glucose excursion in the single oral dose glucose tolerance test using normal mice. In the safety assessment study, no abnormality indicates low toxicity of the compound of the present invention.

By performing the tests described above, the compound of the present invention is confirmed to have favorable properties in one regard, such as solubility, metabolic stability, pharmacokinetics, and the avoidance of an hERG channel inhibition.

Accordingly, the compound of the present invention is expected to be used as a GPR40 agonist for insulin secretagogues and prophylactic and/or therapeutic agents against diabetes (particularly, Type 2 diabetes or borderline type diabetes), obesity, and adiposity.

PREPARATION EXAMPLE

Hereinafter, Examples of the pharmaceutical compositions of the present invention are described.

Preparation Example 1
tablets

| | |
|---|---|
| Compound of Example 2 | 100 g |
| Lactose | 137 g |
| Microcrystalline cellulose | 30 g |
| Hydroxypropylcellulose | 15 g |
| Sodium carboxymethyl starch | 15 g |
| Magnesium stearate | 3 g |

The above components are weighed and then are uniformly mixed. The mixture is formed into tablets to have a weight of 150 mg.

Preparation Example 2
film coating

| | |
|---|---|
| Hydroxypropylmethylcellulose | 9 g |
| Macrogol 6000 | 1 g |
| Titanium oxide | 2 g |

The above components are weighed. Subsequently, hydroxypropylmethylcellulose and macrogol 6000 are dissolved into water to disperse titanium oxide. The resultant liquid is film coated on 300 g of the tablets of Preparation Example 1 to obtain film-coated tablets.

Preparation Example 3
capsules

| | |
|---|---|
| Compound of Example 6 | 50 g |
| Lactose | 435 g |
| Magnesium stearate | 15 g |

The above components are weighed and then are uniformly mixed. The mixture is filled into adequate hard capsules by a weight of 300 mg with a capsule inserter to produce capsules.

Preparation Example 4
capsules

| | |
|---|---|
| Compound of Example 8 | 100 g |
| Lactose | 63 g |
| Corn starch | 25 g |
| Hydroxypropylcellulose | 10 g |
| Talc | 2 g |

The above components are weighed, and then the compound of Example 8, lactose, and corn starch are uniformly mixed. A hydroxypropylcellulose aqueous solution is added to the resultant mixture to produce granules by wet granulation. Talc is uniformly mixed with the granules, and the mixture is filled into adequate hard capsules by a weight of 200 mg to produce capsules.

Preparation Example 5
powders

| | |
|---|---|
| Compound of Example 11 | 200 g |
| Lactose | 790 g |
| Magnesium stearate | 10 g |

The above components are weighed and then are uniformly mixed to produce 20% powdered drugs.

Preparation Example 6
granulse and fine granules

| | |
|---|---|
| Compound of Example 13 | 100 g |
| Lactose | 200 g |
| Microcrystalline cellulose | 100 g |
| Partly pregelatinized starch | 50 g |
| Hydroxypropylcellulose | 50 g |

The above components are weighed, and the compound of Example 13, lactose, microcrystalline cellulose, and partly pregelatinized starch are uniformly mixed. A hydroxypropylcellulose (HPC) aqueous solution is added to the resultant mixture to produce granules or fine granules by wet granulation. The granules or fine granules are dried to be formulations of granules or fine granules.

EXAMPLES

Next, in order to describe the present invention further in detail, there are described Examples which should not be construed as limiting the scope of the present invention.

For the measurement of the nuclear magnetic resonance spectrum (NMR), JEOL JNM-ECX400 FT-NMR (manufactured by JEOL Ltd.), JEOL JNM-ECX300 FT-NMR (manufactured by JEOL Ltd.), or JEOL JNM-EX270 FT-NMR (manufactured by JEOL Ltd.) were used. As the LC-Mass, Waters Fraction Lynx MS system (manufactured by Waters Corporation) was used and as the column, Sun Fire column (4.6 mm×5 cm, 5 μm) (manufactured by Waters Corporation) was used. As a mobile phase, methanol:0.05% acetic acid aqueous solution=1:9 (0 min)→10:0 (5 min)→10:0 (7 min) (gradient condition) or methanol:0.05% trifluoro acetic acid aqueous solution=1:9 (0 min)→10:0 (5 min)→10:0 (7 min) (gradient condition) was used. For the preparative isolation system, gradient conditions accordingly changed according to the type of the compound were used. In the present invention, in the preparative chromatography of a mixture of optical isomers, an enantiomer having a high elution rate is expressed as (A) and an enantiomer having a low elution rate is expressed as (B).

Reference Example 1

Synthesis of Ethyl 3-(4-hydroxyphenyl)Propiolate

According to a method described in [WO 2008/066131 pamphlet, (Reference Example 1)], the subject compound (10.5 g) was obtained from 4-iodophenol (33.0 g) as a light yellow solid.

Reference Example 2

Synthesis of 3-(2,6-dimethylphenyl)Benzyl Chloride

To 3-(2,6-dimethylphenyl)benzyl alcohol (51.9 g) synthesized according to a method described in [WO 2004/041266 pamphlet, (Reference Example 200)], thionyl chloride (130 mL) was gradually added and the resultant reaction mixture was heated under reflux for 3 hours. The reaction mixture was gradually dropped into ice-cooled methanol (inside temperature: 15° C. or less) and the resultant reaction mixture was adjusted to around pH 8 with saturated sodium bicarbonate water, followed by extracting the reaction mixture with ethyl acetate. The resultant organic phase was washed sequentially with a saturated aqueous sodium bicarbonate, water, and saturated saline, and was dried over anhydrous sodium sulfate. From the organic phase, the solvent was distilled off under reduced pressure and the resultant residue was purified by silica gel column chromatography (eluate: n-hexane:ethyl acetate=70:1) to obtain the subject compound (36.1 g) as a colorless oil.

Reference Example 3

Synthesis of 2-((3-bromo-2-methylphenyl)Methoxy) Tetrahydro-2H-pyran

To a suspension of 3-bromo-2-methylbenzyl alcohol (7.80 g) in dichloromethane (78.0 mL), 3,4-dihydro-2H-pyran (7.08 mL) and pyridinium p-toluenesulfonate (0.97 g) were sequentially added and the resultant reaction mixture was stirred at room temperature for 1.5 hours. From the reaction mixture, the solvent was distilled off under reduced pressure and the resultant residue was purified by silica gel column chromatography (eluate: n-hexane:ethyl acetate=100:0 to 95:5) to obtain the subject compound (11.6 g) as a colorless oil.

Reference Example 4

Synthesis of 4-(5,5-dimethyl-1,3,2-dioxaborinan-2-yl)Phenol

A solution of 4-hydroxyphenyl boronic acid (15.0 g) and 2,2-dimethyl-1,3-propanediol (11.4 g) in toluene (100 mL) was heated under reflux for 6 hours 30 minutes (using Dean-Stark apparatus). The resultant reaction mixture was allowed to cool and stand still and therefrom, a precipitates were filtered out and the solvent was distilled off under reduced pressure to obtain the subject compound (21.6 g) as a light gray solid.

Reference Example 5

Synthesis of 4-(5-bromo-4,6-dimethylpyridin-2-yloxy)-2-methylbutan-2-ol

According to a method described in [WO 2009/054423 pamphlet, (Production Example 37)], from 5-bromo-4,6-dimethyl-2-hydroxypyridine (1.50 g) and 3-hydroxy-3-methylbutyl 4-methylbenzenesulfonate (2.11 g), the subject compound (1.50 g) was obtained as a colorless oil.

Reference Example 6

Synthesis of 4-hydroxyphenyl Boronic Acid N-methylimino Diacetic Acid Ester

A suspension of 4-hydroxyphenyl boronic acid (10.3 g) and N-methylimino diacetic acid (11.0 g) in dimethyl sulfoxide (37 mL)-toluene (333 mL) was heated to reflux for 1.5 hours. From the resultant reaction mixture, toluene was distilled off under reduced pressure and the reaction mixture was poured into water (400 mL), followed by stirring the resultant reaction mixture for 1.5 hours. From the reaction mixture, precipitates were filtered and the precipitates were washed with water, followed by drying the deposit under reduced pressure to obtain the subject compound (16.4 g) as a gray white solid.

Example 1

Synthesis of 5-(4-((3-phenoxyphenyl)methoxy)phenyl)isothiazol-3-ol

<Step 1> Synthesis of 3-(4-hydroxyphenyl)Propiolic Acid

To a solution of the compound (1.00 g) obtained in (Reference Example 1) in ethanol (5.0 mL)-water (5.0 mL), lithium hydroxide monohydrate (0.49 g) was added and the resultant reaction mixture was stirred at 60 to 80° C. for 3 hours. To the reaction mixture, a 1N hydrochloric acid aqueous solution was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain the subject compound (0.85 g) as a beige solid.

<Step 2> Synthesis of 3-(4-hydroxyphenyl)Propiolic Acid Amide

To a solution of the compound (0.20 g) obtained in (Example 1) <Step 1> in tetrahydrofuran (3.0 mL), 1,1'-carbonylimidazole (0.24 g) was added and the resultant reaction mixture was stirred at room temperature for 1 hour. To the reaction mixture, 28% aqueous solution of ammonia (1.0 mL) was added and the reaction mixture was stirred at room temperature over one night. To the reaction mixture, water was added and the resultant reaction mixture was extracted with ethyl acetate. The organic phase was washed sequentially with water and saturated saline and was dried over anhydrous sodium sulfate. From the organic phase, the solvent was distilled off under reduced pressure and the resultant residue was purified by silica gel column chromatography twice (NH-silica gel: eluate; ethyl acetate:methanol=100:0 to 0:100, and silica gel: eluate; n-hexane:ethyl acetate=70:30 to 0:100) to obtain the subject compound (45 mg) as a white solid.

<Step 3> Synthesis of 3-(4-((3-phenoxyphenyl)Methoxy)Phenyl)Propiolic Acid Amide To a solution of the compound (40 mg) obtained in (Example 1) <Step 2>, 3-phenoxybenzyl alcohol (65 μL), and triphenylphosphine (98 mg) in tetrahydrofuran (1.0 mL), diethyl azodicarboxylate (2.2 M toluene solution) (0.17 mL) was added under ice-cooling and the resultant reaction mixture was stirred at room temperature over one night. To the reaction mixture, water was added and the resultant reaction mixture was extracted with ethyl acetate. The organic phase was washed sequentially with water and saturated saline and was dried over anhydrous sodium sulfate. From the organic phase, the solvent was distilled off under reduced pressure and the resultant residue was purified by silica gel chromatography (eluate; n-hexane:ethyl acetate=60:40 to 20:80) to obtain a crude product (75 mg) of the subject compound.

<Step 4> Synthesis of 5-(4-((3-phenoxyphenyl)
Methoxy)Phenyl)Isothiazol-3-ol To a solution of the compound (70 mg) obtained in (Example 1) <Step 3> in ethanol (3.0 mL), sodium hydrosulfide n-hydrate (34 mg) was added and the inside of the reaction system was purged with nitrogen, followed by heating the resultant reaction mixture under reflux for 3 hours. To the reaction mixture, a 1N aqueous solution of hydrochloric acid was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain a residue and to a solution of the residue in ethanol (2.0 mL), potassium carbonate (85 mg) and iodine (52 mg) were sequentially added, followed by stirring the resultant reaction mixture at room temperature for 2 hours. To the reaction mixture, a 1N hydrochloric acid and a aqueous solution of sodium thiosulfate were sequentially added and the resultant reaction mixture was stirred at room temperature for 2 hours. The reaction mixture was extracted with ethyl acetate and the organic phase was washed with saturated saline and was dried over anhydrous sodium sulfate. From the organic phase, the solvent was distilled off under reduced pressure and the resultant residue was purified by thin-layer silica gel chromatography (eluate; n-hexane:ethyl acetate=67:33) to obtain a crude product (20 mg) of the subject compound.

Example 2

Synthesis of 5-(4-((3-phenoxyphenyl)Methoxy)Phenyl)Isothiazol-3-ol 1-oxide

To a suspension of the compound (20 mg) obtained in (Example 1) <Step 4> in dichloromethane (1.0 mL), m-chloro perbenzoic acid (content: 65%) (18 mg) was added and the resultant reaction mixture was stirred at room temperature for 3 hours. To the reaction mixture, a aqueous solution of sodium thiosulfate was added and the resultant reaction mixture was extracted with ethyl acetate. The organic phase was washed with saturated saline and was dried over anhydrous sodium sulfate. From the organic phase, the solvent was distilled off under reduced pressure and the resultant residue was purified by thin-layer silica gel column chromatography three times (first time/eluate; n-hexane:ethyl acetate=67:33, second time/eluate; ethyl acetate:methanol=80:20 (NH-silica gel), and third time/eluate; n-hexane:ethyl acetate=67:33) to obtain the subject compound (1.3 mg) as a light yellow solid.

Example 3

Synthesis of 5-(4-(benzyloxy)Phenyl)Isothiazol-3-ol

<Step 1> Synthesis of Ethyl 3-(4-(benzyloxy)Phenyl)Propiolate

To a solution of the compound (1.00 g) obtained in (Reference Example 1) in N,N-dimethylformamide (10.0 mL), benzyl bromide (0.69 mL) and potassium carbonate (1.60 g) were sequentially added and the resultant reaction mixture was stirred at room temperature over one night. To the reaction mixture, water was added and the resultant reaction mixture was extracted with ethyl acetate. The organic phase was washed sequentially with water and saturated saline and was dried over anhydrous sodium sulfate. From the organic phase, the solvent was distilled off under reduced pressure and the resultant residue was purified by silica gel chromatography (eluate; n-hexane:ethyl acetate=100:0 to 80:20) to obtain the subject compound (1.44 g) as a white solid.

<Step 2> Synthesis of 3-(4-(benzyloxy)phenyl)Propiolic Acid

To a solution of the compound (1.0 g) obtained in (Example 3) <Step 1> in ethanol (5.0 mL)-water (5.0 mL), lithium hydroxide monohydrate (0.18 g) was added and the resultant reaction mixture was stirred at room temperature for 1 hour and at 50° C. for 30 minutes. To the reaction mixture, a 1N hydrochloric acid was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain the subject compound (0.87 g) as a white solid.

<Step 3> Synthesis of 3-(4-(benzyloxy)phenyl)Propiolic Acid Amide

To a solution of the compound (0.72 g) obtained in (Example 3) <Step 2> in tetrahydrofuran (15.0 mL), triethylamine (0.44 mL) was added. To the resultant reaction mixture, ethyl chloroformate (0.30 mL) was added under ice-cooling and the reaction mixture was stirred for 15 minutes. To the reaction mixture, a 28% aqueous solution of ammonia (1.50 mL) was added and the resultant reaction mixture was stirred under ice-cooling further for 5 minutes. To the reaction mixture, ice water was added and the resultant reaction mixture was extracted with ethyl acetate. The organic phase was washed sequentially with a 1N hydrochloric acid aqueous solution, a 1N sodium hydroxide aqueous solution, water, and saturated saline and was dried over anhydrous sodium sulfate. From the organic phase, the solvent was distilled off under reduced pressure to obtain the subject compound (0.64 g) as a white solid.

<Step 4> Synthesis of 5-(4-(benzyloxy)Phenyl)Isothiazol-3-ol

To a suspension of sodium hydrosulfide n-hydrate (0.33 g) in ethanol (3.0 mL), the compound (0.50 g) obtained in (Example 3) <Step 3> was added and the resultant reaction mixture was heated under reflux for 2 hours. To the reaction mixture, a 1 N hydrochloric acid was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain a residue and to a suspension of the residue in ethanol (2.0 mL), potassium carbonate (0.83 g) and iodine (0.51 g) were sequentially added, followed by stirring the resultant reaction mixture at room temperature over one night. To the reaction mixture, a 1 N hydrochloric acid and a aqueous solution of sodium sulfite were sequentially added and the resultant reaction mixture was stirred at room temperature. From the reaction mixture, precipitates were collected by filteration to obtain the subject compound (0.35 g) as a yellow solid.

Example 4

Synthesis of 5-(4-(benzyloxy)Phenyl)Isothiazol-3-ol 1-oxide

<Step 1> Synthesis of 5-(4-(benzyloxy)Phenyl)-3-(tert-butyldimethylsiloxy)Isothiazole To a suspension of the compound (0.10 g) obtained in (Example 3) <Step 4> and imidazole (36 mg) in N,N-dimethylformamide (2.0 mL), tert-butyldimethylsilyl chloride (80 mg) was added and the resultant reaction mixture was stirred at room temperature for 1 hour. To the reaction mixture, water was added and the resultant reaction mixture was extracted with ethyl acetate. The organic phase was washed sequentially with water, a saturated aqueous sodium bicarbonate, and saturated saline and was dried over anhydrous sodium sulfate. From the organic phase, the solvent was distilled off under reduced pressure and the resultant residue was purified by silica gel chromatography (eluate; n-hexane:ethyl acetate-90:10 to 70:30) to obtain the subject compound (0.10 g) as a light yellow solid.

<Step 2> Synthesis of 5-(4-(benzyloxy)phenyl)Isothiazol-3-ol 1-oxide

To a suspension of the compound (40 mg) obtained in (Example 4) <Step 1> in dichloromethane (4.0 mL), m-chloro perbenzoic acid (content: 65%) (35 mg) was added under ice-cooling and the resultant reaction mixture was stirred at room temperature for 3 hours. To the reaction mixture, an aqueous solution of sodium thiosulfate was added and the resultant reaction mixture was extracted with ethyl acetate. The organic phase was washed sequentially with a saturated aqueous sodium bicarbonate and saturated saline and was dried over anhydrous sodium sulfate. From the organic phase, the solvent was distilled off under reduced pressure to obtain the subject compound (29 mg) as a light yellow solid.

Example 5

Synthesis of 5-(4-(5-chloro-2,3-dihydro-1H-inden-1-yloxy)Phenyl)Isothiazol-3-ol <Step 1> Synthesis of 3-(4-(5-chloro-2,3-dihydro-1H-inden-1-yloxy)Propiolic Acid To a solution of the compound (0.20 g) obtained in (Reference Example 1), 5-chloro-2,3-dihydro-1H-inden-1-ol (0.27 g), and triphenylphosphine (0.41 g) in tetrahydrofuran (2.0 mL), diethyl azodicarboxylate (2.2 M toluene solution) (0.72 mL) was added under ice-cooling and the resultant reaction mixture was stirred at room temperature for 6 hours. To the reaction mixture, water was added and the resultant reaction mixture was extracted with ethyl acetate. The organic phase was washed with saturated saline and was dried over anhydrous sodium sulfate. From the organic phase, the solvent was distilled off under reduced pressure and the resultant residue was purified by silica gel chromatography (eluate; n-hexane:ethyl acetate=100:0 to 90:10) to obtain an ethyl ester form (0.33 g) of the subject compound. To a solution of the ethyl ester form in ethanol (2.5 mL)-water (2.5 mL), lithium hydroxide monohydrate (49 mg) was added and the resultant reaction mixture was heated with stirring at 60 to 80° C. for 3 hours. To the reaction mixture, a 1 N hydrochloric acid was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain the subject compound (0.18 g) as a light brown solid.

<Step 2> Synthesis of 3-(4-(5-chloro-2,3-dihydro-1H-inden-1-yloxy)Propiolic Acid Amide According to the method of (Example 1) <Step 2>, from the compound (0.18 g) obtained in (Example 5) <Step 1>, the subject compound (75 mg) was obtained as a light yellow solid.

<Step 3> Synthesis of 5-(4-(5-chloro-2,3-dihydro-1H-inden-1-yloxy)Isothiazol-3-ol According to the method of (Example 1) <Step 4>, from the compound (70 mg) obtained in (Example 5) <Step 2>, the subject compound (20 mg) was obtained.

Example 6

Synthesis of 5-(4-(5-chloro-2,3-dihydro-1H-inden-1-yloxy)Phenyl)Isothiazol-3-ol 1-oxide According to the method of (Example 2), from the compound (20 mg) obtained in (Example 5) <Step 3>, the subject compound (4.0 mg) was obtained as a light yellow solid.

Example 7

Synthesis of 5-(4-((3-(2,6-dimethylphenyl)Phenyl)Methoxy)Phenyl)Isothiazol-3-ol <Step 1> Synthesis of 3-(4-((3-(2,6-dimethylphenyl)Phenyl)Methoxy)Phenyl)Propiolic Acid To a solution of the compound (0.50 g) obtained in (Reference Example 1) and the compound (0.61 g) obtained in (Reference Example 2) in N,N-dimethylformamide (10.0 mL), potassium carbonate (0.40 g) and potassium iodide (44 mg) were added and the resultant reaction mixture was stirred at room temperature over one night. To the reaction mixture, water was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain a residue and to a solution of the residue in methanol (15.0 mL)-water (15.0 mL), lithium hydroxide monohydrate (0.12 g) was added, followed by heating the resultant reaction mixture under reflux for 6 hours. To the reaction mixture, a 1 N hydrochloric acid was added and the resultant reaction mixture was extracted with ethyl acetate. The organic phase was washed sequentially with water and saturated saline and was dried over anhydrous sodium sulfate. From the organic phase, the solvent was distilled off under reduced pressure and the resultant residue was triturated with n-hexane-ethyl acetate to obtain the subject compound (0.49 g) as a milky yellow solid.

<Step 2> Synthesis of 3-(4-((3-(2,6-dimethylphenyl)Phenyl)Methoxy)Phenyl)Propiolic Acid Amide To a solution of the compound (0.20 g) obtained in (Example 7) <Step 1> in dichloromethane (2.0 mL), oxalyl chloride (96 μL) and N,N-dimethylformamide (one drop) were sequentially added and the resultant reaction mixture was stirred at room temperature for 1 hour. The reaction mixture was concentrated under reduced pressure to obtain a residue and a solution of the residue in tetrahydrofuran (3.0 mL) was dropped into a 28% aqueous solution of ammonia (1.0 mL) under ice-cooling, followed by stirring the resultant reaction mixture at room temperature over one night. The reaction mixture was concentrated under reduced pressure to obtain a residue and to the residue, water was added, followed by extracting the resultant reaction mixture with ethyl acetate. The organic phase was washed sequentially with water and saturated saline and was dried over anhydrous sodium sulfate. From the organic phase, the solvent was distilled off under reduced pressure and the resultant residue was triturated with diethyl ether to obtain the subject compound (60 mg) as a white solid.

<Step 3> Synthesis of 3-(4-((3-(2,6-dimethylphenyl)Phenyl)Methoxy)Phenyl)Isothiazol-3-ol To a solution of the compound (115 mg) obtained in (Example 7) <Step 2> in ethanol (2.0 mL), sodium hydrosulfide n-hydrate (250 mg) was added and the resultant reaction mixture was heated under reflux for 2 hours. To the reaction mixture, a 1N hydrochloric acid was added and the resultant reaction mixture was extracted with ethyl acetate. The organic phase was washed sequentially with water and saturated saline and was dried over anhydrous sodium sulfate. From the organic phase, the solvent was distilled off under reduced pressure to obtain a residue, and to a solution of a half amount (65 mg) of the obtained residue (130 mg) in ethanol (2.0 mL), potassium carbonate (69 mg) and iodine (55 mg) were sequentially added, followed by stirring the resultant reaction mixture at room temperature for 2 hours. To the reaction mixture, a 1N hydrochloric acid and an aqueous solution of sodium hydrogen sulfite were sequentially added and the resultant reaction mixture was stirred at room temperature for 2 hours. The reaction mixture was extracted with dichloromethane and the organic phase was washed with saturated saline and was dried over anhydrous sodium sulfate. From the organic phase, the solvent was distilled off under reduced pressure and the resultant residue was triturated with ethyl acetate to obtain the subject compound (30 mg) as a light yellow solid.

Example 8

Synthesis of 5-(4-((3-(2,6-dimethylphenyl)Phenyl)Methoxy)Phenyl)Isothiazol-3-ol 1 Oxide

[Method A]
According to the method of (Example 2), from the compound (20 mg) obtained in (Example 7) <Step 3>, the subject compound (7.0 mg) was obtained as a light yellow solid.
[Method B]

<Step 1> Synthesis of 5-chloro-3-(methoxymethoxy)Isothiazole

To a solution of 5-chloro-isothiazol-3-ol (5.00 g) in tetrahydrofuran (50 mL), 1,8-diazabicyclo[5.4.0]undeca-7-ene (8.42 g) was added, and to the resultant reaction mixture, a solution of chloromethyl methyl ether (4.45 g) in tetrahydrofuran (25 mL) was dropped under ice-cooling at an inside temperature of 10° C. or less. After the completion of dropping, the inside temperature was elevated to room temperature and the reaction mixture was stirred for 10 minutes. To the reaction mixture, water was added and the resultant reaction mixture was extracted with ethyl acetate. The organic phase was washed with saturated saline and was dried over anhydrous sodium sulfate. From the organic phase, the solvent was distilled off under reduced pressure to obtain the subject compound (6.15 g) as a brown oil.

<Step 2> Synthesis of 4-(3-(methoxymethoxy)Isothiazol-5-yl)Phenol

To a suspension of the compound (4.00 g) obtained in (Example 8) [Method B] <Step 1>, 4-hydroxyphenyl boronic acid (4.61 g), bis(dibenzylideneacetone) palladium (1.30 g), and 2-dicyclohexylphosphino-2',6'-dimethoxybiphenyl (SPhos; 0.91 g) in 1,4-dioxane (220 mL), a 3M aqueous solution of potassium phosphate (22.3 mL) was added and the resultant reaction mixture was heated with stirring at 100° C. in a nitrogen atmosphere for 2 hours. To the reaction mixture, a 2N hydrochloric acid was added to adjust pH of the reaction mixture to 3 to 4 and the resultant reaction mixture was extracted with ethyl acetate (in process of the reaction, a precipitated insoluble product was filtered out through a pad of Celite). The organic phase was washed with saturated saline and was dried over anhydrous sodium sulfate. From the organic phase, the solvent was distilled off under reduced pressure and the resultant residue was purified by silica gel chromatography and was triturated with dichloromethane to obtain the subject compound (0.80 g) as a light yellow solid.

<Step 3> Synthesis of 5-(4-((3-(2,6-dimethylphenyl)Phenyl)Methoxy)Phenyl)-3-(Methoxymethoxy)Isothiazole According to the method of (Example 7) <Step 1>, from the compound (0.40 g) obtained in (Example 8) [Method B]<Step 2> and the compound (0.47 g) obtained in (Reference Example 2), the subject compound (0.75 g) was obtained as a colorless oil.

<Step 4> Synthesis of 5-(4-((3-(2,6-dimethylphenyl)Phenyl)Methoxy)Phenyl)Isothiazol-3-ol 1-oxide According to the method of (Example 2), from the compound (0.73 g) obtained in (Example 8) [Method B]<Step 3>, the subject compound (96 mg) was obtained as a light yellow solid.

Example 9

Synthesis of 5-(4-((3-(2,6-dimethylphenyl)Phenyl)Methoxy)Phenyl)Isothiazol-3-ol 1,1-dioxide To a suspension of the compound (30 mg) obtained in (Example 7) <Step 3> in dichloromethane (3.0 mL), m-chloro perbenzoic acid (content: 65%) (60 mg) was added and the resultant reaction mixture was stirred at room temperature over one night. To the reaction mixture, a aqueous solution of sodium thiosulfate was added and the resultant reaction mixture was extracted with ethyl acetate. The organic phase was washed with saturated saline and was dried over anhydrous sodium sulfate. From the organic phase, the solvent was distilled off under reduced pressure and the resultant residue was purified by thin-layer silica gel chromatography to obtain the subject compound (7.0 mg) as a light yellow solid.

Example 10

Synthesis of 5-(4-((3-(6-(3-hydroxy-3-methylbutoxy)-4-methylpyridin-3-yl)-2-methylphenyl)Methoxy)Phenyl)Isothiazol-3-ol 1-oxide <Step 1> Synthesis of 5,5-dimethyl-2-(2-methyl-3-((Tetrahydro-2H-pyran-2-yloxy)Methyl)Phenyl)-1,3,2-dioxaborinan To a solution of the compound (2.57 g) obtained in (Reference Example 3) and bis(neopentyl glycolate)diboron (2.65 g) in 1,4-dioxane (45 mL), potassium acetate (2.65 g) and [1,1'-bis(diphenylphosphino)ferrocene]dichloro palladium (II)-dichloromethane adduct (0.74 g) were added and the inside of the reaction system was degassed followed by heating the resultant reaction mixture under reflux for 1 hour. To the reaction mixture, water was added and the resultant reaction mixture was extracted with ethyl acetate. The organic phase was washed with saturated saline and was dried over anhydrous sodium sulfate. From the organic phase, the solvent was distilled off under reduced pressure and the resultant residue was purified by silica gel column chromatography (eluate; n-hexane:ethyl acetate=100:0 to 90:10) to obtain the subject compound (2.21 g) as a colorless oil.

<Step 2> Synthesis of 4-(5-bromo-4-methylpyridin-2-yloxy)-2-methylbutan-2-ol To a suspension of sodium hydride (to which about 40% of a mineral oil was added, 0.23 g) in N,N-dimethylformamide (10 mL), 5-bromo-2-hydroxy-4-methylpyridine (1.00 g) was added under ice-cooling and the resultant reaction mixture was stirred for 30 minutes. To the reaction mixture, 3-hydroxy-3-methylbutyl 4-methylbenzene sulfonate (1.51 g) was added and the resultant reaction mixture was stirred at 60° C. for 4 hours. To the reaction mixture, a aqueous solution of saturated ammonium chloride was added and the resultant reaction mixture was extracted with ethyl acetate. The organic phase was washed with saturated saline and was dried over anhydrous sodium sulfate. From the organic phase, the solvent was distilled off under reduced pressure and the resultant residue was purified by silica gel column chromatography (eluate; n-hexane:ethyl acetate=50:50 to 33:67) to obtain the subject compound (0.92 g) as a light yellow oil.

<Step 3> Synthesis of (3-(6-(3-hydroxy-3-methylbutoxy)-4-methylpyridin-3-yl)-2-methylphenyl)Methanol To a solution of the compound (2.32 g) obtained in (Example 10) <Step 1> and the compound (2.00 g) obtained in (Example 10) <Step 2> in toluene (20 mL), palladium acetate (82 mg), 2-dicyclohexylphosphino-2',6'-dimethoxybiphenyl (SPhos, 0.30 g), and a 7.3M aqueous solution of potassium phosphate (3.0 mL) were sequentially added and the resultant reaction mixture was heated under reflux for 30 minutes. To the reaction mixture, acetic acid (40 mL) and water (10 mL) were added and the reaction mixture was heated under reflux for additional 2 hours. The reaction mixture was subjected to a phase separation and the organic phase was filtered through a pad of Celite. To the resultant filtrate, saturated aqueous sodium bicarbonate was added and the filtrate was extracted with ethyl acetate. The extract was washed with saturated saline and was dried over anhydrous sodium sulfate. From the organic phase, the solvent was distilled off under reduced pressure and the resultant residue was purified by silica gel column chromatography (eluate; n-hexane:ethyl acetate=70:30-50:50-40:60) to obtain the subject compound (0.48 g) as a colorless oil.

The aqueous phase was made basic with a 1N aqueous solution of sodium hydroxide and was extracted with ethyl acetate. The extract was washed with saturated saline and was dried over anhydrous sodium sulfate. From the organic phase, the solvent was distilled off under reduced pressure and the resultant residue was purified by silica gel column chromatography (eluate; n-hexane:ethyl acetate-70:30-50:50-40:60) to obtain the subject compound (0.89 g) as a colorless oil.

In total, the 1.37 g of subject compound was obtained as a colorless oil.

<Step 4> Synthesis of 4-(5-(3-((4-(5,5-dimethyl-1,3,2-dioxaborinan-2-yl)Phenoxy)Methyl)-2-methylphenyl)-4-methylpyridin-2-yloxy)-2-methylbutan-2-ol To a solution of the compound (89 mg) obtained in (Example 10) <Step 3>, the compound (49 mg) obtained in (Reference Example 4), and tri-n-butylphosphine (86 mg) in tetrahydrofuran (2.0 mL), 1,1'-azobis(N,N-dimethylformamide) (73 mg) was added under ice-cooling and the resultant reaction mixture was stirred at room temperature for 2 hours. From the reaction mixture, the solvent was distilled off under reduced pressure and the resultant residue was purified by silica gel column chromatography (eluate; n-hexane:ethyl acetate) to obtain a crude product (59 mg) of the subject compound as a colorless oil.

<Step 5> Synthesis of 5-chloro-isothiazol-3-ol 1-oxide

To a suspension of 5-chloro-isothiazol-3-ol (31.8 g) in dichloromethane (640 mL), m-chloroperbenzoic acid (content: 65%) (60.7 g) was added under ice-cooling and the resultant reaction mixture was stirred at room temperature for 15 hours. The reaction mixture was filtered and the filtrate was concentrated under reduced pressure. To the resultant residue, dichloromethane was added and the resulting precipitates were filtered out. The filtrate was concentrated under reduced pressure and the resultant residue was purified by silica gel chromatography (eluate; n-hexane:ethyl acetate=67:33 to 60:40) to obtain the subject compound (26.0 g) as a white solid.

<Step 6> Synthesis of 5-(4-((3-(6-(3-hydroxy-3-methylbutoxy)-4-methylpyridin-3-yl)-2-methylphenyl)Methoxy)Phenyl)Isothiazol-3-ol 1-oxide A suspension of the compound (56 mg) obtained in (Example 10) <Step 4>, the compound (17 mg) obtained in (Example 10) <Step 5>, bis(dibenzylideneacetone) palladium (6.5 mg), 2-dicyclohexylphosphino-2',6'-dimethoxybiphenyl (SPhos, 4.6 mg), and potassium phosphate (71 mg) in 1,4-dioxane (4.0 mL)-water (0.20 mL) was heated with stirring at 100° C. for 2 hours. The resultant reaction mixture was filtered through a pad of Celite and the filtrate was concentrated under reduced pressure. The resultant residue was purified by thin-layer silica gel column chromatography (eluate; dichloromethane:ethyl acetate:methanol=50:50:5) twice to obtain the subject compound (6.0 mg) as a light yellow solid.

Example 11

Synthesis of 5-(4-((3-(6-(3-hydroxy-3-methylbutoxy)-2-methylpyridin-3-yl)-2-methylphenyl)Methoxy)Phenyl)Isothiazol-3-ol 1-oxide <Step 1> Synthesis of 4-(5-bromo-6-methylpyridin-2-yloxy)-2-methylbutan-2-ol According to the method of (Example 10) <Step 2>, from 5-bromo-2-hydroxy-6-methylpyridine (1.0 g), the subject compound (1.3 g) was obtained as a light yellow oil.

<Step 2> Synthesis of 3-(6-(3-hydroxy-3-methylbutoxy)-2-methylpyridin-3-yl)-2-methylphenyl)Methanol According to the method of (Example 10) <Step 3>, from the compound (2.00 g) obtained in (Example 11) <Step 1> and the compound (2.32 g) obtained in (Example 10) <Step 1>, the subject compound (1.46 g) was obtained as a colorless oil.

<Step 3> Synthesis of 4-(5-(3-((4-(5,5-dimethyl-1,3,2-dioxaborinan-2-yl)Phenoxy)Methyl)-2-methylphenyl)-6-methylpyridin-2-yloxy)-2-methylbutan-2-ol According to the method of (Example 10) <Step 4>, from the compound (0.23 g) obtained in (Example 11) <Step 2> and the compound (0.13 g) obtained in (Reference Example 4), the subject compound (0.10 g) was obtained as a colorless oil.

<Step 4> Synthesis of 5-(4-((3-(6-(3-hydroxy-3-methylbutoxy)-2-methylpyridin-3-yl)-2-methylphenyl)Methoxy)Phenyl)Isothiazol-3-ol 1-oxide According to the method of (Example 10) <Step 6>, from the compound (0.10 g) obtained in (Example 11) <Step 3> and the compound (31 mg) obtained in (Example 10) <Step 5>, the subject compound (23 mg) was obtained as a light yellow solid.

Example 12

Synthesis of 5-(4-((3-(2,4-dimethyl-6-(3-hydroxy-3-methylbutoxy)Pyridin-3-yl)-2-methylphenyl)Methoxy)Phenyl)Isothiazol-3-ol 1-oxide <Step 1> Synthesis of (3-(2,4-dimethyl-6-(3-hydroxy-3-methylbutoxy)Pyridin-3-yl)-2-methylphenyl)Methanol According to the method of (Example 10) <Step 3>, from the compound (2.00 g) obtained in (Reference Example 5) and the compound (2.21 g) obtained in (Example 10) <Step 1>, the subject compound (1.63 g) was obtained as a colorless oil.

<Step 2> Synthesis of 4-(5-(3-((4-(5,5-dimethyl-1,3,2-dioxaborinan-2-yl)Phenoxy)Methyl)-2-methylphenyl)-4,6-dimethylpyridin-2-yloxy)-2-methylbutan-2-ol According to the method of (Example 10) <Step 4>, from the compound (96 mg) obtained in (Example 12) <Step 1> and the compound (60 mg) obtained in (Reference Example 4), the subject compound (43 mg) was obtained as a colorless oil.

<Step 3> Synthesis of 5-(4-((3-(2,4-dimethyl-6-(3-hydroxy-3-methylbutoxy)Pyridin-3-yl)-2-methylphenyl)Methoxy)Phenyl)Isothiazol-3-ol 1-oxide According to the method of (Example 10) <Step 6>, from the compound (41 mg) obtained in (Example 12) <Step 2> and the compound (12 mg) obtained in (Example 10) <Step 5>, the subject compound (14 mg) was obtained as a light yellow solid.

Example 13

Synthesis of 5-(4-((3-(2,6-dimethyl-4-(3-hydroxy-3-methylbutoxy)Phenyl)-2-methylphenyl)Methoxy)Phenyl)Isothiazol-3-ol 1-oxide <Step 1> Synthesis of Methyl 3-(5,5-dimethyl-1,3,2-dioxaborinan-2-yl)-2-methyl Benzoate According to the method of (Example 10) <Step 1>, from methyl 3-bromo-2-methyl benzoate (1.0 g), the subject compound (0.96 g) was obtained as a light orange oil.

<Step 2> Synthesis of 4-(4-bromo-3,5-dimethylphenoxy)-2-methylbutan-2-ol

According to the method of (Example 10) <Step 2>, from 4-bromo-3,5-dimethylphenol (3.60 g) and 3-hydroxy-3-methylbutyl 4-methylbenzene sulfonate (5.09 g), the subject compound (5.24 g) was obtained as a colorless oil.

<Step 3> Synthesis of Methyl 3-(2,6-dimethyl-4-(3-hydroxy-3-methylbutoxy)phenyl)-2-methyl Benzoate According to the method of (Example 10) <Step 3>, from the compound (0.46 g) obtained in (Example 13) <Step 1> and the compound (0.50 g) obtained in (Example 13) <Step 2>, the subject compound (0.62 g) was obtained as a brown oil.

<Step 4> Synthesis of (3-(2,6-dimethyl-4-(3-hydroxy-3-methylbutoxy)Phenyl)-2-methylphenyl)Methanol To a suspension of lithium aluminum hydride (64 mg) in tetrahydrofuran (8.0 mL), a solution of the compound (0.60 g) obtained in (Example 13) <Step 3> in tetrahydrofuran (2.0 mL) was added under ice-cooling and the resultant reaction mixture was stirred at room temperature for 3 hours. To the reaction mixture, a 1N hydrochloric acid was added and the resultant reaction mixture was extracted with ethyl acetate. The organic phase was washed with saturated saline and was dried over anhydrous sodium sulfate. From the organic phase, the solvent was distilled off under reduced pressure to obtain the subject compound (0.48 g) as a light gray solid.

<Step 5> Synthesis of 4-(4-(3-((4-(5,5-dimethyl-1,3,2-dioxaborinan-2-yl)Phenoxy)Methyl)-2-methylphenyl)-3,5-dimethylphenyloxy)-2-methylbutan-2-ol According to the method of (Example 10) <Step 4>, from the compound (0.23 g) obtained in (Example 13) <Step 4> and the compound (0.17 g) obtained in (Reference Example 4), a crude product (0.11 g) of the subject compound was obtained as a light yellow solid.

<Step 6> Synthesis of 5-(4-((3-(2,6-dimethyl-4-(3-hydroxy-3-methylbutoxy)Phenyl)-2-methylphenyl)Methoxy)Phenyl)Isothiazol-3-ol 1-oxide According to the method of (Example 10) <Step 6>, from the compound (0.11 g) obtained in (Example 13) <Step 5> and the compound (65 mg) obtained in (Example 10) <Step 5>, the subject compound (18 mg) was obtained as a white solid.

Example 14

Optical Resolution of 5-(4-((3-(2,6-dimethylphenyl)Phenyl)Methoxy)Phenyl)Isothiazol-3-ol 1-oxide The compound (50 mg) obtained in (Example 8) was subjected to an optical resolution using a preparative chromatography (column: CHIRALPAK IC (2.0 cm×25 cm) (manufactured by Daicel Chemical Industries, Ltd.), eluate: acetonitrile:acetic (v/v), flow rate: 8 mL/min, detection: UV 330 nm, column temperature: 40° C.) to obtain each enantiomer of the subject compound.

Primary fraction (25 mg, light yellow solid, >99% ee, retention time 5.3 min (enantiomer A: Example 14-(A)))

Secondary fraction (25 mg, light yellow solid, >99% ee, retention time 7.1 min (enantiomer B: Example 14-(B)))

The optical purity and the retention time were determined under the following conditions.

Column: CHIRALPAK IC (0.46 cm×25 cm) (manufactured by Daicel Chemical Industries, Ltd.), Eluate: acetonitrile:acetic acid=100:0.1 (v/v), Flow rate: 1.0 mL/min, Detection: UV 330 nm, Column temperature: 40° C.

Example 15

Synthesis of 5-(4-((3-(2,6-dimethylphenyl)Phenyl)Methoxy)Phenyl)Isothiazol-3-ol 1-oxide(A)

<Step 1> Optical Resolution of (Rac)-5-chloro-isothiazol-3-ol 1-oxide

The compound (30.5 g) obtained in (Example 10) <Step 5> was subjected to an optical resolution using a preparative chromatography (column: CHIRALPAK AS-H (5 cm×25 cm) (manufactured by Daicel Chemical Industries, Ltd.), eluate: carbon dioxide:methanol=86:14 (v/v), flow rate: 200 g/sec, detection: UV 238 nm, room temperature) to obtain each enantiomer of the subject compound.

Primary fraction (14.7 g, white solid, >99% ee, retention time 4.8 min (enantiomer A: Example 15-1 (A)))

Secondary fraction (14.1 g, white solid, >98% ee, retention time 5.3 min (enantiomer B: Example 15-1 (B)))

The optical purity and the retention time were determined under the following conditions.

Column: CHIRALPAK AD-H (0.46 cm×25 cm) (manufactured by Daicel Chemical Industries, Ltd.), Eluate: methanol:acetic acid=100:0.1 (v/v), Flow rate: 1.0 mL/min, Detection: UV 282 nm, Column temperature: 40° C.

<Step 2> Synthesis of 2-(4-((3-(2,6-dimethylphenyl)Phenyl)Methoxy)Phenyl)-5,5-dimethyl-1,3,2-dioxaborinan According to the method of (Example 10) <Step 4>, from 3-(2,6-dimethylphenyl)benzyl alcohol (1.00 g) and the compound (0.97 g) obtained in (Reference Example 4), the subject compound (1.02 g) was obtained as a yellow oil.

<Step 3> Synthesis of 5-(4-((3-(2,6-dimethylphenyl)Phenyl)Methoxy)Phenyl)Isothiazol-3-ol 1-oxide(A)

According to the method of (Example 10) <Step 6>, from the enantiomer A (Example 15-1 (A)) (45 mg) obtained in (Example 15) <Step 1> and the compound (0.10 g) obtained in (Example 15) <Step 2>, the subject compound (55 mg) was obtained as a white solid.

The retention time in the chiral column of the subject compound agreed with that of the enantiomer A (Example 14-(A)) obtained in (Example 14).

Hereinafter, the compound synthesized using the enantiomer A (Example 15-1(A)) obtained in (Example 15) <Step 1> is expressed as "name of the compound+(A)" and the compound synthesized using the enantiomer B (Example 15-1(B)) obtained in (Example 15) <Step 1> is expressed as "name of the compound+(B)".

Example 16

Synthesis of 5-(4-((3-(2,6-dimethylphenyl)Phenyl)Methoxy)Phenyl)Isothiazol-3-ol 1-oxide (B)

According to the method of (Example 10) <Step 6>, from the enantiomer B (Example 15-1 (B)) (45 mg) obtained in (Example 15) <Step 1> and the compound (0.10 g) obtained in (Example 15) <Step 2>, the subject compound (58 mg) was obtained as a white solid.

The retention time in the chiral column of the subject compound agreed with that of the enantiomer B (Example 14-(B)) obtained in (Example 14).

Example 17

Synthesis of 5-(4-((3-(2,6-dimethyl-4-(2-ethoxyethoxy)Phenyl)Phenyl)Methoxy)Phenyl)Isothiazol-3-ol 1-oxide(A)

<Step 1> Synthesis of 1-bromo-2,6-dimethyl-4-(2-ethoxyethoxy)Benzene

According to a method described in [WO 2005/063729 pamphlet, (Reference Example 31)], from 4-bromo-3,5-dimethylphenol (10.0 g) and 2-chloroethyl ethyl ether (5.94 mL), the subject compound (12.8 g) was obtained as a colorless oil.

<Step 2> Synthesis of (3-(2,6-dimethyl-4-(2-ethoxyethoxy)Phenyl)Phenyl)Methanol To a mixed solution of the compound (6.40 g) obtained in (Example 17) <Step 1> and 3-(hydroxymethyl)phenyl boronic acid (3.56 g) in 1,4-dioxane (70 mL)-water (7 mL), bis(dibenzylideneacetone) palladium (1.35 g), 2-dicyclohexylphosphino-2',6'-dimethoxybiphenyl (SPhos; 1.92 g), and potassium phosphate monohydrate (10.8 g) were sequentially added and the resultant reaction mixture was heated with stirring at 100° C. for 4 hours. To the reaction mixture, water was added and the resultant reaction mixture was extracted with ethyl acetate. The extract was washed with saturated saline and was dried over anhydrous sodium sulfate. From the organic phase, the solvent was distilled off under reduced pressure and the resultant residue was purified by silica gel column chromatography (eluate; n-hexane:ethyl acetate=80:20 to 75:25) to obtain the subject compound (4.13 g) as a colorless oil.

<Step 3> Synthesis of 4-((3-(2,6-dimethyl-4-(2-ethoxyethoxy)phenyl)Phenyl)Methoxy)Phenyl Boronic Acid N-methylimino Diacetic Acid Ester According to the method of (Example 10) <Step 4>, from the compound (1.50 g) obtained in (Example 17) <Step 2> and the compound (1.49 g) obtained in (Reference Example 6), the subject compound (2.37 g) was obtained as a white amorphous solid.

<Step 4> Synthesis of 5-(4-((3-(2,6-dimethyl-4-(2-ethoxyethoxy)Phenyl)Phenyl)Methoxy)Phenyl)Isothiazol-3-ol 1-oxide(A)

To a solution of the compound (0.20 g) obtained in (Example 17) <Step 3> in 1,4-dioxane (3.7 mL), a 1N aqueous solution of sodium hydroxide (1.1 mL) was added and the resultant reaction mixture was stirred at room temperature for 1.5 hours. To the reaction mixture, the enantiomer A (Example 15-1 (A)) (74 mg) obtained in (Example 15) <Step 1>, 2-dicyclohexylphosphino-2',6'-dimethoxybiphenyl (SPhos; 31 mg), and palladium acetate (8.4 mg) were sequentially added and the resultant reaction mixture was heated with stirring at 90° C. for 3 hours. To the reaction mixture, a saturated aqueous solution of ammonium chloride was added and the resultant reaction mixture was extracted with ethyl acetate. The extract was washed with saturated saline and was dried over anhydrous sodium sulfate. From the organic phase, the solvent was distilled off under reduced pressure and the resultant residue was subjected to a preparative purification by LC/MS to obtain the subject compound (9.2 mg) as a light yellow amorphous solid.

The compounds of (Example 18) to (Example 43) below were synthesized by the same method as or a method equivalent to the method of (Example 17) from each corresponding commercially available raw material or a raw material synthesized from a publicly known compound via a corresponding substituted phenyl boronic acid ester.

Example 18

5-(4-((3-(2,6-dimethyl-4-(2-ethoxyethoxy)Phenyl)-2-methylphenyl)Methoxy)Phenyl)Isothiazol-3-ol 1-oxide(A)

Example 19

5-(4-((3-(2,4-dimethyl-6-(2-ethoxyethoxy)Pyridin-3-yl)Phenyl)Methoxy)Phenyl)Isothiazol-3-ol 1-oxide (A)

Example 20

5-(4-((3-(6-(2-ethoxyethoxy)-2-methylpyridin-3-yl)-2-methylphenyl)Methoxy)Phenyl)Isothiazol-3-ol 1-oxide(A)

Example 21

5-(4-((3-(4,6-dimethyl-2-(2-ethoxyethoxy)Pyrimidin-5-yl)-2-methylphenyl)Methoxy)Phenyl)Isothiazol-3-ol 1-oxide(A)

Example 22

5-(4-((3-(2,6-dimethyl-4-(2-ethoxyethoxy)-3-fluorophenyl)Phenyl)Methoxy)Phenyl)Isothiazol-3-ol 1-oxide(A)

Example 23

5-(4-((3-(2,6-dimethyl-4-(3-(Methylsulfonyl)Propoxy)Phenyl)-2-methylphenyl)Methoxy)Phenyl) Isothiazol-3-ol 1-oxide(A)

Example 24

5-(4-((3-(2,4-dimethyl-6-(3-(Methylsulfonyl)Propoxy)Pyridin-3-yl)Phenyl)Methoxy)Phen yl)Isothiazol-3-ol 1-oxide(A)

Example 25

5-(4-((3-(2-methyl-6-(3-(Methylsulfonyl)Propoxy) Pyridin-3-yl)-2-methylphenyl)Methoxy)Phenyl) Isothiazol-3-ol 1-oxide(A)

Example 26

5-(4-((3-(4,6-dimethyl-2-(3-(Methylsulfonyl)Propoxy)Pyrimidin-5-yl)-2-methylphenyl)Methoxy) Phenyl)Isothiazol-3-ol 1-oxide(A)

Example 27

5-(4-((3-(2,6-dimethyl-3-fluoro-4-(3-(Methylsulfonyl)Propoxy)Phenyl)Phenyl)Methoxy)Phenyl) Isothiazol-3-ol 1-oxide(A)

Example 28

5-(4-((3-(2,6-dimethyl-4-((1,1-dioxidotetrahydro-2H-thiopyran-4-yl)Oxy)Phenyl)Phenyl)Methoxy) Phenyl)Isothiazol-3-ol 1-oxide(A)

Example 29

5-(4-((3-(2,6-dimethyl-4-((1,1-dioxidotetrahydro-2H-thiopyran-4-yl)Oxy)Phenyl)-2-methylphenyl) Methoxy)Phenyl)Isothiazol-3-ol 1-oxide(A)

Example 30

5-(4-((3-(2,4-dimethyl-6-(3-hydroxy-3-methylbutoxy)Pyridin-3-yl)Phenyl)Methoxy)Phenyl)Isothiazol-3-ol 1-oxide(A)

Example 31

5-(4-((3-(2,6-dimethyl-4-(3-hydroxy-3-methylbutoxy)Phenyl)-2-methylphenyl)Methoxy)Phenyl)Isothiazol-3-ol 1-oxide(A)

Example 32

5-(4-((3-(2,6-dimethyl-3-fluoro-4-(3-hydroxy-3-methylbutoxy)Phenyl)Phenyl)Methoxy)Phenyl)Isothiazol-3-ol 1-oxide(A)

Example 33

5-(4-((3-(2,6-dimethyl-4-(3-(2-oxopyrrolidin-1-yl)Propoxy)Phenyl)Phenyl)Methoxy)Phenyl)Isothiazol-3-ol 1-oxide(A)

Example 34

5-(4-((3-(2,6-dimethyl-4-(3-(2-oxopyrrolidin-1-yl)Propoxy)Phenyl)-2-methylphenyl)Methoxy)Phenyl)Isothiazol-3-ol 1-oxide(A)

Example 35

5-(4-((3-(2,4-dimethyl-6-(3-(2-oxopyrrolidin-1-yl)Propoxy)Pyridin-3-yl)Phenyl)Methoxy)Phenyl)Isothiazol-3-ol 1-oxide(A)

Example 36

5-(4-((3-(2-methyl-6-(3-(2-oxopyrrolidin-1-yl)Propoxy)Pyridin-3-yl)-2-methylphenyl)Methoxy)Phenyl)Isothiazol-3-ol 1-oxide(A)

Example 37

5-(4-((3-(4,6-dimethyl-2-(3-(2-oxopyrrolidin-1-yl)Propoxy)Pyrimidin-5-yl)-2-methylphenyl)Methoxy)Phenyl)Isothiazol-3-ol 1-oxide(A)

Example 38

5-(4-((3-(2,6-dimethyl-3-fluoro-4-(3-(2-oxopyrrolidin-1-yl)Propoxy)Phenyl)Phenyl)Methoxy)Phenyl)Isothiazol-3-ol 1-oxide(A)

Example 39

5-(4-((3-(2,4-dimethyl-6-(2-(2-oxopyrrolidin-1-yl)Ethoxy)Pyridin-3-yl)Phenyl)Methoxy)Phenyl)Isothiazol-3-ol 1-oxide(A)

Example 40

5-(4-((3-(2-methyl-6-(2-(2-oxopyrrolidin-1-yl)Ethoxy)Pyridin-3-yl)-2-methylphenyl)Methoxy)Phenyl)Isothiazol-3-ol 1-oxide(A)

Example 41

5-(4-((3-(2,6-dimethyl-4-(2-(2-oxopyrrolidin-1-yl)Ethoxy)Phenyl)-2-methylphenyl)Methoxy)Phenyl)Isothiazol-3-ol 1-oxide(A)

Example 42

5-(4-((3-(2,6-dimethyl-4-((3-methyl-3-oxetanyl)Methoxy)Phenyl)-2-methylphenyl)Methoxy)Phenyl)Isothiazol-3-ol 1-oxide(A)

Example 43

5-(4-((3-(2,6-dimethyl-3-fluoro-4-((3-methyl-3-oxetanyl)Methoxy)Phenyl)Phenyl)Methoxy)Phenyl)Isothiazol-3-ol 1-oxide(A)

Example 44

Synthesis of 5-(4-((3-(2,6-dimethyl-4-(3-(Methylsulfonyl)Propoxy)Phenyl)Phenyl)Methoxy)Phenyl)Isothiazol-3-ol 1-oxide(A)

<Step 1> Synthesis of (3-(2,6-dimethyl-4-((Tert-butyldimethylsilyl)Oxy)Phenyl)Phenyl)Methanol According to the method of (Example 17) <Step 2>, from 1-bromo-4-((tert-butyldimethylsilyl)oxy)-2,6-dimethylbenzene (15.0 g) synthesized according to a method described in [WO 2005/063729 pamphlet], the subject compound (10.4 g) was obtained as an orange solid.

<Step 2> Synthesis of 4-((3-(2,6-dimethyl-4-((Tert-butyldimethylsilyl)Oxy)Phenyl)Phenyl)Methoxy) Phenyl Boronic Acid N-methylimino Diacetic Acid Ester According to the method of (Example 17) <Step 3>, from the compound (0.20 g) obtained in (Example 44) <Step 1>, the subject compound (0.24 g) was obtained as a light yellow amorphous solid.

<Step 3> Synthesis of 4-((3-(2,6-dimethyl-4-hydroxyphenyl)Phenyl)Methoxy)Phenyl Boronic Acid N-methylimino Diacetic Acid Ester To a solution of the compound (4.18 g) obtained in (Example 44) <Step 2> in tetrahydrofuran (70 mL), a 1N tetrabutylammonium fluoride tetrahydrofuran solution (14.6 mL) was added under ice-cooling and the resultant reaction mixture was stirred under ice-cooling for 30 minutes. To the reaction mixture, water was added and the resultant reaction mixture was extracted with ethyl acetate. The organic phase was washed with saturated saline and was dried over anhydrous sodium sulfate. From the organic phase, the solvent was distilled off under reduced pressure and the resultant residue was purified by silica gel column chromatography (eluate; n-hexane:ethyl acetate=33:67 to 20:80) to obtain the subject compound (1.06 g) as a beige amorphous solid.

<Step 4> Synthesis of 443-(2,6-dimethyl-4-(3-(Methylsulfonyl)Propoxy)Phenyl)Phenyl)Methoxy)Phenyl Boronic Acid N-methylimino Diacetic Acid Ester According to the method of (Example 17) <Step 1>, from the compound (0.20 g) obtained in (Example 44) <Step 3> and 3-(methylsulfonyl)propyl 4-methylbenzenesulfonate (0.14 g) synthesized according to a method described in [WO 2007/018314 pamphlet], the subject compound (79 mg) was obtained as a white solid.

<Step 5> Synthesis of 5-(4-((3-(2,6-dimethyl-4-(3-(Methylsulfonyl)Propoxy)Phenyl)Phenyl)Methoxy) Phenyl)Iso thiazol-3-ol 1-oxide(A)

According to the method of (Example 17) <Step 4>, from the compound (76 mg) obtained in (Example 44) <Step 4>, the subject compound (15 mg) was obtained as a beige solid.

The compounds of (Example 45) to (Example 46) below were synthesized by the same method as or a method equivalent to the method of (Example 44) from each corresponding commercially available raw material or a raw material synthesized from a publicly known compound via a corresponding substituted phenyl boronic acid ester.

Example 45

5-(4-((3-(2,6-dimethyl-4-(2-(2-oxopyrrolidin-1-yl) Ethoxy)Phenyl)Phenyl)Methoxy)Phenyl) isothiazol-3-ol 1-oxide(A)

Example 46

5-(4-((3-(2,6-dimethyl-4-((3-methyl-3-oxetanyl) Methoxy)Phenyl)Phenyl)Methoxy)Phenyl) isothiazol-3-ol 1-oxide(A)

Example 47

Synthesis of 5-(4-((3-(2,6-dimethyl-4-(3-hydroxypropoxy)Phenyl)Phenyl)Methoxy)Phenyl)Isothiazol-3-ol 1-oxide(A)

<Step 1> Synthesis of 1-bromo-4-(3-((Tert-butyldimethylsilyl)Oxy)Propoxy)-2,6-dimethylbenzene According to the method of (Example 17) <Step 1>, from 4-bromo-3,5-dimethylphenol (4.00 g) and 3-((tert-butyldimethylsilyl)oxy)propyl bromide (5.55 g), the subject compound (7.60 g) was obtained as a colorless oil.

<Step 2> Synthesis of (3-(2,6-dimethyl-4-(3-(tert-butyldimethylsilyl)Oxy)Propoxyphenyl)Phenyl) Methanol According to the method of (Example 10) <Step 4>, from the compound (3.60 g) obtained in (Example 47) <Step 1>, the subject compound (1.34 g) was obtained as a brown oil.

<Step 3> Synthesis of 4-((3-(4-(3-((tert-butyldimethylsilyl)Oxy)Propoxy)-2,6-dimethylphenyl)Phenyl) Methoxy)Phenyl Boronic Acid N-methylimino Diacetic Acid Ester According to the method of (Example 17) <Step 3>, from the compound (1.20 g) obtained in (Example 47) <Step 2>, the subject compound (1.21 g) was obtained as a light yellow amorphous solid.

<Step 4> Synthesis of 5-(4-((3-(2,6-dimethyl-4-(3-hydroxypropoxy)Phenyl)Phenyl)Methoxy)Phenyl) Isothiazol-3-ol 1-oxide(A)

To a solution of the compound (0.20 g) obtained in (Example 47) <Step 3> in 1,4-dioxane (3.2 mL), a 1N aqueous solution of sodium hydroxide (0.9 mL) was added, and the resultant reaction mixture was stirred at room temperature for 1.5 hours. To the reaction mixture, the enantiomer A (Example 15-1 (A)) (62 mg) obtained in (Example 15) <Step 1>, 2-dicyclohexylphosphino-2',6'-dimethoxybiphenyl (SPhos; 26 mg), and palladium acetate (7.1 mg) were sequentially added, and the resultant reaction mixture was heated with stirring at 100° C. for 2 hours. To the reaction mixture, a aqueous solution of saturated ammonium chloride was added, and the resultant reaction mixture was extracted with ethyl acetate. The organic phase was washed with saturated saline and was dried over anhydrous sodium sulfate. From the organic phase, the solvent was distilled off under reduced pressure, and the resultant residue was dissolved in ethanol (5.0 mL)-tetrahydrofuran (5.0 mL). To the resultant solution, concentrated hydrochloric acid (4.1 mL) was added, and the resultant reaction mixture was stirred at room temperature for 8 hours. To the reaction mixture, a saturated aqueous sodium bicarbonate was added to make the reaction mixture weak acidic, and the reaction mixture was extracted with ethyl acetate. The organic phase was washed with saturated saline and was dried over anhydrous sodium sulfate. From the organic phase, the solvent was distilled off under reduced pressure, and the resultant residue was subjected to a preparative purification by LC/MS to obtain the subject compound (23 mg) as a light yellow amorphous solid.

The compounds of (Example 48) to (Example 62) below were synthesized by the same method as or a method equivalent to the method of (Example 47) from each corresponding commercially available raw material or a raw material synthesized from a publicly known compound via a corresponding substituted phenyl boronic acid ester.

Example 48

5-(4-((3-(2,6-dimethyl-4-(3-hydroxypropoxy)phenyl)-2-methylphenyl)Methoxy)Phenyl)Isothiazol-3-ol 1-oxide(A)

Example 49

5-(4-((3-(2,4-dimethyl-6-(3-hydroxypropoxy)pyridin-3-yl)Phenyl)Methoxy)Phenyl)Isothiazol-3-ol 1-oxide(A)

Example 50

5-(4-((3-(2-methyl-6-(3-hydroxypropoxy)Pyridin-3-yl)-2-methylphenyl)Methoxy)Phenyl)Isothiazol-3-ol 1-oxide(A)

Example 51

5-(4-((3-(2,6-dimethyl-4-(2-hydroxyethoxy)Phenyl)-2-methylphenyl)Methoxy)Phenyl)Isothiazol-3-ol 1-oxide(A)

Example 52

5-(4-((3-(2-methyl-6-(2-hydroxyethoxy)Pyridin-3-yl)-2-methylphenyl)Methoxy)Phenyl)Isothiazol-3-ol 1-oxide(A)

Example 53

5-(4-((3-(2,4-dimethyl-6-(2-hydroxyethoxy)Pyridin-3-yl)Phenyl)Methoxy)Phenyl)Isothiazol-3-ol 1-oxide (A)

Example 54

5-(4-((3-(4,6-dimethyl-2-(2-hydroxyethoxy)Pyrimidin-5-yl)-2-methylphenyl)Methoxy)Phenyl)Isothiazol-3-ol 1-oxide(A)

Example 55

5-(4-((3-(4-((2R)-2,3-dihydroxypropoxy)-2,6-dimethylphenyl)Phenyl)Methoxy)Phenyl)Isothiazol-3-ol 1-oxide(A)

Example 56

5-(4-((3-(4-((2R)-2,3-dihydroxypropoxy)-2,6-dimethylphenyl)-2-methylphenyl)Methoxy)Phenyl)Isothiazol-3-ol 1-oxide(A)

Example 57

5-(4-((3-(6-((2R)-2,3-dihydroxypropoxy)-2-methylpyridin-3-yl)-2-methylphenyl)Methoxy)Phenyl)Isothiazol-3-ol 1-oxide(A)

Example 58

5-(4-((3-(2-((2R)-2,3-dihydroxypropoxy)-4,6-dimethylpyrimidin-5-yl)-2-methylphenyl)Methoxy)Phenyl)Isothiazol-3-ol 1-oxide(A)

Example 59

5-(4-((3-(4-((2R)-2,3-dihydroxypropoxy)-2,6-dimethyl-3-fluorophenyl)Phenyl)Methoxy)Phenyl)Isothiazol-3-ol 1-oxide(A)

Example 60

5-(4-((3-(6-((2S)-2,3-dihydroxypropoxy)-2-methylpyridin-3-yl)-2-methylphenyl)Methoxy)Phenyl)Isothiazol-3-ol 1-oxide(A)

Example 61

5-(4-((3-(2,6-dimethyl-4-((3S)-3-hydroxybutoxy)Phenyl)-2-methylphenyl)Methoxy)Phenyl)Isothiazol-3-ol 1-oxide(A)

Example 62

5-(4-((3-(2-methyl-6-((3S)-3-hydroxybutoxy)pyridin-3-yl)-2-methylphenyl)Methoxy)Phenyl)Isothiazol-3-ol 1-oxide(A)

Example 63

Synthesis of 5-(4-((3-(2,6-dimethyl-4-((3R)-3-hydroxybutoxy)Phenyl)Phenyl)Methoxy)Phenyl) Isothiazol-3-ol 1-oxide(A)

<Step 1> Synthesis of (3R)-3-acetoxybutoxy 4-methylbenzenesulfonate

A hydroxy group of (3R)-3-hydroxybutoxy 4-methylbenzenesulfonate (35.0 g) synthesized according to a method of [Tetrahedron: Asymmetry vol. 5 (1), p. 117 to 118 (1994)] was acetylated according to an ordinary method to obtain the subject compound (15.6 g) as a yellow oil.

<Step 2> Synthesis of 4-((3R)-3-acetoxybutoxy)-1-bromo-2,6-dimethylbenzene

According to the method of (Example 17) <Step 1>, from 4-bromo-3,5-dimethylphenol (5.00 g) and the compound (7.83 g) obtained in (Example 63) <Step 1>, the subject compound (4.09 g) was obtained as a colorless oil.

<Step 3> Synthesis of (3-(4-((3R)-3-acetoxybutoxy)-2,6-dimethylphenyl)Phenyl)Methanol According to the method of (Example 10) <Step 4>, from the compound (2.00 g) obtained in (Example 63) <Step 2>, the subject compound (1.36 g) was obtained as a brown oil.

<Step 4> Synthesis of 4-((3-(4-((3R)-3-acetoxybutoxy)-2,6-dimethylphenyl)Phenyl)Methoxy)Phenyl Boronic Acid N-methylimino Diacetic Acid Ester According to the method of (Example 17) <Step 3>, from the compound (1.20 g) obtained in (Example 63) <Step 3>, the subject compound (1.83 g) was obtained as a white solid.

<Step 5> Synthesis of 5-(4-((3-(2,6-dimethyl-4-((3R)-3-hydroxybutoxy)Phenyl)Phenyl)Methoxy) Phenyl)Isothiazol-3-ol 1-oxide(A)

To a solution of the compound (0.40 g) obtained in (Example 63) <Step 4> in 1,4-dioxane (7.0 mL), a 1N sodium hydroxide aqueous solution (2.1 mL) was added, and the resultant reaction mixture was stirred at room temperature for 1.5 hours. To the reaction mixture, the enantiomer A (Example 15-1 (A)) (137 mg) obtained in (Example 15) <Step 1>, 2-dicyclohexylphosphino-2',6'-dimethoxybiphenyl (SPhos; 57 mg), and palladium acetate (39 mg) were sequentially added, and the resultant reaction mixture was heated with stirring at 100° C. for 2 hours. To the reaction mixture, a saturated aqueous solution of ammonium chloride was added, and the resultant reaction mixture was extracted with ethyl acetate. The organic phase was washed with saturated saline and was dried over anhydrous sodium sulfate. From the organic phase, the solvent was distilled off under reduced pressure, and the resultant residue was dissolved in ethanol (5.0 mL). To the resultant solution, a 1N aqueous solution of sodium hydroxide (4.9 mL) was added, and the resultant reaction mixture was stirred at room temperature for 8 hours. To the reaction mixture, a saturated aqueous solution of ammonium chloride was added to make the reaction mixture weak acidic, and the reaction mixture was extracted with ethyl acetate. The organic phase was washed with saturated saline and was dried over anhydrous sodium sulfate. From the organic phase, the solvent was distilled off under reduced pressure, and the resultant residue was subjected to a preparative purification by LC/MS to obtain the subject compound (29 mg) as a light yellow amorphous solid.

The compounds of (Example 64) to (Example 65) below were synthesized by the same method as or a method equivalent to the method of (Example 63) from each corresponding commercially available raw material or a raw material synthesized from a publicly known compound via a corresponding substituted phenyl boronic acid ester.

Example 64

5-(4-((3-(2,6-dimethyl-4-((3R)-3-hydroxybutoxy)Phenyl)-2-methylphenyl)Methoxy)Phenyl)Isothiazol-3-ol 1-oxide(A)

Example 65

5-(4-((3-(2-methyl-6-((3R)-3-hydroxybutoxy)Pyridin-3-yl)-2-methylphenyl)Methoxy)Phenyl)Isothiazol-3-ol 1-oxide(A)

Example 66

Synthesis of 5-(4-((1R)-4-bromo-2,3-dihydro-1H-inden-1-yloxy)Phenyl)Isothiazol-3-ol 1-oxide(A)

<Step 1> Synthesis of 4-((1R)-4-bromo-2,3-dihydro-1H-inden-1-yloxy)Phenyl Boronic Acid N-methylimino Diacetic Acid Ester According to the method of (Example 17) <Step 3>, from (1S)-4-bromo-2,3-dihydro-1H-inden-1-ol (153 mg) that is commercially available or can be obtained by a publicly known method, the subject compound (178 mg) was obtained as an amorphous solid.

<Step 2> Synthesis of 5-(4-((1R)-4-bromo-2,3-dihydro-1H-inden-1-yloxy)Phenyl)Isothiazol-3-ol 1-oxide(A)

According to the method of (Example 17) <Step 4>, from the compound (178 mg) obtained in (Example 66) <Step 1>, the subject compound (25 mg) was obtained as an amorphous solid.

The compounds of (Example 67) to (Example 69) below were synthesized by the same method as or a method equivalent to the method of (Example 66) from each corresponding commercially available raw material or a raw material synthesized from a publicly known compound via a corresponding substituted phenyl boronic acid ester.

Example 67

5-(4-((1S)-4-bromo-2,3-dihydro-1H-inden-1-yloxy)Phenyl)Isothiazol-3-ol 1-oxide(A)

Example 68

5-(4-(4-chloro-2,3-dihydro-1H-inden-1-yloxy)Phenyl)Isothiazol-3-ol 1-oxide(A)

Example 69

5-(4-(4-trifluoromethyl-2,3-dihydro-1H-inden-1-yloxy)Phenyl)Isothiazol-3-ol 1-oxide (A)

The compounds of (Example 70) to (Example 76) below were synthesized by the same method as or a method equivalent to the method of (Example 17) from each corresponding commercially available raw material or a raw material synthesized from a publicly known compound via a corresponding substituted phenyl boronic acid ester.

Example 70

N-[3-[4-[3-[[4-(3-hydroxy-1-oxo-isothiazol-5-yl)Phenoxy]methyl]phenyl]-3,5-dimethylphenoxy]propyl]acetamide(A)

Example 71

N-[3-[5-[3-[[4-(3-hydroxy-1-oxo-isothiazol-5-yl)Phenoxy]methyl]-2-methylphenyl]-6-methylpyridin-2-yl]oxypropyl]acetamide(A)

Example 72

N-[3-[4-[3-[[4-(3-hydroxy-1-oxo-isothiazol-5-yl)Phenoxy]methyl]phenyl]-3,5-dimethylphenoxy]propyl]methanesulfonamide(A)

Example 73

5-[4-[[3-[2,5-dimethyl-4-(3-methylsulfonylpropoxy)Phenyl]phenyl]methoxy]phenyl]isothiazol-3-ol 1-oxide(A)

Example 74

5-[4-[[3-[2,5-dimethyl-6-(3-methylsulfonylpropoxy)Pyridin-3-yl]phenyl]methoxy]phenyl]isothiazol-3-ol 1-oxide(A)

Example 75

5-[4-[[3-[4-(3-hydroxy-3-methylbutoxy)-2,5-dimethylphenyl]phenyl]methoxy]phenyl] isothiazol-3-ol 1-oxide(A)

Example 76

5-[4-[[3-[4-(3-hydroxy-3-methylbutoxy)-2,6-dimethylphenyl]phenyl]methoxy]phenyl]isothiazol-3-ol 1-oxide(A)

The compounds of (Example 77) to (Example 78) below were synthesized by the same method as or a method equivalent to the method of (Example 47) from each corresponding commercially available raw material or a raw material synthesized from a publicly known compound via a corresponding substituted phenyl boronic acid ester.

Example 77

2-[[4-[3-[[4-(3-hydroxy-1-oxo-isothiazol-5-yl)Phenoxy]methyl]phenyl]-3,5-dimethylphenoxy]methyl]propane-1,3-diol (A)

Example 78

5-[4-[[3-[4-(3-aminopropoxy)-2,6-dimethylphenyl]phenyl]methoxy]phenyl]isothiazol-3-ol 1-oxide(A)

Example 79

Synthesis of 5-[2-chloro-4-[[3-[2,4-dimethyl-6-(3-methylsulfonylpropoxy)Pyridin-3-yl]phenyl]methoxy]phenyl]isothiazol-3-ol 1-oxide(A)

<Step 1> Synthesis of 3-[3-(Bromomethyl)phenyl]-2,4-dimethyl-6-(3-methylsulfonylpropoxy)Pyridine

[3-[2,4-dimethyl-6-(3-methylsulfonylpropoxy)pyridin-3-yl]phenyl]methanol (0.30 g) synthesized according to the methods in (Reference Example 5) and (Example 11) <Step 2> and carbon tetrabromide (0.34 g) were dissolved in methylene chloride (1.8 mL) and to the resultant solution, a solution of triphenylphosphine (0.34 g) in methylene chloride (0.9 mL) was added, followed by stirring the resultant reaction mixture at room temperature for 3 hours. From the reaction mixture, the solvent was distilled off under reduced pressure, and the resultant residue was purified by silica gel column chromatography (eluate; n-hexane:ethyl acetate=3:2) to obtain the subject compound (0.21 g) as a colorless liquid.

<Step 2> Synthesis of [2-chloro-4-[[3-[2,4-dimethyl-6-(3-methylsulfonylpropoxy)pyridin-3-yl]phenyl]methoxy]phenyl]boronic Acid According to the method of (Example 100) <Step 2> described below, from the compound (0.19 g) obtained in (Example 79) <Step 1>, the subject compound (84 mg) was obtained as a beige amorphous.

<Step 3> Synthesis of 5-[2-chloro-4-[[3-[2,4-dimethyl-6-(3-methylsulfonylpropoxy)Pyridin-3-yl]phenyl]methoxy]phenyl]isothiazol-3-ol 1-oxide(A)

According to the method of (Example 100) <Step 2> described below, from the compound (70 mg) obtained in (Example 79) <Step 2>, the subject compound (11 mg) was obtained as a light yellow solid.

Example 80

Synthesis of 1-oxo-5-[4-[[7-(Trifluoromethyl)-2,3-dihydro-1-benzofuran-3-yl]oxy]phenyl]-1,2-thiazol-3-ol (A)

<Step 1> Synthesis of 6-methyl-2-[4-[[7-(Trifluoromethyl)-2,3-dihydro-1-benzofuran-3-yl]oxy]phenyl]-1,3,6,2-dioxazaborocane-4,8-dione According to the method of (Example 17) <Step 3>, from 7-(trifluoromethyl)-2,3-dihydrobenzofuran-3-ol (0.30 g) synthesized according to a method described in [WO 2009/157418 pamphlet, (Example 47)], the subject compound (0.15 g) was obtained as an amorphous.

<Step 2> Synthesis of 1-oxo-5-[4-[[7-(Trifluoromethyl)-2,3-dihydro-1-benzofuran-3-yl]oxy]phenyl]-1,2-thiazol-3-ol (A)

According to the method of (Example 17) <Step 4>, from the compound (0.15 mg) obtained in (Example 80) <Step 1>, the subject compound (59 mg) was obtained as a light yellow solid.

The compounds of (Example 81) to (Example 99) below were synthesized by the same method as or a method equivalent to the method of (Example 80) from each corresponding commercially available raw material or a raw material synthesized from a publicly known compound via a corresponding substituted phenyl boronic acid ester.

Example 81

5-[4-[[8-(Trifluoromethyl)-3,4-dihydro-2H-chromen-4-yl]oxy]phenyl]isothiazol-3-ol 1-oxide(A)

Example 82

5-[4-[(2,2-dimethyl-4H-1,3-benzodioxin-5-yl]methoxy]phenyl]isothiazol-3-ol 1-oxide (A)

Example 83

5-[4-[[7-(Trifluoromethyl)-3,4-dihydro-2H-chromen-4-yl]oxy]phenyl]isothiazol-3-ol 1-oxide(A)

Example 84

5-[4-[[(2,6-dimethylphenyl)Methoxy]phenyl]isothiazol-3-ol 1-oxide(A)

Example 85

5-[4-[(5,5,8,8-tetramethyl-6,7-dihydronaphthalen-2-yl]methoxy]phenyl]isothiazol-3-ol 1-oxide(A)

Example 86

5-[4-[(2,3-dichlorophenyl)Methoxy]phenyl]isothiazol-3-ol 1-oxide(A)

Example 87

5-[4-[(1R)-1-(3-chlorophenyl)Ethoxy]phenyl]isothiazol-3-ol 1-oxide(A)

Example 88

5-[4-[(1R)-1-(3-bromophenyl)Ethoxy]phenyl]isothiazol-3-ol 1-oxide(A)

Example 89

5-[4-[(3-chlorophenyl)methoxy]phenyl]isothiazol-3-ol 1-oxide(A)

Example 90

5-[4-[(1S)-1-(3-bromophenyl)Ethoxy]phenyl]isothiazol-3-ol 1-oxide(A)

Example 91

5-[4-[(3-bromo-2-methylphenyl)Methoxy]phenyl]isothiazol-3-ol 1-oxide(A)

Example 92

5-[4-[2-(4-methoxyphenyl)Ethoxy]phenyl]isothiazol-3-ol 1-oxide(A)

Example 93

5-[4-[[3-(4,4-difluoropiperidin-1-yl)Phenyl]methoxy]phenyl]isothiazol-3-ol 1-oxide(A)

Example 94

5-[4-[[3-(2,6-dimethylphenyl)-2-methoxyphenyl]methoxy]phenyl]isothiazol-3-ol 1-oxide (A)

Example 95

5-[4-(2,3-dihydro-1-benzofuran-7-ylmethoxy)Phenyl]isothiazol-3-ol 1-oxide(A)

Example 96

5-[4-[[(3S)-1-(2,6-dimethylphenyl)Piperidin-3-yl]methoxy]phenyl]isothiazol-3-ol 1-oxide (A)

Example 97

5-[4-[[(3R)-1-(2,6-dimethylphenyl)Piperidin-3-yl]methoxy]phenyl]isothiazol-3-ol 1-oxide(A)

Example 98

5-[4-[[3-(4,4-difluoropiperidin-1-yl)-2-methoxyphenoxy]methyl]phenyl]isothiazol-3-ol 1-oxide(A)

Example 99

5-[4-[[3-(Trifluoromethyl)Phenyl]methoxy]phenyl]isothiazol-3-ol 1-oxide

Example 100

Synthesis of 5-[4-[2-chloro-4-(Trifluoromethyl)Phenoxy]phenyl]isothiazol-3-ol 1-oxide <Step 1> Synthesis of [4-[2-chloro-4-(Trifluoromethyl)Phenoxy]phenyl]boronic Acid A solution of 2-chloro-1-fluoro-4-(trifluoromethyl)benzene (0.95 g), (4-hydroxyphenyl)boronic acid (0.66 g), and potassium carbonate (1.65 g) in DMSO (5.0 mL) was heated with stirring at 130° C. for 20 hours. The resultant reaction mixture was left to be cooled down and was poured into an ice water, and pH of the resultant reaction mixture was adjusted to around 2 with a 10% hydrochloric acid, followed by extracting the reaction mixture with ethyl acetate. From the organic phase, the solvent was distilled off under reduced pressure, and the resultant residue was purified by silica gel column chromatography (eluate; n-hexane:ethyl acetate 100:0 to 50:50) to obtain the subject compound (0.20 g) as a white solid.

<Step 2> Synthesis of 5-[4-[2-chloro-4-(Trifluoromethyl)Phenoxy]phenyl]isothiazol-3-ol 1-oxide To the compound (0.10 g) obtained in (Example 100) <Step 1>, the compound (53 mg) obtained in (Example 10) <Step 5>, tris(dibenzylideneacetone)dipalladium (14.5 mg), and 2-dicyclohexylphosphino-2',4',6'-triisopropylbiphenyl (XPhos; 30 mg), 1,4-dioxane (3.0 mL) was added and thereto, a solution in which potassium carbonate (87 mg) was dissolved in water (1.5 mL) was added, followed by heating the resultant reaction mixture with stirring at 90° C. for 1 hour. The reaction mixture was left to be cooled down and to the reaction mixture, a 1M hydrochloric acid was added to adjust pH thereof to around 2, followed by extracting the reaction mixture with ethyl acetate. The organic phase was washed with saturated saline and was dried over anhydrous sodium sulfate. From the organic phase, the solvent was distilled off under reduced pressure, and the resultant residue was purified by silica gel column chromatography (eluate; n-hexane:ethyl acetate 30:70) to obtain the subject compound (95 mg) as a yellow solid.

Example 101

Synthesis of 5-[4-[(3-bromophenyl)Methylamino]phenyl]isothiazol-3-ol 1-oxide

<Step 1> Synthesis of N-[(3-bromophenyl)Methyl]-4-(4,4,5,5-tetramethyl-1,3,2-dioxaborolan-2-yl)Aniline 4-(4,4,5,5-tetramethyl-1,3,2-dioxaborolan-2-yl)aniline (1.0 g) and 3-bromobenzaldehyde (0.93 g) were dissolved in methanol (15 mL) and to the resultant solution, sodium triacetoxyborohydride (1.2 g) was added, followed by stirring the resultant reaction mixture at room temperature for 2 hours. To the reaction mixture, 3-bromobenzaldehyde (0.17 g) and sodium triacetoxyborohydride (0.6 g) were further added, and the reaction mixture was stirred further for 1.5 hours. To the resultant reaction mixture, a saturated ammonium chloride aqueous solution was added, and the reaction mixture was extracted with ethyl acetate. The organic phase was washed with saturated saline and was dried over anhydrous sodium sulfate. From the organic phase, the solvent was distilled off under reduced pressure, and the resultant residue was purified by silica gel column chromatography (eluate; n-hexane:ethyl acetate 30:1 to 10:1) to obtain the subject compound (0.67 g) as a colorless oil.

<Step 2> Synthesis of N-[(3-bromophenyl)Methyl]-N-[4-(4,4,5,5-tetramethyl-1,3,2-dioxaborolan-2-yl)Phenyl]Carbamic Acid Tert-butyl Ester The compound (0.20 g) obtained in (Example 101) <Step 1> was dissolved in tetrahydrofuran (5.0 mL) and to the resultant solution, triethylamine (0.14 mL), N,N-dimethylaminopyridine (6.3 mg), and di-tert-butyl dicarbonate (0.14 g) were added, followed by stirring the resultant reaction mixture at room temperature for 1.5 hours. Then, the reaction mixture was stirred at 40° C. for 30 minutes and thereto, further N,N-dimethylaminopyridine (63 mg) was added, followed by heating the resultant reaction mixture under reflux for 1 hour. To the reaction mixture, di-tert-butyl dicarbonate (0.14 g) was added, and triethylamine (0.14 mL) was added, followed by heating the reaction mixture under reflux for 4.5 hours. Then, to the reaction mixture, di-tert-butyl dicarbonate (0.14 g) was added, and the reaction mixture was heated under reflux for additional 2.5 hours. To the reaction mixture, a saturated aqueous solution of ammonium chloride was added, and the reaction mixture was extracted with ethyl acetate. The organic phase was washed with saturated saline and was dried over anhydrous sodium sulfate. From the organic phase, the solvent was distilled off under reduced pressure, and the resultant residue was purified by silica gel column chromatography (eluate; n-hexane:ethyl acetate 97:3) to obtain the subject compound (0.22 g) as a colorless oil.

<Step 3> Synthesis of 5-[4-[(3-bromophenyl)Methylamino]phenyl]isothiazol-3-ol 1-oxide To a solution of the compound (50 mg) obtained in (Example 101) <Step 2> in THF (0.5 mL) and water (0.25 mL), potassium hydrogen difluoride (24 mg) was added, and the resultant reaction mixture was stirred at room temperature for 4 hours. From the reaction mixture, the solvent was distilled off under reduced pressure, and the resultant residue was dissolved in 1,4-dioxane (2.0 mL) and water (1.0 mL). To the resultant solution, the compound (23 mg) obtained in (Example 10) <Step 5>, 2-dicyclohexylphosphino-2',6'-dimethoxybiphenyl (SPhos; 4.2 mg), and bis(dibenzylideneacetone) palladium (2.9 mg) were sequentially added. The inside of the reaction system was degassed, and the reaction mixture was heated under reflux for 2 hours. The reaction mixture was left to be cooled down and to the reaction mixture, a saturated aqueous solution of ammonium chloride was added, followed by extracting the reaction mixture with ethyl acetate. The organic phase was washed with saturated saline and was dried over anhydrous sodium sulfate. From the organic phase, the solvent was distilled off under reduced pressure, and the resultant residue was dissolved in methylene chloride (1.0 mL). To the resultant solution, trifluoro acetic acid (39 µL) was added, and the resultant reaction mixture was stirred at room temperature for 3.5 hours. Further, to the reaction mixture, trifluoro acetic acid (0.39 mL) was added, and the resultant reaction mixture was stirred at room temperature for 1.5 hours. From the reaction mixture, the solvent was distilled off, and the resultant residue was subjected to a preparative purification by LC/MS to obtain the subject compound (14 mg) as a yellow solid.

Example 102

Synthesis of 5-[4-[(3-bromophenyl)Methoxy]phenyl]isothiazol-3-ol 1-oxide(A)

<Step 1> Synthesis of 2-[4-[(3-bromophenyl)Methoxy]-phenyl]-6-methyl-1,3,6,2-dioxazaborocane-4,8-dione 3-bromobenzyl bromide (0.60 g) and the compound (0.50 g) of (Reference Example 6) were dissolved in dimethylformamide (5.0 mL) and to the resultant solution, potassium carbonate (0.83 g) was added, followed by heating the resultant reaction mixture with stirring at 80° C. for 6 hours. The reaction mixture was left to be cooled down and to the reaction mixture, water was added, followed by extracting the resultant reaction mixture with ethyl acetate. The organic phase was washed with saturated saline and was dried over anhydrous sodium sulfate. From the organic phase, the solvent was distilled off under reduced pressure, and the resultant residue was purified by silica gel column chromatography to obtain the subject compound (0.30 g) as a colorless amorphous.

<Step 2> Synthesis of 5-[4-[(3-bromophenyl)Methoxy]phenyl]isothiazol-3-ol 1-oxide(A)

According to the method of (Example 17) <Step 4>, from the compound (0.30 g) obtained in (Example 102) <Step 1>, the subject compound (0.20 g) was obtained as a light yellow solid.

Example 103

Synthesis of 5-[4-[(3-bromophenoxy)Methyl]phenyl]isothiazol-3-ol 1-oxide

<Step 1> Synthesis of [4-[(3-bromophenoxy)Methyl]phenyl]boronic Acid 3-bromophenol (0.50 g) was dissolved in acetone, and to the resultant solution, potassium carbonate (1.49 g), potassium iodide (14 mg), and 4-bromomethylphenyl boronic acid (0.62 g) were added, followed by heating the resultant reaction mixture under reflux for 3 hours. The reaction mixture was left to be cooled down, and to the reaction mixture, water was added, and a 2M hydrochloric acid was added to adjust pH of the reaction mixture to 2 to 3, followed by extracting the reaction mixture with ethyl acetate. The organic phase was washed with saturated saline and was dried over anhydrous sodium sulfate. From the organic phase, the solvent was distilled off under reduced pressure, and the resultant residue was purified by silica gel column chromatography to obtain the subject compound (0.45 g) as a colorless solid.

<Step 2> Synthesis of 5-[4-[(3-bromophenoxy)Methyl]phenyl]isothiazol-3-ol 1-oxide According to the method of (Example 100) <Step 2>, from the compound (0.21 g) obtained in (Example 103) <Step 1>, the subject compound (80 mg) was obtained as a light orange solid.

The compound of (Example 104) below was synthesized by the same method as or a method equivalent to the method of (Example 103) from a corresponding commercially available raw material via a corresponding substituted phenyl boronic acid.

Example 104

5-[3-[(3-bromophenyl)Methoxy]phenyl]isothiazol-3-ol 1-oxide

Example 105

Synthesis of

5-[4-[(2R)-1-(3-propan-2-yloxyphenyl)Propan-2-yl]oxyphenyl]isothiazol-3-ol 1-oxide <Step 1> Synthesis of 5-(4-hydroxyphenyl)-1,2-thiazol-3-ol According to the method of (Example 1) <Step 4>, from the compound (10 g) obtained in (Example 1) <Step 2>, the subject compound (7.8 g) was obtained as a beige solid.

\<Step 2\> Synthesis of 5-(4-hydroxyphenyl)Isothiazol-3-ol 1-oxide(A)

The compound (1.0 g) obtained in (Example 105) \<Step 1\> was suspended in acetone (20 mL)-water (10 mL), and to the resultant suspension, OXONE® (3.2 g) was added, followed by heating the resultant reaction mixture with stirring at 50° C. for 1 hour. A precipitated solid was filtered out, and to the filtrate, a saturated aqueous solution of sodium thiosulfate was added until the filtrate became not reacted with a KI starch paper. The solvent in the filtrate was distilled off under reduced pressure to around the half volume and the deposited solid was filtered and dried under reduced pressure to obtain the subject compound (0.90 g) as a beige solid.

\<Step 3\> Synthesis of 5-(4-hydroxyphenyl)-1-oxo-2-trityl-1,2-thiazol-3-one To the compound (5.0 g) obtained in (Example 105) \<Step 2\>, molecular sieves 4A (10 g), and triphenylmethyl chloride (26.7 g), dimethylformamide (20 mL) and diisopropylethylamine (9.0 mL) were added and the resultant reaction mixture was stirred at room temperature for 1 hour. The reaction mixture was filtered through a apd of Celite, and to the filtrate, ethyl acetate and water were added to extract the resultant reaction mixture with ethyl acetate. The organic phase was washed with saturated saline and was dried over sodium sulfate anhydride. From the organic phase, the solvent was distilled off under reduced pressure, and the resultant residue was suspended in methanol to filter an insoluble product in the resultant suspension. The obtained filtrate was concentrated and the resultant residue was purified by silica gel column chromatography to obtain a mixture (2.0 g) containing the subject compound as a light yellow solid.

\<Step 4\> Synthesis of 1-oxo-5-[4-[(2R)-1-(3-propan-2-yl(oxyphenyl)Propan-2-yl]oxyphenyl]-2-trityl-1,2-thiazol-3-one According to the method of (Example 10) \<Step 4\>, from the compound (0.56 g) obtained in (Example 105) \<Step 3\> and (S)-1-(3-isopropoxyphenyl)propan-2-ol (0.20 g) described in [WO 2009/147990 pamphlet, (Example 20)], the subject compound (0.31 g) was obtained as a beige solid.

\<Step 5\> Synthesis of 5-[4-[(2R)-1-(3-propan-2-yloxyphenyl)Propan-2-yl]oxyphenyl]isothiazol-3-ol 1-oxide The compound (0.31 g) obtained in (Example 105) \<Step 4\> was dissolved in ethyl acetate (4.0 mL) and to the resultant solution, a 4N hydrochloric acid-ethyl acetate solution (4.0 mL) was added, followed by stirring the resultant reaction mixture at room temperature for 14 hours. From the organic phase, the solvent was distilled off under reduced pressure and the resultant residue was reprecipitated in diethyl ether to obtain the subject compound (0.13 g) as a white solid.

The compound of (Example 106) below was synthesized by the same method as or a method equivalent to the method of (Example 105).

Example 106

5-[4-[2-(3-phenoxyphenyl)Ethoxy]phenyl]isothiazol-3-ol 1-oxide

Example 107

Synthesis of 5-[4-[[(1R)-4-(2,6-dimethylphenyl)-2,3-dihydro-1H-inden-1-yl]oxy]phenyl]isothiazol-3-ol 1-oxide(A)

To the compound (50 mg) obtained in (Example 66), 2,6-dimethylphenyl boronic acid (53 mg), tris(dibenzylideneacetone)dipalladium (7.0 mg), and 2-dicyclohexylphosphino-2',4',6'-triisopropylbiphenyl (XPhos; 12 mg), 1,4-dioxane (1.0 mL) was added and thereto, a solution in which potassium carbonate (34 mg) was dissolved in water (0.5 mL) was added, followed by heating the resultant reaction mixture with stirring at 100° C. for 4 hours. The reaction mixture was left to be cooled down and to the reaction mixture, a 1M hydrochloric acid was added to adjust pH of the reaction mixture to around 2, followed by extracting the reaction mixture with ethyl acetate. The organic phase was washed with saturated saline and was dried over sodium sulfate anhydride. From the organic phase, the solvent was distilled off under reduced pressure and the resultant residue was subjected to a preparative purification by LC/MS to obtain the subject compound (21 mg) as a colorless solid.

The compounds of (Example 108) to (Example 123) below were synthesized by the same method as or a method equivalent to the method of (Example 107) using as a raw material, each corresponding boronic acid.

Example 108

5-[4-[[(1R)-4-(Cyclohexen-1-yl)-2,3-dihydro-1H-inden-1-yl]oxy]phenyl]isothiazol-3-ol 1-oxide(A)

Example 109

5-[4-[[(1R)-4-cyclopropyl-2,3-dihydro-1H-inden-1-yl]oxy]phenyl]isothiazol-3-ol 1-oxide (A)

Example 110

5-[4-[[(1R)-4-phenyl)-2,3-dihydro-1H-inden-1-yl]oxy]phenyl] isothiazol-3-ol 1-oxide(A)

Example 111

5-[4-[[(1R)-4-pyridin-3-yl-2,3-dihydro-1H-inden-1-yl]oxy]phenyl]isothiazol-3-ol 1-oxide (A)

Example 112

5-[4-[[(1R)-4-(6-methoxypyridin-3-yl)-2,3-dihydro-1H-inden-1-yl]oxy]phenyl]isothiazol-3-ol 1-oxide (A)trifluoro Acetic Acid Salt

Example 113

5-[4-[[(1R)-4-(2-methylpyridin-3-yl)-2,3-dihydro-1H-inden-1-yl]oxy]phenyl]isothiazol-3-ol 1-oxide (A)trifluoro Acetic Acid Salt

Example 114

5-[4-[[(1R)-4-(2-methoxypyridin-3-yl)-2,3-dihydro-1H-inden-1-yl]oxy]phenyl]isothiazol-3-ol 1-oxide (A)

Example 115

5-[4-[[(1R)-4-(4-methoxy-2,6-dimethylphenyl)-2,3-dihydro-1H-inden-1-yl]oxy]phenyl]isothiazol-3-ol 1-oxide(A)

Example 116

5-[4-[[(1R)-4-(2,6-dimethoxypyridin-3-yl)-2,3-dihydro-1H-inden-1-yl]oxy]phenyl]isothiazol-3-ol 1-oxide(A)

Example 117

5-[4-[[(1R)-4-[2-(Trifluoromethyl)Pyridin-3-yl]-2,3-dihydro-1,4-inden-1-yl]oxy]phenyl] isothiazol-3-ol 1-oxide(A)

Example 118

5-[4-[[(1R)-4-(6-(Piperidin-1-yl)Pyridin-3-yl)-2,3-dihydro-1H-inden-1-yl]oxy]phenyl] isothiazol-3-ol 1-oxide(A)

Example 119

5-[4-[[(1R)-4-(6-methoxy-2-methylpyridin-3-yl)-2,3-dihydro-1H-inden-1-yl]oxy]phenyl]isothiazol-3-ol 1-oxide(A)trifluoro Acetic Acid Salt

Example 120

5-[4-[[(1R)-4-(4,4-dimethylcyclohexen-1-yl)-2,3-dihydro-1H-inden-1-yl]oxy]phenyl]isothiazol-3-ol 1-oxide(A)

Example 121

5-[4-[[(1R)-4-(3,6-dihydro-2H-pyran-4-yl)-2,3-dihydro-1H-inden-1-yl]oxy]phenyl]isothiazol-3-ol 1-oxide(A)

Example 122

5-[4-[[(1R)-4-(Pyridin-4-yl)-2,3-dihydro-1H-inden-1-yl]oxy]phenyl]isothiazol-3-ol 1-oxide(A)trifluoro Acetic Acid Salt

Example 123

5-[4-[[(1R)-4-(2-methoxypyrimidin-5-yl)-2,3-dihydro-1H-inden-1-yl]oxy]phenyl]isothiazol-3-ol 1-oxide(A)

Example 124

Synthesis of 5-[4-[(4-phenoxy-2,3-dihydro-1H-inden-1-yl)Oxy]phenyl]isothiazol-3-ol 1-oxide(A)

<Step 1> Synthesis of 4-phenoxy-2,3-dihydroinden-1-one

To phenyl boronic acid (1.0 g) and 4-hydroxy-2,3-dihydro-1H-inden-1-one (1.0 g), methylene chloride (67 mL) was added and thereto, copper (II) acetate (1.4 g), molecular sieves 4A (1.9 g), and triethylamine (4.7 mL) were added, followed by stirring the resultant reaction mixture at room temperature in an oxygen atmosphere for 19 hours. The reaction mixture was filtered through a pad of Celite and the filtered substance was washed with ethyl acetate. To the resultant filtrate, a 1M aqueous solution of sodium hydroxide was added and the resultant mixture was filtered through a pad of Celite again. The resultant filtrate was phase-separated into an aqueous phase and an organic phase and the aqueous phase was extracted with ethyl acetate to combine the resultant organic phase with the above organic phase. The combined organic phase was washed with saturated saline and was dried over sodium sulfate anhydride. From the organic phase, the solvent was distilled off under reduced pressure and the resultant residue was purified by silica gel column chromatography to obtain the subject compound (1.1 g) as an orange solid.

<Step 2> Synthesis of 4-phenoxy-2,3-dihydro-1H-inden-1-ol

The compound (1.03 g) obtained in (Example 124) <Step 1> was suspended in methanol (9 mL) and to the resultant suspension, sodium borohydride (87 mg) was added, followed by stirring the resultant reaction mixture at room temperature for 1.5 hours. The reaction mixture was concentrated to around the half volume under reduced pressure, and to the resultant reaction mixture, water was added, followed by extracting the resultant reaction mixture with ethyl acetate. The organic phase was washed with saturated saline and was dried over sodium sulfate anhydride. From the organic phase, the solvent was distilled off under reduced pressure to obtain the subject compound (1.1 g) as a yellow oil.

<Step 3> Synthesis of 6-methyl-2-[4-[(4-phenoxy-2,3-dihydro-1H-inden-1-yl)oxy]phenyl]-1,3,6,2-dioxazaborocane-4,8-dione According to the method of (Example 10) <Step 4>, from the compound (1.0 g) obtained in (Example 124) <Step 2>, a mixture (0.20 g) containing the subject compound was obtained as an amorphous.

<Step 4> Synthesis of 5-[4-[(4-phenoxy-2,3-dihydro-1H-inden-1-yl)Oxy]phenyl]isothiazol-3-ol 1-oxide(A)

According to the method of (Example 17) <Step 4>, from the compound (0.20 g) obtained in (Example 124) <Step 3>, the subject compound (17 mg) was obtained as an amorphous.

The compounds of (Example 125) to (Example 127) below were synthesized by the same method as or a method equivalent to the method of (Example 124) from each corresponding commercially available raw material or a raw material synthesized from a publicly known compound via a corresponding substituted phenyl boronic acid ester.

Example 125

5-[4-[[4-(2-methylpyridin-3-yl)Oxy-2,3-dihydro-1H-inden-1-yl]oxy]phenyl]isothiazol-3-ol 1-oxide(A)

Example 126

5-[4-[[4-(2-methoxypyridin-4-yl)Oxy-2,3-dihydro-1H-inden-1-yl]oxy]phenyl]isothiazol-3-ol 1-oxide (A)

Example 127

5-[4-[(4-pyridin-4-yloxy-2,3-dihydro-1H-inden-1-yl)Oxy]phenyl]isothiazol-3-ol 1-oxide (A)

Example 128

Synthesis of 5-[4-[[3-(2-methoxypyridin-3-yl)phenyl)Methoxy]phenyl]isothiazol-3-ol 1-oxide(A)

According to the method of (Example 107), from the compound (50 mg) obtained in (Example 102), the subject compound (4 mg) was obtained as a light yellow solid.

Example 129

Synthesis of

5-[4-[(4-phenylmethoxy-2,3-dihydro-1H-inden-1-yl)Oxy]phenyl]isothiazol-3-ol 1-oxide (A)

<Step 1> Synthesis of
4-phenylmethoxy-2,3-dihydro-1H-inden-1-ol

To a suspension of 60% sodium hydride (0.18 g) in dimethylformamide (22 mL), 4-hydroxy-2,3-dihydro-1H-inden-1-one (1.0 g) was added and the resultant reaction mixture was stirred at room temperature for 1 hour. Then, into the reaction mixture, a solution of benzyl bromide (1.3 g) in DMF (15 mL) was added dropwise at 80° C. and at the same temperature, the resultant reaction mixture was heated with stirring for 30 minutes. Further, to the reaction mixture, sodium hydride (0.09 g) and benzyl bromide (0.30 g) were further added and the resultant reaction mixture was heated with stirring for 2 hours. To the reaction mixture, a saturated aqueous solution of ammonium chloride was added and the resultant reaction mixture was extracted with ethyl acetate. The organic phase was washed with saturated saline and was dried over sodium sulfate anhydride. From the organic phase, the solvent was distilled off under reduced pressure and the resultant residue was purified by silica gel column chromatography (eluate; n-hexane:ethyl acetate=5:1) to obtain 4-benzyloxy-2,3-dihydro-1H-inden-1-one (1.2 g) as a white solid. The obtained white solid was subjected to a reaction according to the method of (Example 124) <Step 2> to obtain the subject compound (1.1 g) as a white solid.

<Step 2> Synthesis of 6-methyl-2-[4-[(4-phenylmethoxy-2,3-dihydro-1H-inden-1-yl)Oxy]phenyl]-1,3,6,2-dioxazaborocane-4,8-dione According to the methods of (Example 124) <Step 2> and <Step 3>, from the compound (1.0 g) obtained in (Example 129) <Step 1>, the subject compound (1.1 g) was obtained as a beige amorphous.

<Step 3> Synthesis of 5-[4-[(4-phenylmethoxy-2,3-dihydro-1H-inden-1-yl)Oxy]phenyl]isothiazol-3-ol 1-oxide (A)

According to the method of (Example 17) <Step 4>, from the compound (0.10 mg) obtained in (Example 129) <Step 2>, the subject compound (28 mg) was obtained as an amorphous.

The compounds of (Example 130) to (Example 133) below were synthesized by the same method as or a method equivalent to the method of (Example 129) from each corresponding commercially available raw material or a raw material synthesized from a publicly known compound via a corresponding substituted phenyl boronic acid ester.

Example 130

5-[4-[[4-(2,2,2-trifluoroethoxy)-2,3-dihydro-1H-inden-1-yl]oxy]phenyl]isothiazol-3-ol 1-oxide(A)

Example 131

5-[4-[(4-cyclohexyloxy-2,3-dihydro-1H-inden-1-yl)Oxy]phenyl]isothiazol-3-ol 1-oxide (A)

Example 132

5-[4-[[4-(Oxan-4-yloxy)-2,3-dihydro-1H-inden-1-yl]oxy]phenyl]isothiazol-3-ol 1-oxide (A)

Example 133

5-[4-[[4-(2-ethoxyethoxy)-2,3-dihydro-1H-inden-1-yl]oxy]phenyl]isothiazol-3-ol 1-oxide (A)

Example 134

Synthesis of 5-[4-[[4-(1-methylpiperidine-4-yl)Oxy-2,3-dihydro-1H-inden-1-yl]oxy]phenyl]-1-oxo-iso thiazol-3-yl]oxy Sodium Salt <Step 1> Synthesis of 6-methyl-2-[4-[[4-(1-methylpiperidin-4-yl)Oxy-2,3-dihydro-1,1-inden-1-yl]oxy]phenyl]-1,3,6,2-dioxazaborocane-4,8-dione According to the methods of (Example 129) <Step 1> and <Step 2>, from (2,3-dihydro-1H-indene-1,4-diol (1.0 g), the subject compound (0.55 g) was obtained as a light brown solid.

<Step 2> Synthesis of 5-[4-[[4-(1-methylpiperidine-4-yl)Oxy-2,3-dihydro-1H-inden-1-yl]oxy]phenyl]-1-oxo-iso thiazol-3-yl]oxy Sodium To a solution of the compound (0.20 g) obtained in (Example 17) <Step 3> in 1,4-dioxane (3.7 mL), a 1N aqueous solution of sodium hydroxide (1.1 mL) was added and the resultant reaction mixture was stirred at room temperature for 1.5 hours. To the reaction mixture, the enantiomer A (Example 15-1 (A)) (74 mg) obtained in (Example 15) <Step 1>, 2-dicyclohexylphosphino-2',6'-dimethoxybiphenyl (SPhos; 31 mg), and bis(dibenzylideneacetone) palladium (26 mg) were sequentially added and the resultant reaction mixture was heated with stirring at 90° C. for 3 hours. To the reaction mixture, a 1M aqueous solution of sodium hydroxide was added and from the resultant reaction mixture, the solvent was distilled off under reduced pressure, followed by adding water to the resultant residue to filter a deposited solid. The obtained solid was washed with ethanol and ethyl acetate and the resultant solid was suspended in ethyl acetate. The resultant suspension was irradiated with a supersonic wave and an insoluble solid was filtered, followed by washing the resultant solid with ethyl acetate and by drying the solid under reduced pressure to obtain the subject compound (0.10 g) as a sodium salt thereof as a light brown solid.

Example 135

Synthesis of 5-[4-[[(1R)-4-[6-(3-hydroxy-3-methylbutoxy)-2-methylpyridin-3-yl]-2,3-dihydro-1H-inden-1-yl]oxy]phenyl]isothiazol-3-ol 1-oxide(A)

<Step 1> Synthesis of 4-[5-(5,5-dimethyl-1,3,2-dioxaborinan-2-yl)-6-methylpyridin-2-yl]oxy-2-methylbutan-2-ol According to the method of (Example 10) <Step 1>, from the compound (0.3 g) of (Example 11) <Step 1>, the subject compound (0.3 g) was obtained as colorless oil.

<Step 2> Synthesis of 5-[4-[[(1R)-4-[6-(3-hydroxy-3-methylbutoxy)-2-methylpyridin-3-yl]-2,3-dihydro-1H-inden-1-yl]oxy]phenyl]isothiazol-3-ol 1-oxide (A)

According to the method of (Example 107), from the compound (49 mg) of (Example 135) <Step 1> and the compound (50 mg) of (Example 66), the subject compound (12 mg) was obtained as a colorless amorphous.

The compounds of (Example 136) to (Example 140) below were synthesized by the same method as or a method equivalent to the method of (Example 135) from each corresponding commercially available raw material or a raw material synthesized from a publicly known compound via a corresponding substituted phenyl boronic acid ester.

Example 136

5-[4-[[(1R)-4-[6-(2-ethoxyethoxy)-2-methylpyridin-3-yl]-2,3-dihydro-1H-inden-1-yl]oxy]phenyl]isothiazol-3-ol 1-oxide(A)

Example 137

5-[4-[[(1R)-4-[2-methyl-6-(3-methylsulfonylpropoxy)Pyridin-3-yl]-2,3-dihydro-1H-inden-1-yl]oxy]phenyl]isothiazol-3-ol 1-oxide(A)

Example 138

5-[4-[[(1R)-4-[2,6-dimethyl-4-(3-methylsulfonylpropoxy)Phenyl]-2,3-dihydro-1H-inden-1-yl]oxy]phenyl]isothiazol-3-ol 1-oxide(A)

Example 139

5-[4-[[(1R)-4-[4-(2-ethoxyethoxy)-2,6-dimethylphenyl]-2,3-dihydro-1H-inden-1-yl]oxy]phenyl]isothiazol-3-ol 1-oxide(A)

Example 140

5-[4-[[(1R)-4-[4-(3-hydroxy-3-methylbutoxy)-2,6-dimethylphenyl]-2,3-dihydro-1H-inden-1-yl]oxy]phenyl]isothiazol-3-ol 1-oxide(A)

Example 141

Synthesis of 5-[4-[(3-bromophenyl)Methoxymethyl]phenyl]isothiazol-3-ol 1-oxide

<Step 1> Synthesis of [4-[(3-bromophenyl)Methoxymethyl]phenyl]boronic Acid

According to the method of (Example 129) <Step 1>, from (3-bromophenyl)methanol (0.50 g) and (4-(hydroxymethyl)phenyl)boronic acid (0.69), the subject compound (0.25 g) was obtained as a colorless solid.

<Step 2> Synthesis of 5-[4-[(3-bromophenyl)Methoxymethyl]phenyl]isothiazol-3-ol 1-oxide According to the method of (Example 100) <Step 2>, from the compound (0.12 g) of (Example 141) <Step 1>, the subject compound (7.8 mg) was obtained as a light yellow solid.

Example 142

Synthesis of 5-(4-((1R)-4-trifluoromethyl-2,3-dihydro-1H-inden-1-yloxy)Phenyl)Isothiazol-3-ol 1-oxide(A)

According to the method of (Example 66), from (1S)-4-trifluoromethylindan-1-ol synthesized according to the method described in [WO 2009/157418 pamphlet, (Example 51)], the subject compound was synthesized.

Example 143

Synthesis of 5-(4-((1R)-4-chloro-2,3-dihydro-1H-inden-1-yloxy)Phenyl)Isothiazol-3-ol 1-oxide(A)

According to the method of (Example 66), from (1S)-4-chloroindan-1-ol synthesized according to the method described in [WO 2009/157418 pamphlet, (Example 52)], the subject compound was synthesized.

Example 144

Synthesis of 5-[4-[[(1R)-4-(6-fluoropyridin-3-yl)-2,3-dihydro-1H-inden-1-yl]oxy]phenyl]isothiazol-3-ol 1-oxide(A)

According to the method of (Example 107), the subject compound was synthesized.

Here, in all of the above Examples, by using the enantiomer (B) of Example 15-1 (B) instead of the enantiomer (A) of Example 15-1 (A), the enantiomer (B) of a compound corresponding to each Example can be produced.

The structures of the final compounds synthesized in the above (Example 1) to (Example 144) are shown in the figures below (Structural Formulae I to 5 and Tables 2 to 4). LC/MS data and NMR data (no mark: 400 MHz NMR, *: 300 MHz NMR, **: 270 MHz NMR) of these final compounds of Examples are also shown in Tables below (Tables 8 to 11 and Tables 16 to 18). The structures of the intermediate compounds synthesized in Examples respectively and the compounds of Reference Examples are shown in the figures below (Structural Formulae 6 to 10 and Tables 5 to 7) and LC/MS data of these intermediate compounds and the compounds of Reference Examples and NMR data (no mark: 400 MHz NMR, *: 300 MHz NMR, **: 270 MHz NMR) of these intermediate compounds and the compounds of Reference Examples are also shown in Tables below (Tables 12 to 15 and Tables 19 to 22). Here, with respect to the intermediate compound, for example, the compound obtained in (Example 1) <Step 1> is expressed as "(Example 1-1)".

147
-continued
Example 12
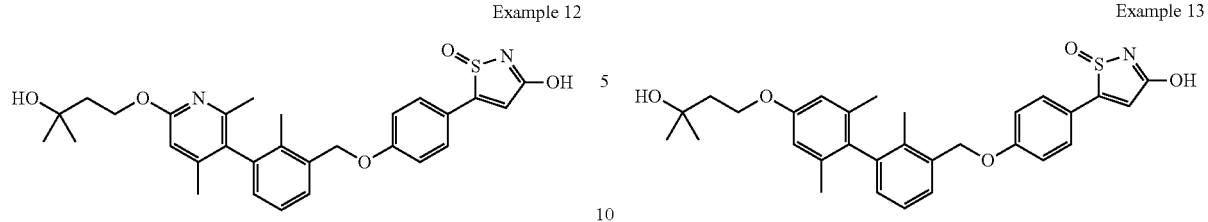
148
-continued
Example 13
TABLE 2
| Example | Structural Formula |
| --- | --- |
| 14-(A) | |
| 14-(B) | |
| 17 | |
| 18 | |
| 19 | |

TABLE 2-continued

| Example | Structural Formula |
| --- | --- |
| 20 | |
| 21 | |
| 22 | |
| 23 | |
| 24 | |
| 25 | |

TABLE 2-continued

| Example | Structural Formula |
|---------|-------------------|
| 26 | |
| 27 | |
| 28 | |
| 29 | |
| 30 | |
| 31 | |

TABLE 2-continued

| Example | Structural Formula |
|---|---|
| 32 | |
| 33 | |
| 34 | |

TABLE 3

| Example | Structural Formula |
|---|---|
| 35 | |
| 36 | |
| 37 | |

TABLE 3-continued
| Example | Structural Formula |
|---|---|
| 38 | 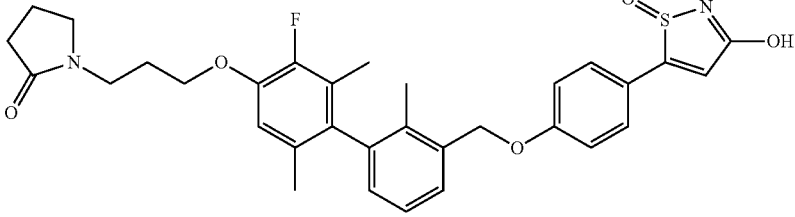 |
| 39 | 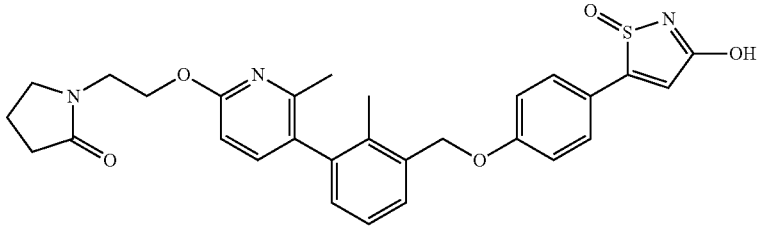 [SMILES: Cc1nc(OCCN2CCCC2=O)ccc1-c1cccc(COc2ccc(C3=CC(O)=NS3=O)cc2)c1C] |
| 40 | 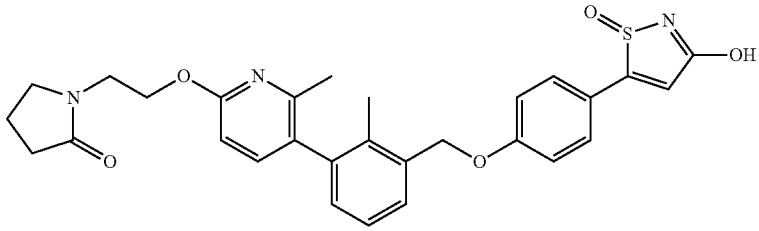 [SMILES: Cc1nc(OCCN2CCCC2=O)ccc1-c1cccc(COc2ccc(C3=CC(O)=NS3=O)cc2)c1C] |
| 41 | 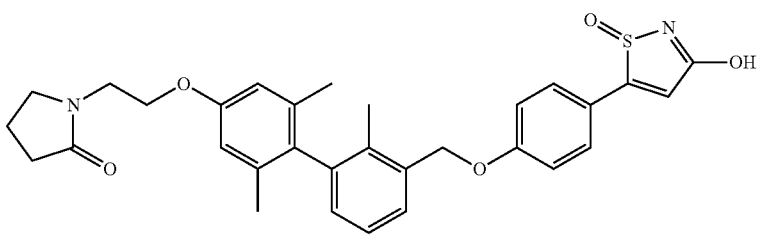 [SMILES: Cc1cc(OCCN2CCCC2=O)cc(C)c1-c1cccc(COc2ccc(C3=CC(O)=NS3=O)cc2)c1C] |
| 42 | 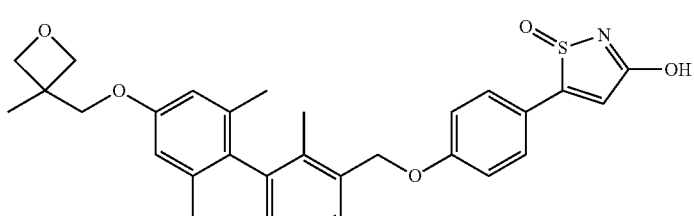 |
| 43 | 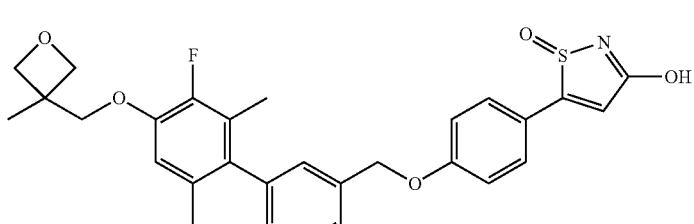 |

TABLE 3-continued

| Example | Structural Formula |
|---------|--------------------|
| 44 | |
| 45 | |
| 46 | |
| 47 | |
| 48 | |
| 49 | |

TABLE 3-continued

| Example | Structural Formula |
|---|---|
| 50 | (structure) |
| 51 | (structure) |
| 52 | (structure) |
| 53 | (structure) |
| 54 | (structure) |

TABLE 4

| Example | Structural Formula |
|---|---|
| 55 | (structure) |

TABLE 4-continued

| Example | Structural Formula |
|---|---|
| 56 | |
| 57 | |
| 58 | |
| 59 | |
| 60 | |
| 61 | |

TABLE 4-continued
| Example | Structural Formula |
|---|---|
| 62 | 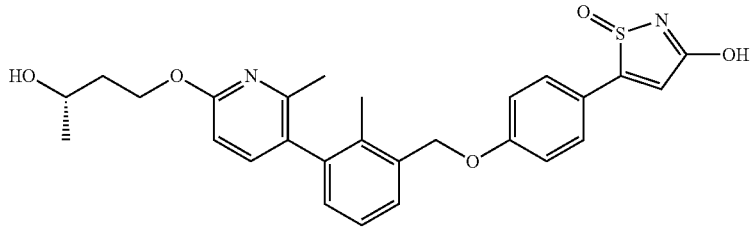 [SMILES: Cc1nc(OCC[C@H](C)O)ccc1-c1cccc(COc2ccc(C3=CC(O)=NS3=O)cc2)c1C] |
| 63 | 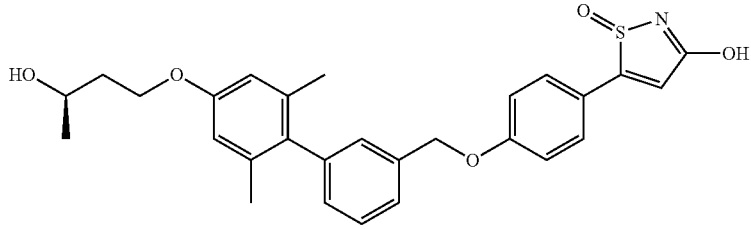 [SMILES: Cc1cc(OCC[C@@H](C)O)cc(C)c1-c1cccc(COc2ccc(C3=CC(O)=NS3=O)cc2)c1] |
| 64 | 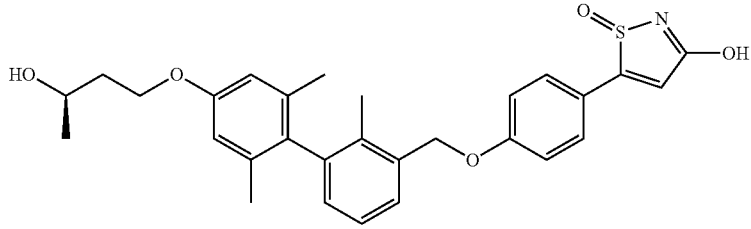 [SMILES: Cc1cc(OCC[C@@H](C)O)cc(C)c1-c1cccc(COc2ccc(C3=CC(O)=NS3=O)cc2)c1C] |
| 65 | 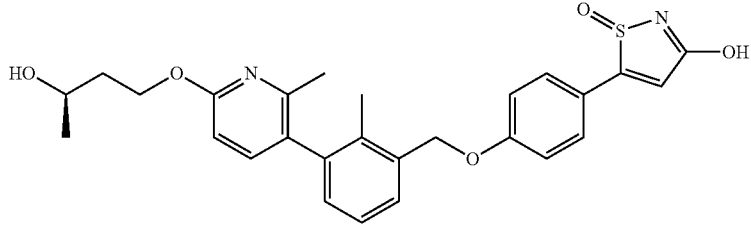 [SMILES: Cc1nc(OCC[C@@H](C)O)ccc1-c1cccc(COc2ccc(C3=CC(O)=NS3=O)cc2)c1C] |
| 66 | 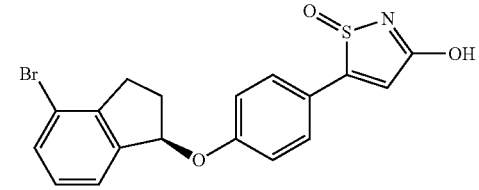 [SMILES: O=S1N=C(O)C=C1c1ccc(O[C@@H]2CCc3c(Br)cccc32)cc1] |
| 67 | 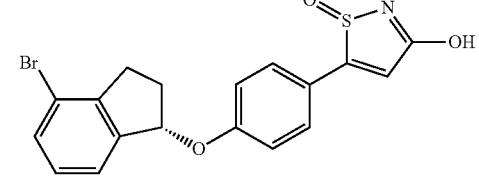 |
| 68 | 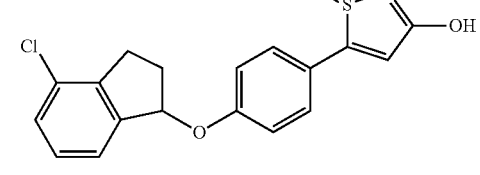 |

TABLE 4-continued
| Example | Structural Formula |
| --- | --- |
| 69 | 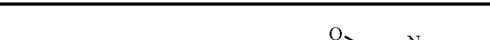 |
Structural Formula 2
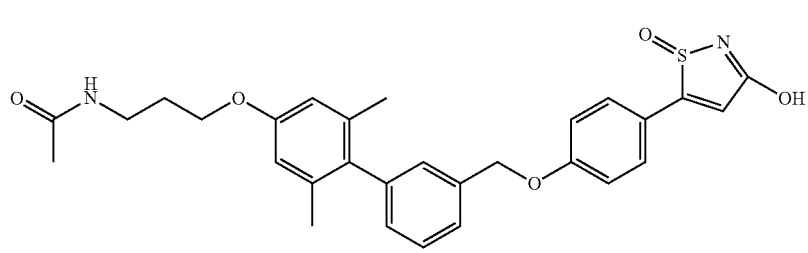
Example 70
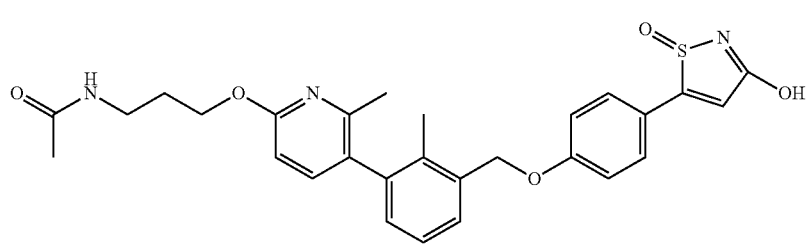
Example 71
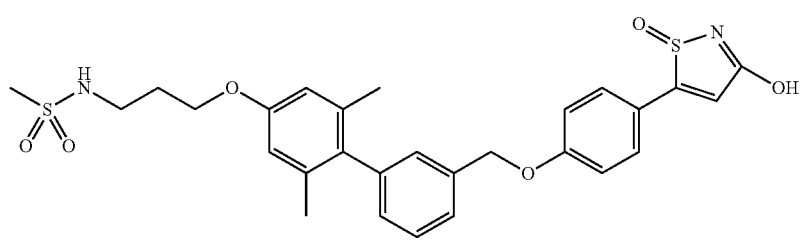
Example 72
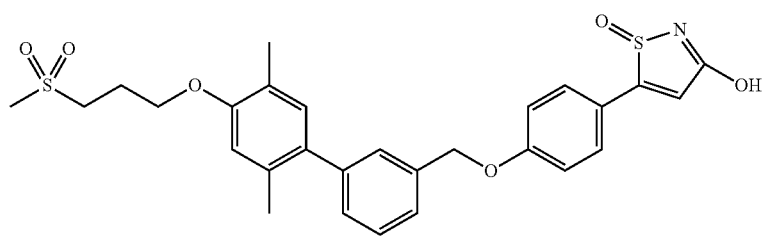
Example 73
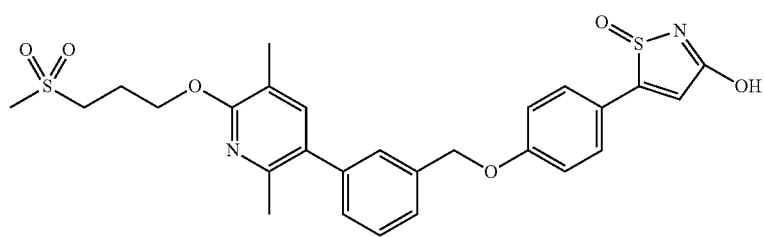
Example 74

-continued
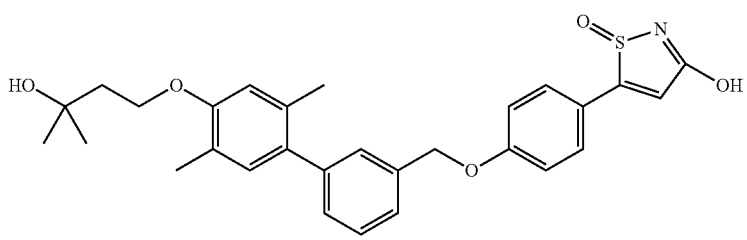
Example 75
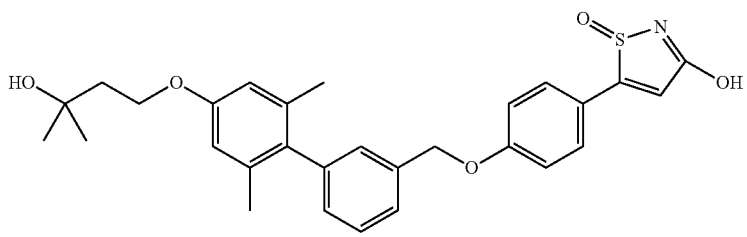
Example 76
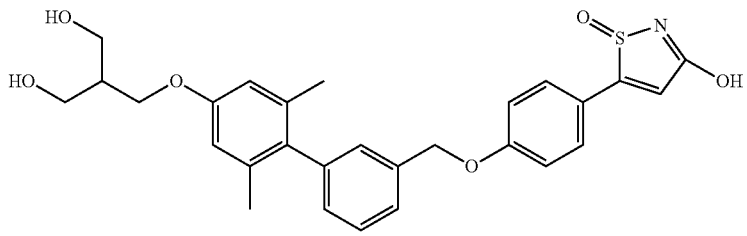
Example 77
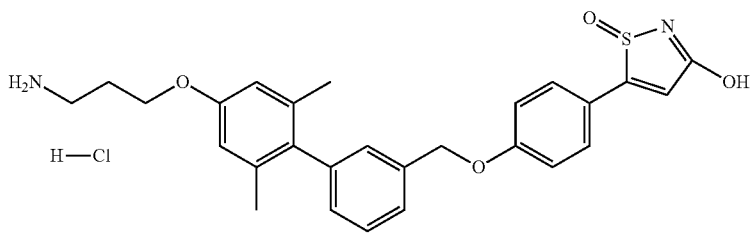
Example 78
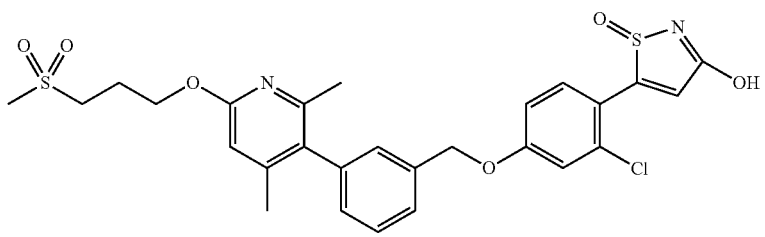
Example 79
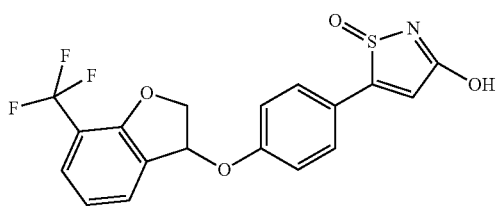
Example 80
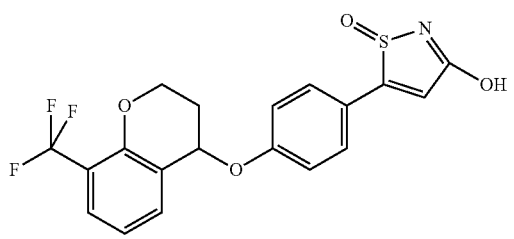
Example 81

-continued
Example 82
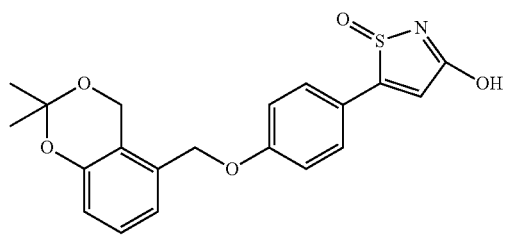
Example 83
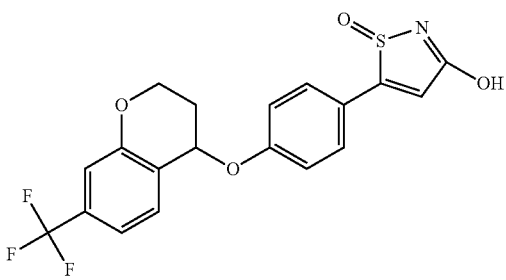
Example 84
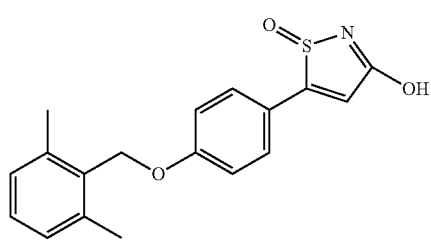
Example 85
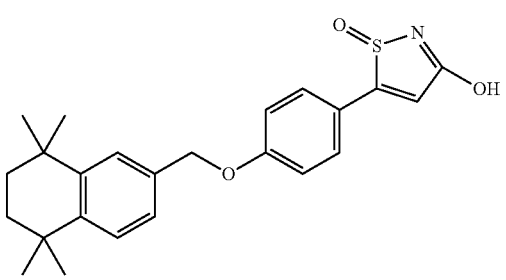
Example 86
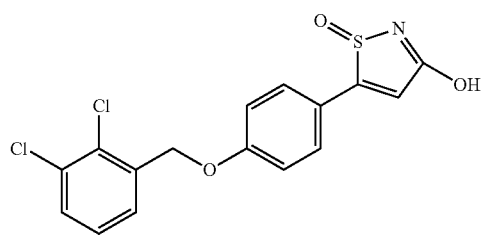
Example 87
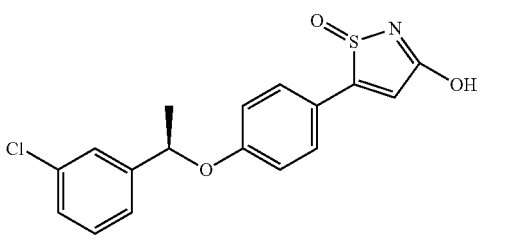
Example 88
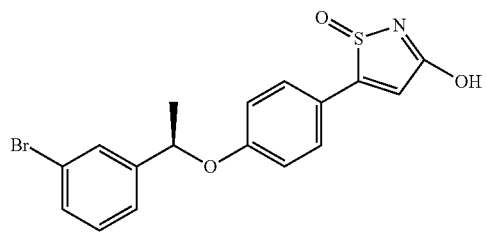
Example 89
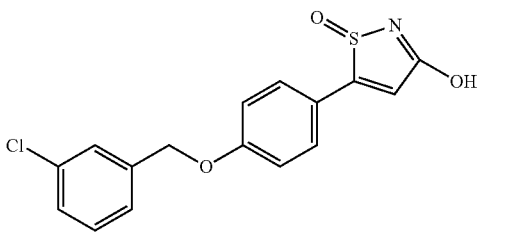
Example 90
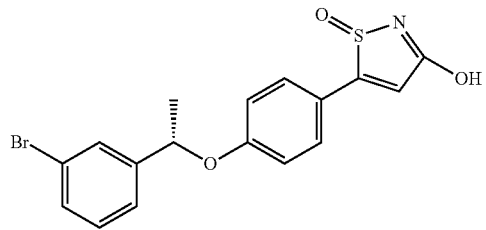
Example 91
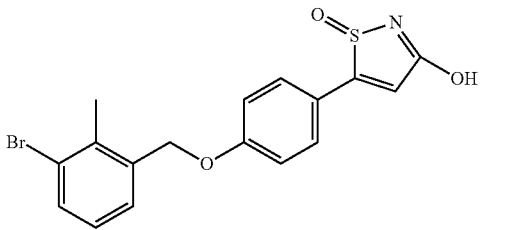
Structural Formula 3
Example 92
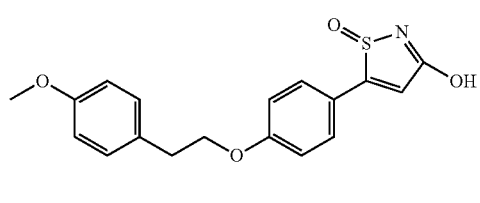
Example 93
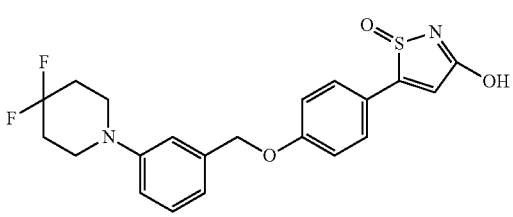

Example 94
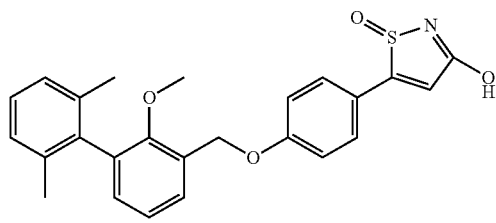
Example 95
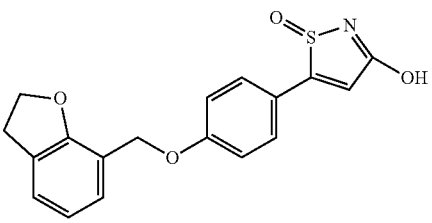
Example 96
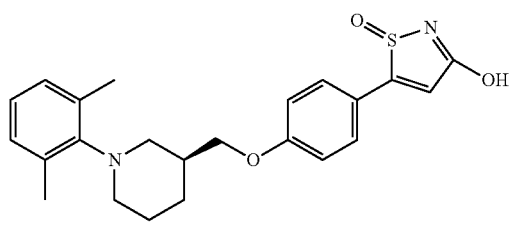
Example 97
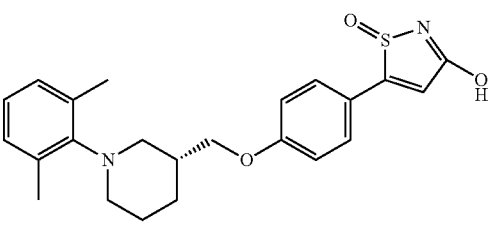
Example 98
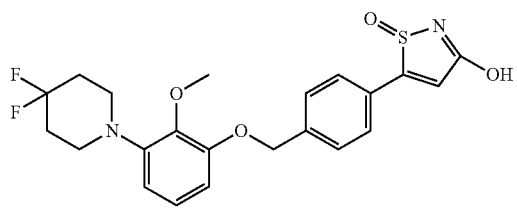
Example 99
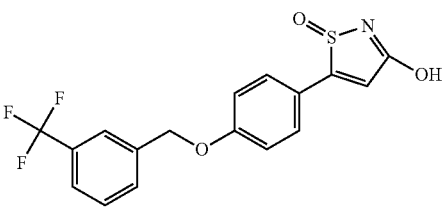
Example 100
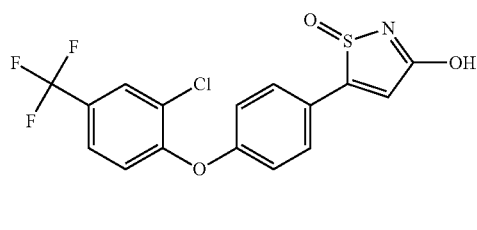
Example 101
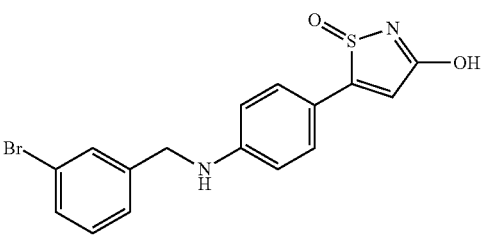
Example 102
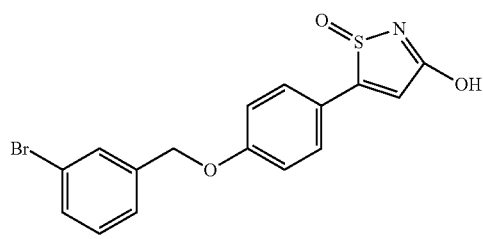
Example 103
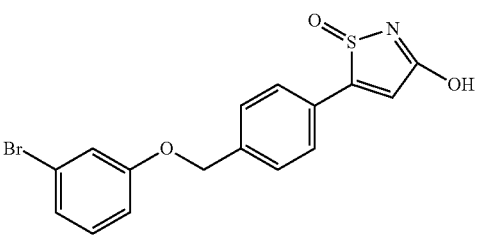
Example 104
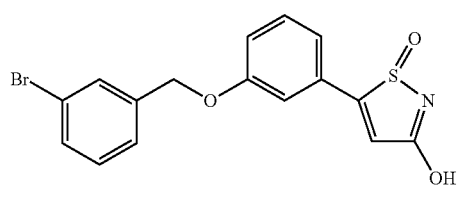
Example 105
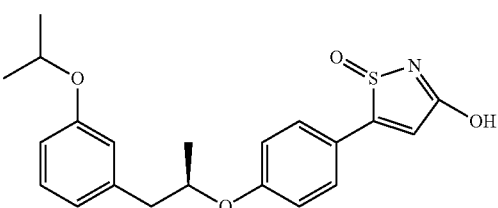

-continued
Example 106
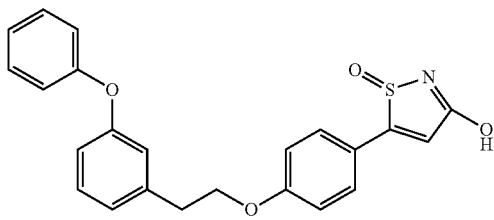
Example 108
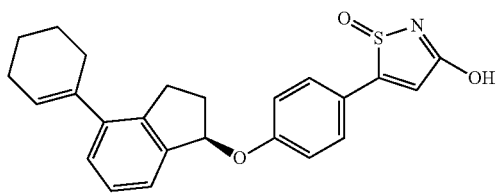
Example 110
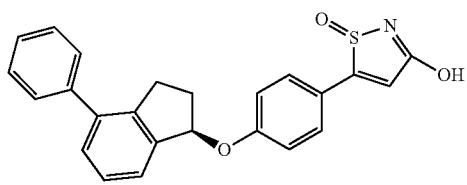
Example 112
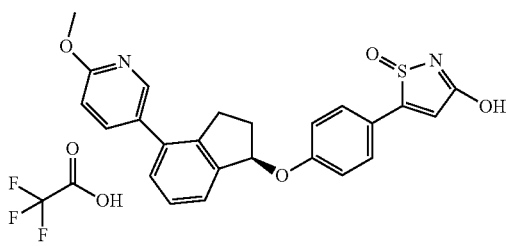
Example 114
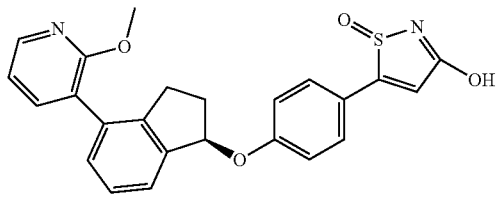
Example 116
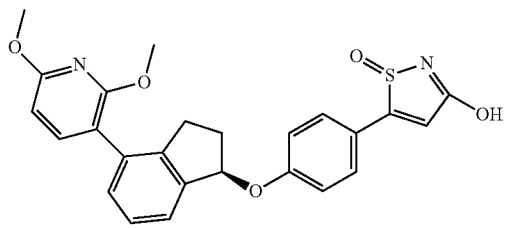
Example 107
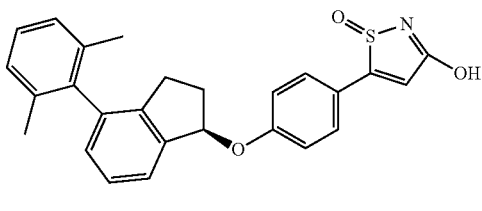
Example 109
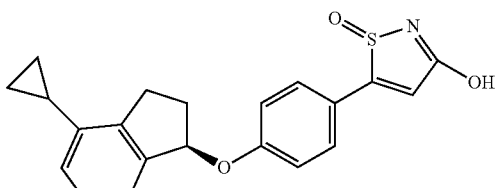
Example 111
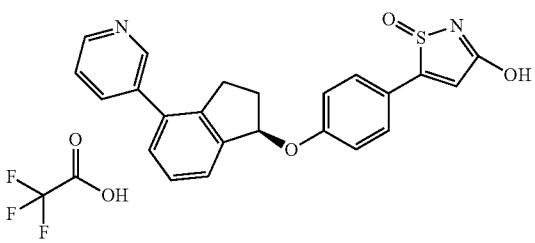
Example 113
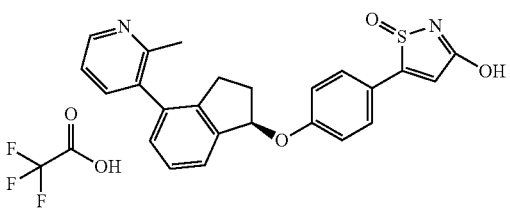
Example 115
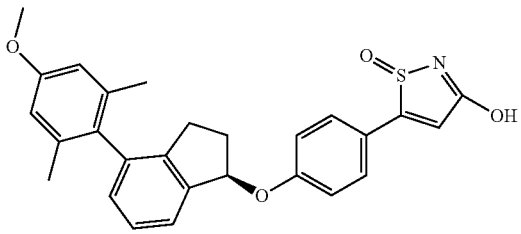
Example 117
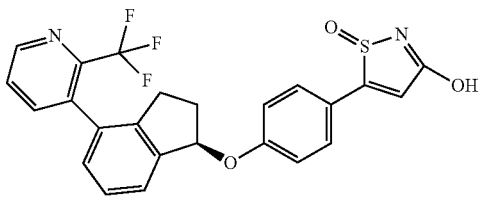

-continued
Example 118
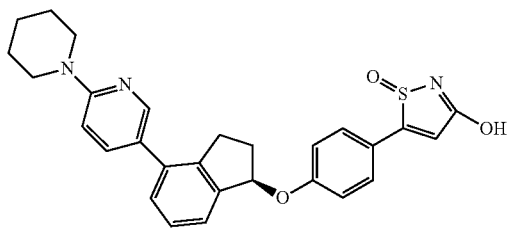
Example 119
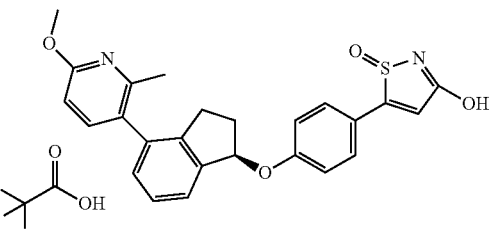
Example 120
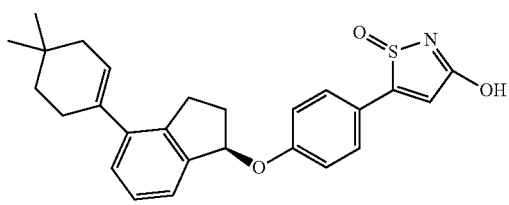
Example 121
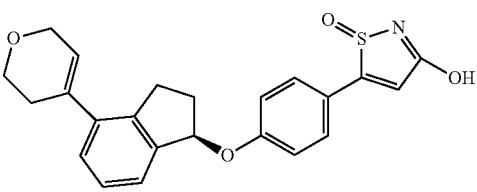
Example 122
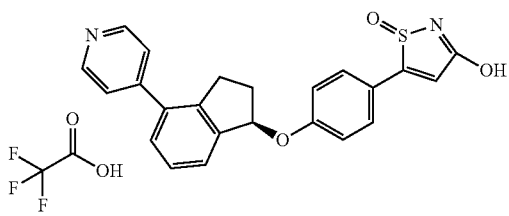
Example 123
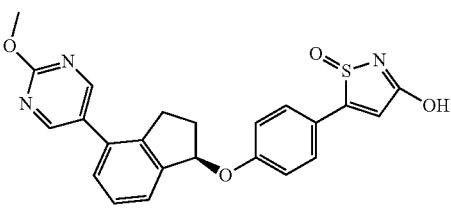
Example 124
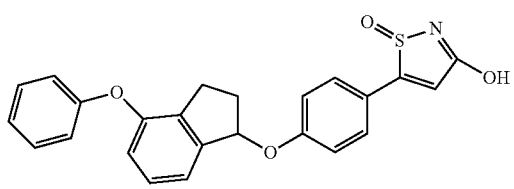
Example 125
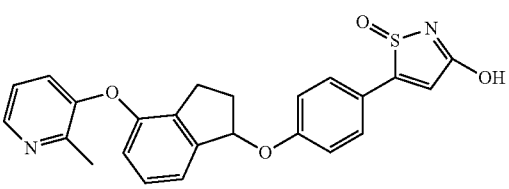
Example 126
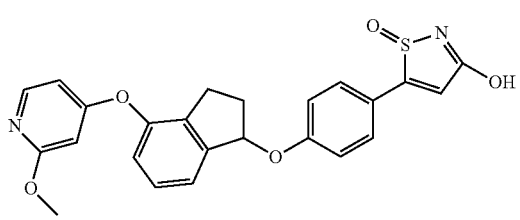
Example 127
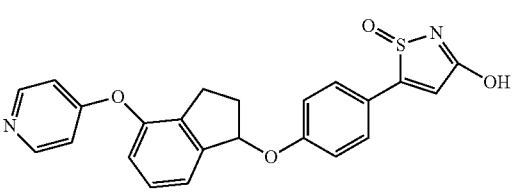
Example 128
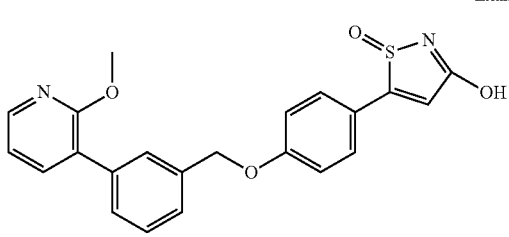
Example 129
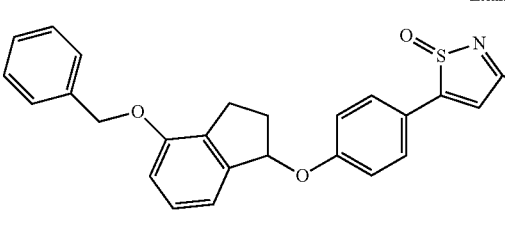
Example 130
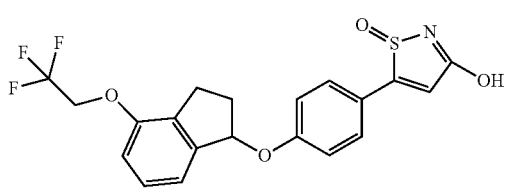
Example 131
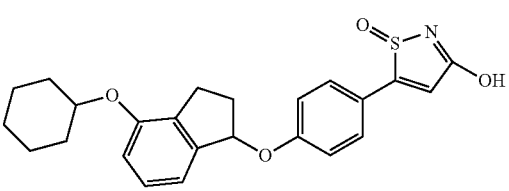

-continued
Example 132
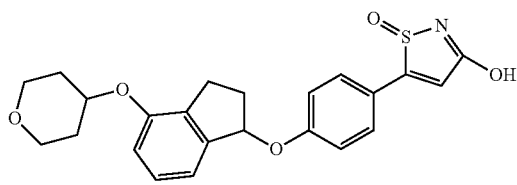
Example 133
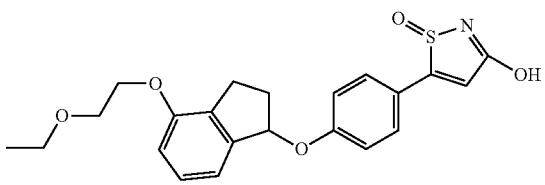
Example 134
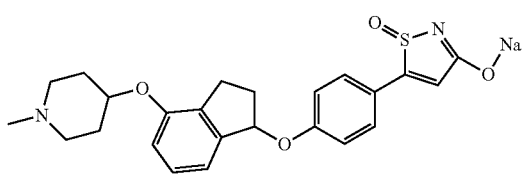
Example 135
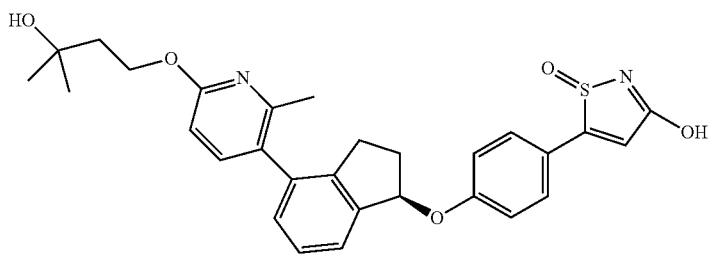
Example 136
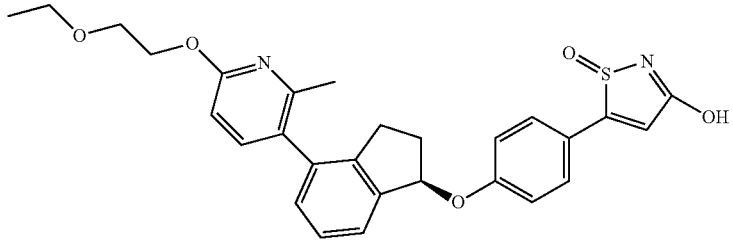
Example 137
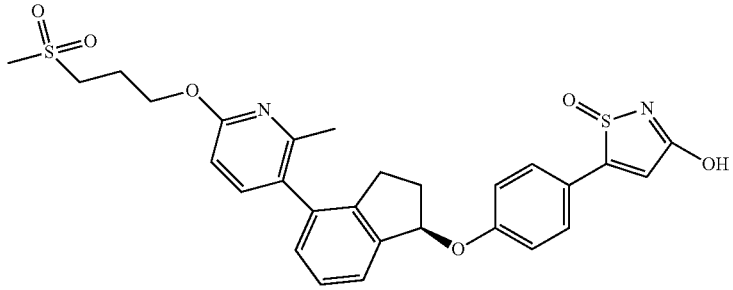
Example 138
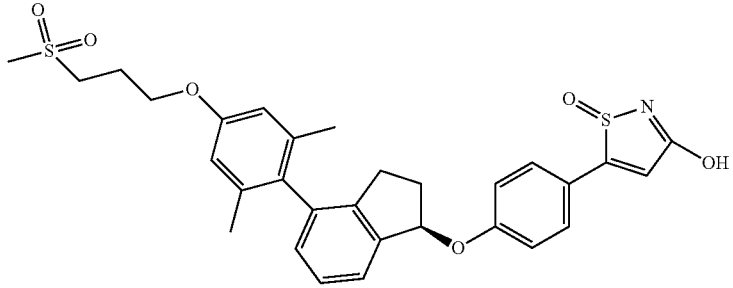

-continued
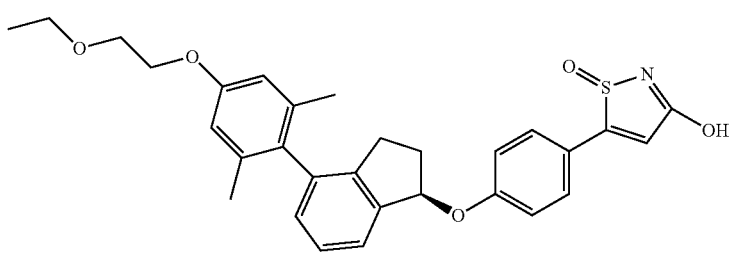
Example 139
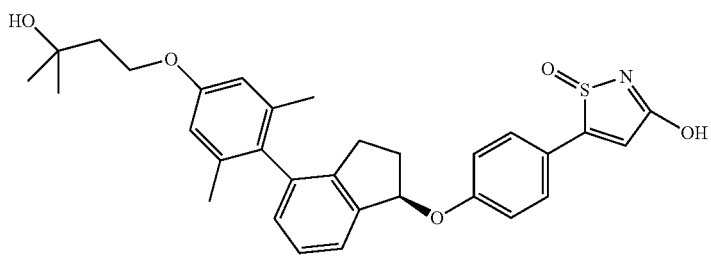
Example 140
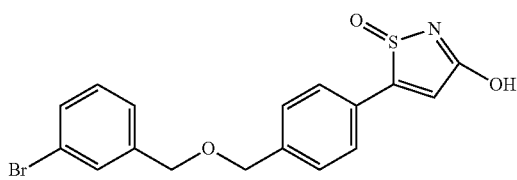
Example 141
Structural Formula 5
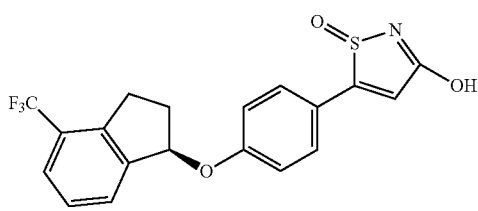
Example 142
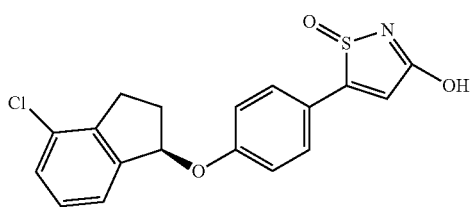
Example 143
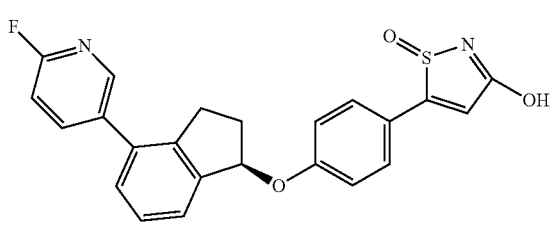
Example 144
Structural Formula 6
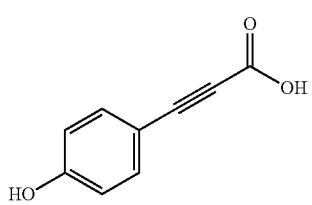
Example 1-1
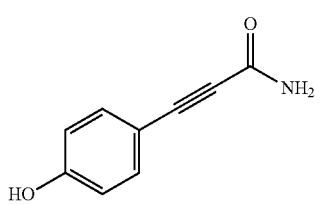
Example 1-2

-continued
Example 1-3
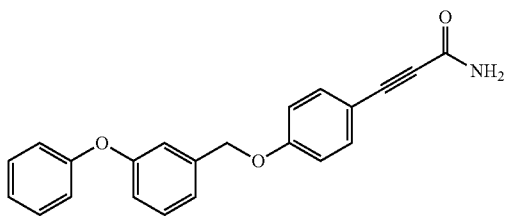
Example 3-1
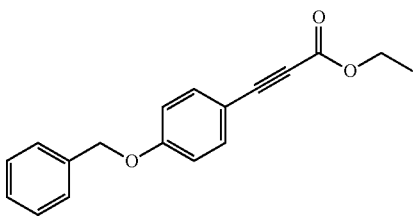
Example 3-2
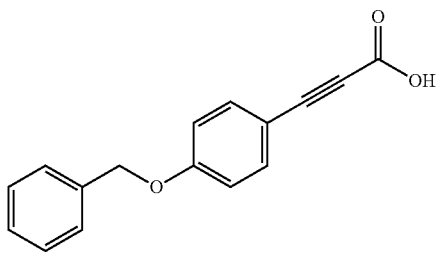
Example 3-3
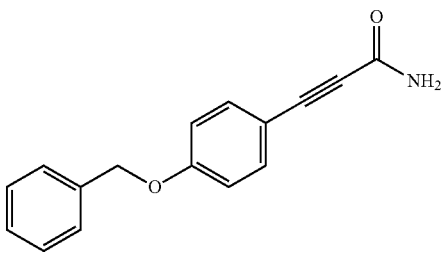
Example 4-1
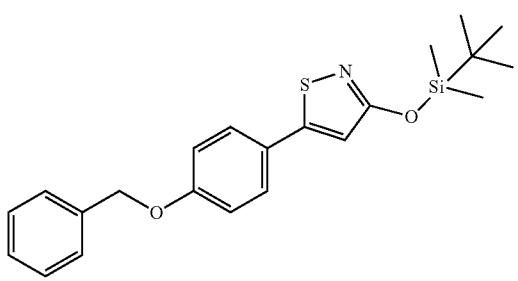
Example 5-1
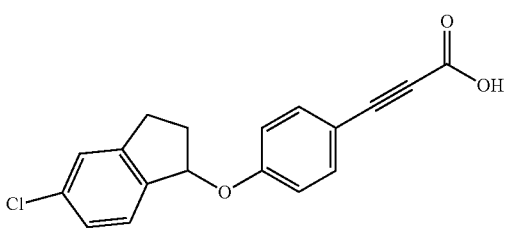
Example 5-2
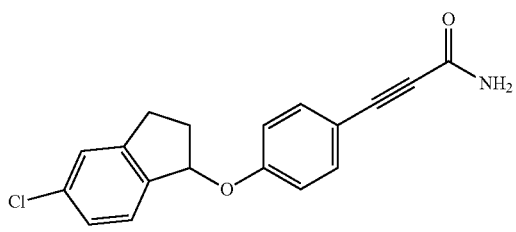
Example 7-1
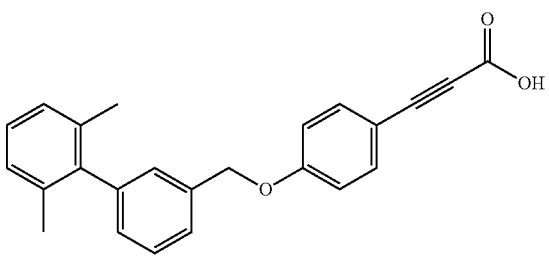
Example 7-2
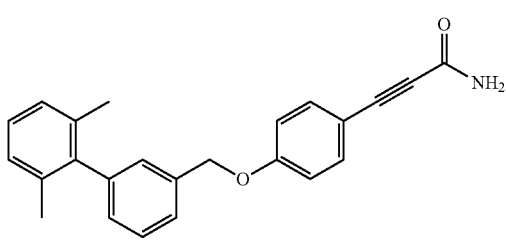
Example 8-1
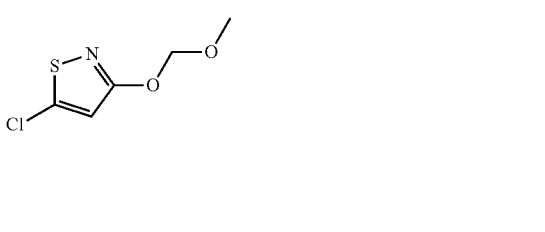
Example 8-2
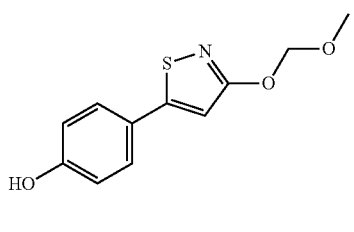
Example 8-3
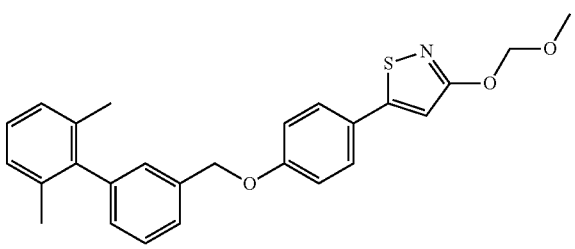

-continued
Example 10-1
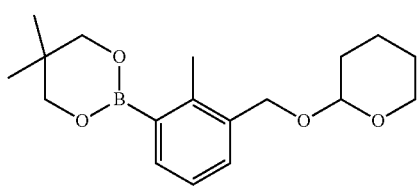
Example 10-2
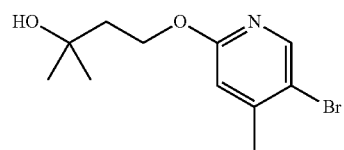
Example 10-3
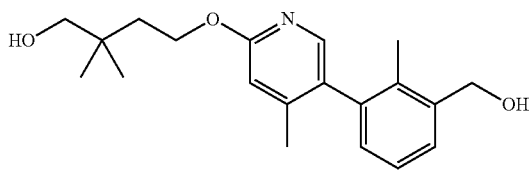
Example 10-4
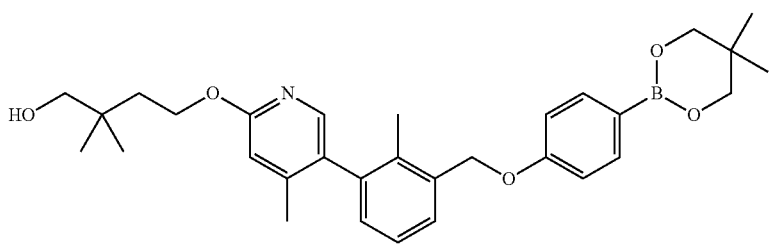
Structural Formula 7
Example 10-5
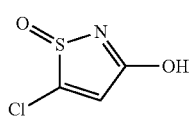
Example 11-1
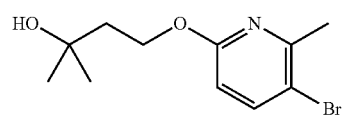
Example 11-2
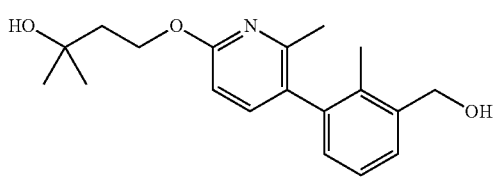
Example 11-3
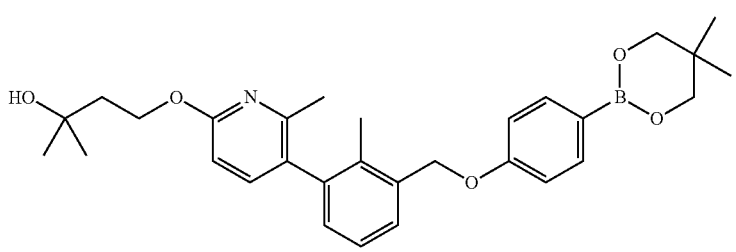
Example 12-1
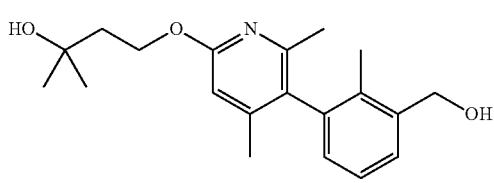
Example 12-2
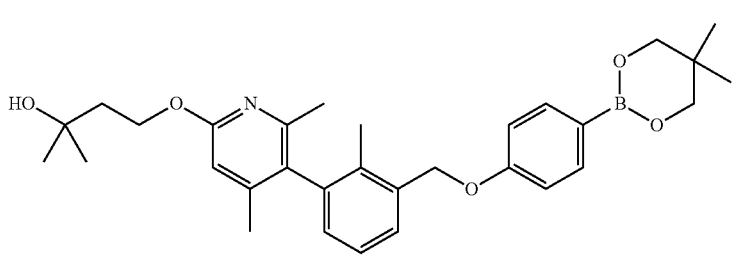

Example 13-1
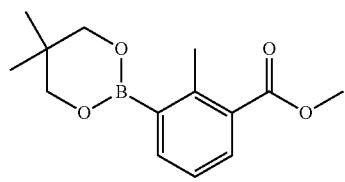
Example 13-2
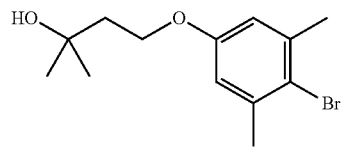
Example 13-3
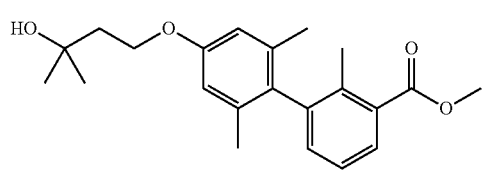
Example 13-4
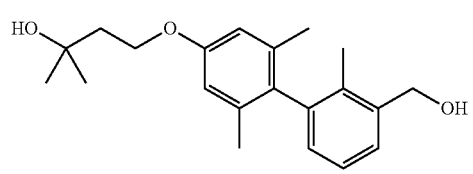
Example 13-5
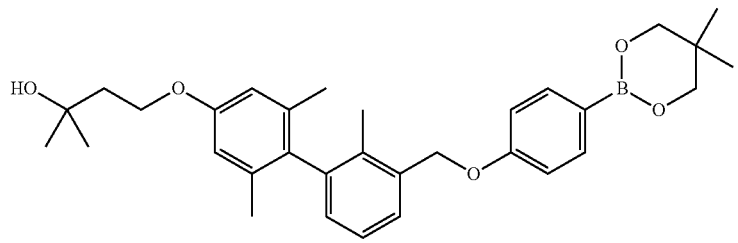
Reference Example 1
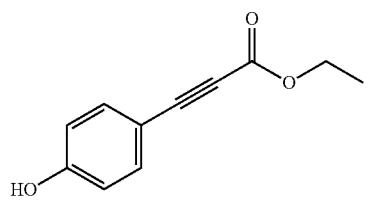
Reference Example 2
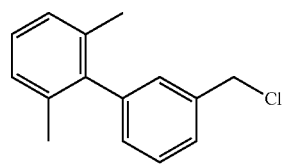
Reference Example 3
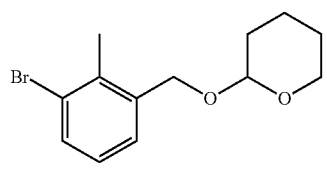
Reference Example 4
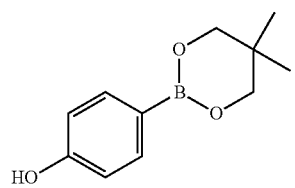
Reference Example 5
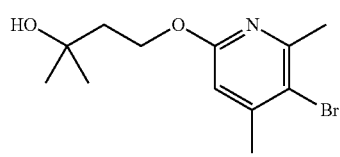
Example 15-1(A)
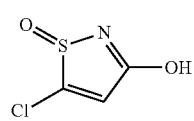
Reference Example 15-1(B)
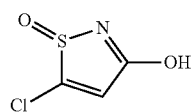
Example 15-2
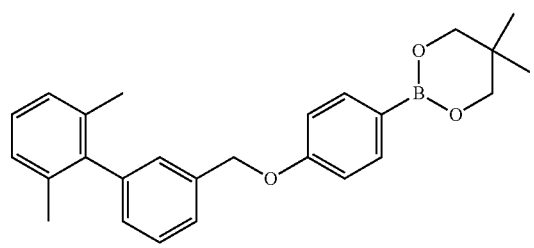

-continued
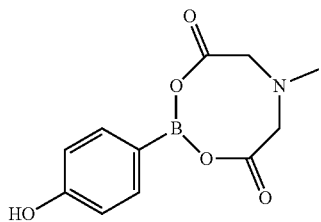
Reference Example 6
TABLE 5
Substituted boronic acid ester (1)
Example  Structural Formula
17
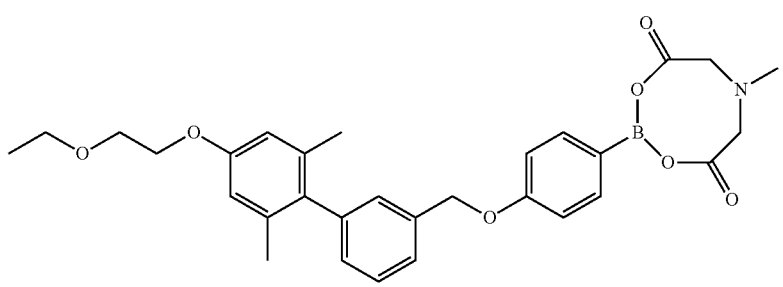 [SMILES: CCOCCOc1cc(C)c(-c2cccc(COc3ccc(B4OC(=O)CN(C)CC(=O)O4)cc3)c2)c(C)c1]
18
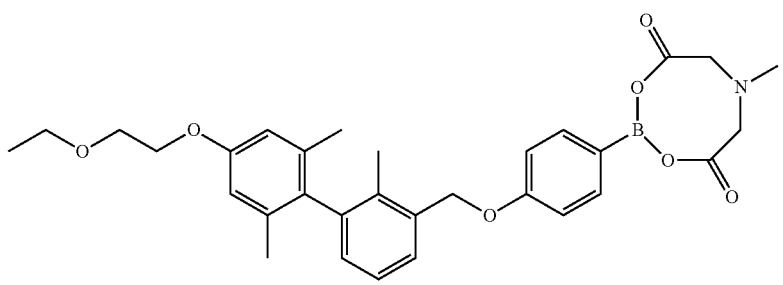 [SMILES: CCOCCOc1cc(C)c(-c2cccc(COc3ccc(B4OC(=O)CN(C)CC(=O)O4)cc3)c2C)c(C)c1]
19
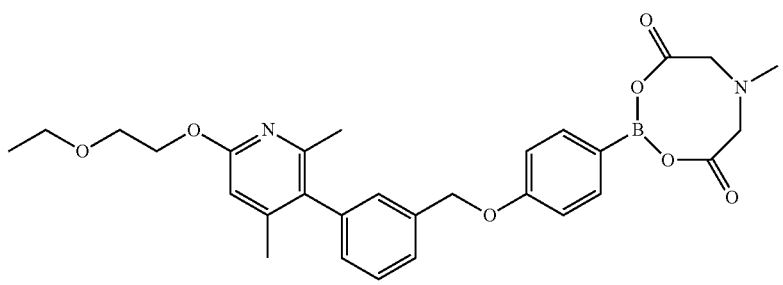 [SMILES: CCOCCOc1cc(C)c(-c2cccc(COc3ccc(B4OC(=O)CN(C)CC(=O)O4)cc3)c2)c(C)n1]
20
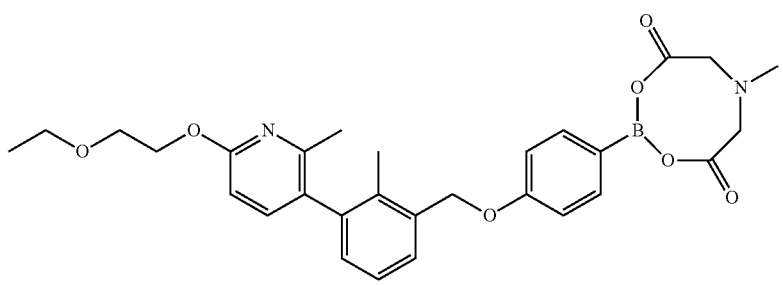 [SMILES: CCOCCOc1ccc(-c2cccc(COc3ccc(B4OC(=O)CN(C)CC(=O)O4)cc3)c2C)c(C)n1]

TABLE 5-continued
Substituted boronic acid ester (1)
Example | Structural Formula
21
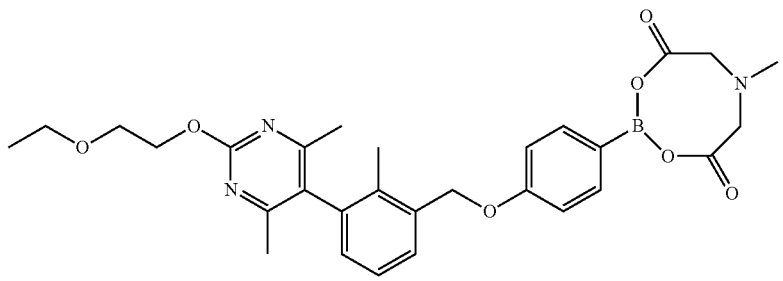 [SMILES: CCOCCOc1nc(C)c(-c2cccc(COc3ccc(B4OC(=O)CN(C)CC(=O)O4)cc3)c2C)c(C)n1]
22
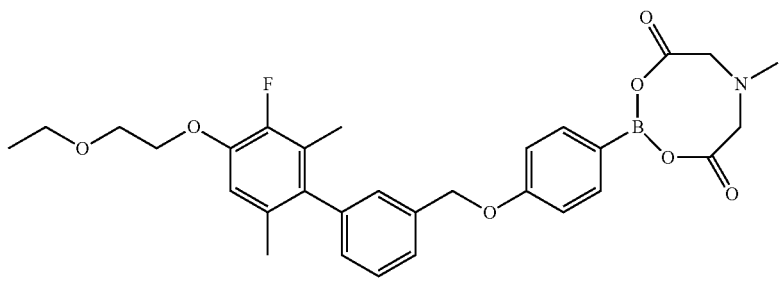 [SMILES: CCOCCOc1cc(C)c(-c2cccc(COc3ccc(B4OC(=O)CN(C)CC(=O)O4)cc3)c2)c(C)c1F]
23
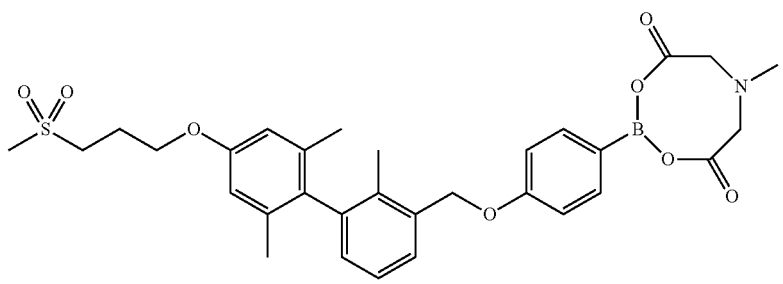
24
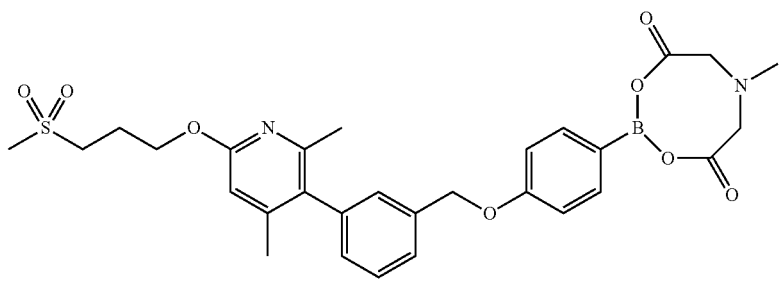
25
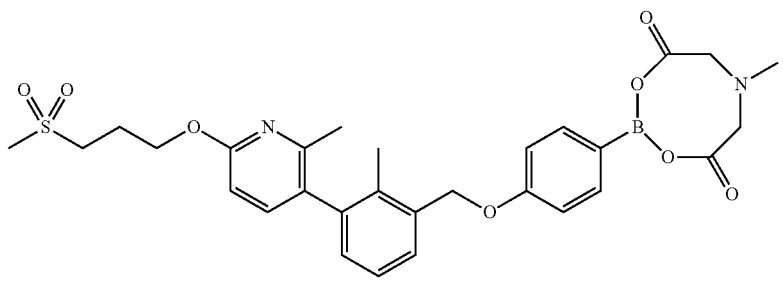

TABLE 5-continued
Substituted boronic acid ester (1)
| Example | Structural Formula |
|---|---|
| 26 | 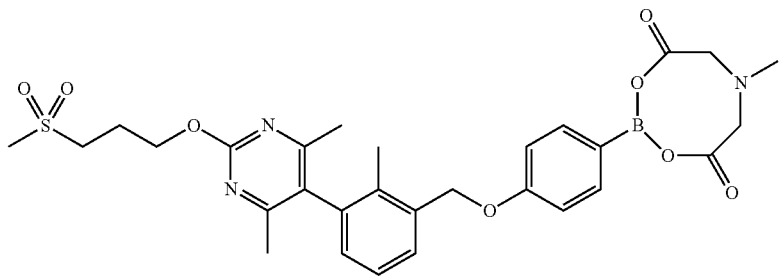 |
| 27 | 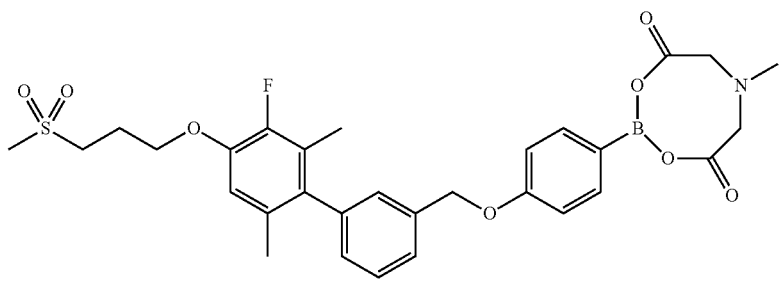 |
| 28 | 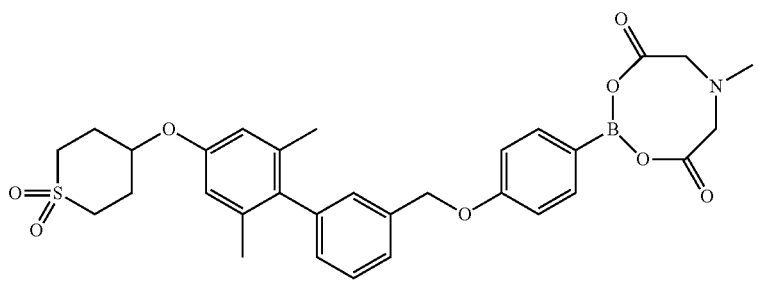 [SMILES: Cc1cc(OC2CCS(=O)(=O)CC2)cc(C)c1-c1cccc(COc2ccc(B3OC(=O)CN(C)CC(=O)O3)cc2)c1] |
| 29 | 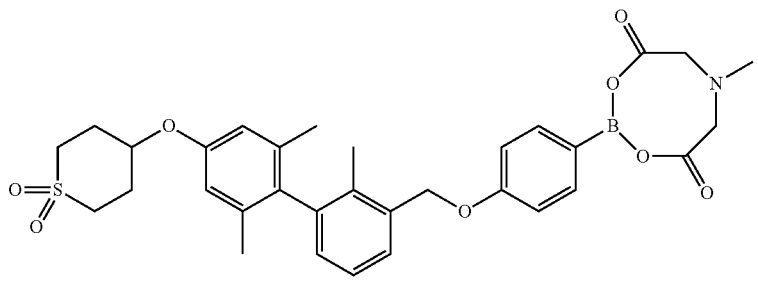 [SMILES: Cc1cc(OC2CCS(=O)(=O)CC2)cc(C)c1-c1cccc(COc2ccc(B3OC(=O)CN(C)CC(=O)O3)cc2)c1C] |
| 30 | 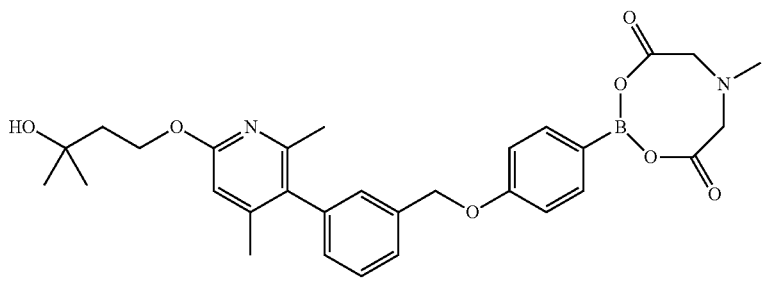 [SMILES: Cc1cc(OCCC(C)(C)O)nc(C)c1-c1cccc(COc2ccc(B3OC(=O)CN(C)CC(=O)O3)cc2)c1] |

TABLE 5-continued
Substituted boronic acid ester (1)
Example | Structural Formula
31
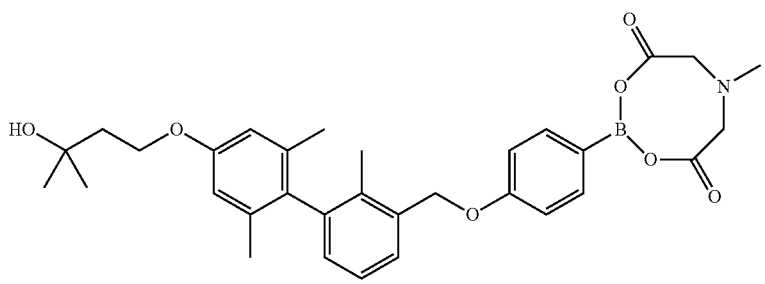 [SMILES: Cc1cc(OCCC(C)(C)O)cc(C)c1-c1cccc(COc2ccc(B3OC(=O)CN(C)CC(=O)O3)cc2)c1C]
32
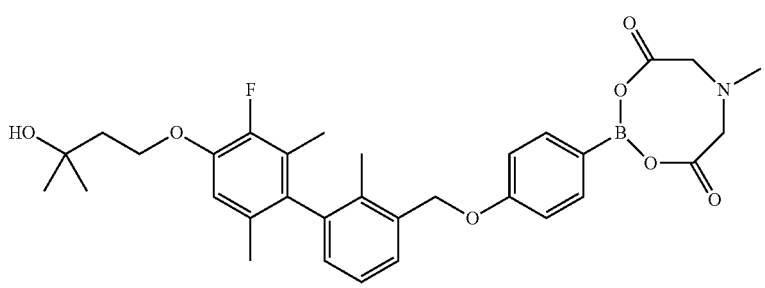 [SMILES: Cc1cc(OCCC(C)(C)O)c(F)c(C)c1-c1cccc(COc2ccc(B3OC(=O)CN(C)CC(=O)O3)cc2)c1C]
33
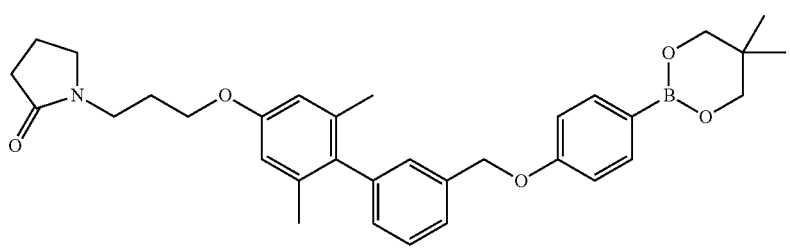 [SMILES: Cc1cc(OCCCN2CCCC2=O)cc(C)c1-c1cccc(COc2ccc(B3OCC(C)(C)CO3)cc2)c1]
34
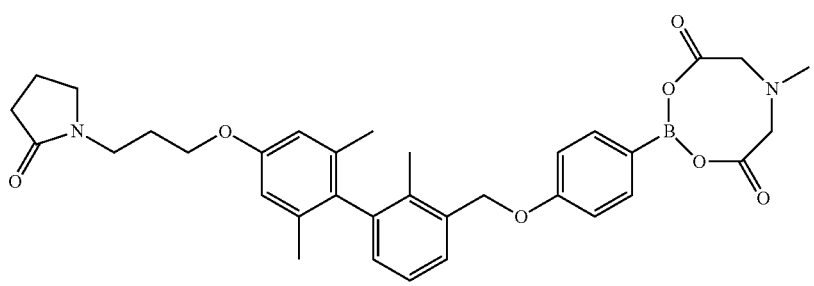 [SMILES: Cc1cc(OCCCN2CCCC2=O)cc(C)c1-c1cccc(COc2ccc(B3OC(=O)CN(C)CC(=O)O3)cc2)c1C]
35
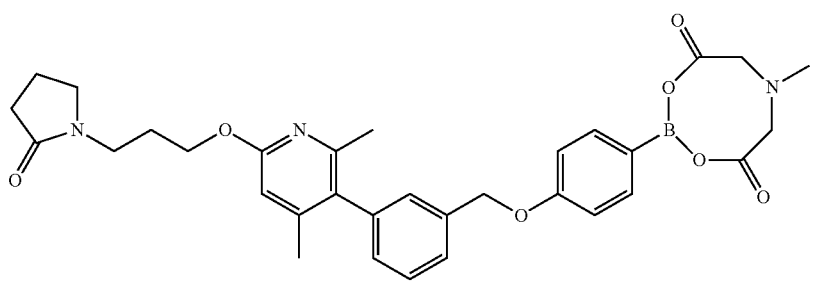 [SMILES: Cc1cc(OCCCN2CCCC2=O)nc(C)c1-c1cccc(COc2ccc(B3OC(=O)CN(C)CC(=O)O3)cc2)c1]

TABLE 5-continued
Substituted boronic acid ester (1)
Example Structural Formula
36
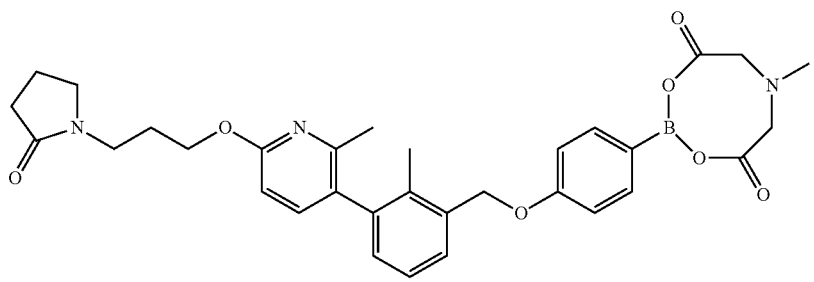 [SMILES: Cc1nc(OCCCN2CCCC2=O)ccc1-c1cccc(COc2ccc(B3OC(=O)CN(C)CC(=O)O3)cc2)c1C]
TABLE 6
Substituted boronic acid ester (2)
Example Structural Formula
37
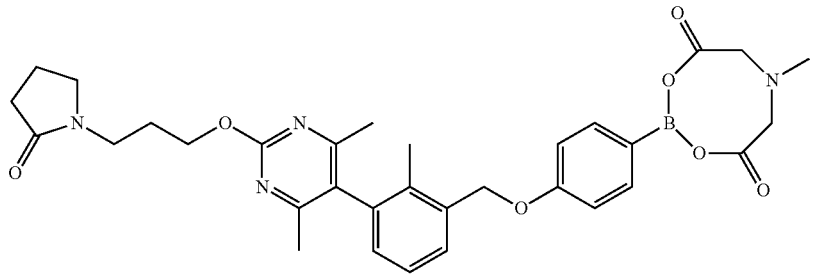 [SMILES: Cc1nc(OCCCN2CCCC2=O)nc(C)c1-c1cccc(COc2ccc(B3OC(=O)CN(C)CC(=O)O3)cc2)c1C]
38
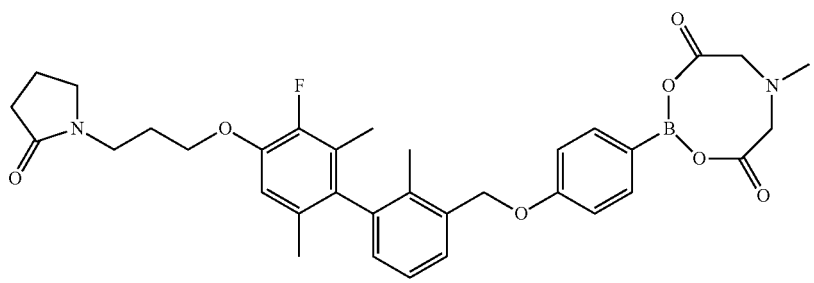 [SMILES: Cc1cc(OCCCN2CCCC2=O)c(F)c(C)c1-c1cccc(COc2ccc(B3OC(=O)CN(C)CC(=O)O3)cc2)c1C]
39
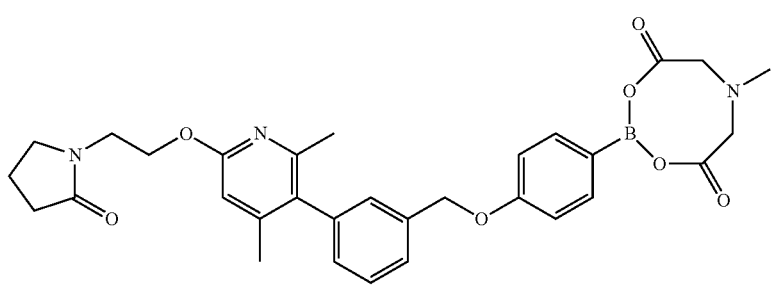 [SMILES: Cc1cc(OCCN2CCCC2=O)nc(C)c1-c1cccc(COc2ccc(B3OC(=O)CN(C)CC(=O)O3)cc2)c1]

TABLE 6-continued
Substituted boronic acid ester (2)
Example Structural Formula
40
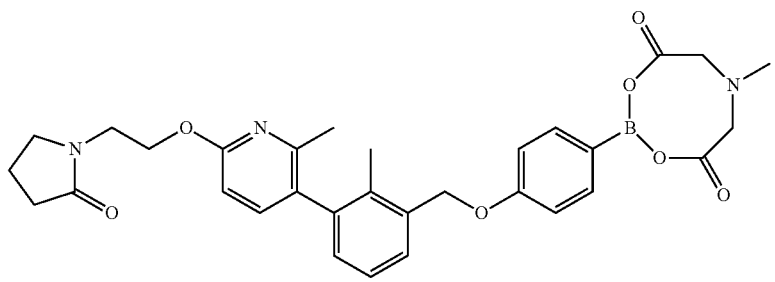 [SMILES: Cc1nc(OCCN2CCCC2=O)ccc1-c1cccc(COc2ccc(B3OC(=O)CN(C)CC(=O)O3)cc2)c1C]
41
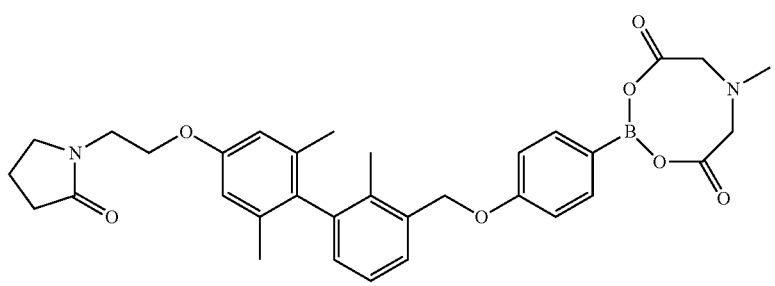 [SMILES: Cc1cc(OCCN2CCCC2=O)cc(C)c1-c1cccc(COc2ccc(B3OC(=O)CN(C)CC(=O)O3)cc2)c1C]
42
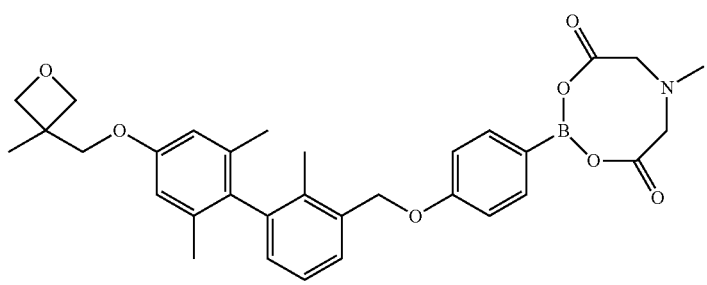
43
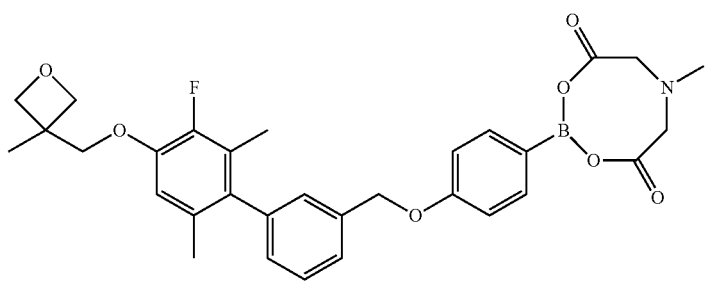
44
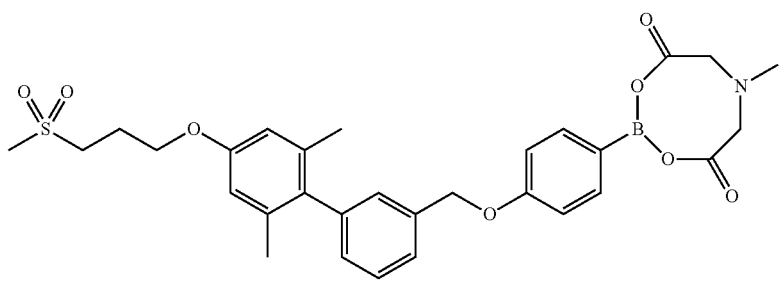

TABLE 6-continued
Substituted boronic acid ester (2)
Example | Structural Formula
---|---
45
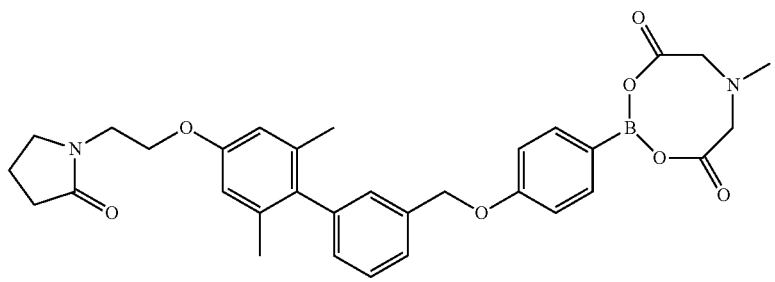 [SMILES: Cc1cc(OCCN2CCCC2=O)cc(C)c1-c1cccc(COc2ccc(B3OC(=O)CN(C)CC(=O)O3)cc2)c1]
46
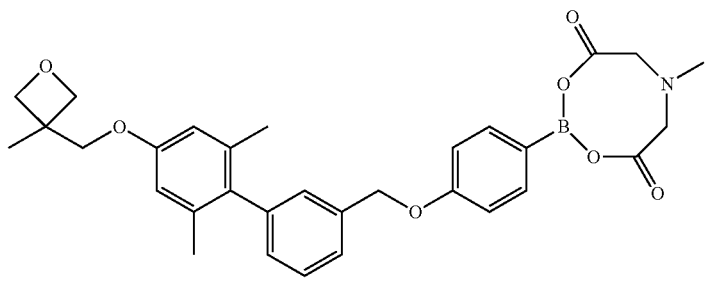
47
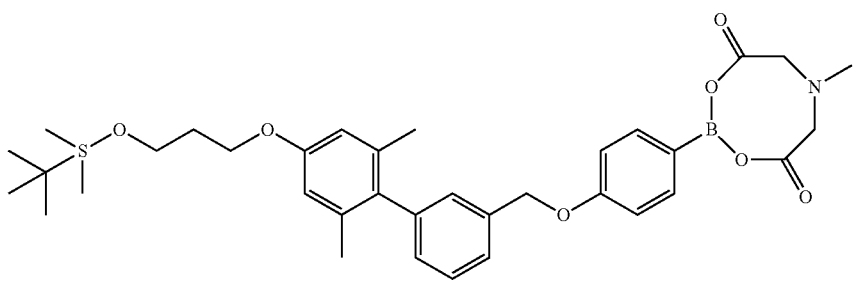 [SMILES: Cc1cc(OCCCOS(C)(C)C(C)(C)C)cc(C)c1-c1cccc(COc2ccc(B3OC(=O)CN(C)CC(=O)O3)cc2)c1]
48
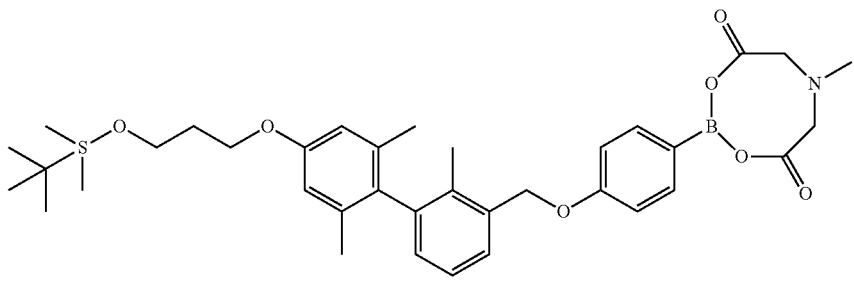 [SMILES: Cc1cc(OCCCOS(C)(C)C(C)(C)C)cc(C)c1-c1cccc(COc2ccc(B3OC(=O)CN(C)CC(=O)O3)cc2)c1C]
49
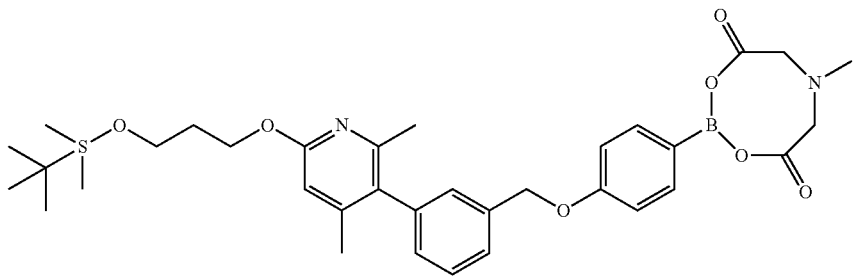 [SMILES: Cc1cc(OCCCOS(C)(C)C(C)(C)C)nc(C)c1-c1cccc(COc2ccc(B3OC(=O)CN(C)CC(=O)O3)cc2)c1]

TABLE 6-continued
Substituted boronic acid ester (2)
Example  Structural Formula
50
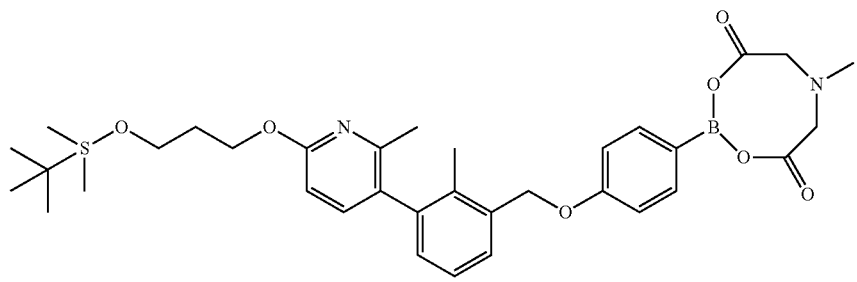 [SMILES: Cc1nc(OCCCOS(C)(C)C(C)(C)C)ccc1-c1cccc(COc2ccc(B3OC(=O)CN(C)CC(=O)O3)cc2)c1C]
51
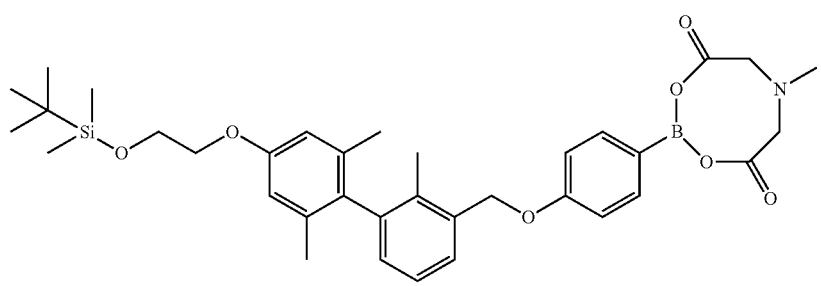 [SMILES: Cc1cc(OCCO[Si](C)(C)C(C)(C)C)cc(C)c1-c1cccc(COc2ccc(B3OC(=O)CN(C)CC(=O)O3)cc2)c1C]
52
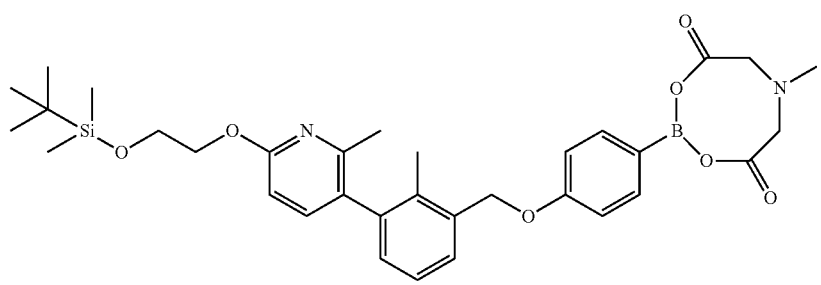 [SMILES: Cc1nc(OCCO[Si](C)(C)C(C)(C)C)ccc1-c1cccc(COc2ccc(B3OC(=O)CN(C)CC(=O)O3)cc2)c1C]
53
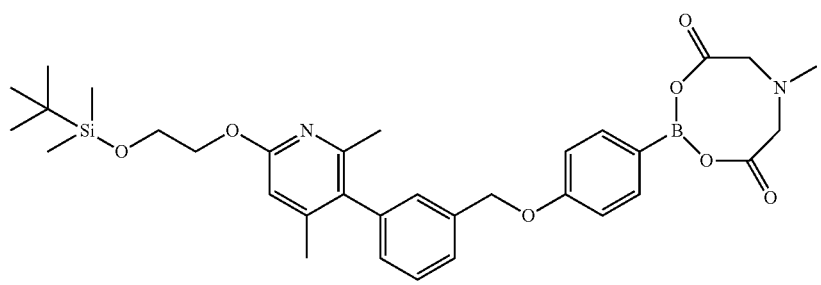 [SMILES: Cc1cc(OCCO[Si](C)(C)C(C)(C)C)nc(C)c1-c1cccc(COc2ccc(B3OC(=O)CN(C)CC(=O)O3)cc2)c1]
54
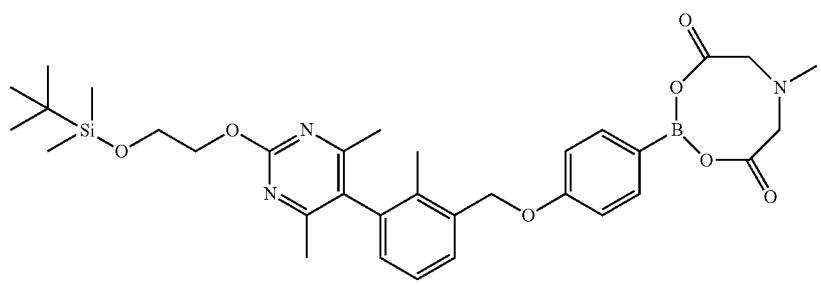 [SMILES: Cc1nc(OCCO[Si](C)(C)C(C)(C)C)nc(C)c1-c1cccc(COc2ccc(B3OC(=O)CN(C)CC(=O)O3)cc2)c1C]

TABLE 6-continued
Substituted boronic acid ester (2)
Example  Structural Formula
55
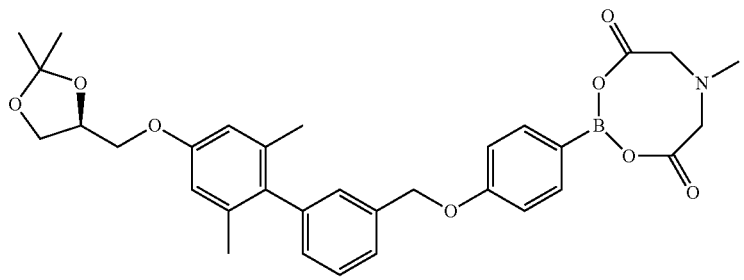 [SMILES: Cc1cc(OC[C@H]2COC(C)(C)O2)cc(C)c1-c1cccc(COc2ccc(B3OC(=O)CN(C)CC(=O)O3)cc2)c1]
56
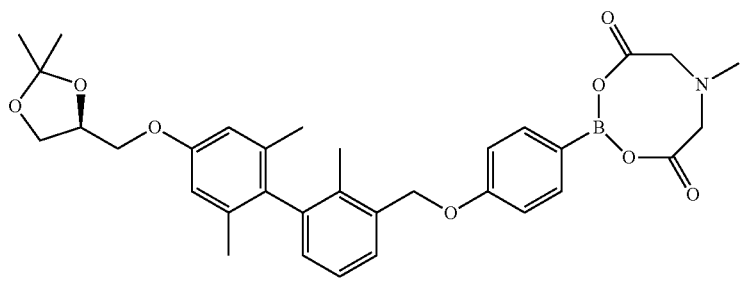 [SMILES: Cc1cc(OC[C@H]2COC(C)(C)O2)cc(C)c1-c1cccc(COc2ccc(B3OC(=O)CN(C)CC(=O)O3)cc2)c1C]
TABLE 7
Substituted boronic acid ester (3)
Example  Structural Formula
57
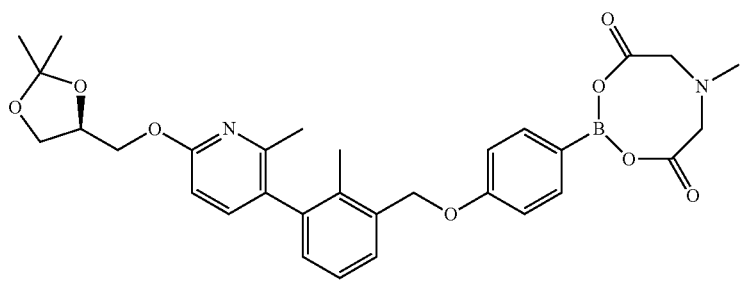
58
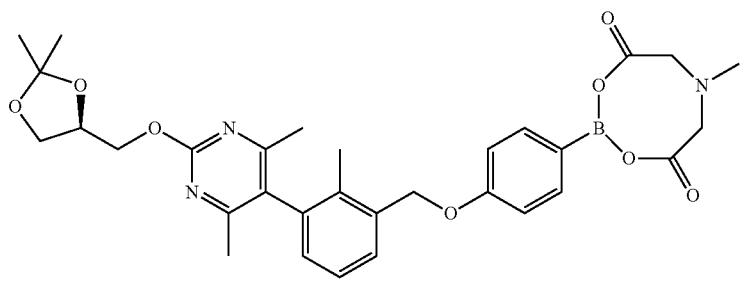 [SMILES: Cc1nc(OC[C@H]2COC(C)(C)O2)nc(C)c1-c1cccc(COc2ccc(B3OC(=O)CN(C)CC(=O)O3)cc2)c1C]

TABLE 7-continued
Substituted boronic acid ester (3)
Example Structural Formula
59
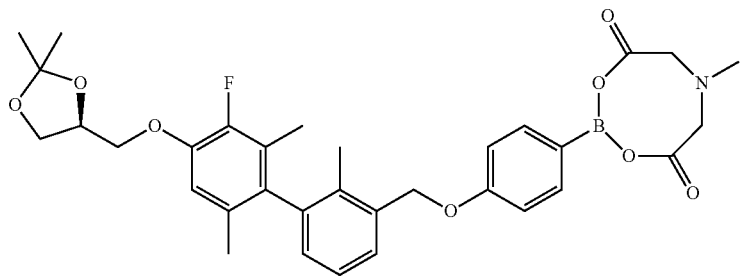 [SMILES: Cc1cc(OC[C@H]2COC(C)(C)O2)c(F)c(C)c1-c1cccc(COc2ccc(B3OC(=O)CN(C)CC(=O)O3)cc2)c1C]
60
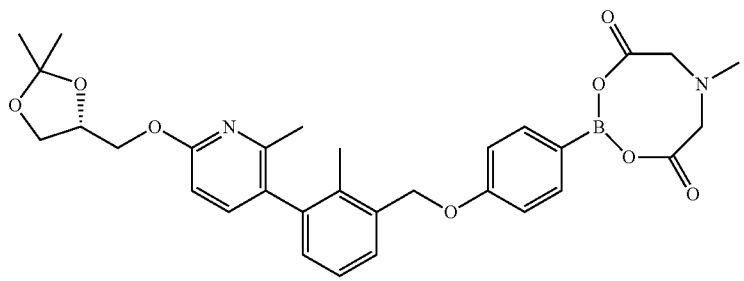 [SMILES: Cc1nc(OC[C@@H]2COC(C)(C)O2)ccc1-c1cccc(COc2ccc(B3OC(=O)CN(C)CC(=O)O3)cc2)c1C]
61
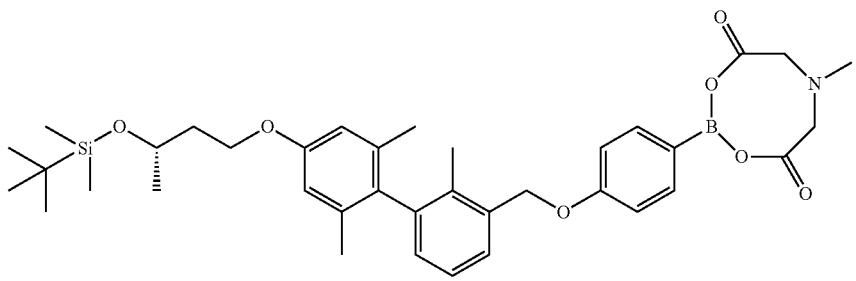 [SMILES: Cc1cc(OCC[C@H](C)O[Si](C)(C)C(C)(C)C)cc(C)c1-c1cccc(COc2ccc(B3OC(=O)CN(C)CC(=O)O3)cc2)c1C]
62
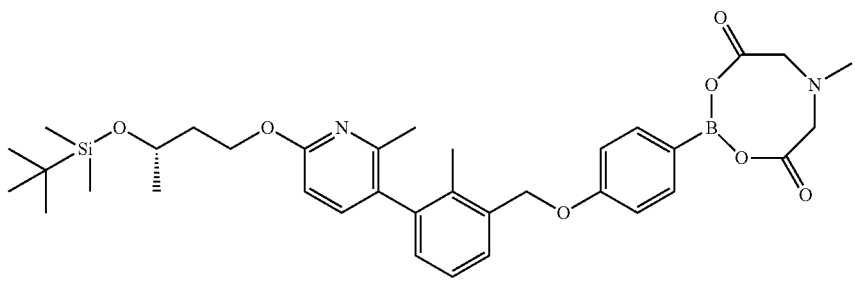 [SMILES: Cc1nc(OCC[C@H](C)O[Si](C)(C)C(C)(C)C)ccc1-c1cccc(COc2ccc(B3OC(=O)CN(C)CC(=O)O3)cc2)c1C]
63
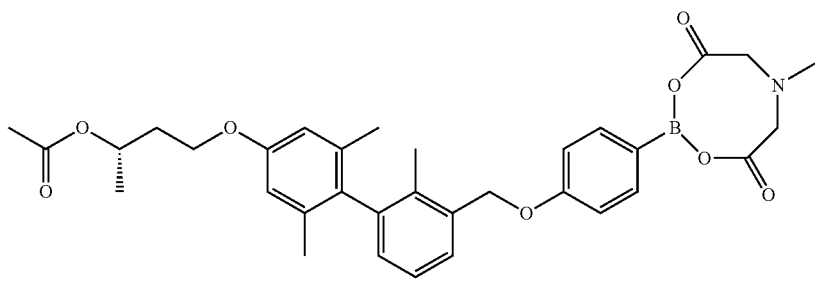 [SMILES: CC(=O)O[C@@H](C)CCOc1cc(C)c(-c2cccc(COc3ccc(B4OC(=O)CN(C)CC(=O)O4)cc3)c2C)c(C)c1]

US 8,476,287 B2
207	208
TABLE 7-continued
Substituted boronic acid ester (3)
| Example | Structural Formula |
|---|---|
| 64 | 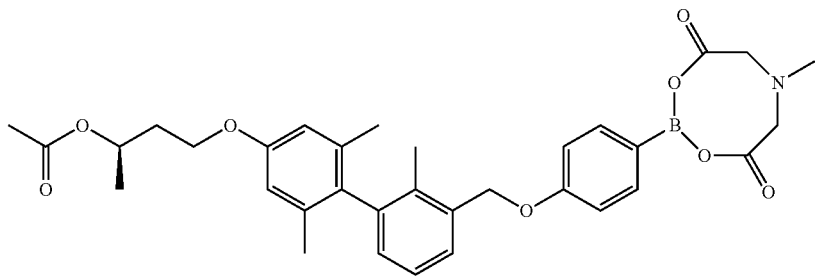 [SMILES: CC(=O)O[C@H](C)CCOc1cc(C)c(-c2cccc(COc3ccc(B4OC(=O)CN(C)CC(=O)O4)cc3)c2C)c(C)c1] |
| 65 | 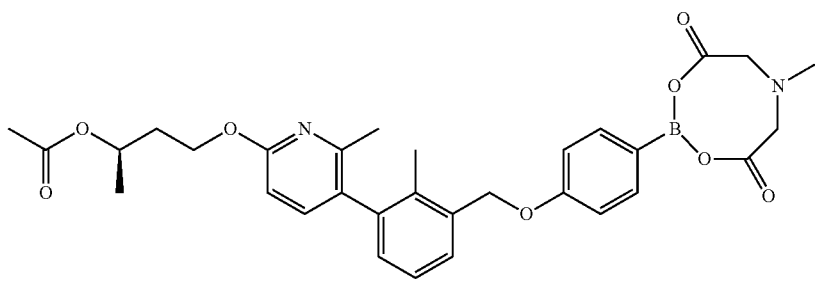 [SMILES: CC(=O)O[C@H](C)CCOc1ccc(-c2cccc(COc3ccc(B4OC(=O)CN(C)CC(=O)O4)cc3)c2C)c(C)n1] |
| 66 | 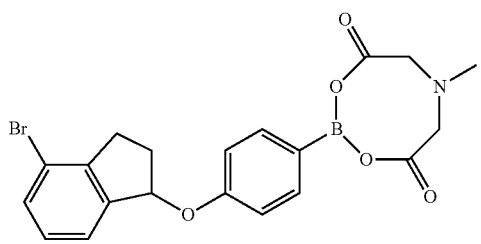 [SMILES: CN1CC(=O)OB(c2ccc(OC3CCc4c(Cl)cccc43)cc2)OC(=O)C1] |
| 67 | 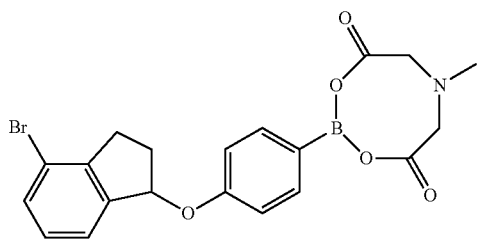 |
| 68 | 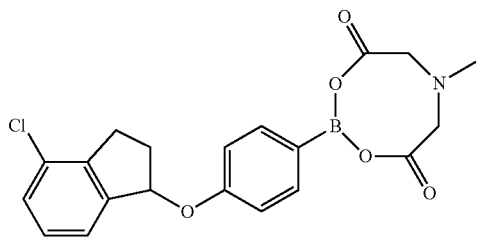 |
| 69 | 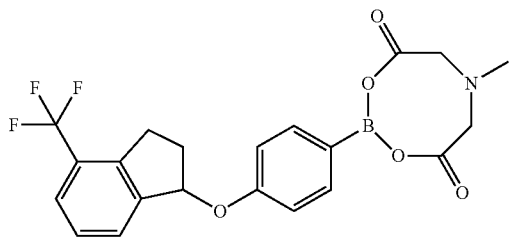 [SMILES: CN1CC(=O)OB(c2ccc(OC3CCc4c3cccc4C(F)(F)F)cc2)OC(=O)C1] |

Structural Formula 8
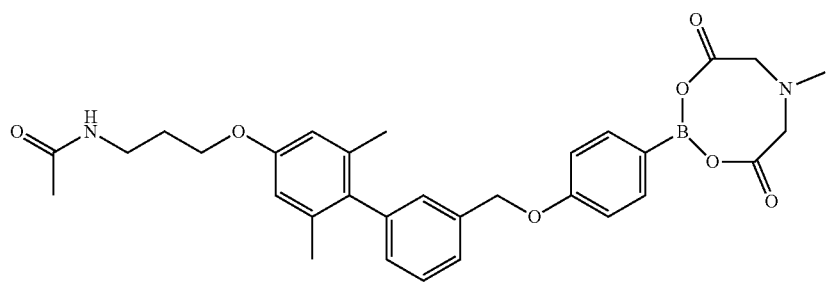
Example 70-1
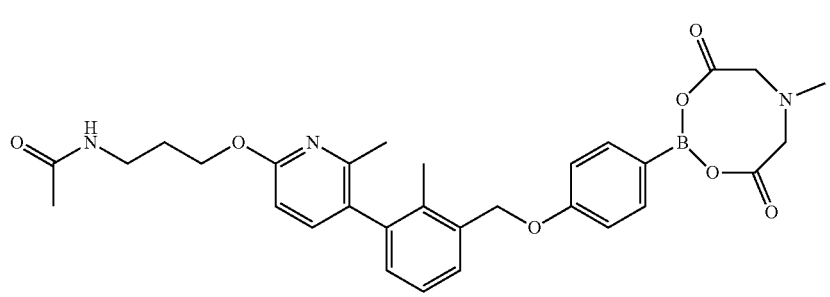
Example 71-1
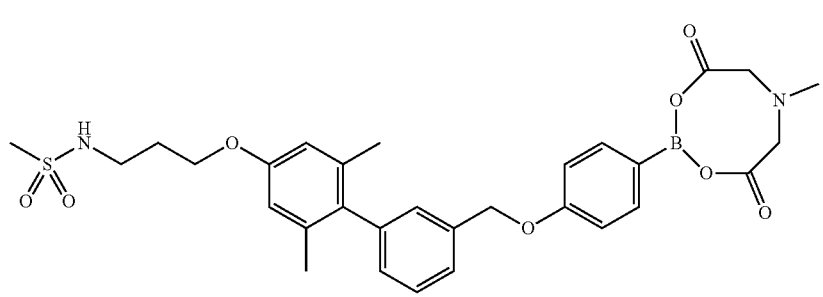
Example 72-1
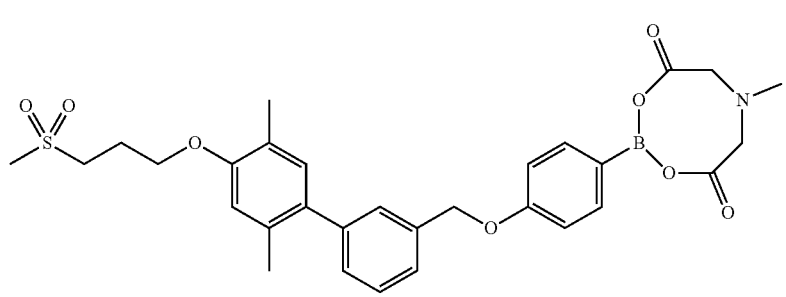
Example 73-1
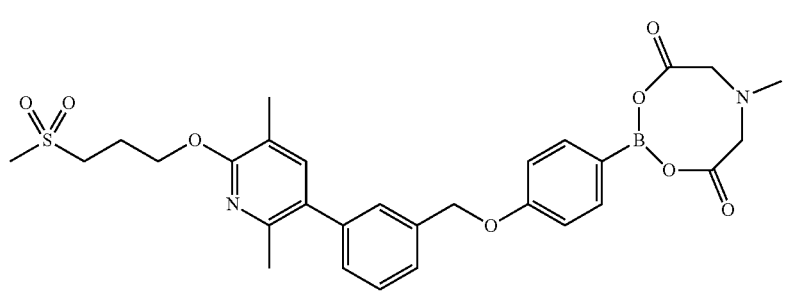
Example 74-1

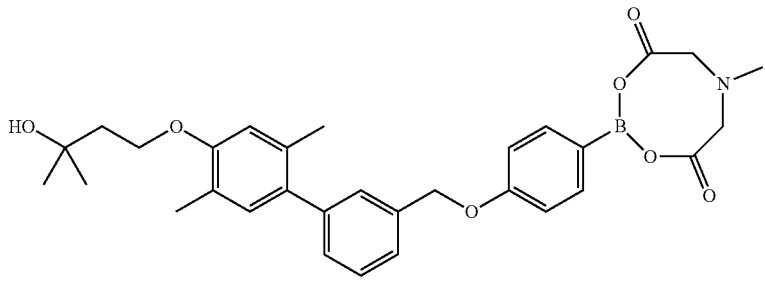
Example 75-1
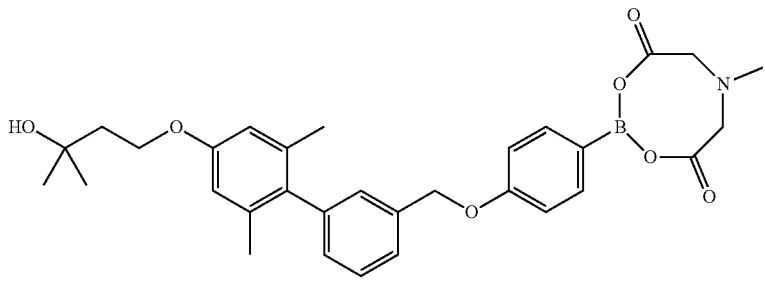
Example 76-1
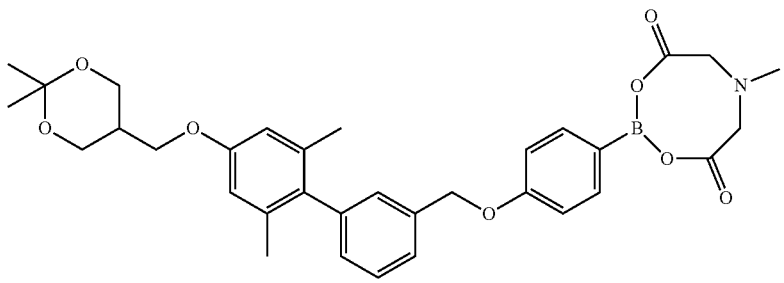
Example 77-1
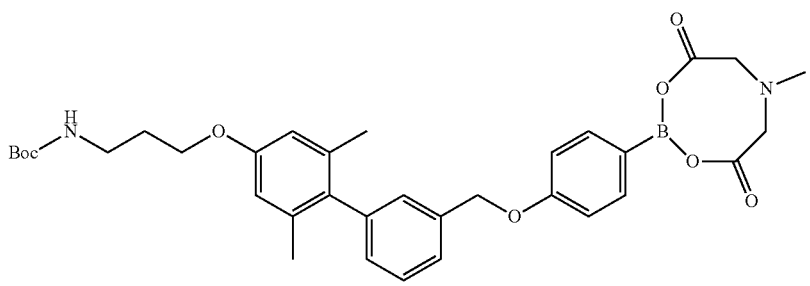
Example 78-1
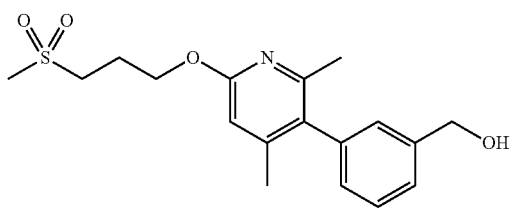
Example 79-1
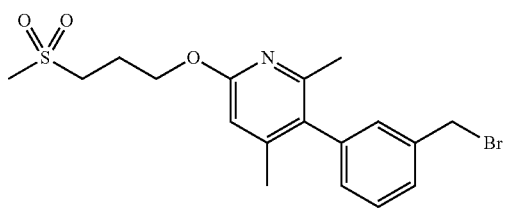
Example 79-2
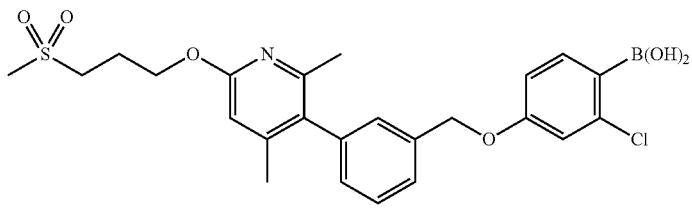
Example 79-3

Example 80-1
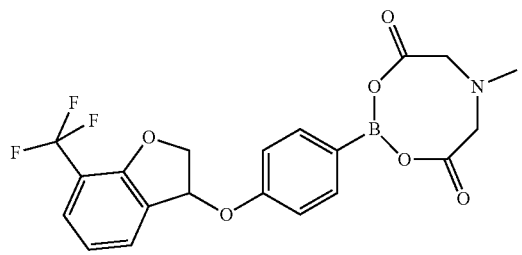
Example 81-1
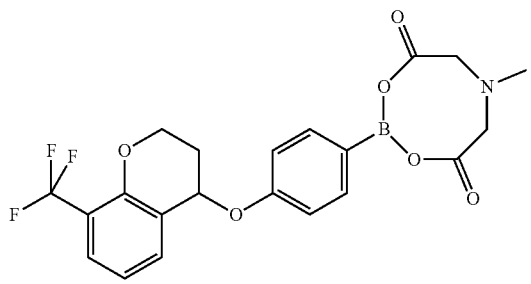
Example 82-1
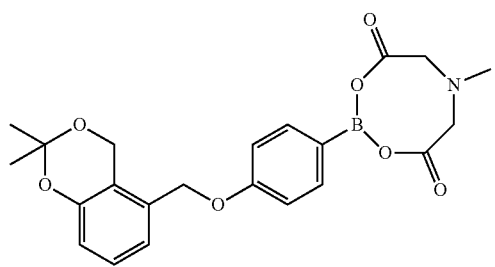
Example 83-1
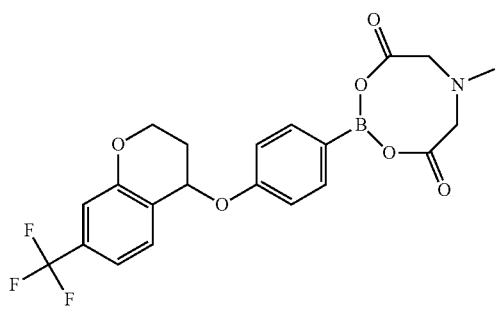
Example 84-1
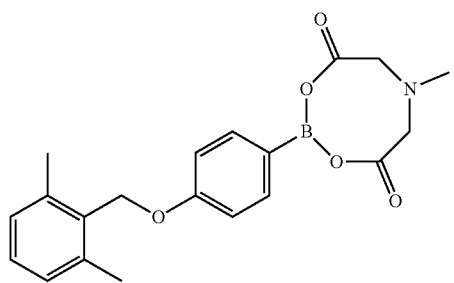
Example 85-1
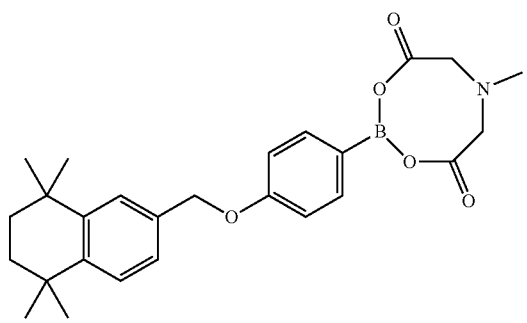
Example 86-1
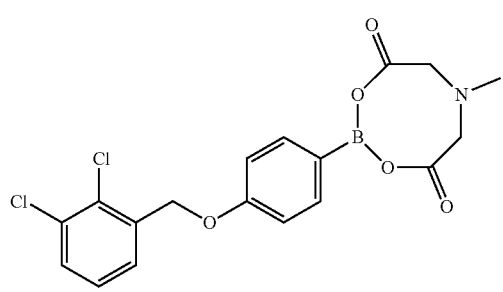
Example 87-1
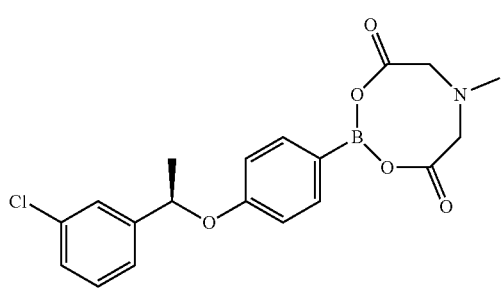
Example 88-1
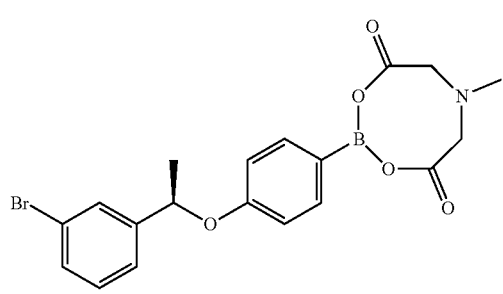

Structural Formula 9
Example 89-1
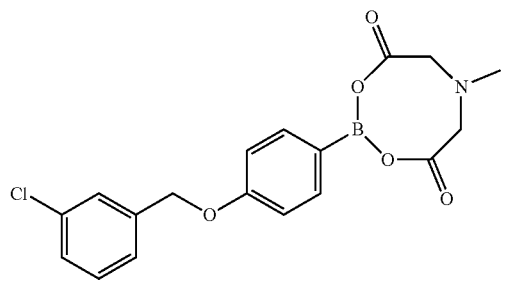
Example 90-1
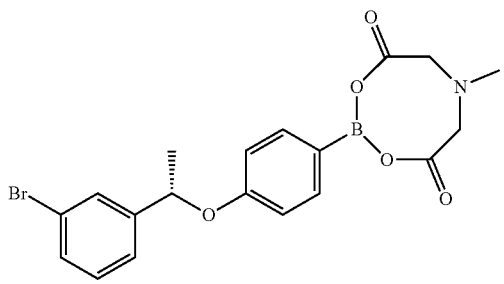
Example 91-1
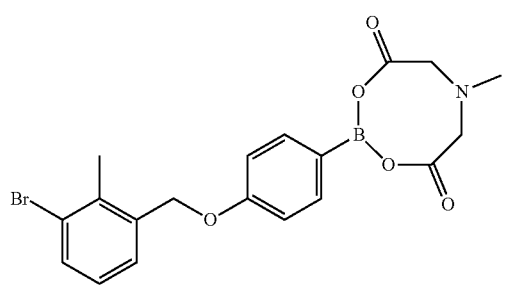
Example 92-1
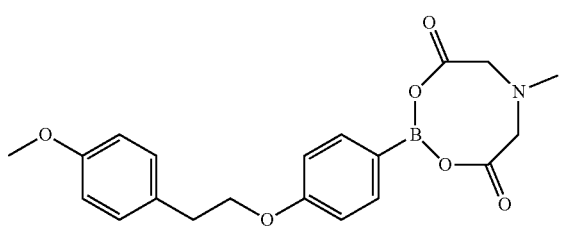
Example 93-1
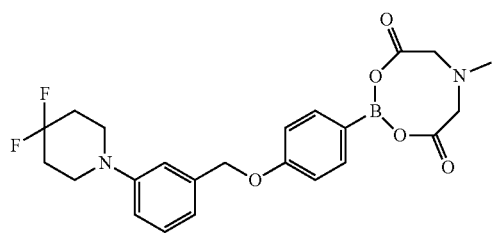
Example 94-1
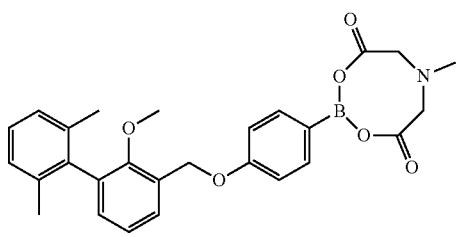
Example 95-1
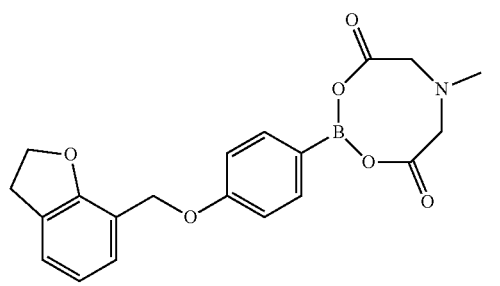
Example 96-1
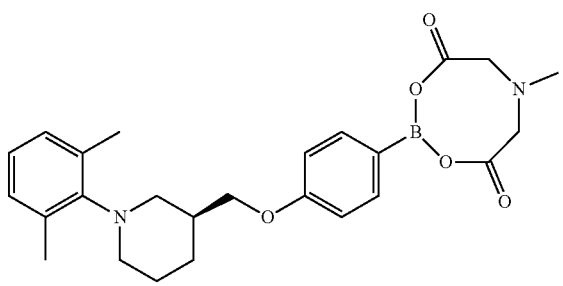
Example 97-1
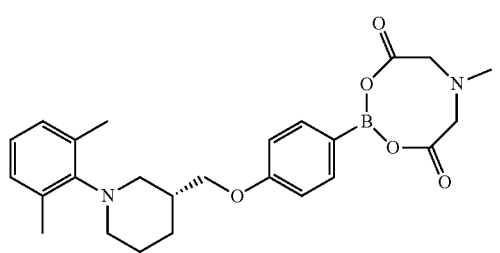
Example 98-1
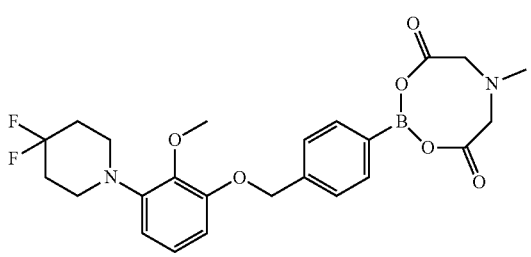

-continued
Example 99-1
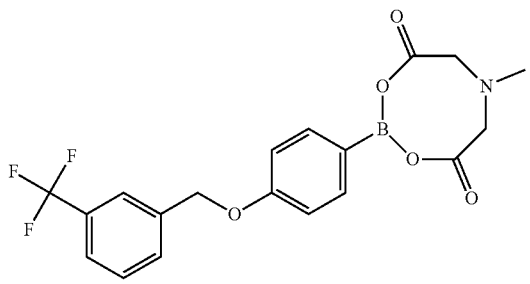
Example 100-1
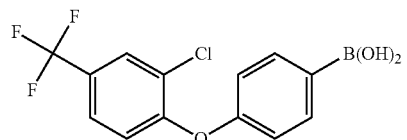
Example 101-1
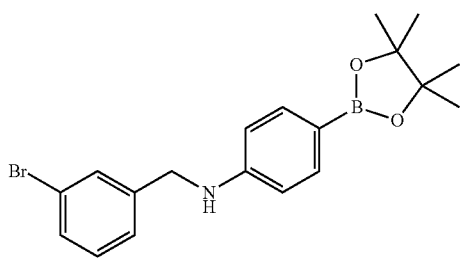
Example 101-2
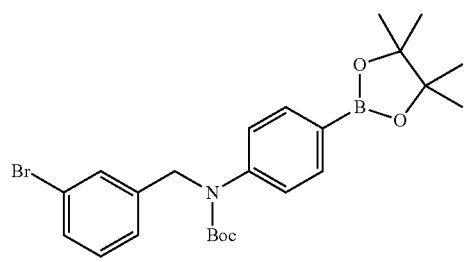
Example 102-1
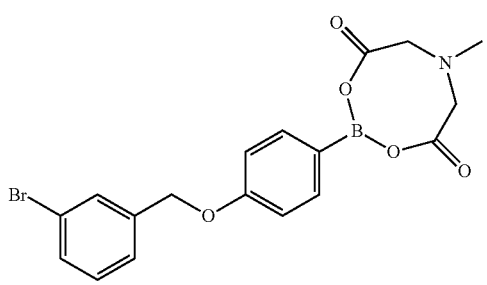
Example 103-1
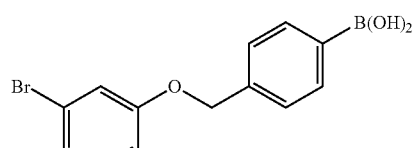
Example 104-1
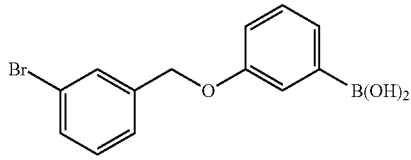
Example 105-1
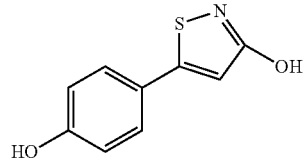
Example 105-2
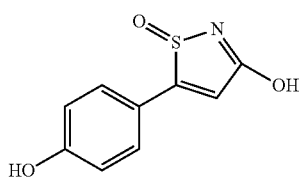
Example 105-3
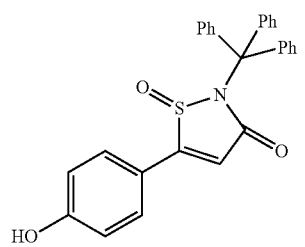
Example 105-4
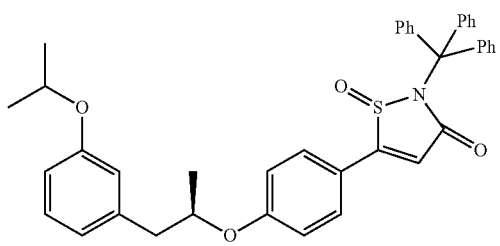
Example 106-1

Example 124-3
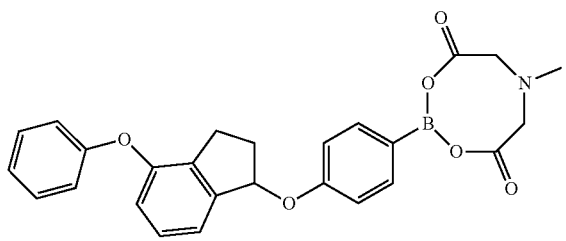
Example 124-2
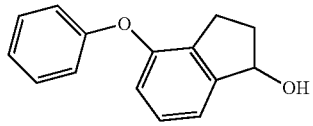
Example 124-1
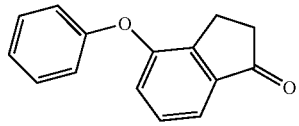
Example 125-1
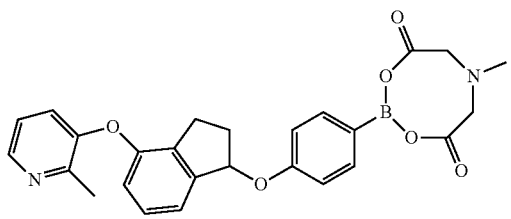
Example 126-1
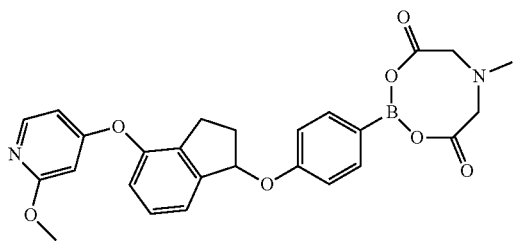
Structural Formula 10
Example 127-1
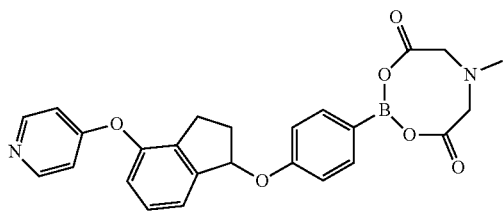
Example 129-1
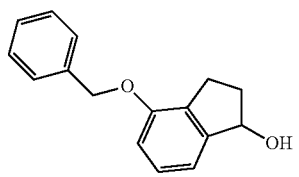
Example 129-2
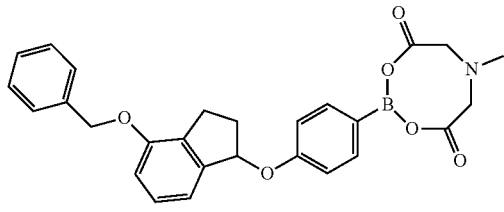
Example 130-1
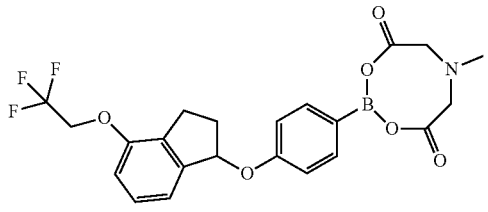
Example 131-1
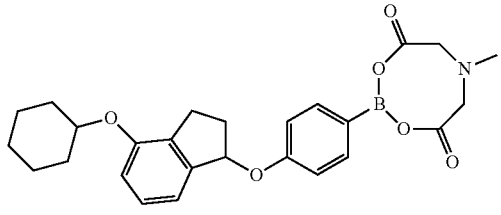
Example 132-1
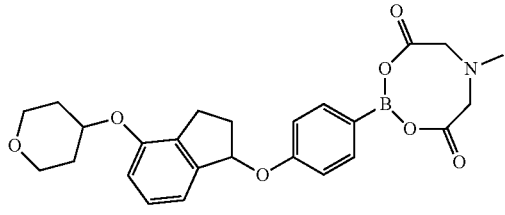
Example 133-1
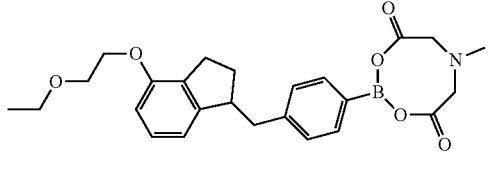
Example 134-1
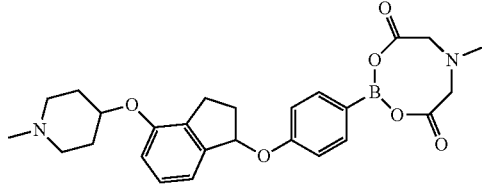

-continued
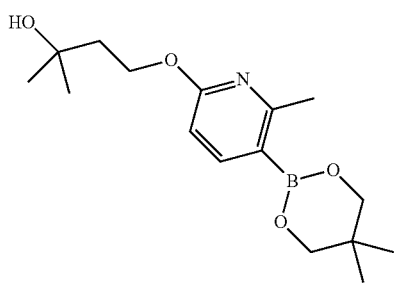
Example 135-1
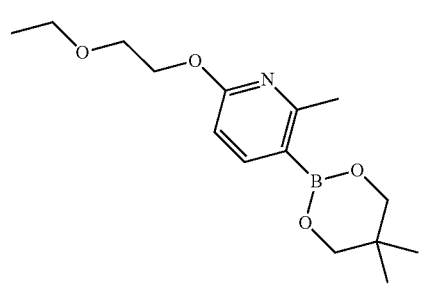
Example 136-1
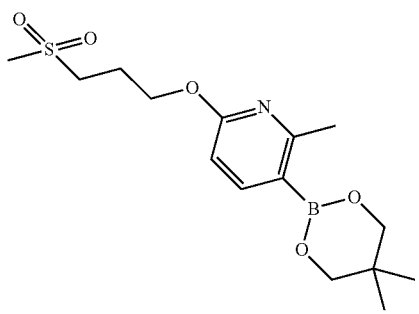
Example 137-1
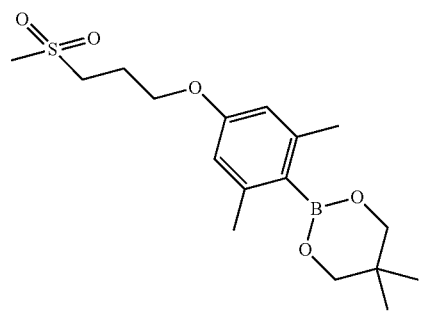
Example 138-1
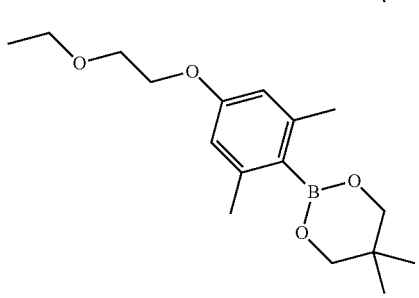
Example 139-1
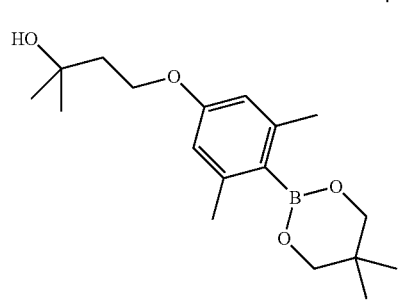
Example 140-1
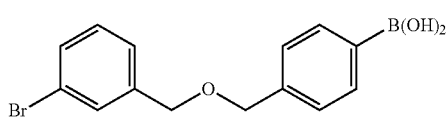
Example 141-1
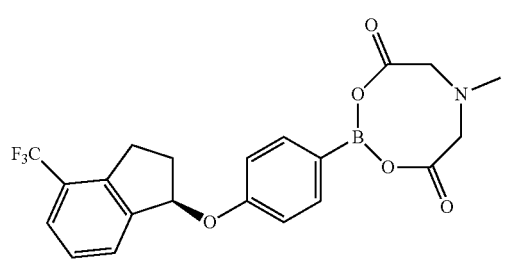
Example 142-1
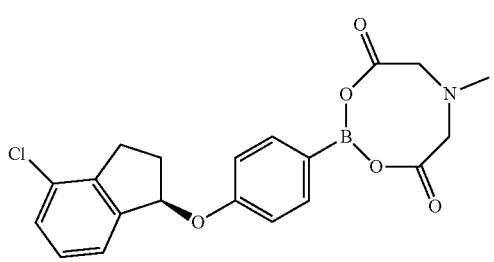
Example 143-1
TABLE 8
| Example | MS-ESI (m/z) [M + H]⁺ | Retention time (min.) |
|---|---|---|
| 1 | 376 | 6.35 |
| 2 | 392 | 6.08 |
| 3 | 284 | 5.83 |
TABLE 8-continued
| Example | MS-ESI (m/z) [M + H]⁺ | Retention time (min.) |
|---|---|---|
| 4 | 300 | 5.28 |
| 5 | 342* | 6.32 |
| 6 | 358* | 6.00 |

TABLE 8-continued

| Example | MS-ESI (m/z) [M + H]⁺ | Retention time (min.) |
| --- | --- | --- |
| 7 | 388 | 6.58 |
| 8 | 404 | 6.53 |
| 10 | 507 | 6.02 |
| 11 | 507 | 6.05 |
| 12 | 521 | 6.13 |
| 13 | 518* | 6.32 |

*[M − H]⁻

TABLE 9

| Example | MS-ESI (m/z) [M + H]⁺ | Retention time (min.) |
| --- | --- | --- |
| 14- (A) | 404 | 6.42 |
| 14- (B) | 404 | 6.43 |
| 15 | 404 | 6.58 |
| 16 | 404 | 6.58 |
| 17# | 492 | 6.08 |
| 18# | 506 | 6.16 |
| 19# | 493 | 6.07 |
| 20# | 493 | 5.73 |
| 21 | 508 | 5.92 |
| 22# | 510 | 6.07 |
| 23# | 554 | 5.71 |
| 24# | 541 | 4.54 |
| 25# | 541 | 5.11 |
| 26# | 556 | 5.21 |
| 27# | 558 | 5.60 |
| 28# | 552 | 5.73 |
| 29# | 566 | 5.78 |
| 30# | 507 | 4.83 |
| 31# | 542** | 6.12 |
| 32# | 524 | 6.02 |
| 33# | 545 | 5.97 |
| 34# | 559 | 5.81 |
| 35# | 546 | 4.50 |
| 36 | 544* | 5.85 |
| 37# | 561 | 5.31 |
| 38# | 563 | 5.83 |
| 39# | 532 | 4.72 |
| 40# | 532 | 5.37 |
| 41# | 545 | 5.77 |
| 42# | 518 | 6.07 |
| 43# | 522 | 6.05 |
| 44 | 540 | 5.78 |
| 45 | 531 | 6.08 |
| 46 | 526** | 6.33 |
| 47# | 478 | 5.77 |
| 48# | 492 | 5.89 |
| 49# | 479 | 4.30 |
| 50# | 479 | 5.03 |
| 51# | 478 | 5.59 |
| 52 | 465 | 5.09 |
| 53# | 465 | 4.26 |
| 54# | 480 | 5.15 |
| 55# | 494 | 5.45 |
| 56 | 508 | 5.68 |
| 57# | 495 | 4.90 |
| 58# | 510 | 4.97 |
| 59# | 512 | 5.52 |
| 60# | 495 | 4.90 |
| 61# | 506 | 6.08 |
| 62# | 493 | 5.35 |
| 63# | 492 | 6.01 |
| 64 | 504* | 6.28 |
| 65# | 493 | 5.37 |
| 66 | 404 | 5.93 |
| 67 | 404 | 5.95 |
| 68# | 360 | 5.85 |
| 69# | 394 | 5.88 |

TFA based
*[M − H]⁻
**[M + Na]⁺

TABLE 10

| Example | MS-ESI (m/z) [M + H]⁺ | Retention time (min.) |
| --- | --- | --- |
| 70 | 519 | 5.93 |
| 71 | 520 | 5.65 |
| 72 | 555 | 5.90 |
| 73# | 540 | 5.77 |
| 74 | 541 | 5.88 |
| 75 | 528** | 6.53 |
| 76 | 528** | 6.37 |
| 77 | 530** | 5.75 |
| 78 | 477 (free) | 4.03 |
| 79 | 575 | 6.00 |
| 80 | 418** | 5.62 |
| 81 | 432** | 5.87 |
| 82 | 408** | 5.52 |
| 83 | 432** | 6.07 |
| 84 | 328 | 5.73 |
| 85 | 410 | 6.67 |
| 86 | 368 | 6.10 |
| 87 | 348 | 5.72 |
| 88 | 392 | 5.75 |
| 89 | 334 | 5.70 |
| 90 | 392 | 5.75 |
| 91 | 392 | 6.12 |
| 92 | 344 | 5.55 |
| 93 | 419 | 5.73 |
| 94# | 434 | 6.17 |
| 95 | 364** | 5.40 |
| 96 | 411 | 7.10 |
| 97 | 411 | 6.90 |
| 98 | 449 | 5.90 |
| 99 | 368 | 5.59 |
| 100 | 388 | 6.40 |
| 101 | 377 | 5.32 |
| 102 | 378 | 5.70 |
| 103 | 378 | 5.65 |
| 104 | 378 | 6.00 |
| 105 | 386 | 6.03 |
| 106 | 406 | 6.27 |
| 107# | 430 | 6.35 |
| 108# | 406 | 6.46 |
| 109# | 366 | 5.99 |
| 110# | 402 | 6.12 |
| 111# | 403 | 4.13 |
| 112# | 433 | 5.77 |
| 113# | 417 | 3.94 |
| 114# | 433 | 5.67 |
| 115# | 482** | 6.25 |
| 116# | 463 | 6.13 |
| 117# | 471 | 5.75 |
| 118# | 486 | 5.87 |
| 119# | 447 | 5.65 |
| 120# | 434 | 6.73 |
| 121# | 430** | 5.53 |
| 122# | 403 | 3.95 |
| 123# | 434 | 5.37 |
| 124 | 440** | 6.45 |
| 125 | 433 | 5.63 |
| 126 | 449 | 6.02 |
| 127 | 419 | 4.70 |
| 128 | 407 | 5.75 |
| 129 | 432 | 6.37 |

TFA based
*[M − H]⁻
**[M + Na]⁺

TABLE 11

| Example | MS-ESI (m/z) [M + H]⁺ | Retention time (min.) |
| --- | --- | --- |
| 130 | 424 | 5.88 |
| 131 | 446** | 6.77 |
| 132 | 448** | 5.60 |
| 133 | 424 | 5.73 |
| 134 | 439 (free) | 3.13 |

TABLE 11-continued

| Example | MS-ESI (m/z) [M + H]+ | Retention time (min.) |
|---|---|---|
| 135 | 519 | 6.08 |
| 136 | 505 | 6.23 |
| 137 | 553 | 5.58 |
| 138 | 566 | 5.92 |
| 139 | 518 | 6.53 |
| 140 | 532 | 6.46 |
| 141 | 392 | 5.58 |
| 142# | 394 | 5.67 |
| 143# | 360 | 5.85 |
| 144# | 421 | 5.48 |

TFA based
*[M − H]−
**[M + Na]+

TABLE 12

| Example | MS-ESI (m/z) [M + H]+ | Retention time (min.) |
|---|---|---|
| 1-2 | 162 | 2.88 |
| 1-3 | 344 | 5.95 |
| 3-1 | 281 | 6.37 |
| 3-3 | 252 | 5.37 |
| 4-1 | 398 | 7.32 |
| 5-2 | 312 | 5.85 |
| 8-1 | 180 | 4.85 |
| 8-2 | 236* | 4.98 |
| 8-3 | 432 | 7.00 |
| 10-2 | 296** | 5.72 |
| 10-3 | 338** | 5.32 |
| 10-5 | 150* | 0.92 |
| 11-1 | 296** | 5.77 |
| 11-2 | 338** | 5.28 |
| 12-1 | 330 | 5.35 |
| 13-2 | 309** | 6.22 |
| 13-3 | 379** | 6.23 |
| 13-4 | 351** | 5.78 |
| Reference Example 1 | 189* | 4.98 |
| Reference Example 3 | 307** | 6.37 |
| Reference Example 5 | 310** | 6.02 |

*[M − H]−
**[M + Na]+

TABLE 13

| Example | MS-ESI (m/z) [M + H]+ | Retention time (min.) |
|---|---|---|
| 15-1 (A) | 150* | 0.95 |
| 15-1 (B) | 150* | 0.93 |
| Reference Example 6 | 248* | 1.18 |

*[M − H]−

TABLE 14

Substituted boronic acid ester

| Example | MS-ESI (m/z) [M + H]+ | Retention time (min.) |
|---|---|---|
| 17 | 532 | 5.87 |
| 18 | 546 | 5.95 |
| 19# | 533 | 5.18 |
| 20 | 533 | 5.67 |
| 21 | 548 | 5.48 |
| 22 | 550 | 6.03 |
| 23 | 592* | 5.42 |
| 24# | 581 | 4.32 |
| 25 | 581 | 5.28 |
| 26 | 596 | 5.05 |

TABLE 14-continued

Substituted boronic acid ester

| Example | MS-ESI (m/z) [M + H]+ | Retention time (min.) |
|---|---|---|
| 27 | 598 | 5.57 |
| 28 | 592 | 5.58 |
| 29 | 606 | 5.65 |
| 30 | 547 | 5.62 |
| 31 | 582** | 5.98 |
| 32 | 586** | 5.98 |
| 34 | 599 | 5.75 |
| 35 | 586 | 5.73 |
| 36 | 586 | 5.47 |
| 37 | 601 | 5.25 |
| 38 | 603 | 5.82 |
| 39 | 572 | 5.72 |
| 40 | 572 | 5.68 |
| 41 | 585 | 5.67 |
| 42# | 558 | 6.08 |
| 43 | 562 | 6.03 |
| 44 | 580 | 5.49 |
| 45 | 571 | 5.60 |
| 46 | 544 | 6.02 |
| 47# | 632 | 6.97 |
| 48# | 668** | 6.97 |
| 49 | 633 | 6.73 |
| 50 | 633 | 6.75 |
| 51 | 632 | 6.77 |
| 52 | 619 | 6.75 |
| 53 | 619 | 6.67 |
| 54 | 634 | 6.47 |
| 55# | 574 | 5.98 |
| 56 | 586* | 6.13 |
| 57 | 575 | 5.77 |
| 58 | 590 | 5.62 |
| 59 | 592 | 6.13 |
| 60 | 575 | 5.77 |
| 61 | 682** | 7.10 |
| 62 | 647 | 6.92 |
| 63 | 574 | 6.15 |
| 64 | 610** | 6.15 |
| 65 | 575 | 5.95 |

TFA based
*[M − H]−
**[M + Na]+

TABLE 15

| Example | MS-ESI (m/z) [M + H]+ | Retention time (min.) |
|---|---|---|
| 70-1 | 559 | 5.58 |
| 71-1 | 560 | 5.28 |
| 72-1 | 593* | 5.57 |
| 73-1 | 580 | 5.60 |
| 74-1 | 581 | 5.48 |
| 75-1 | 568** | 6.02 |
| 76-1 | 568** | 5.92 |
| 77-1 | 610** | 6.07 |
| 78-1 | 639** | 6.43 |
| 79-1 | 412 | 5.68 |
| 79-2 | 504 | 5.82 |
| 80-1 | 458** | 5.23 |
| 81-1 | 472** | 5.37 |
| 82-1 | 448** | 5.22 |
| 83-1 | 472** | 5.62 |
| 84-1 | 390** | 5.33 |
| 86-1 | 406* | 5.68 |
| 87-1 | 386* | 5.43 |
| 88-1 | 430* | 5.45 |
| 89-1 | 372* | 5.32 |
| 90-1 | 430* | 5.43 |
| 91-1 | 430* | 5.70 |
| 92-1 | 382* | 5.10 |
| 93-1 | 459 | 5.38 |
| 94-1 | 496** | 5.98 |

TABLE 15-continued

| Example | MS-ESI (m/z) [M + H]+ | Retention time (min.) |
|---|---|---|
| 95-1 | 380* | 5.00 |
| 97-1 | 451 | 6.32 |
| 98-1 | 487* | 5.73 |
| 99-1 | 406* | 5.38 |
| 100-1 | 315* | 6.23 |
| 101-1 | 388 | 6.35 |
| 101-2 | 510** | 6.78 |
| 102-1 | 416* | 5.40 |
| 103-1 | 305* | 5.98 |
| 104-1 | 305* | 5.87 |
| 105-1 | 194 | 3.77 |
| 105-2# | 210 | 2.92 |
| 105-3 | 474** | 5.93 |
| 105-4 | 650** | 6.75 |
| 106-1 | 670** | 6.83 |
| 124-1 | 225 | 5.60 |
| 124-2 | 209 (—H2O) | 5.55 |
| 125-1 | 473 | 5.20 |
| 126-1 | 489 | 5.62 |
| 127-1 | 459 | 4.27 |
| 129-1 | 239 | 5.63 |
| 129-2 | 494** | 5.93 |
| 130-1 | 462* | 5.47 |
| 131-1 | 486** | 6.17 |
| 132-1 | 488** | 5.22 |
| 133-1 | 476** | 5.23 |
| 134-1# | 479 | 3.80 |
| 138-1 | 377** | 5.33 |
| 139-1 | 329** | 5.95 |
| 140-1 | 343** | 5.94 |
| 141-1 | 321 | 5.90 |
| 142-1 | 432* | 5.68 |
| 143-1 | 398* | 5.63 |

TFA based
*[M − H]−
**[M + Na]+

TABLE 16

| Example | NMR data (δ: ppm) <*: 300 MHz> |
|---|---|
| 1* | (DMSO-d6) 7.60 (2H, d, J = 9 Hz), 7.45-7.34 (3H, m), 7.28-6.89 (9H, m), 5.18 (2H, s) |
| 2 | (DMSO-d6) 11.98 (1H, bs), 7.70 (2H, d, J = 9 Hz), 7.45-7.37 (3H, m), 7.24 (1H, d, J = 8 Hz), 7.16 (1H, dd, J = 7, 7 Hz), 7.13-7.06 (3H, m), 7.02 (2H, d, J = 9 Hz), 6.99-6.93 (1H, m), 6.67 (1H, bs), 5.18 (2H, s) |
| 3* | (DMSO-d6) 11.48 (1H, bs), 7.60 (2H, d, J = 9 Hz), 7.53-7.30 (5H, m), 7.11 (2H, d, J = 9 Hz), 6.91 (1H, s), 5.18 (2H, s) |
| 4 | (DMSO-d6) 11.28 (1H, bs), 7.82 (2H, d, J = 9 Hz), 7.50-7.45 (2H, m), 7.44-7.39 (2H, m), 7.38-7.33 (1H, m), 7.21 (2H, d, J = 9 Hz), 7.09 (1H, s), 5.23 (2H, s) |
| 5* | (DMSO-d6) 7.62 (2H, d, J = 9 Hz), 7.45-7.39 (2H, m), 7.33-7.27 (1H, m), 7.14 (2H, d, J = 9 Hz), 6.93 (1H, s), 5.96-5.89 (1H, m), 3.30-1.90 (4H, m) |
| 6 | (CDCl3) 7.74 (2H, d, J = 9 Hz), 7.35 (1H, d, J = 8 Hz), 7.33-7.22 (2H, m), 7.11 (2H, d, J = 9 Hz), 6.65 (1H, s), 5.81 (1H, dd, J = 7, 4 Hz), 3.21-3.11 (1H, m), 3.01-2.92 (1H, m), 2.68-2.57 (1H, m), 2.30-2.20 (1H, m) |
| 7 | (CDCl3) 7.53-7.40 (2H, m), 7.50 (2H, d, J = 9 Hz), 7.24-7.10 (5H, m), 7.03 (2H, d, J = 9 Hz), 6.65 (1H, s), 5.18 (2H, s), 2.03 (6H, s) |
| 8* | (DMSO-d6) 11.40 (1H, bs), 7.81 (2H, d, J = 9 Hz), 7.53-7.43 (2H, m), 7.26-7.08 (7H, m), 7.07 (1H, s), 5.29 (2H, s), 1.96 (6H, s) |
| 9 | (DMSO-d6) 7.75 (2H, d, J = 9 Hz), 7.53-7.43 (2H, m), 7.23 (1H, s), 7.19-7.07 (6H, m), 6.51 (1H, s), 5.24 (2H, s), 1.96 (6H, s) |
| 10* | (DMSO-d6) 11.49 (1H, bs), 7.83 (1H, s), 7.81 (2H, d, J = 9 Hz), 7.49 (1H, d, J = 7 Hz), 7.33-7.23 (1H, m), 7.24 (2H, d, J = 9 Hz), 7.12 (1H, d, J = 7 Hz), 7.03 (1H, s), 6.75 (1H, s), 5.25 (2H, s), 4.38 (1H, s), 4.37 (2H, t, J = 7 Hz), 2.03 (3H, s), 1.97 (3H, s), 1.89-1.80 (2H, m), 1.17 (6H, s) |
| 11* | (DMSO-d6) 11.28 (1H, bs), 7.82 (2H, d, J = 9 Hz), 7.48 (1H, d, J = 7 Hz), 7.39 (1H, d, J = 8 Hz), 7.32-7.23 (1H, m), 7.24 (2H, d, J = 9 Hz), 7.12 (1H, d, J = 7 Hz), 7.06 (1H, s), 6.66 (1H, d, J = 9 Hz), 5.25 (2H, s), 4.38 (1H, s), 4.43-4.33 (2H, m), 2.12 (3H, s), 2.04 (3H, s), 1.89-1.82 (2H, m), 1.18 (6H, s) |
| 12* | (DMSO-d6) 11.37 (1H, bs), 7.76 (2H, d, J = 9 Hz), 7.47 (1H, d, J = 7 Hz), 7.30 (1H, dd, J = 8, 8 Hz), 7.20 (2H, d, J = 9 Hz), 7.03 (1H, d, J = 7 Hz), 6.84 (1H, s), 6.58 (1H, s), 5.24 (2H, s), 4.42-4.28 (2H, m), 4.37 (1H, s), 2.00 (3H, s), 1.96 (3H, s), 1.88-1.79 (2H, m), 1.85 (3H, s), 1.17 (6H, s) |
| 13* | (DMSO-d6) 11.30 (1H, bs), 7.84 (2H, d, J = 9 Hz), 7.45 (1H, d, J = 7 Hz), 7.33-7.24 (1H, m), 7.26 (2H, d, J = 9 Hz), 7.11 (1H, s), 6.99 (1H, d, J = 7 Hz), 6.72 (2H, s), 5.27 (2H, s), 4.39 (1H, s), 4.09 (2H, t, J = 7 Hz), 1.94 (3H, s), 1.89-1.82 (2H, m), 1.86 (6H, s), 1.19 (6H, s) |

TABLE 17

| Example | NMR data (δ: ppm) <*: 300 MHz> |
|---|---|
| 14-(A) | (DMSO-d6) 11.27 (1H, s), 7.81 (2H, d, J = 9 Hz), 7.54-7.44 (2H, m), 7.28-7.05 (8H, m), 5.29 (2H, s), 1.95 (6H, s) |
| 14-(B) | (DMSO-d6) 11.28 (1H, s), 7.81 (2H, d, J = 9 Hz), 7.53-7.43 (2H, m), 7.25-7.07 (8H, m), 5.28 (2H, s), 1.95 (6H, s) |
| 15* | (CDCl3) 7.74-7.65 (1H, m), 7.70 (2H, d, J = 9 Hz), 7.50-7.36 (2H, m), 6.62 (1H, s), 7.23-7.05 (7H, m), 5.19 (2H, s), 2.01 (6H, s) |
| 16* | (CDCl3) 7.73-7.57 (1H, m), 7.70 (2H, d, J = 9 Hz), 7.50-7.35 (2H, m), 6.62 (1H, s), 7.23-7.05 (7H, m), 5.19 (2H, s), 2.01 (6H, s) |

TABLE 17-continued

| Example | NMR data (δ: ppm) <*: 300 MHz> |
|---|---|
| 17 | (DMSO-d$_6$) 11.27 (1H, s), 7.80 (2H, d, J = 9 Hz), 7.51-7.40 (2H, m), 7.24-7.16 (3H, m), 7.08 (1H, d, J = 7 Hz), 7.07 (1H, s), 6.71, (2H, s), 5.27 (2H, s), 4.10-4.05 (2H, m), 3.72-3.66 (2H, m), 3.51 (2H, q, J = 7 Hz), 1.92 (6H, s), 1.14 (3H, t, J = 7 Hz) |
| 33 | (DMSO-d$_6$) 11.27 (1H, s), 7.80 (2H, d, J = 9 Hz), 7.50-7.40 (2H, m), 7.23-7.18 (3H, m), 7.11-7.06 (1H, m), 7.09 (1H, s), 6.68 (2H, s), 5.26 (2H, s), 3.95 (2H, t, J = 6 Hz), 3.39-3.30 (4H, m), 2.21 (2H, t, J = 8 Hz), 1.98-1.84 (10H, m) |
| 44 | (DMSO-d$_6$) 7.79 (2H, d, J = 9 Hz), 7.50-7.39 (2H, m), 7.23-7.16 (3H, m), 7.11-7.03 (2H, m), 6.71 (2H, s), 5.26 (2H, s), 4.08 (2H, t, J = 6 Hz), 3.31-3.24 (2H, m), 3.03 (3H, s), 2.19-2.09 (2H, m), 1.92 (6H, s) |
| 46 | (DMSO-d$_6$) 11.26 (1H, s), 7.80 (2H, d, J = 9 Hz), 7.50-7.37 (2H, m), 7.23-7.16 (1H, m), 7.20 (2H, d, J = 9 Hz), 7.11-7.05 (2H, m), 6.75 (2H, s), 5.27 (2H, s), 4.49 (2H, d, J = 6 Hz), 4.31 (2H, d, J = 6 Hz), 4.04 (2H, s), 1.92 (6H, s), 1.37 (3H, s) |
| 47 | (DMSO-d$_6$) 11.27 (1H, s), 7.81 (2H, d, J = 9 Hz), 7.49-7.40 (2H, m), 7.24-7.17 (3H, m), 7.08 (2H, d, J = 7 Hz), 6.69 (2H, s), 5.27 (2H, s), 4.54 (1H, t, J = 5 Hz), 4.03 (2H, t, J = 6 Hz), 3.56 (2H, q, J = 6 Hz), 1.91 (6H, s), 1.89-1.82 (2H, m) |
| 56* | (DMSO-d$_6$) 7.82 (2H, d, J = 9 Hz), 7.44 (1H, d, J = 8 Hz), 7.31-7.22 (1H, m), 7.24 (2H, d, J = 9 Hz), 7.07 (1H, s), 6.97 (1H, d, J = 6 Hz), 6.72 (2H, s), 5.25 (2H, s), 4.93 (1H, d, J = 5 Hz), 4.66 (1H, t, J = 6 Hz), 4.04-3.94 (1H, m), 3.91-3.73 (2H, m), 3.45 (2H, t, J = 6 Hz), 3.16 (1H, d, J = 5 Hz), 1.93 (3H, s), 1.85 (6H, s) |
| 63 | (DMSO-d$_6$) 11.28 (1H, s), 7.83-7.76 (2H, m), 7.50-7.39 (2H, m), 7.24-7.16 (3H, m), 7.08 (2H, d, J = 9 Hz), 6.68 (2H, s), 5.26 (2H, s), 4.58-4.53 (1H, m), 4.09-3.95 (2H, m), 3.87-3.74 (1H, m), 1.91 (6H, s), 1.81-1.68 (2H, m), 1.15-1.08 (3H, m) |
| 66* | (DMSO-d$_6$) 11.28 (1H, s), 7.83 (2H, d, J = 9 Hz), 7.57 (1H, d, J = 8 Hz), 7.46-7.41 (1H, m), 7.27-7.19 (1H, m), 7.23 (2H, d, J = 9 Hz), 7.11 (1H, s), 6.10 (1H, dd, J = 7, 4 Hz), 3.11-2.97 (1H, m), 2.97-2.83 (1H, m), 2.71-2.58 (1H, m), 2.15-2.00 (1H, m) |

TABLE 18

| Example | NMR data (δ: ppm) <*: 300 MHz> |
|---|---|
| 107 | $^1$H-NMR (DMSO-D$_6$) δ: 11.30 (1H, s), 7.83 (2H, d, J = 9 Hz), 7.42 (1H, d, J = 7 Hz), 7.36 (1H, t, J = 7 Hz), 7.26 (2H, d, J = 9 Hz), 7.20-7.11 (3H, m), 7.09 (1H, s), 7.07-7.04 (1H, m), 6.09 (1H, dd, J = 4, 6 Hz), 2.65-2.39 (3H, m), 2.04-1.95 (1H, m), 1.94 (3H, s), 1.91 (3H, s). |
| 114* | $^1$H-NMR (DMSO-D$_6$) δ: 11.29 (1H, s), 8.21 (1H, dd, J = 5, 2 Hz), 7.84 (2H, d, J = 9 Hz), 7.66 (1H, dd, J = 7, 2 Hz), 7.47-7.40 (1H, m), 7.33-7.23 (2H, m), 7.26 (2H, d, J = 9 Hz), 7.13-7.06 (1H, m), 7.10 (1H, s), 6.10-6.03 (1H, m), 3.86 (3H, s), 2.93-2.80 (1H, m), 2.79-2.51 (2H, m), 2.08-1.93 (1H, m). |
| 115* | $^1$H-NMR (DMSO-D$_6$) δ: 11.29 (1H, s), 7.84 (2H, d, J = 9 Hz), 7.40 (1H, d, J = 7 Hz), 7.33 (1H, t, J = 7 Hz), 7.26 (2H, d, J = 9 Hz), 7.11 (1H, s), 7.05-7.00 (1H, m), 6.71 (2H, s), 6.12-6.04 (1H, m), 3.75 (3H, s), 2.67-2.38 (3H, m), 2.05-1.95 (1H, m), 1.91 (3H, s), 1.88 (3H, s). |
| 124 | $^1$H-NMR (CDCl$_3$) δ: 7.74 (2H, d, J = 9 Hz), 7.56 (1H, s), 7.37-7.30 (2H, m), 7.28-7.19 (2H, m), 7.14 (2H, d, J = 9 Hz), 7.12-7.07 (1H, m), 7.01-6.96 (2H, m), 6.94-6.89 (1H, m), 6.65 (1H, s), 5.91-5.86 (1H, m), 3.12-3.01 (1H, m), 2.92-2.82 (1H, m), 2.68-2.56 (1H, m), 2.28-2.15 (1H, m). |
| 125 | $^1$H-NMR (CDCl$_3$) δ: 8.29 (1H, t, J = 3 Hz), 7.74 (2H, d, J = 9 Hz), 7.28-7.20 (2H, m), 7.13 (2H, d, J = 9 Hz), 7.11-7.09 (2H, m), 6.78-6.73 (1H, m), 6.65 (1H, s), 5.92-5.85 (1H, m), 3.19-3.00 (1H, m), 3.00-2.80 (1H, m), 2.73-2.56 (1H, m), 2.55 (3H, s), 2.32-2.17 (1H, m). |
| 129* | $^1$H-NMR (CDCl$_3$) δ: 7.73 (2H, d, J = 9 Hz), 7.51 (1H, s), 7.47-7.30 (5H, m), 7.22 (1H, d, J = 8 Hz), 7.12 (2H, d, J = 9 Hz), 7.05 (1H, d, J = 8 Hz), 6.88 (1H, d, J = 8 Hz), 6.63 (1H, s), 5.90-5.83 (1H, m), 5.13 (2H, s), 3.23-3.09 (1H, m), 3.05-2.90 (1H, m), 2.71-2.54 (1H, m), 2.31-2.14 (1H, m). |
| 135 | $^1$H-NMR (CDCl$_3$) δ: 7.75 (2H, d, J = 9 Hz), 7.57 (1H, s), 7.46 (1H, d, J = 8 Hz), 7.39 (1H, d, J = 8 Hz), 7.35 (1H, t, J = 8 Hz), 7.19 (1H, d, J = 8 Hz), 7.16 (2H, d, J = 9 Hz), 6.66 (1H, s), 6.63 (1H, d, J = 8 Hz), 5.96-5.89 (1H, m), 4.58 (2H, t, J = 6 Hz), 3.01 (1H, s), 2.98-2.84 (1H, m), 2.77-2.54 (2H, m), 2.30 (3H, s), 2.28-2.14 (1H, m), 2.04 (2H, t, J = 6 Hz), 1.34 (6H, s). |
| 137 | $^1$H-NMR (CDCl$_3$) δ: 7.76 (2H, d, J = 9 Hz), 7.52 (1H, s), 7.46 (1H, d, J = 8 Hz), 7.40 (1H, d, J = 8 Hz), 7.36 (1H, t, J = 8 Hz), 7.19 (1H, d, J = 8 Hz), 7.16 (2H, d, J = 9 Hz), 6.66 (1H, s), 6.62 (1H, d, J = 8 Hz), 5.96-5.89 (1H, m), 4.50 (2H, t, J = 6 Hz), 3.32-3.25 (2H, m), 2.98 (3H, s), 2.96-2.83 (1H, m), 2.78-2.55 (2H, m), 2.43-2.33 (2H, m), 2.29 (3H, s), 2.26-2.14 (1H, m). |

TABLE 19

| Example | NMR data (δ: ppm) <*: 300 MHz, **: 270 MHz> |
|---|---|
| 1-1* | (DMSO-d$_6$) 13.52 (1H, bs), 10.29 (1H, bs), 7.46 (2H, d, J = 9 Hz), 6.83 (2H, d, J = 9 Hz) |
| 1-2* | (DMSO-d$_6$) 10.19 (1H, bs), 8.01 (1H, bs), 7.54 (1H, bs), 7.38 (2H, dd, J = 9, 2 Hz), 6.81 (2H, dd, J = 9, 2 Hz) |
| 1-3* | (DMSO-d$_6$) 8.06 (1H, bs), 7.60 (1H, bs), 7.50 (2H, d, J = 9 Hz), 7.45-7.35 (3H, m), 7.22 (1H, d, J = 7 Hz), 7.20-7.13 (1H, m), 7.11-6.94 (4H, m), 7.07 (2H, d, J = 9 Hz), 5.17 (2H, s) |
| 3-1 | (CDCl$_3$) 7.53 (2H, d, J = 9 Hz), 7.44-7.31 (5H, m), 6.95 (2H, d, J = 9 Hz), 5.09 (2H, s), 4.28 (2H, q, J = 7 Hz), 1.35 (3H, t, J = 7 Hz) |

TABLE 19-continued

| Example | NMR data (δ: ppm) <*: 300 MHz, **: 270 MHz> |
|---|---|
| 3-2* | (DMSO-d$_6$) 13.62 (1H, bs), 7.58 (2H, d, J = 9 Hz), 7.48-7.30 (5H, m), 7.10 (2H, d, J = 9 Hz), 5.17 (2H, s) |
| 3-3 | (CDCl$_3$) 7.50 (2H, d, J = 9 Hz), 7.45-7.32 (5H, m), 6.96 (2H, d, J = 9 Hz), 5.84 (2H, bs), 5.09 (2H, s) |
| 4-1* | (DMSO-d$_6$) 7.64 (2H, d, J = 9 Hz), 7.50-7.31 (5H, m), 7.11 (2H, d, J = 9 Hz), 7.09 (1H, s), 5.18 (2H, s), 0.98 (9H, s), 0.32 (6H, s) |
| 5-1* | (CDCl$_3$) 7.59 (2H, d, J = 9 Hz), 7.34 (1H, d, J = 8 Hz), 7.31 (1H, s), 7.24 (1H, d, J = 8 Hz), 6.98 (2H, d, J = 9 Hz), 5.76 (1H, dd, J = 7, 4 Hz), 3.22-3.09 (1H, m), 3.01-2.87 (1H, m), 2.68-2.55 (1H, m), 2.30-2.18 (1H, m) |
| 5-2* | (DMSO-d$_6$) 8.07 (1H, bs), 7.60 (1H, bs), 7.53 (2H, d, J = 9 Hz), 7.46-7.39 (2H, m), 7.33-7.27 (1H, m), 7.12 (2H, d, J = 9 Hz), 5.95-5.88 (1H, m), 3.13-3.00 (1H, m), 2.97-2.85 (1H, m), 2.67-2.50 (1H, m), 2.12-2.00 (1H, m) |
| 7-1* | (CDCl$_3$) 7.56 (2H, d, J = 9 Hz), 7.50-7.36 (2H, m), 7.22-7.07 (5H, m), 7.01-6.92 (2H, m), 5.17 (2H, s), 2.01 (6H, s) |
| 7-2* | (CDCl$_3$) 7.50-7.43 (1H, m), 7.49 (2H, d, J = 9 Hz), 7.42-7.37 (1H, m), 7.22-7.09 (5H, m), 6.96 (2H, d, J = 9 Hz), 5.76 (1H, bs), 5.53 (1H, bs), 5.16 (2H, s), 2.01 (6H, s) |
| 8-1* | (CDCl$_3$) 6.60 (1H, s), 5.45 (2H, s), 3.54 (3H, s) |
| 8-2* | (CDCl$_3$) 10.04 (1H, bs), 7.53 (2H, d, J = 9 Hz), 7.11 (1H, s), 6.85 (2H, d, J = 9 Hz), 5.43 (2H, s), 3.44 (3H, s) |
| 8-3* | (DMSO-d$_6$) 7.62 (2H, d, J = 9 Hz), 7.50-7.28 (2H, m), 7.24-7.00 (8H, m), 5.42 (2H, s), 5.23 (2H, s), 3.42 (3H, s), 1.92 (6H, s) |
| 10-1 | (CDCl$_3$) 7.77-7.62 (1H, m), 7.42 (1H, d, J = 7 Hz), 7.19-7.13 (1H, m), 4.81 (1H, d, J = 12 Hz), 4.71 (1H, t, J = 4 Hz), 4.50 (1H, d, J = 12 Hz), 3.97-3.88 (1H, m), 3.78 (4H, s), 3.59-3.51 (1H, m), 2.50 (3H, s), 1.92-1.48 (6H, m), 1.04 (6H, s) |
| 10-2* | (CDCl$_3$) 8.16 (1H, s), 6.63 (1H, s), 4.45 (2H, t, J = 7 Hz), 2.33 (3H, s), 2.23 (1H, bs), 1.96 (2H, t, J = 7 Hz), 1.29 (6H, s) |

TABLE 20

| Example | NMR data |
|---|---|
| 10-3 | (CDCl$_3$) 7.84 (1H, s), 7.42 (1H, d, J = 7 Hz), 7.29-7.23 (1H, m), 7.08-7.03 (1H, m), 6.66 (1H, s), 4.77 (2H, d, J = 5 Hz), 4.58-4.48 (2H, m), 2.61 (1H, bs), 2.06 (3H, s), 2.04-1.99 (2H, m), 2.00 (3H, s), 1.72-1.65 (1H, m), 1.33 (6H, s) |
| 10-4* | (CDCl$_3$) 7.88 (1H, s), 7.76 (2H, d, J = 9 Hz), 7.49-7.44 (1H, m), 7.29-7.22 (1H, m), 7.11-7.06 (1H, m), 6.99 (2H, d, J = 9 Hz), 6.66 (1H, s), 5.10 (2H, s), 4.57-4.50 (2H, m), 3.75 (4H, s), 2.59 (1H, bs), 2.07 (3H, s), 2.05-1.98 (2H, m), 2.02 (3H, s), 1.32 (6H, s), 1.02 (6H, s) |
| 10-5 | (CDCl$_3$) 8.12 (1H, bs), 6.68 (1H, s) |
| 11-1* | (CDCl$_3$) 7.61 (1H, d, J = 9 Hz), 6.45 (1H, d, J = 9 Hz), 4.47 (2H, t, J = 7 Hz), 2.54 (3H, s), 2.43 (1H, bs), 1.97 (2H, t, J = 7 Hz), 1.29 (6H, s) |
| 11-2 | (CDCl$_3$) 7.39 (1H, d, J = 7 Hz), 7.30 (1H, d, J = 8 Hz), 7.27-7.21 (1H, m), 7.07-7.03 (1H, m), 6.61 (1H, d, J = 8 Hz), 4.77 (2H, d, J = 5 Hz), 4.61-4.51 (2H, m), 3.02 (1H, bs), 2.19 (3H, s), 2.07 (3H, s), 2.02 (2H, t, J = 6 Hz), 1.62 (1H, t, J = 5 Hz), 1.32 (6H, s) |
| 11-3* | (CDCl$_3$) 7.76 (2H, d, J = 9 Hz), 7.47-7.41 (1H, m), 7.33 (1H, d, J = 8 Hz), 7.28-7.21 (1H, m), 7.12-7.06 (1H, m), 6.99 (2H, d, J = 9 Hz), 6.61 (1H, d, J = 8 Hz), 5.12 (1H, d, J = 12 Hz), 5.08 (1H, d, J = 12 Hz), 4.60-4.51 (2H, m), 3.75 (4H, s), 3.00 (1H, bs), 2.20 (3H, s), 2.07 (3H, s), 2.06-1.99 (2H, m), 1.32 (6H, s), 1.02 (6H, s) |
| 12-1* | (CDCl$_3$) 7.40 (1H, d, J = 8 Hz), 7.30-7.21 (1H, m), 7.00-6.94 (1H, m), 6.51 (1H, s), 4.77 (2H, bs), 4.61-4.47 (2H, m), 3.23 (1H, bs), 2.08 (3H, s), 2.05-1.99 (2H, m), 1.99 (3H, s), 1.89 (3H, s), 1.64 (1H, bs), 1.31 (6H, s) |
| 12-2 | (DMSO-d$_6$) 7.64 (2H, d, J = 8 Hz), 7.46 (1H, d, J = 8 Hz), 7.32-7.25 (1H, m), 7.04-6.97 (1H, m), 7.02 (2H, d, J = 8 Hz), 6.58 (1H, s), 5.16 (2H, s), 4.38 (1H, s), 4.34 (2H, t, J = 7 Hz), 3.73 (4H, s), 2.00 (3H, s), 1.94 (3H, s), 1.88-1.80 (2H, m), 1.84 (3H, s), 1.17 (6H, s), 0.95 (6H, s) |
| 13-1* | (CDCl$_3$) 7.79 (2H, d, J = 8 Hz), 7.20 (1H, t, J = 8 Hz), 3.89 (3H, s), 3.80 (4H, s), 2.71 (3H, s), 1.06 (6H, s) |
| 13-2* | (CDCl$_3$) 6.67 (2H, s), 4.14 (2H, t, J = 6 Hz), 2.39 (6H, s), 2.21 (1H, bs), 1.99 (2H, t, J = 6 Hz), 1.32 (6H, s) |
| 13-3* | (CDCl$_3$) 7.84 (1H, dd, J = 8, 1 Hz), 7.33-7.25 (1H, m), 7.17 (1H, dd, J = 8, 1 Hz), 6.70 (2H, s), 4.22 (2H, t, J = 6 Hz), 3.92 (3H, s), 2.43 (1H, bs), 2.20 (3H, s), 2.03 (2H, t, J = 6 Hz), 1.91 (6H, s), 1.35 (6H, s) |
| 13-4* | (CDCl$_3$) 7.37 (1H, d, J = 8, 1 Hz), 7.30-7.22 (1H, m), 6.98 (1H, d, J = 8, 1 Hz), 6.69 (2H, s), 4.78 (2H, d, J = 6 Hz), 4.22 (2H, t, J = 6 Hz), 2.48 (1H, bs), 2.03 (2H, t, J = 6 Hz), 1.98 (3H, s), 1.92 (6H, s), 1.57 (1H, t, J = 6 Hz), 1.35 (6H, s) |
| 13-5* | (CDCl$_3$) 7.77 (2H, d, J = 9 Hz), 7.46-7.41 (1H, m), 7.29-7.22 (1H, m), 7.05-7.00 (1H, m), 7.00 (2H, d, J = 9 Hz), 6.70 (2H, s), 5.11 (2H, s), 4.22 (2H, t, J = 6 Hz), 3.77 (4H, s), 2.47 (1H, bs), 2.03 (2H, t, J = 6 Hz), 1.99 (3H, s), 1.93 (6H, s), 1.35 (6H, s), 1.03 (6H, s) |
| Reference Example 1 | (CDCl$_3$) 7.50 (2H, d, J = 9 Hz), 6.83 (2H, d, J = 9 Hz), 5.22 (1H, bs), 4.30 (2H, q, J = 7 Hz), 1.37 (3H, t, J = 7 Hz) |
| Reference Example 2** | (CDCl$_3$) 7.46-7.33 (2H, m), 7.21-7.07 (5H, m), 4.63 (2H, s), 2.03 (6H, s) |
| Reference Examples 3* | (CDCl$_3$) 7.50 (1H, d, J = 8 Hz), 7.34 (1H, d, J = 8 Hz), 7.04 (1H, dd, J = 8 Hz), 4.82 (1H, d, J = 12 Hz), 4.71 (1H, t, J = 3 Hz), 4.51 (1H, d, J = 12 Hz), 3.97-3.82 (1H, m), 3.62-3.53 (1H, m), 2.43 (3H, s), 1.95-1.50 (6H, m) |

TABLE 20-continued

| | |
|---|---|
| Reference Example 4* | (CDCl$_3$) 7.71 (2H, d, J = 8 Hz), 6.82 (2H, d, J = 8 Hz), 4.82 (1H, bs), 3.76 (4H, s), 1.03 (6H, s) |
| Reference Example 5 | (CDCl$_3$) 6.47 (1H, s), 4.47 (2H, t, J = 6 Hz), 2.62 (1H, bs), 2.57 (3H, s), 2.35 (3H, s), 1.97 (2H, t, J = 6 Hz), 1.30 (6H, s) |

TABLE 21

| Example | NMR data (δ: ppm) <*: 300 MHz> |
|---|---|
| 15-1 (A)* | (CDCl$_3$) 7.65 (1H, bs), 6.69 (1H, s) |
| 15-1 (B)* | (CDCl$_3$) 7.71 (1H, bs), 6.69 (1H, s) |
| 15-2* | (CDCl$_3$) 7.77-7.68 (2H, m), 7.47-7.34 (2H, m), 7.23-7.03 (5H, m), 6.99-6.92 (2H, m), 5.14 (2H, s), 3.75 (4H, s), 2.02 (6H, s), 1.01 (6H, s) |
| 17-3 | (CDCl$_3$) 7.45-7.35 (4H, m), 7.18 (1H, s), 7.11-7.06 (1H, m), 6.99 (2H, d, J = 9 Hz), 6.69 (2H, s), 5.11 (2H, s), 4.16-4.12 (2H, m), 3.95 (2H, d, J = 16 Hz), 3.80 (2H, t, J = 5 Hz), 3.75 (2H, d, J = 16 Hz), 3.62 (2H, q, J = 7 Hz), 2.53 (3H, s), 1.98 (6H, s), 1.25 (3H, t, J = 7 Hz) |
| 44-3* | (DMSO-d$_6$) 7.50-7.37 (2H, m), 7.33 (2H, d, J = 9 Hz), 7.16 (1H, s), 7.10-7.02 (1H, m), 6.99 (2H, d, J = 9 Hz), 6.70 (2H, s), 5.16 (2H, s), 4.30 (2H, d, J = 17 Hz), 4.14-3.97 (4H, m), 3.31-3.22 (2H, m), 3.03 (3H, s), 2.47 (3H, s), 2.20-2.07 (2H, m), 1.91 (6H, s) |
| 47-3 | (CDCl$_3$) 7.43 (2H, d, J = 9 Hz), 7.41-7.36 (2H, m), 7.19 (1H, s), 7.12-7.08 (1H, s), 7.00 (2H, d, J = 9 Hz), 6.66 (2H, s), 5.12 (2H, s), 4.07 (2H, t, J = 6 Hz), 3.90 (2H, d, J = 16 Hz), 3.81 (2H, t, J = 6 Hz), 3.75 (2H, d, J = 16 Hz), 2.55 (3H, s), 2.04-1.94 (2H, m), 1.99 (6H, s), 0.91 (9H, s), 0.07 (6H, s) |
| 63-4 | (CDCl$_3$) 7.47-7.35 (4H, m), 7.17 (1H, s), 7.08 (1H, d, J = 7 Hz), 6.99 (2H, d, J = 9 Hz), 6.63 (2H, s), 5.20-5.06 (2H, m), 5.12 (1H, s), 4.01 (2H, t, J = 6 Hz), 3.89 (2H, d, J = 16 Hz), 3.74 (2H, d, J = 16 Hz), 2.54 (3H, s), 2.12-1.99 (2H, m), 2.05 (3H, s), 1.98 (6H, s), 1.32 (3H, d, J = 6 Hz) |
| 66-1 | (CDCl$_3$) 7.48 (1H, d, J = 8 Hz), 7.47 (2H, d, J = 9 Hz), 7.35 (1H, d, J = 8 Hz), 7.13 (1H, t, J = 8 Hz), 7.01 (2H, d, J = 9 Hz), 5.84 (1H, dd, J = 7, 4 Hz), 3.90 (2H, d, J = 16 Hz), 3.76 (2H, d, J = 16 Hz), 3.20-3.09 (1H, m), 3.00-2.89 (1H, m), 2.66-2.54 (1H, m), 2.59 (3H, s), 2.27-2.16 (1H, m) |
| Reference Example 6* | (DMSO-d$_6$) 9.41 (1H, s), 7.21 (2H, d, J = 8 Hz), 6.73 (2H, d, J = 8 Hz), 4.27 (2H, d, J = 17 Hz), 4.04 (2H, d, J = 17 Hz), 2.45 (3H, s) |

TABLE 22

| Example | NMR data (δ: ppm) <*: 300 MHz> |
|---|---|
| 85-1 | $^1$H-NMR (CDCl$_3$) δ: 7.45 (2H, d, J = 8 Hz), 7.36-7.31 (2H, m), 7.20 (1H, dd, J = 8, 2 Hz), 7.02 (2H, d, J = 9 Hz), 4.99 (2H, s), 3.88 (2H, d, J = 16 Hz), 3.75 (2H, d, J = 16 Hz), 2.56 (3H, s), 1.69 (4H, s), 1.28 (12H, s). |
| 105-1* | $^1$H-NMR (DMSO-D$_6$) δ: 11.41 (1H, brs), 9.95 (1H, s), 7.47 (2H, d, J = 9 Hz), 6.83 (2H, d, J = 9 Hz), 6.82 (1H, s). |
| 105-2 | $^1$H-NMR (DMSO-D$_6$) δ: 11.20 (1H, s), 10.39 (1H, s), 7.70 (2H, d, J = 9 Hz), 6.98 (1H, s), 6.92 (2H, d, J = 9 Hz). |
| 124-3 | $^1$H-NMR (CDCl$_3$) δ: 7.47 (2H, d, J = 9 Hz), 7.35-7.29 (2H, m), 7.24-7.21 (2H, m), 7.11-7.05 (1H, m), 7.04 (2H, d, J = 9 Hz), 6.99-6.95 (2H, m), 6.91-6.87 (1H, m), 5.85-5.79 (1H, m), 3.94 (2H, d, J = 16 Hz), 3.77 (2H, d, J = 16 Hz), 3.09-2.98 (1H, m), 2.89-2.78 (1H, m), 2.64-2.53 (1H, m), 2.59 (3H, s), 2.24-2.14 (1H, m). |
| 127-1* | $^1$H-NMR (CDCl$_3$) δ: 8.46 (2H, d, J = 6 Hz), 7.48 (2H, d, J = 9 Hz), 7.38-7.31 (2H, m), 7.08-6.99 (1H, m), 7.03 (2H, d, J = 9 Hz), 6.84-6.79 (2H, m), 5.87-5.80 (1H, m), 3.91 (2H, d, J = 16 Hz), 3.77 (2H, d, J = 16 Hz), 3.06-2.88 (1H, m), 2.86-2.69 (1H, m), 2.67-2.50 (1H, m), 2.60 (3H, s), 2.28-2.11 (1H, m). |
| 135-1* | $^1$H-NMR (CDCl$_3$) δ: 7.92 (1H, d, J = 8 Hz), 6.51 (1H, d, J = 8 Hz), 4.55 (2H, t, J = 6 Hz), 3.77 (4H, s), 2.64 (3H, s), 1.98 (2H, t, J = 6 Hz), 1.29 (6H, s), 1.03 (6H, s). |
| 136-1* | $^1$H-NMR (CDCl$_3$) δ: 7.90 (1H, d, J = 8 Hz), 6.57 (1H, d, J = 8 Hz), 4.52-4.46 (2H, m), 3.81-3.75 (6H, m), 3.77 (6H, s), 3.60 (2H, q, J = 7 Hz), 2.62 (3H, s), 1.24 (3H, t, J = 7 Hz), 1.03 (6H, s). |
| 137-1* | $^1$H-NMR (CDCl$_3$) δ: 7.93 (1H, d, J = 8 Hz), 6.50 (1H, d, J = 8 Hz), 4.46 (2H, t, J = 6 Hz), 3.77 (4H, s), 3.28-3.20 (2H, m), 2.95 (3H, s), 2.62 (3H, s), 2.40-2.26 (2H, m), 1.04 (6H, s). |

The invention claimed is:
1. A compound of Formula (I):

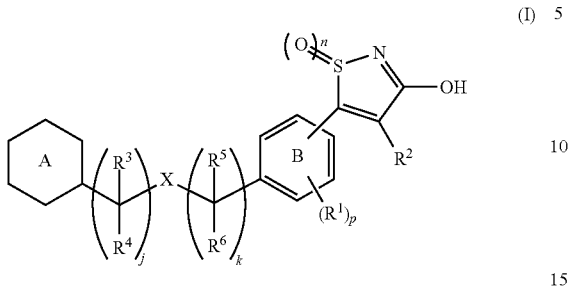

where n is an integer of 1; p is an integer of 0 to 4; j is an integer of 0 to 3; k is an integer of 0 to 2;
a ring A is a $C_{6-14}$ aryl group which is optionally substituted with 1 to 5 L(s) or a 3- to 14-membered heterocyclic group which is optionally substituted with 1 to 5 L(s);
a ring B is a benzene ring, a pyridine ring, or a pyrimidine ring;
X is an oxygen atom, a sulfur atom, or —$NR^7$—;
$R^1$ are independently a group arbitrarily selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group;
$R^2$ is a hydrogen atom, a halogen atom, a $C_{1-6}$ alkyl group, a $C_{2-6}$ alkenyl group, a $C_{2-6}$ alkynyl group, a $C_{1-6}$ alkoxy group, or a cyano group;
$R^3, R^4, R^5, R^6$, and $R^7$ are independently a group arbitrarily selected from a hydrogen atom, a $C_{1-6}$ alkyl group, a halogenated $C_{1-6}$ alkyl group, a $C_{2-6}$ alkenyl group, and a $C_{2-6}$ alkynyl group;
Ls are independently a halogen atom, —OH, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{1-10}$ alkenyloxy group which is optionally substituted with 1 to 5 substituent(s) RI, a $C_{1-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, a —$S(O)_iR^a$ (i is an integer of 0 to 2) group, or a —$NR^bR^c$ group;
$R^a$ is a group arbitrarily selected from a $C_{1-6}$ alkyl group and a halogenated $C_{1-6}$ alkyl group;
$R^b$ and $R^c$ are independently a group arbitrarily selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with —OH or a $C_{1-6}$ alkoxy group), a $C_{1-6}$ alkylsulfonyl group, an arylcarbonyl group, and a heterocyclic carbonyl group, where $R^b$ and $R^c$ optionally form together with a nitrogen atom to which $R^b$ and $R^c$ are bonded, a 3- to 8-membered cyclic group, where in the cyclic group, one carbon atom is optionally substituted with an atom arbitrarily selected from an oxygen atom, a sulfur atom, and a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;
where the substituents RI are optionally the same as or different from each other and are each a group arbitrarily selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with a $C_{1-6}$ alkyl group), 1 to 5-$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a —$NR^{b1}R^{c1}$ group, and a non-aromatic heterocyclic oxy group;
the substituents RII are optionally the same as or different from each other and are each a group arbitrarily selected from the substituents RI and a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s));
$R^d$ and $R^e$ are independently a hydrogen atom or a $C_{1-6}$ alkyl group;
$R^{b1}$ and $R^{c1}$ are independently a group arbitrarily selected from a hydrogen atom, a $C_{1-6}$ alkyl group, a $C_{2-7}$ alkanoyl group, and a $C_{1-6}$ alkylsulfonyl group, where $R^{b1}$ and $R^{c1}$ optionally form together with a nitrogen atom to which $R^{b1}$ and $R^{c1}$ are bonded, a 3- to 8-membered cyclic group, where in the cyclic group, one carbon atom is optionally substituted with an atom arbitrarily selected from an oxygen atom, a sulfur atom, and a nitrogen atom (the nitrogen atom is optionally substituted with a $C_{1-6}$ alkyl group) or with a carbonyl group, or a pharmaceutically acceptable salt of the compound, or a pharmaceutically acceptable solvate of the salt or a pharmaceutically acceptable solvate of the compound.

2. The compound according to claim 1 of Formula (II):

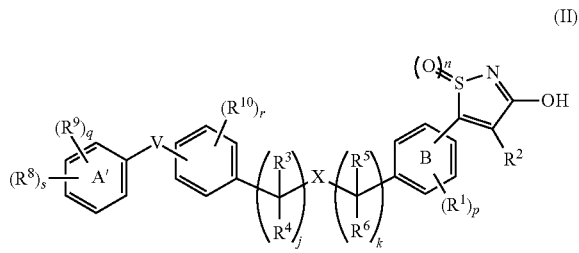

where n, p, j, k, the ring B, X, $R^1$, $R^2$, $R^3$, $R^4$, $R^5$, and $R^6$ are the same as defined in Formula (I), q and r are independently an integer of 0 to 4; s is an integer of 0 to 2; a ring A' is a benzene ring, a pyridine ring, or a pyrimidine ring; V is a single bond or an oxygen atom;

$R^8$s are independently a $C_{1-6}$ alkoxy group which is substituted with 1 to 5 substituent(s) RIII or a non-aromatic heterocyclic oxy group; where the substituents RIII are each a group arbitrarily selected from —OH, a $C_{1-6}$ alkoxy group, a non-aromatic heterocyclic group (the heterocyclic group is optionally substituted with a $C_{1-6}$ alkyl group), a —S(O)$_i$R$^a$ (i is an integer of 0 to 2, and R$^a$ is the same as defined above) group, a —SO$_2$NR$^d$R$^e$ (R$^d$ and R$^e$ are the same as defined above) group, a —CONR$^d$R$^e$ (R$^d$ and R$^e$ are the same as defined above) group, and a —NR$^{b1}$R$^{c1}$ (R$^{b1}$ and R$^{c1}$ are the same as defined above) group;

$R^9$ and $R^{10}$ are independently a halogen atom, a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group(s)), or a $C_{1-6}$ alkoxy group (the $C_{1-6}$ alkoxy group is optionally substituted with 1 to 5 halogen atom(s), or a pharmaceutically acceptable salt of the compound, or a pharmaceutically acceptable solvate of the salt or a pharmaceutically acceptable solvate of the compound.

3. The compound according to claim 2 of Formula (II-B):

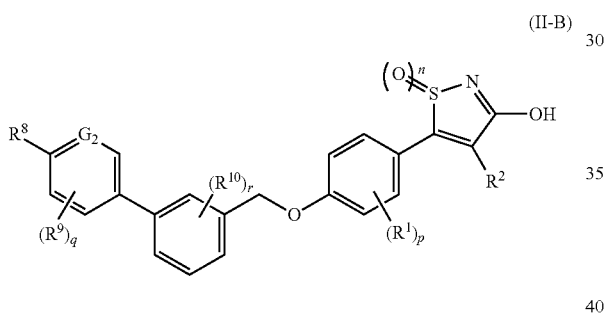

where n, p, $R^1$, and $R^2$ are the same as defined in Formula (I), q, r, $R^8$, $R^9$, and $R^{10}$ are the same as defined in Formula (II), and $G_2$ is a =CH— group, a =CR$^9$— group, or a nitrogen atom, or a pharmaceutically acceptable salt of the compound, or a pharmaceutically acceptable solvate of the salt or a pharmaceutically acceptable solvate of the compound.

4. The compound according to claim 3, wherein r is 0 or 1, $R^{10}$ is a $C_{1-4}$ alkyl group, q is 1, 2, or 3, $R^9$s are independently a halogen atom or a $C_{1-4}$ alkyl group, $R^8$ is a $C_{1-6}$ alkoxy group (the $C_{1-6}$ alkoxy group is substituted with 1 to 5 —OH, 1 to 5 ethoxy, 1 to 5 methylsulfonyl, 1 to 5 sulfamoyl, 1 to 5 methyl sulfamoyl, 1 to 5 dimethylsulfamoyl, 1 to 5 carbamoyl, 1 to 5 methylcarbamoyl, 1 to 5 dimethylcarbamoyl, 1 to 5 —NH$_2$, 1 to 5 acetylamino, 1 to 5 methylsulfonylamino, 1 to 5 2-oxo-1-pyrrolidinyl, or 1 to 5 3-methyloxetane-3-yl) or is a (1,1-dioxytetrahydro-2H-thiopyran-4-yl) oxy group, and $G_2$ is a =CH— group or a nitrogen atom, or a pharmaceutically acceptable salt of the compound, or a pharmaceutically acceptable solvate of the salt or a pharmaceutically acceptable solvate of the compound.

5. The compound according to claim 4, wherein r is 0 or 1, $R^{10}$ is a methyl group, q is 1, 2, or 3, $R^9$s are independently a fluorine atom or a methyl group, $R^8$ is a $C_{2-6}$ alkoxy group (the $C_{2-6}$ alkoxy group is substituted with 1 or 2 -OH, 1 or 2 ethoxy, 1 or 2 methylsulfonyl, 1 or 2 —NH$_2$, 1 or 2 acetylamino, 1 or 2 methylsulfonylamino, 1 or 2 2-oxo-1-pyrrolidinyl, or 1 or 2 3-methyloxetane-3-yl), or is a (1,1-dioxytetrahydro-2H-thiopyran-4-yl) oxy group, and $G_2$ is a =CH— group or a nitrogen atom, or a pharmaceutically acceptable salt of the compound, or a pharmaceutically acceptable solvate of the salt or a pharmaceutically acceptable solvate of the compound.

6. The compound according to claim 5, wherein $R^8$ is a 2-hydroxyethoxy group, a 3-hydroxypropoxy group, a 3-hydroxybutoxy group, a 3-hydroxy-3-methylbutoxy group, a 2,3-dihydroxypropoxy group, a 3-hydroxy-2-hydroxymethylpropoxy group, a 2-ethoxyethoxy group, a 3-(methylsulfonyl)propoxy group, a 3-aminopropoxy group, a 3-acetylaminopropoxy group, a 3-methylsulfonylaminopropoxy group, a 2-(2-oxopyrrolidine-1-yl)ethoxy group, a 3-(2-oxopyrrolidine-1-yl)propoxy group, a (3-methyl-3-oxetanyl)methoxy group, or a (1,1-dioxytetrahydro-2H-thiopyran-4-yl) oxy or a pharmaceutically acceptable salt of the compound, or a pharmaceutically acceptable solvate of the salt or a pharmaceutically acceptable solvate of the compound.

7. The compound according to claim 1 of Formula (III):

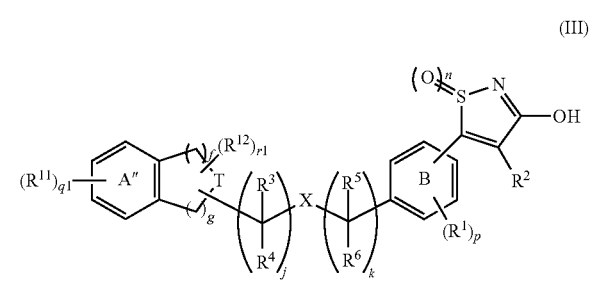

where n, p, j, k, the ring B, X, $R^1$, $R^2$, $R^3$, $R^4$, $R^5$, and $R^6$ are the same as defined in Formula (I), f is an integer of 0 or 2; g is an integer of 1 to 4; q1 is an integer of 0 to 4; r1 is an integer of 0 to 2;

a ring A" is a benzene ring or a pyridine ring;

T is —CH$_2$—, an oxygen atom, —S(O)$_i$— (i is an integer of 0 to 2), or —NR$^7$ (the definition of R$^7$ is the same as R$^7$ of Formula (I), $R^{12}$s are independently a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a —S(O)$_i$R$^a$ (i is an integer of 0 to 2, and R$^a$ is the same as defined in Formula (I)) group, or a —NR$^b$R$^c$ (the definitions of R$^b$ and R$^c$ are the same as R$^b$ and R$^c$ of Formula (I)) group;

the definition of $R^{11}$ is the same as L of Formula (I);

the substituents RI described above are the same as defined in Formula (I), or a pharmaceutically acceptable salt of the compound, or a pharmaceutically acceptable solvate of the salt or a pharmaceutically acceptable solvate of the compound.

8. The compound according to claim 7 of Formula (III-B):

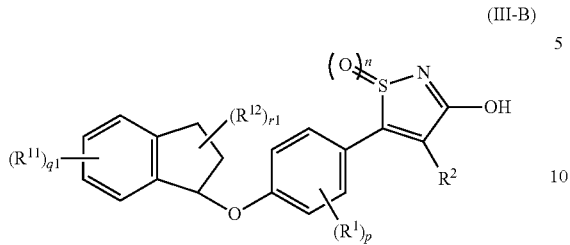

(III-B)

where n, p, $R^1$, and $R^2$ are the same as defined in Formula (I), and q1, r1, $R^{11}$, and $R^{12}$ are the same as defined in Formula (III), or a pharmaceutically acceptable salt of the compound, or a pharmaceutically acceptable solvate of the salt or a pharmaceutically acceptable solvate of the compound.

9. The compound according to claim 8, wherein
r1 is 0, q1 is an integer of 1 or 2, and $R^{11}$ is a halogen atom, a cyano group, a $C_{1-10}$ alkyl group (the $C_{1-10}$ alkyl group is optionally substituted with 1 to 5 halogen atom(s), 1 to 5 —OH, or 1 to 5 $C_{1-4}$ alkoxy group(s)), a $C_{1-10}$ alkenyl group (the $C_{1-10}$ alkenyl group is optionally substituted with 1 to 5 halogen atom(s), 1 to 5 —OH, or 1 to 5 $C_{1-4}$ alkoxy group(s)), a $C_{1-10}$ alkoxy group (the $C_{1-10}$ alkoxy group is optionally substituted with 1 to 5 halogen atom(s), 1 to 5 —OH, or 1 to 5 $C_{1-4}$ alkoxy group(s)), a $C_{1-10}$ alkenyloxy group (the $C_{1-10}$ alkenyloxy group is optionally substituted with 1 to 5 halogen atom(s), 1 to 5 —OH, or 1 to 5 $C_{1-4}$ alkoxy group(s)), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, an aryloxy group which is optionally substituted with 1 to 5 substituent(s) RIIa, a heteroaryloxy group which is optionally substituted with 1 to 5 substituent(s) RIIa, a non-aromatic heterocyclic oxy group which is optionally substituted with 1 to 5 substituent(s) RIIa, an aralkyloxy group which is optionally substituted with 1 to 5 substituent(s) RIIa (the substituents RIIa are optionally the same as or different from each other and are optionally each a group arbitrarily selected from a halogen atom, a $C_{1-6}$ alkoxy group (the $C_{1-6}$ alkoxy group is optionally substituted with 1 to 5 halogen atom(s), 1 to 5 —OH, 1 to 5 $C_{1-4}$ alkoxy group(s), 1 to 5 non-aromatic heterocyclic group(s) (the heterocyclic group is optionally substituted with a $C_{1-6}$ alkoxy group), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a non-aromatic heterocyclic oxy group, and a $C_{1-6}$ alkyl group (the $C_{1-6}$ alkyl group is optionally substituted with 1 to 5 halogen atom(s), 1 to 5 —OH, 1 to 5 $C_{1-4}$ alkoxy group(s), or 1 to 5 NR$^{b1}$R$^{c1}$ group(s)), or a pharmaceutically acceptable salt of the compound, or a pharmaceutically acceptable solvate of the salt or a pharmaceutically acceptable solvate of the compound.

10. A pharmaceutical composition comprising a compound of claim 1 or a pharmaceutically acceptable salt of the compound, or a pharmaceutically acceptable solvate of the compound or a pharmaceutically acceptable solvate of the salt.

11. A compound of Formula (I-I):

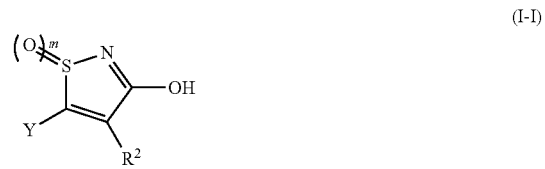

(I-I)

where $R^2$ is a hydrogen atom, a halogen atom, a $C_{1-6}$ alkyl group, a $C_{2-6}$ alkenyl group, a $C_{2-6}$ alkynyl group, a $C_{1-6}$ alkoxy group, or a cyano group; Y is a halogen atom, and m is an integer of 1, the case where Y and $R^2$ are both chlorine atoms is excluded, a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

12. A compound selected from:
5-(4-((3-phenoxyphenyl)methoxy)phenyl)isothiazol-3-ol 1-oxide;
5-(4-(benzyloxy)phenyl)isothiazol-3-ol 1-oxide;
5-(4-(5-chloro-2,3-dihydro-1H-inden-1-yloxy)phenyl) isothiazol-3-ol 1-oxide;
5-(4-((3-(2,6-dimethylphenyl)phenyl)methoxy)phenyl) isothiazol-3-ol 1-oxide;
5-(4-((3-(6-(3-hydroxy-3-methylbutoxy)-4-methylpyridin-3-yl)-2-methylphenyl)methoxy)phenyl)isothiazol-3-ol 1-oxide;
5-(4-((3-(6-(3-hydroxy-3-methylbutoxy)-2-methylpyridin-3-yl)-2-methylphenyl)methoxy)phenyl)isothiazol-3-ol 1-oxide;
5-(4-((3-(2,4-dimethyl-6-(3-hydroxy-3-methylbutoxy)pyridin-3-yl)-2-methylphenyl)methoxy)phenyl)isothiazol-3-ol 1-oxide;
5-(4-((3-(2,6-dimethyl-4-(3-hydroxy-3-methylbutoxy) phenyl)-2-methylphenyl)methoxy)phenyl)isothiazol-3-ol 1-oxide;
5-(4-((3-(2,6-dimethylphenyl)phenyl)methoxy)phenyl) isothiazol-3-ol 1-oxide;
5-(4-((3-(2,6-dimethyl-4-(2-ethoxyethoxy)phenyl)phenyl)methoxy)phenyl)isothiazol-3-ol 1-oxide;
5-(4-((3-(2,6-dimethyl-4-(2-ethoxyethoxy)phenyl)-2-methylphenyl)methoxy)phenyl)isothiazol-3-ol 1-oxide;
5-(4-((3-(2,4-dimethyl-6-(2-ethoxyethoxy)pyridin-3-yl) phenyl)methoxy)phenyl)isothiazol-3-ol 1-oxide;
5-(4-((3-(6-(2-ethoxyethoxy)-2-methylpyridin-3-yl)-2-methylphenyl)methoxy)phenyl)isothiazol-3-ol 1-oxide;
5-(4-((3-(4,6-dimethyl-2-(2-ethoxyethoxy)pyrimidin-5-yl)-2-methylphenyl)methoxy)phenyl)isothiazol-3-ol 1-oxide;
5-(4-((3-(2,6-dimethyl-4-(2-ethoxyethoxy)-3-fluorophenyl)phenyl)methoxy)phenyl)isothiazol-3-ol 1-oxide;
5-(4-((3-(2,6-dimethyl-4-(3-(methylsulfonyl)propoxy) phenyl)-2-methylphenyl)methoxy)phenyl)isothiazol-3-ol 1-oxide;
5-(4-((3-(2,4-dimethyl-6-(3-(methylsulfonyl)propoxy)pyridin-3-yl)phenyl)methoxy)phenyl)isothiazol-3-ol 1-oxide;
5-(4-((3-(2-methyl-6-(3-(methylsulfonyl)propoxy)pyridin-3-yl)-2-methylphenyl)methoxy)phenyl)isothiazol-3-ol 1-oxide;

5-(4-((3-(4,6-dimethyl-2-(3-(methylsulfonyl)propoxy)pyrimidin-5-yl)-2-methylphenyl)methoxy)phenyl)isothiazol-3-ol 1-oxide;
5-(4-((3-(2,6-dimethyl-3-fluoro-4-(3-(methylsulfonyl)propoxy)phenyl)phenyl)methoxy)phenyl)isothiazol-3-ol 1-oxide;
5-(4-((3-(2,6-dimethyl-4-((1,1-dioxidetetrahydro-2H-thiopyran-4-yl)oxy)phenyl)phenyl)methoxy)phenyl)isothiazol-3-ol 1-oxide;
5-(4-((3-(2,6-dimethyl-4-((1,1-dioxidetetrahydro-2H-thiopyran-4-yl)oxy)phenyl)-2-methylphenyl)methoxy)phenyl)isothiazol-3-ol 1-oxide;
5-(4-((3-(2,4-dimethyl-6-(3-hydroxy-3-methylbutoxy)pyridin-3-yl)phenyl)methoxy)phenyl)isothiazol-3-ol 1-oxide;
5-(4-((3-(2,6-dimethyl-4-(3-hydroxy-3-methylbutoxy)phenyl)-2-methylphenyl)methoxy)phenyl)isothiazol-3-ol 1-oxide;
5-(4-((3-(2,6-dimethyl-3-fluoro-4-(3-hydroxy-3-methylbutoxy)phenyl)phenyl)methoxy)phenyl)isothiazol-3-ol 1-oxide;
5-(4-((3-(2,6-dimethyl-4-(3-(2-oxopyrrolidin-1-yl)propoxy)phenyl)phenyl)methoxy)phenyl)isothiazol-3-ol 1-oxide;
5-(4-((3-(2,6-dimethyl-4-(3-(2-oxopyrrolidin-1-yl)propoxy)phenyl)-2-methylphenyl)methoxy)phenyl)isothiazol-3-ol 1-oxide;
5-(4-((3-(2,4-dimethyl-6-(3-(2-oxopyrrolidin-1-yl)propoxy)pyridin-3-yl)phenyl)methoxy)phenyl)isothiazol-3-ol 1-oxide;
5-(4-((3-(2-methyl-6-(3-(2-oxopyrrolidin-1-yl)propoxy)pyridin-3-yl)-2-methylphenyl)methoxy)phenyl)isothiazol-3-ol 1-oxide;
5-(4-((3-(4,6-dimethyl-2-(3-(2-oxopyrrolidin-1-yl)propoxy)pyrimidin-5-yl)-2-methylphenyl)methoxy)phenyl)isothiazol-3-ol 1-oxide;
5-(4-((3-(2,6-dimethyl-3-fluoro-4-(3-(2-oxopyrrolidin-1-yl)propoxy)phenyl)phenyl)methoxy)phenyl)isothiazol-3-ol 1-oxide;
5-(4-((3-(2,4-dimethyl-6-(2-(2-oxopyrrolidin-1-yl)ethoxy)pyridin-3-yl)phenyl)methoxy)phenyl)isothiazol-3-ol 1-oxide;
5-(4-((3-(2-methyl-6-(2-(2-oxopyrrolidin-1-yl)ethoxy)pyridin-3-yl)-2-methylphenyl)methoxy)phenyl)isothiazol-3-ol 1-oxide;
5-(4-((3-(2,6-dimethyl-4-(2-(2-oxopyrrolidin-1-yl)ethoxy)phenyl)-2-methylphenyl)methoxy)phenyl)isothiazol-3-ol 1-oxide;
5-(4-((3-(2,6-dimethyl-4-((3-methyl-3-oxetanyl)methoxy)phenyl)-2-methylphenyl)methoxy)phenyl)isothiazol-3-ol 1-oxide;
5-(4-((3-(2,6-dimethyl-3-fluoro-4-((3-methyl-3-oxetanyl)methoxy)phenyl)phenyl)methoxy)phenyl)isothiazol-3-ol 1-oxide;
5-(4-((3-(2,6-dimethyl-4-(3-(methylsulfonyl)propoxy)phenyl)phenyl)methoxy)phenyl)isothiazol-3-ol 1-oxide;
5-(4-((3-(2,6-dimethyl-4-(2-(2-oxopyrrolidin-1-yl)ethoxy)phenyl)phenyl)methoxy)phenyl)isothiazol-3-ol 1-oxide;
5-(4-((3-(2,6-dimethyl-4-((3-methyl-3-oxetanyl)methoxy)phenyl)phenyl)methoxy)phenyl)isothiazol-3-ol 1-oxide;
5-(4-((3-(2,6-dimethyl-4-(3-hydroxypropoxy)phenyl)phenyl)methoxy)phenyl)isothiazol-3-ol 1-oxide;
5-(4-((3-(2,6-dimethyl-4-(3-hydroxypropoxy)phenyl)-2-methylphenyl)methoxy)phenyl)isothiazol-3-ol 1-oxide;
5-(4-((3-(2,4-dimethyl-6-(3-hydroxypropoxy)pyridin-3-yl)phenyl)methoxy)phenyl)isothiazol-3-ol 1-oxide;
5-(4-((3-(2-methyl-6-(3-hydroxypropoxy)pyridin-3-yl)-2-methylphenyl)methoxy)phenyl)isothiazol-3-ol 1-oxide;
5-(4-((3-(2,6-dimethyl-4-(2-hydroxyethoxy)phenyl)-2-methylphenyl)methoxy)phenyl)isothiazol-3-ol 1-oxide;
5-(4-((3-(2-methyl-6-(2-hydroxyethoxy)pyridin-3-yl)-2-methylphenyl)methoxy)phenyl)isothiazol-3-ol 1-oxide;
5-(4-((3-(2,4-dimethyl-6-(2-hydroxyethoxy)pyridin-3-yl)phenyl)methoxy)phenyl)isothiazol-3-ol 1-oxide;
5-(4-((3-(4,6-dimethyl-2-(2-hydroxyethoxy)pyrimidin-5-yl)-2-methylphenyl)methoxy)phenyl)isothiazol-3-ol 1-oxide;
5-(4-((3-(4-((2R)-2,3-dihydroxypropoxy)-2,6-dimethylphenyl)phenyl)methoxy)phenyl)isothiazol-3-ol 1-oxide;
5-(4-((3-(4-((2R)-2,3-dihydroxypropoxy)-2,6-dimethylphenyl)-2-methylphenyl)methoxy)phenyl)isothiazol-3-ol 1-oxide;
5-(4-((3-(6-((2R)-2,3-dihydroxypropoxy)-2-methylpyridin-3-yl)-2-methylphenyl)methoxy)phenyl)isothiazol-3-ol 1-oxide;
5-(4-((3-(2-((2R)-2,3-dihydroxypropoxy)-4,6-dimethylpyrimidin-5-yl)-2-methylphenyl)methoxy)phenyl)isothiazol-3-ol 1-oxide;
5-(4-((3-(4-((2R)-2,3-dihydroxypropoxy)-2,6-dimethyl-3-fluorophenyl)phenyl)methoxy)phenyl)isothiazol-3-ol 1-oxide;
5-(4-((3-(6-((2S)-2,3-dihydroxypropoxy)-2-methylpyridin-3-yl)-2-methylphenyl)methoxy)phenyl)isothiazol-3-ol 1-oxide;
5-(4-((3-(2,6-dimethyl-4-((3S)-3-hydroxybutoxy)phenyl)-2-methylphenyl)methoxy)phenyl)isothiazol-3-ol 1-oxide;
5-(4-((3-(2-methyl-6-((3S)-3-hydroxybutoxy)pyridin-3-yl)-2-methylphenyl)methoxy)phenyl)isothiazol-3-ol 1-oxide;
5-(4-((3-(2,6-dimethyl-4-((3R)-3-hydroxybutoxy)phenyl)phenyl)methoxy)phenyl)isothiazol-3-ol 1-oxide;
5-(4-((3-(2,6-dimethyl-4-((3R)-3-hydroxybutoxy)phenyl)-2-methylphenyl)methoxy)phenyl)isothiazol-3-ol 1-oxide;
5-(4-((3-(2-methyl-6-((3R)-3-hydroxybutoxy)pyridin-3-yl)-2-methylphenyl)methoxy)phenyl)isothiazol-3-ol 1-oxide;
5-(4-((1R)-4-bromo-2,3-dihydro-1H-inden-1-yloxy)phenyl)isothiazol-3-ol 1-oxide;
5-(4-((1S)-4-bromo-2,3-dihydro-1H-inden-1-yloxy)phenyl)isothiazol-3-ol 1-oxide;
5-(4-(4-chloro-2,3-dihydro-1H-inden-1-yloxy)phenyl)isothiazol-3-ol 1-oxide;
5-(4-(4-trifluoromethyl-2,3-dihydro-1H-inden-1-yloxy)phenyl)isothiazol-3-ol 1-oxide;
N-[3-[4-[3-[[4-(3-hydroxy-1-oxo-isothiazol-5-yl)phenoxy]methyl]phenyl]-3,5-dimethylphenoxy]propyl]acetamide;
N-[3-[5-[3-[[4-(3-hydroxy-1-oxo-isothiazol-5-yl)phenoxy]methyl]-2-methylphenyl]-6-methylpyridin-2-yl]oxypropyl]acetamide;
N-[3-[4-[3-[[4-(3-hydroxy-1-oxo-isothiazol-5-yl)phenoxy]methyl]phenyl]-3,5-dimethylphenoxy]propyl]methanesulfonamide;
5-[4-[[3-[2,5-dimethyl-4-(3-methylsulfonylpropoxy)phenyl]phenyl]methoxy]phenyl]isothiazol-3-ol 1-oxide;

5-[4-[[3-[2,5-dimethyl-6-(3-methylsulfonylpropoxy)pyridin-3-yl]phenyl]methoxy]phenyl]isothiazol-3-ol 1-oxide;

5-[4-[[3-[4-(3-hydroxy-3-methylbutoxy)-2,5-dimethylphenyl]phenyl]methoxy]phenyl]isothiazol-3-ol 1-oxide;

5-[4-[[3-[4-(3-hydroxy-3-methylbutoxy)-2,6-dimethylphenyl]phenyl]methoxy]phenyl]isothiazol-3-ol 1-oxide;

2-[[4-[3-[[4-(3-hydroxy-1-oxo-isothiazol-5-yl)phenoxy]methyl]phenyl]-3,5-dimethylphenoxy]methyl]propane-1,3-diol;

5-[4-[[3-[4-(3-aminopropoxy)-2,6-dimethylphenyl]phenyl]methoxy]phenyl]isothiazol-3-ol 1-oxide;

5-[2-chloro-4-[[3-[2,4-dimethyl-6-(3-methylsulfonylpropoxy)pyridin-3-yl]phenyl]methoxy]phenyl]isothiazol-3-ol 1-oxide;

1-oxo-5-[4-[[7-(trifluoromethyl)-2,3-dihydro-1-benzofuran-3-yl]oxy]phenyl]-1,2-thiazol-3-ol;

5-[4-[[8-(trifluoromethyl)-3,4-dihydro-2H-chromen-4-yl]oxy]phenyl]isothiazol-3-ol 1-oxide;

5-[4-[(2,2-dimethyl-4H-1,3-benzodioxin-5-yl)methoxy]phenyl]isothiazol-3-ol 1-oxide;

5-[4-[[7-(trifluoromethyl)-3,4-dihydro-2H-chromen-4-yl]oxy]phenyl]isothiazol-3-ol 1-oxide;

5-[4-[(2,6-dimethylphenyl)methoxy]phenyl]isothiazol-3-ol 1-oxide;

5-[4-[(5,5,8,8-tetramethyl-6,7-dihydronaphthalen-2-yl)methoxy]phenyl]isothiazol-3-ol 1-oxide;

5-[4-[(2,3-dichlorophenyl)methoxy]phenyl]isothiazol-3-ol 1-oxide;

5-[4-[(1R)-1-(3-chlorophenyl)ethoxy]phenyl]isothiazol-3-ol 1-oxide;

5-[4-[(1R)-1-(3-bromophenyl)ethoxy]phenyl]isothiazol-3-ol 1-oxide;

5-[4-[(3-chlorophenyl)methoxy]phenyl]isothiazol-3-ol 1-oxide;

5-[4-[(1S)-1-(3-bromophenyl)ethoxy]phenyl]isothiazol-3-ol 1-oxide;

5-[4(3-bromo-2-methylphenyl)methoxy]phenyl]isothiazol-3-ol 1-oxide;

5-[4-[2-(4-methoxyphenyl)ethoxy]phenyl]isothiazol-3-ol 1-oxide;

5-[4-[[3-(4,4-difluoropiperidin-1-yl)phenyl]methoxy]phenyl]isothiazol-3-ol 1-oxide;

5-[4-[[3-(2,6-dimethylphenyl)-2-methoxyphenyl]methoxy]phenyl]isothiazol-3-ol 1-oxide;

5-[4-(2,3-dihydro-1-benzofuran-7-ylmethoxy)phenyl]isothiazol-3-ol 1-oxide;

5-[4-[[(3S)-1-(2,6-dimethylphenyl)piperidin-3-yl]methoxy]phenyl]isothiazol-3-ol 1-oxide;

5-[4-[[(3R)-1-(2,6-dimethylphenyl)piperidin-3-yl]methoxy]phenyl]isothiazol-3-ol 1-oxide;

5-[4-[[3-(4,4-difluoropiperidin-1-yl)-2-methoxyphenoxy]methyl]phenyl]isothiazol-3-ol 1-oxide;

5-[4-[[3-(trifluoromethyl)phenyl]methoxy]phenyl]isothiazol-3-ol 1-oxide;

5-[4-[2-chloro-4-(trifluoromethyl)phenoxy]phenyl]isothiazol-3-ol 1-oxide;

5-[4-[(3-bromophenyl)methylamino]phenyl]isothiazol-3-ol 1-oxide;

5-[4-[(3-bromophenyl)methoxy]phenyl]isothiazol-3-ol 1-oxide;

5-[4-[(3-bromophenoxy)methyl]phenyl]isothiazol-3-ol 1-oxide;

5-[3-[(3-bromophenyl)methoxy]phenyl]isothiazol-3-ol 1-oxide;

5-[4-[(2R)-1-(3-propane-2-yloxyphenyl)propan-2-yl]oxyphenyl]isothiazol-3-ol 1-oxide;

5-[4-[2-(3-phenoxyphenyl)ethoxy]phenyl]isothiazol-3-ol 1-oxide;

5-[4-[[(1R)-4-(2,6-dimethylphenyl)-2,3-dihydro-1H-inden-1-yl]oxy]phenyl]isothiazol-3-ol 1-oxide;

5-[4-[[(1R)-4-(cyclohexene-1-yl)-2,3-dihydro-1H-inden-1-yl]oxy]phenyl]isothiazol-3-ol 1-oxide;

5-[4-[[(1R)-4-cyclopropyl-2,3-dihydro-1H-inden-1-yl]oxy]phenyl]isothiazol-3-ol 1 oxide;

5-[4-[[(1R)-4-phenyl-2,3-dihydro-1H-inden-1-yl]oxy]phenyl]isothiazol-3-ol 1-oxide;

5-[4[[(1R)-4-pyridin-3-yl-2,3-dihydro-1H-inden-1-yl]oxy]phenyl]isothiazol-3-ol 1-oxide;

5-[4-[[(1R)-4-(6-methoxypyridin-3-yl)-2,3-dihydro-1H-inden-1-yl]oxy]phenyl]isothiazol-3-ol 1-oxide trifluoroacetate salt;

5-[4-[[(1R)-4-(2-methylpyridin-3-yl)-2,3-dihydro-1H-inden-1-yl]oxy]phenyl]isothiazol-3-ol 1-oxide trifluoroacetate salt;

5-[4-[[(1R)-4-(2-methoxypyridin-3-yl)-2,3-dihydro-1H-inden-1-yl]oxy]phenyl]isothiazol-3-ol 1-oxide;

5-[4-[[(1R)-4-(4-methoxy-2,6-dimethylphenyl)-2,3-dihydro-1H-inden-1-yl]oxy]phenyl]isothiazol-3-ol 1-oxide;

5-[4-[[(1R)-4-(2,6-dimethoxypyridin-3-yl)-2,3-dihydro-1H-inden-1-yl]oxy]phenyl]isothiazol-3-ol 1-oxide;

5-[4-[[(1R)-4-[2-(trifluoromethyl)pyridin-3-yl]-2,3-dihydro-1H-inden-1-yl]oxy]phenyl]isothiazol-3-ol 1-oxide;

5-[4-[[(1R)-4-(6-(piperidin-1-yl)pyridin-3-yl)-2,3-dihydro-1H-inden-1-yl]oxy]phenyl]isothiazol-3-ol 1-oxide;

5-[4-[[(1R)-4-(6-methoxy-2-methylpyridin-3-yl)-2,3-dihydro-1H-inden-1-yl]oxy]phenyl]isothiazol-3-ol 1-oxide trifluoroacetate salt;

5-[4-[[(1R)-4-(4,4-dimethylcyclohexen-1-yl)-2,3-dihydro-1H-inden-1-yl]oxy]phenyl]isothiazol-3-ol 1-oxide;

5-[4-[[(1R)-4-(3,6-dihydro-2H-pyran-4-yl)-2,3-dihydro-1H-inden-1-yl]oxy]phenyl]isothiazol-3-ol 1-oxide;

5-[4-[[(1R)-4-(pyridin-4-yl)-2,3-dihydro-1H-inden-1-yl]oxy]phenyl]isothiazol-3-ol 1-oxide trifluoroacetate salt;

5-[4-[[(1R)-4-(2-methoxypyrimidin-5-yl)-2,3-dihydro-1H-inden-1-yl]oxy]phenyl]isothiazol-3-ol 1-oxide;

5-[4-[(4-phenoxy-2,3-dihydro-1H-inden-1-yl)oxy]phenyl]isothiazol-3-ol 1-oxide;

5-[4-[[4-(2-methylpyridin-3-yl)oxy-2,3-dihydro-1H-inden-1-yl]oxy]phenyl]isothiazol-3-ol 1-oxide;

5-[4-[[4-(2-methoxypyridin-4-yl)oxy-2,3-dihydro-1H-inden-1-yl]oxy]phenyl]isothiazol-3-ol 1-oxide;

5-[4-[(4-pyridin-4-yloxy-2,3-dihydro-1H-inden-1-yl)oxy]phenyl]isothiazol-3-ol 1-oxide;

5-[4-[[3-(2-methoxypyridin-3-yl)phenyl]methoxy]phenyl]isothiazol-3-ol 1-oxide;

5-[4-[(4-phenylmethoxy-2,3-dihydro-1H-inden-1-yl)oxy]phenyl]isothiazol-3-ol 1-oxide;

5-4-[[4-(2,2,2-trifluoroethoxy)-2,3-dihydro-1H-inden-1-yl]oxy]phenyl]isothiazol-3-ol 1-oxide;

5-[4-[(4-cyclohexyloxy-2,3-dihydro-1H-inden-1-yl)oxy]phenyl]isothiazol-3-ol 1-oxide;

5-[4-[[4-(oxane-4-yloxy)-2,3-dihydro-1H-inden-1-yl]oxy]phenyl]isothiazol-3-ol 1-oxide;

5-[4-[[4-(2-ethoxyethoxy)-2,3-dihydro-1H-inden-1-yl]oxy]phenyl]isothiazol-3-ol 1-oxide;

[5-[4-[[4-(1-methylpiperidin-4-yl)oxy-2,3-dihydro-1H-inden-1-yl]oxy]phenyl]-1-oxo-isothiazol-3-yl]oxysodium salt;

5-[4-[[(1R)-4-[6-(3-hydroxy-3-methylbutoxy)-2-methylpyridin-3-yl]-2,3-dihydro-1H-inden-1-yl]oxy]phenyl]isothiazol-3-ol 1-oxide;

5-[4-[[(1R)-4-[6-(2-ethoxyethoxy)-2-methylpyridin-3-yl]-2,3-dihydro-1H-inden-1-yl]oxy]phenyl]isothiazol-3-ol 1-oxide;
5-[4-[[(1R)-4-[2-methyl-6-(3-methylsulfonylpropoxy)pyridin-3-yl]-2,3-dihydro-1H-inden-1-yl]oxy]phenyl]isothiazol-3-ol 1-oxide;
5-[4-[[(1R)-4-[2,6-dimethyl-4-(3-methylsulfonylpropoxy)phenyl]-2,3-dihydro-1H-inden-1-yl]oxy]phenyl]isothiazol-3-ol 1-oxide;
5-[4-[[(1R)-4-[4-(2-ethoxyethoxy)-2,6-dimethylphenyl]-2,3-dihydro-1H-inden-1-yl]oxy]phenyl]isothiazol-3-ol 1-oxide;
5-[4-[[(1R)-4-[4-(3-hydroxy-3-methylbutoxy)-2,6-dimethylphenyl]-2,3-dihydro-1H-inden-1-yl]oxy]phenyl]isothiazol-3-ol 1-oxide;
5-[4-[(3-bromophenyl)methoxymethyl]phenyl]isothiazol-3-ol 1-oxide;
5-(4-((1R)-4-trifluoromethyl-2,3-dihydro-1H-inden-1-yloxy)phenyl)isothiazol-3-ol 1-oxide;
5-(4-((1R)-4-chloro-2,3-dihydro-1H-inden-1-yloxy)phenyl)isothiazol-3-ol 1-oxide; or
5-[4-[[(1R)-4-(6-fluoropyridin-3-yl)-2,3-dihydro-1H-inden-1-yl]oxy]phenyl]isothiazol-3-ol 1-oxide;
or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

13. A compound selected from:
1) 5-(4-((3-(2,6-dimethyl-4-(2-ethoxyethoxy)phenyl)phenyl)methoxy)phenyl)-isothiazol-3-ol 1-oxide;
2) 5-(4-((3-(2,4-dimethyl-6-(3-hydroxy-3-methylbutoxy)pyridin-3-yl)phenyl)-methoxy)-phenyl)isothiazol-3-ol 1-oxide;
3) 5-(4-((3-(2,6-dimethyl-3-fluoro-4-(3-(2-oxopyrrolidin-1-yl)propoxy)phenyl)-phenyl)-methoxy)phenyl)isothiazol-3-ol 1-oxide;
4) 5-(4-((3-(2,6-dimethyl-3-fluoro-4-((3-methyl-3-oxetanyl)methoxy)phenyl)-phenyl)-methoxy)phenyl)isothiazol-3-ol 1-oxide;
5) 5-(4-((3-(2,6-dimethyl-4-(3-(methylsulfonyl)propoxy)phenyl)phenyl)methoxy)-phenyl)-isothiazol-3-ol 1-oxide;
6) 5-(4-((3-(2,6-dimethyl-4-(3-hydroxypropoxy)phenyl)phenyl)methoxy)phenyl)-isothiazol-3-ol 1-oxide;
7) 5-(4-((3-(2,4-dimethyl-6-(3-hydroxypropoxy)pyridin-3-yl)phenyl)methoxy)-phenyl)-isothiazol-3-ol 1-oxide;
8) 5-(4-((3-(4-((2R)-2,3-dihydroxypropoxy)-2,6-dimethyl-3-fluorophenyl)-phenyl)-methoxy)phenyl)isothiazol-3-ol 1-oxide;
9) 5-(4-((3-(2,6-dimethyl-4-((3R)-3-hydroxybutoxy)phenyl)phenyl)methoxy)-phenyl)-isothiazol-3-ol 1-oxide;
10) N-[3-[4-[3-[[4-(3-hydroxy-1-oxo-isothiazol-5-yl)phenoxy]methyl]phenyl]-3,5-di-methylphenoxy]propyl]methanesulfonamide;
11) 5-[4-[[3-[4-(3-aminopropoxy)-2,6-dimethylphenyl]phenyl]methoxy]phenyl]-isothiazol-3-ol 1-oxide;
12) 5-[4-[[(1R)-4-(6-methoxy-2-methylpyridin-3-yl)-2,3-dihydro-1H-inden-1-yl]-oxy]-phenyl]isothiazol-3-ol 1-oxide trifluoroacetate salt;
13) 5-[4-[[(1R)-4-[6-(3-hydroxy-3-methylbutoxy)-2-methylpyridin-3-yl]-2,3-dihydro-1H-inden-1-yl]oxy]phenyl]isothiazol-3-ol 1-oxide;
14) 5-[4-[[(1R)-4-[6-(2-ethoxyethoxy)-2-methylpyridin-3-yl]-2,3-dihydro-1H-inden-1-yl]-oxy]phenyl]isothiazol-3-ol 1-oxide; and
15) 5-[4[[(1R)-4-[4-(3-hydroxy-3-methylbutoxy)-2,6-dimethylphenyl]-2,3-dihydro-1H-inden-1-yl]oxy]phenyl]isothiazol-3-ol 1-oxide;
or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

14. The compound of claim 13, wherein the compound is 5-(4-((3-(2,6-dimethyl-4-(2-ethoxyethoxy)phenyl)phenyl)methoxy)phenyl)isothiazol-3-ol 1-oxide;
or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

15. The compound of claim 13, wherein the compound is 5-(4-((3-(2,4-dimethyl-6-(3-hydroxy-3-methylbutoxy)pyridin-3-yl)phenyl)methoxy)phenyl)isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

16. The compound of claim 13, wherein the compound is 5-(4-((3-(2,6-dimethyl-3-fluoro-4-(3-(2-oxopyrrolidin-1-yl)propoxy)phenyl)phenyl)methoxy)phenyl)isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

17. The compound of claim 13, wherein the compound is 5-(4-((3-(2,6-dimethyl-3-fluoro-4-((3-methyl-3-oxetanyl)methoxy)phenyl)phenyl)methoxy)phenyl)isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

18. The compound of claim 13, wherein the compound is 5-(4-((3-(2,6-dimethyl-4-(3-(methylsulfonyl)propoxy)phenyl)phenyl)methoxy)phenyl)isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

19. The compound of claim 13, wherein the compound is 5-(4-((3-(2,6-dimethyl-4-(3-hydroxypropoxy)phenyl)phenyl)methoxy)phenyl)isothiazol-3-ol 1-oxide; or a pharmaceutically acceptable salt of the compound, or a pharmaceu- 20. The compound of claim 13, wherein the compound is 5-(4-((3-(2,4-dimethyl-6-(3-hydroxypropoxy)pyridin-3-yl)phenyl)methoxy)phenyl)isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

21. The compound of claim 13, wherein the compound is 5 (4 ((3 (4 ((2R)-2,3-dihydroxypropoxy) 2,6-dimethyl-3-fluorophenyl)phenyl)methoxy)phenyl)isothiazole 3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

22. The compound of claim 13, wherein the compound is 5-(4-((3-(2,6-dimethyl-4-((3R)-3-hydroxybutoxy)phenyl)phenyl)methoxy)phenyl)isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

23. The compound of claim 13, wherein the compound is N-[3-[4-[3-[[4-(3-hydroxy-1-oxo-isothiazol-5-yl)phenoxy]methyl]phenyl]-3,5-dimethylphenoxy]propyl]methanesulfonamide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

24. The compound of claim 13, wherein the compound is 5-[4-[[3-[4-(3-aminopropoxy)-2,6-dimethylphenyl]phenyl]methoxy]phenyl]isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

25. The compound of claim 13, wherein the compound is 5-[4-[[(1R)-4-(6-methoxy-2-methylpyridine 3 yl) 2,3-dihydro 1H-indene-1-yl]oxy]phenyl]isothiazole 3-ol 1 oxide trifluoroacetate salt; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

26. The compound of claim 13, wherein the compound is 5-[4-[[(1R)-4-[6-(3-hydroxy-3-methylbutoxy)-2-methylpyridin-3-yl]-2,3-dihydro-1H-inden-1-yl]oxy]phenyl]isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

27. The compound of claim 13, wherein the compound is 5-[4-[[(1R)-4-[6-(2-ethoxyethoxy)-2-methylpyridin-3-yl]-2,3-dihydro-1H-inden-1-yl]oxy]phenyl]isothiazol-3-ol 1-oxide; or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

28. The compound of claim 13, wherein the compound is 5-[4-[[(1R)-4-[4-(3-hydroxy-3-methylbutoxy)-2,6-dimethylphenyl]-2,3-dihydro-1H-inden-1-yl]oxy]phenyl]isothiazol-3-ol 1-oxide;
or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the optical isomer, or a pharmaceutically acceptable solvate of the salt or a pharmaceutically acceptable solvate of the optical isomer.

29. A pharmaceutical composition comprising a compound of claim 13, or a pharmaceutically acceptable salt of the compound, or a pharmaceutically acceptable solvate of the compound or a pharmaceutically acceptable solvate of the salt.

30. A pharmaceutical composition comprising a compound of claim 1, or a pharmaceutically acceptable salt of the compound, or a pharmaceutically acceptable solvate of the compound or a pharmaceutically acceptable solvate of the salt, and
a compound selected from a group consisting of a PPAR gamma agonist, a biguanide agent, a sulfonylurea, a rapid-acting insulin secretagogue, an alpha-glucosidase inhibitor, insulin or an insulin derivative, GLP-1 and a GLP-1 agonist, a DPP-IV inhibitor, an alpha-2 antagonist, an SGLT2 inhibitor, omega-3 fatty acids, an HMG-CoA reductase inhibitor, an HMG-CoA synthase inhibitor, a cholesterol absorption inhibitor, an acyl-CoA-cholesterol acyltransferase (ACAT) inhibitor, a CETP inhibitor, a squalene synthase inhibitor, an antioxidant, a PPAR alpha agonist, a PPAR delta agonist, an LXR agonist, an FXR agonist, an MTTP inhibitor, a squalene epoxidase inhibitor, a bile acid absorption inhibitor, a CB-1 receptor antagonist, a monoamine reuptake inhibitor, a serotonin reuptake inhibitor, a lipase inhibitor, a neuropeptide Y (NPY) receptor antagonist, a peptide YY (PYY) receptor antagonist, and an adrenergic beta-3 receptor agonist.

31. The pharmaceutical composition of claim 30, wherein the DPP-IV inhibitor is selected from sitagliptin, vildagliptin, alogliptin, saxagliptin, linagliptin, and teneligliptin, or a pharmaceutically acceptable salt thereof.

32. The pharmaceutical composition of claim 30, wherein the DPP-IV inhibitor is sitagliptin, or a pharmaceutically acceptable salt thereof.

33. A method for treating diabetes comprising the administration to a patient of an effective amount of the compound of claim 1, or a pharmaceutically acceptable salt of the compound, or a pharmaceutically acceptable solvate of the compound or a pharmaceutically acceptable solvate of the salt.

34. A method for treating diabetes comprising the administration to a patient of an effective amount of the compound of claim 1, or a pharmaceutically acceptable salt of the compound, or a pharmaceutically acceptable solvate of the compound or a pharmaceutically acceptable solvate of the salt, and a compound selected from a group consisting of a PPAR gamma agonist, a biguanide agent, a sulfonylurea, a rapid-acting insulin secretagogue, an alpha-glucosidase inhibitor, insulin or an insulin derivative, GLP-1 and a GLP-1 agonist, a DPP-IV inhibitor, an alpha-2 antagonist, an SGLT2 inhibitor, omega-3 fatty acids, an HMG-CoA reductase inhibitor, an HMG-CoA synthase inhibitor, a cholesterol absorption inhibitor, an acyl-CoA-cholesterol acyltransferase (ACAT) inhibitor, a CETP inhibitor, a squalene synthase inhibitor, an antioxidant, a PPAR alpha agonist, a PPAR delta agonist, an LXR agonist, an FXR agonist, an MTTP inhibitor, a squalene epoxidase inhibitor, a bile acid absorption inhibitor, a CB-1 receptor antagonist, a monoamine reuptake inhibitor, a serotonin reuptake inhibitor, a lipase inhibitor, a neuropeptide Y (NPY) receptor antagonist, a peptide YY (PYY) receptor antagonist, and an adrenergic beta-3 receptor agonist.

35. The method of claim 34, wherein the DPP-IV inhibitor is selected from sitagliptin, vildagliptin, alogliptin, saxagliptin, linagliptin, and teneligliptin, or a pharmaceutically acceptable salt thereof.

36. The method of claim 34, wherein the DPP-IV inhibitor is sitagliptin, or a pharmaceutically acceptable salt thereof.

* * * * *